(12) United States Patent
Dillon et al.

(10) Patent No.: US 7,595,405 B2
(45) Date of Patent: Sep. 29, 2009

(54) TETRAZOLE-SUBSTITUTED ARYLAMIDES AS P2X₃ AND P2X₂/₃ ANTAGONISTS

(75) Inventors: Michael Patrick Dillon, San Francisco, CA (US); Ronald Charles Hawley, Mountain View, CA (US); Li Chen, Shanghai (CN); Lichun Feng, Shanghai (CN); Minmin Yang, Shanghai (CN)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/823,808

(22) Filed: Jun. 28, 2007

(65) Prior Publication Data

US 2008/0004442 A1 Jan. 3, 2008

Related U.S. Application Data

(60) Provisional application No. 60/817,298, filed on Jun. 29, 2006.

(51) Int. Cl.
*C07D 257/04* (2006.01)

(52) U.S. Cl. .................. 548/254; 544/238; 544/333; 544/405; 546/348; 548/146; 548/579

(58) Field of Classification Search ............ 544/238, 544/333, 359, 405; 546/348; 548/146, 254
See application file for complete search history.

(56) References Cited

U.S. PATENT DOCUMENTS

| 2003/0187076 A1 | 10/2003 | Agoston et al. |
| 2007/0037974 A1* | 2/2007 | Brotherton-Pleiss et al. ...... 544/120 |

FOREIGN PATENT DOCUMENTS

| DE | 100 55 713 A1 | 5/2002 |
| WO | WO 94/26709 A1 | 11/1994 |
| WO | WO 01/02379 A1 | 1/2001 |
| WO | WO 02/00647 A1 | 1/2002 |
| WO | WO 2004/009816 A1 | 1/2004 |
| WO | WO 2004/094395 A2 | 11/2004 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Patani, et al. in Chem. Rev., 96, 1996, pp. 3147-3176.*

* cited by examiner

*Primary Examiner*—James O Wilson
*Assistant Examiner*—Douglas M Willis
(74) *Attorney, Agent, or Firm*—Robert C. Hall

(57) ABSTRACT

Compounds of the formula I:

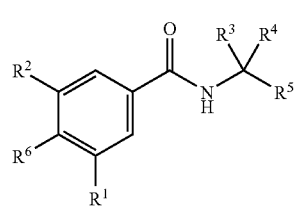

or a pharmaceutically acceptable salt thereof, wherein, $R^1$ is optionally substituted tetrazolyl, $R^2$ is optionally substituted phenyl, optionally substituted pyridinyl or optionally substituted thienyl, and $R^3$, $R^4$, $R^5$ and $R^6$ are as defined herein. Also provided are methods of using the compounds for treating diseases associated with the $P2X_3$ and/or a $P2X_{2/3}$ receptor antagonist and methods of making the compounds.

30 Claims, No Drawings

TETRAZOLE-SUBSTITUTED ARYLAMIDES AS P2X$_3$ AND P2X$_{2/3}$ ANTAGONISTS

CROSS REFERENCE TO RELATED APPLICATIONS

This application claims the benefit of priority of U.S. Provisional Patent Application Ser. No. 60/817,298 filed Jun. 29, 2006, the disclosure of which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION (1) Field of the Invention

This invention pertains to compounds useful for treatment of diseases associated with P2X purinergic receptors, and more particularly to P2X$_3$ and/or P2X$_{2/3}$ antagonists usable for treatment of genitourinary, pain, gastrointestinal and respiratory diseases, conditions and disorders.

(2) Description of Related Art

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, P2X$_1$; P2X$_2$; P2X$_3$; P2X$_4$; P2X$_5$; and P2X$_7$; and three heteromeric receptors P2X$_{2/3}$, P2X$_{4/6}$, P2X$_{1/5}$ (See, e.g., Chen, et al. (1995) Nature 377:428-431; Lewis, et al. (1995) Nature 377:432-435; and Burnstock (1997) Neurophamacol. 36:1127-1139). The structure and chromosomal mapping of mouse genomic P2X$_3$ receptor subunit has also been described (Souslova, et al. (1997) Gene 195:101-111). In vitro, co-expression of P2X$_2$ and P2X$_3$ receptor subunits is necessary to produce ATP-gated currents with the properties seen in some sensory neurons (Lewis, et al. (1995) Nature 377:432-435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). P2X$_3$ receptors have been identified on nociceptive neurons in the tooth pulp (Cook et al., Nature 387:505-508 (1997)). ATP released from damaged cells may thus lead to pain by activating P2X$_3$ and/or P2X$_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that P2X$_2$ and P2X$_3$ are involved in nociception, and that modulators of P2X receptors are potentially useful as analgesics.

Other researchers have shown that P2X$_3$ receptors are expressed in human colon, and are expressed at higher levels in inflamed colon than in normal colon (Y. Yiangou et al, *Neurokastroenterol Mot* (2001) 13:365-69). Other researchers have implicated the P2X$_3$ receptor in detection of distension or intraluminal pressure in the intestine, and initiation of reflex contractions (X. Bian et al., *J Physiol* (2003) 551.1: 309-22), and have linked this to colitis (G. Wynn et al., *Am J Physiol Gastrointest Liver Physiol* (2004) 287:G647-57).

Inge Brouns et al. (*Am J Respir Cell Mol Biol* (2000) 23:52-61) found that P2X$_3$ receptors are expressed in pulmonary neuroepithelial bodies (NEBs), implicating the receptor in pain transmission in the lung. More recently, others have implicated P2X$_2$ and P2X$_3$ receptors in pO$_2$ detection in pulmonary NEBs (W. Rong et al., *J Neurosci* (2003) 23(36): 11315-21).

There is accordingly a need for compounds that act as modulators of P2X receptors, including antagonists of P2X$_3$ and P2X$_{2/3}$ receptors, as well as a need for methods of treating diseases, conditions and disorders mediated by P2X$_3$ and/or P2X$_{2/3}$ receptors. The present invention satisfies these needs as well as others.

BRIEF SUMMARY OF THE INVENTION

The invention provides compounds of the formula (I):

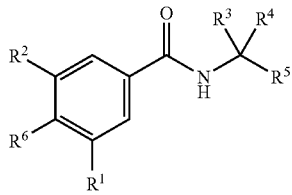

I or a pharmaceutically acceptable salt thereof,
wherein:
$R^1$ is optionally substituted tetrazolyl;
$R^2$ is optionally substituted phenyl, optionally substituted pyridinyl, optionally substituted pyrimidinyl, optionally substituted pyridazinyl or optionally substituted thiophenyl;
$R^3$ is:
  hydrogen;
  $C_{1-6}$alkyl;
  hetero-$C_{1-6}$alkyl; or
  cyano;
$R^4$ is:
  hydrogen;
  $C_{1-6}$alkyl; or
  hetero-$C_{1-6}$alkyl;
  or $R^3$ and $R^4$ together with the atom to which they are attached may form a $C_{3-6}$ carbocyclic ring;
$R^5$ is:
  $C_{1-6}$alkyl;
  hetero-$C_{1-6}$alkyl;
  halo-$C_{1-6}$alkyl;
  N—$C_{1-6}$alkylamino;
  N,N-di-($C_{1-6}$alkyl)-amino;
  $C_{3-7}$cycloalkyl;
  aryl;
  heteroaryl;
  heterocyclyl;
  $C_{3-7}$cycloalkyl-$C_{1-6}$alkyl;
  heteroaryl-$C_{1-6}$alkyl;
  heterocyclyl-$C_{1-6}$alkyl;
  aryloxy-$C_{1-6}$alkyl;
  —$(CR^aR^b)_m$—C(O)—$R^8$ wherein:
    m is 0 or 1;
    $R^a$ and $R^b$ each independently is:
      hydrogen; or
      $C_{1-6}$alkyl; and
    $R^8$ is:
      hydrogen;
      $C_{1-6}$alkyl;
      hetero-$C_{1-6}$alkyl;
      $C_{3-7}$cycloalkyl;
      aryl;
      heteroaryl;
      heterocyclyl;
      $C_{3-7}$cycloalkyl-$C_{1-6}$alkyl;
      aryl-$C_{1-6}$alkyl;
      heteroaryl-$C_{1-6}$alkyl;
      heterocyclyl-$C_{1-6}$alkyl;
      $C_{3-7}$cycloalkyloxy;
      aryloxy;
      heteroaryloxy;
      heterocyclyloxy;
      $C_{3-7}$cycloalkyloxy-$C_{1-6}$alkyl;
      aryloxy-$C_{1-6}$alkyl;
      heteroaryloxy-$C_{1-6}$alkyl;
      heterocyclyloxy-$C_{1-6}$alkyl; or
      —$NR^9R^{10}$, wherein:
        $R^9$ is:
          hydrogen; or
          $C_{1-6}$alkyl; and
        $R^{10}$ is:
          hydrogen;
          $C_{1-6}$-alkyl;
          hetero-$C_{1-6}$alkyl;
          $C_{3-7}$cycloalkyl;
          aryl;
          heteroaryl;
          heterocyclyl;
          $C_{3-7}$cycloalkyl-$C_{1-6}$alkyl;
          aryl-$C_{1-6}$-alkyl;
          heteroaryl-$C_{1-6}$-alkyl; or
          heterocyclyl-$C_{1-6}$alkyl; and
  or $R^4$ and $R^5$ together with the atom to which they are attached may form a $C_{3-6}$ carbocyclic ring that is optionally substituted with hydroxy;
  or $R^4$ and $R^5$ together with the atom to which they are attached may form a $C_{4-6}$ heterocyclic ring containing one or two heteroatoms each independently selected from O, N and S;
  or $R^3$, $R^4$ and $R^5$ together with the atom to which they are attached may form a six-membered heteroaryl containing one or two nitrogen atoms, and which is optionally substituted with halo, amino or $C_{1-6}$alkyl;
$R^6$ is:
  $C_{1-6}$alkyl;
  $C_{1-6}$alkyloxy;
  halo;
  $C_{1-6}$haloalkyl; or
  cyano;
  provided that when $R^1$ is tetrazol-1-yl, $R^2$ is 4-methylphenyl, $R^3$ is methyl, $R^4$ is hydrogen and $R^6$ is hydrogen, then $R^5$ is not furan-2-yl.

The invention also provides and pharmaceutical compositions comprising the compounds, methods of using the compounds, and methods of preparing the compounds.

BRIEF DESCRIPTION OF THE SEVERAL VIEWS OF THE DRAWING(S)

Not Applicable

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl means a moiety of the formula —R'—R"—R'" where R' is alkylene, R" is —$SO_2$— and R'" is alkyl as defined herein.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and $R^1$ is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R' wherein R is alkylene and R' is aryl as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", phenyl", "heteroaryl" "cycloalkyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Respiratory disorder" refers to, without limitation, chronic obstructive pulmonary disease (COPD), asthma, bronchospasm, and the like.

"Gastrointestinal disorder" ("GI disorder") refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

All patents and publications identified herein are incorporated herein by reference in their entirety.

Compounds of the Invention

The invention provides compounds of the formula I:

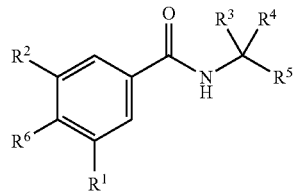

or a pharmaceutically acceptable salt thereof,
wherein:
$R^1$ is optionally substituted tetrazolyl;
$R^2$ is optionally substituted phenyl, optionally substituted pyridinyl, optionally substituted pyrimidinyl, optionally substituted pyridazinyl or optionally substituted thiophenyl;
$R^3$ is:
hydrogen;
$C_{1-6}$alkyl;
hetero-$C_{1-6}$alkyl; or
cyano;
$R^4$ is:
hydrogen;
$C_{1-6}$alkyl; or
hetero-$C_{1-6}$alkyl;
or $R^3$ and $R^4$ together with the atom to which they are attached may form a $C_{3-6}$ carbocyclic ring;
$R^5$ is:
$C_{1-6}$alkyl;
hetero-$C_{1-6}$alkyl;
halo-$C_{1-6}$alkyl;
N—$C_{1-6}$alkylamino;
N,N-di-($C_{1-6}$alkyl)-amino;
$C_{3-7}$cycloalkyl;
aryl;
heteroaryl;
heterocyclyl;
$C_{3-7}$cycloalkyl-$C_{1-6}$alkyl;
heteroaryl-$C_{1-6}$alkyl;
heterocyclyl-$C_{1-6}$alkyl;
aryloxy-$C_{1-6}$alkyl;
—$(CR^aR^b)_m$—C(O)—$R^8$ wherein:
  m is 0 or 1;
  $R^a$ and $R^b$ each independently is:
    hydrogen; or
    $C_{1-6}$alkyl; and
  $R^8$ is:
    hydrogen;
    $C_{1-6}$alkyl;
    hetero-$C_{1-6}$alkyl;
    $C_{3-7}$cycloalkyl;
    aryl;
    heteroaryl;
    heterocyclyl;
    $C_{3-7}$cycloalkyl-$C_{1-6}$alkyl;
    aryl-$C_{1-6}$alkyl;
    heteroaryl-$C_{1-6}$alkyl;
    heterocyclyl-$C_{1-6}$alkyl;
    $C_{3-7}$cycloalkyloxy;
    aryloxy;
    heteroaryloxy;
    heterocyclyloxy;
    $C_{3-7}$cycloalkyloxy-$C_{1-6}$alkyl;

aryloxy-$C_{1-6}$alkyl;
heteroaryloxy-$C_{1-6}$alkyl;
heterocyclyloxy-$C_{1-6}$alkyl; or
—$NR^9R^{10}$, wherein:
  $R^9$ is:
    hydrogen; or
    $C_{1-6}$alkyl; and
  $R^{10}$ is:
    hydrogen;
    $C_{1-6}$alkyl;
    hetero-$C_{1-6}$alkyl;
    $C_{3-7}$cycloalkyl;
    aryl;
    heteroaryl;
    heterocyclyl;
    $C_{3-7}$cycloalkyl-$C_{1-6}$alkyl;
    aryl-$C_{1-6}$alkyl;
    heteroaryl-$C_{1-6}$alkyl; or
    heterocyclyl-$C_{1-6}$alkyl; and or $R^4$ and $R^5$ together with the atom to which they are attached may form a $C_{3-6}$ carbocyclic ring that is optionally substituted with hydroxy;

or $R^4$ and $R^5$ together with the atom to which they are attached may form a $C_{4-6}$ heterocyclic ring containing one or two heteroatoms each independently selected from O, N and S;

or $R^3$, $R^4$ and $R^5$ together with the atom to which they are attached may form a six-membered heteroaryl containing one or two nitrogen atoms, and which is optionally substituted with halo, amino or $C_{1-6}$alkyl;

$R^6$ is:
    $C_{1-6}$alkyl;
    $C_{1-6}$alkyloxy;
    halo;
    $C_{1-6}$haloalkyl; or
    cyano;

provided that when $R^1$ is tetrazol-1-yl, $R^2$ is 4-methyl-phenyl, $R^3$ is methyl, $R^4$ is hydrogen and $R^6$ is hydrogen, then $R^5$ is not furan-2-yl.

In many embodiments of formula I, $R^2$ is optionally substituted phenyl, such as phenyl optionally substituted once, twice or three times, preferably once or twice, with any of $C_{1-6}$alkyl, $C_{1-6}$alkyloxy, halo, $C_{1-6}$haloalkyl, hetero-$C_{1-6}$alkyl, $C_{1-6}$alkylsulfonyl or cyano.

In certain embodiments $R^2$ is phenyl substituted once or twice with halo or methyl.

In many embodiments of formula I, $R^2$ is phenyl substituted at the 4-position with methyl or halo and optionally substituted at the 2- and 6-positions with halo.

In many embodiments of formula I, $R^2$ is phenyl substituted at the 4-position with methyl or halo and optionally substituted at the 2-position with halo.

In certain embodiments of formula I, $R^2$ is 4-methyl-phenyl, 2-fluoro-4-methyl-phenyl, 2-chloro-4-fluoro-phenyl, 4-chloro-2-fluoro-phenyl, 2,4-dichloro-phenyl, 2,4-difluoro-phenyl, or 2-chloro-4-methyl-phenyl.

In certain embodiments of formula I, $R^2$ is 4-methyl-phenyl or 4-chloro-phenyl.

In certain embodiments of formula I, $R^2$ is 4-methyl-phenyl.

In certain embodiments of formula I, $R^2$ is 2-fluoro-4-methyl-phenyl.

In certain embodiments of formula I, $R^2$ is 2-chloro-4-fluoro-phenyl.

In certain embodiments of formula I, $R^2$ is 4-chloro-2-fluoro-phenyl.

In certain embodiments of formula I, $R^2$ is 2,4-dichloro-phenyl.

In certain embodiments of formula I, $R^2$ is 2,4-difluoro-phenyl.

In certain embodiments of formula I, $R^2$ is 2-chloro-4-methyl-phenyl.

In many embodiments of formula I, $R^2$ is optionally substituted pyridinyl. Exemplary pyridinyl include pyridin-2-yl, and pyridin-2-one-1-yl, each optionally substituted once, twice or three times, preferably once or twice, with any of $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. Preferred pyridyl include 4-methyl-pyridin-2-yl, 4-fluoro-pyridin-2-yl and 4-methyl-pyridin-2-one-1-yl.

In certain embodiments of formula I, $R^2$ is pyridin 2-yl substituted with methyl or halo at the 5-position.

In certain embodiments of formula I, $R^2$ is pyridin 2-yl substituted with methyl or halo at the 5-position and optionally substituted with halo at the 3-position.

In certain embodiments of formula I, $R^2$ is 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-ppyridin-2-yl.

In certain embodiments of formula I, $R^2$ is 5-methyl-pyridin-2-yl.

In certain embodiments of formula I, $R^2$ is 5-chloro-pyridin-2-yl.

In certain embodiments of formula I, $R^2$ is 5-fluoro-pyridin-2-yl.

In certain embodiments of formula I, $R^2$ is 5-methyl-3-fluoro-pyridin-2-yl.

In certain embodiments of formula I, $R^2$ is 5-methyl-3-chloro-pyridin-2-yl.

In certain embodiments of formula I, $R^2$ is 3,5-difluoro-pyridin-2-yl.

In certain embodiments of formula I, $R^2$ is 3,5-dichloro-pyridin-2-yl.

In certain embodiments of formula I, $R^2$ is optionally substituted pyridazinyl. In such embodiments $R^2$ may be 6-chloro-pyridazinyl or 6-methyl-pyridazinyl, preferably 6-chloro-pyridazinyl.

In certain embodiments of formula I, $R^2$ is optionally substituted thiophenyl. In such embodiments $R^2$ may be thiophen-2-yl optionally substituted with $C_{1-6}$alkyl or halo. Preferred thiophenyl include 3-methyl-thiophen-2-yl, 5-methyl-thiophen-2-yl and 5-chloro-thiophen-2-yl.

In many embodiments of formula I, $R^3$ is hydrogen. In certain embodiments of formula I, $R^6$ may be methyl.

In many embodiments of formula I, $R^3$ is hydrogen.

In many embodiments of formula I, $R^3$ is $C_{1-6}$alkyl. A preferred $C_{1-6}$alkyl in such embodiments is methyl.

In many embodiments of formula I, $R^4$ is $C_{1-6}$alkyl. A preferred $C_{1-6}$alkyl in such embodiments is methyl.

In many embodiments of formula I, $R^3$ is hydrogen and $R^4$ is $C_{1-6}$alkyl, preferably methyl.

In certain embodiments of formula I, $R^3$ and $R^4$ are hydrogen.

In certain embodiments of formula I, $R^3$ and $R^4$ together with the atom to which they are attached may form a $C_{3-6}$ carbocyclic ring.

In certain embodiments of formula I, $R^3$ and $R^4$ together with the atom to which they are attached may form a cyclopropyl group.

In certain embodiments of formula I, $R^4$ and $R^5$ together with the atom to which they are attached form a $C_{3-6}$ carbocyclic ring that is optionally substituted with hydroxy.

In certain embodiments of formula I, $R^4$ and $R^5$ together with the atom to which they are attached form a cyclopropyl.

In certain embodiments of formula I, $R^3$ is hydrogen and $R^4$ and $R^5$ together with the atom to which they are attached form a cyclopropyl.

In certain embodiments of formula I, $R^3$ is hydrogen and $R^4$ and $R^5$ together with the atom to which they are attached form a cyclopentyl optionally substituted with hydroxy.

In certain embodiments of formula I, $R^4$ and $R^5$ together with the atom to which they are attached form a $C_{4-6}$ heterocyclic ring containing one or two heteroatoms each independently selected from O, N and S.

In certain embodiments of formula I, $R^4$ and $R^5$ together with the atom to which they are attached form a piperidinyl group or oxetanyl ring group.

In certain embodiments of formula I, $R^4$ and $R^5$ together with the atom to which they are attached form a piperidin-3-yl group or an oxetan-3-yl group.

In certain embodiments of formula I, $R^3$, $R^4$ and $R^5$ together with the atom to which they are attached form a six-membered heteroaryl containing one or two nitrogen atoms, and which is optionally substituted with halo, amino or $C_{1-6}$alkyl.

In certain embodiments of formula I, $R^3$, $R^4$ and $R^5$ together with the atom to which they are attached form a heteroaryl selected from 2-oxo-1,2-dihydro-pyrimidinyl, pyridinyl, pyrimidinyl, pyridazinyl or pyridazinyl, each optionally substituted with methyl or amino.

In certain embodiments of formula I, $R^3$, $R^4$ and $R^5$ together with the atom to which they are attached form a heteroaryl selected from 2-oxo-1,2-dihydro-pyrimidin-4-yl, 2-oxo-1,2-dihydro-pyrimidin-4-yl, 1-methyl-2-oxo-1,2-dihydro-pyrimidin-4-yl, 6-methyl-pyridin-3-yl, pyridazin-4-yl, 6-amino-pyridin-2-yl, 2-aminopyrimidin-4-yl or 2-amino-pyrimidin-3-yl.

In many embodiments of formula I, $R^1$ is tetrazol-1-yl optionally substituted at the 5-position with $C_{1-6}$alkyl.

In certain embodiments of formula I, $R^1$ is tetrazol-5-yl optionally substituted at the 1-position with $C_{1-6}$alkyl, halo-$C_{1-6}$alkyl, hetero-$C_{1-6}$alkyl, $C_{3-6}$-cycloalkyl, $C_{3-6}$cycloalkyl-$C_{1-6}$alkyl or cyano. Preferably in such embodiments the 1-position is substituted with $C_{1-6}$alkyl.

In certain embodiments of formula I, $R^1$ is tetrazol-1-yl optionally substituted at the 5-position with $C_{1-6}$alkyl, halo-$C_{1-6}$alkyl, hetero-$C_{1-6}$alkyl, $C_{3-6}$-cycloalkyl, $C_{3-6}$cycloalkyl-$C_{1-6}$alkyl or cyano.

In certain embodiments of formula I, $R^1$ is tetrazol-1-yl substituted at the 5-position with $C_{1-6}$alkyl.

In certain embodiments of formula I, $R^1$ is tetrazol-1-yl substituted at the 5-position with halo-$C_{1-4}$alkyl.

In certain embodiments of formula I, $R^1$ is tetrazol-1-yl substituted at the 5-position with hetero-$C_{1-6}$alkyl selected from hydroxy-$C_{1-6}$alkyl, $C_{1-6}$alkoxy-$C_{1-6}$alkyl, $C_{1-6}$alkylamino-$C_{1-6}$alkyl, or N,N-di-($C_{1-6}$alkyl)-amino-$C_{1-6}$alkyl.

In certain embodiments of formula I, $R^1$ is tetrazol-1-yl substituted at the 5-position with halo-$C_{1-6}$alkyl.

In certain embodiments of formula I, $R^1$ is tetrazol-1-yl optionally substituted at the 5-position with methyl, ethyl, n-propyl, n-butyl, isopropyl, isobutyl, tert-butyl, cyclopropyl, cyclopropylmethyl, trifluoromethyl, pentafluoro-ethyl, 1,1-difluoro-ethyl, 1-methoxy-ethyl, 1-ethoxy-ethyl, 2-methoxy-1-methyl-ethyl, 1-hydroxy-ethyl, or dimethylamino-methyl.

In certain embodiments of formula I, $R^1$ is tetrazol-1-yl substituted at the 5-position with methyl, ethyl, n-propyl, isopropyl, n-butyl, isobutyl, tert-butyl, cyclopropyl or cyclopropylmethyl.

In certain embodiments of formula I, $R^5$ is: $C_{1-6}$alkyl; $C_{1-6}$alkyloxy-$C_{1-6}$alkyl; hydroxy-$C_{1-6}$alkyl; $C_{1-6}$alkylsulfanyl-$C_{1-6}$alkyl; $C_{1-6}$alkylsulfonyl-$C_{1-6}$alkyl; amino-$C_{1-6}$alkyl; N—$C_{1-6}$alkyl-amino-$C_{1-6}$alkyl; N,N-di-$C_{1-6}$alkyl-amino-$C_{1-6}$alkyl; $C_{3-7}$cycloalkyl; optionally substituted phenyl; heteroaryl, or heterocyclyl-$C_{1-6}$alkyl.

In certain embodiments of formula I, $R^5$ is N—$C_{1-6}$alkyl-amino-$C_{1-6}$alkyl substituted with halo.

In certain embodiments of formula I, $R^5$ is: $C_{1-6}$alkyloxy-$C_{1-6}$alkyl; hydroxy-$C_{1-6}$alkyl; heteroaryl, or heterocyclyl-$C_{1-6}$alkyl.

In certain embodiments of formula I, $R^5$ is $C_{1-6}$alkyloxy-$C_{1-6}$alkyl. One preferred $C_{1-6}$alkyloxy-$C_{1-6}$alkyl is methoxymethyl.

In certain embodiments of formula I, $R^5$ is hydroxy-$C_{1-6}$alkyl. One preferred hydroxy-$C_{1-6}$alkyl is hydroxymethyl.

In certain embodiments of formula I, $R^5$ is heteroaryl.

In certain embodiments where $R^5$ is heteroaryl, such heteroaryl may be pyridinyl, pyrimidinyl, pyrazinyl, pyridazinyl, pyrazolyl, imidazolyl, thienyl, thiazolyl, oxazolyl, isoxazolyl, triazolyl, oxadiazolyl, 3-oxo-2,3-dihydro-isoxazolyl, tetrazolyl, imidazo[2,1-b]thiazolyl, imidazo[1,2-a]pyridinyl, imidazo[4,5-b]pyridinyl, and benzimidazolyl, each of which may be optionally substituted one, two or three times with a group or groups independently selected from $C_{1-6}$alkyl, $C_{1-6}$alkoxy, $C_{1-6}$alkoxy-$C_{1-6}$alkyl, halo-$C_{1-6}$alkyl, halo, amino, N—$C_{1-6}$alkyl-amino, or N,N-di-($C_{1-6}$alkyl)-amino. More preferably, such heteroarly may be optionally substituted once or twice with a group or groups independently selected from methyl, ethyl, n-propyl, fluoro, chloro, trifluoromethyl, amino, methylamino or dimethylamino.

In certain embodiments where $R^5$ is heteroaryl, such heteroaryl may be pyridinyl, pyrimidinyl, pyrazinyl, pyridazinyl, pyrazolyl or thiazolyl, each of which may be optionally substituted once or twice with a group or groups independently selected from methyl, ethyl, n-propyl, fluoro, chloro, amino, methylamino or dimethylamino.

In certain embodiments where $R^5$ is heteroaryl, such heteroaryl may be pyridinyl, pyrimidinyl, or pyrazinyl, each of which may be optionally substituted once or twice with a group or groups independently selected from methyl, fluoro, chloro, amino, methylamino or dimethylamino.

In certain embodiments of formula I, where $R^5$ is heteroaryl, such heteroaryl may be thiophen-2-yl, pyridin-2-yl, pyridin-3-yl, pyridin-4-yl, oxazol-2-yl, pyrimidin-2-yl, pyridazin-4-yl, pyrazin-2-yl, 5-methyl-pyrazin-2-yl, imidazol-1-yl, pyrazol-1-yl, 3,5-dimethyl-pyrazol-1-yl, 2-methyl-thiazol-4-yl, 3-(2-chloro-phenyl)-[1,2,4]-oxadiazol-5-yl, 3-(pyridin-4-yl)-[1,2,4]-oxadiazol-5-yl, pyridazin-3-yl, 2-methyl-pyrazol-3-yl, thiazol-5-yl, 1-methyl-imidazol-2-yl, 6-chloro-pyrimidin-4-yl, 4-ethyl-[1,2,4]-triazol-3-yl, 1,3,5-trimethyl-pyrazol-4-yl, 1,5-dimethyl-pyrazol-4-yl, 1,3-dimethyl-pyrazol-4-yl, 3-(2-methoxy-ethyl)-[1,2,4]-oxadiazol-5-yl, 3-(pyridin-3-yl-[1,2,4]-oxadiazol-5-yl, tetrazol-5-yl, pyrazol-3-yl, 4-amino-2-methyl-pyrimidin-5-yl, 2-amino-pyrimidin-4-yl, 6-methoxy-pyridazin-3-yl, 3-oxo-2,3-dihydro-isoxazol-5-yl, 3-methyl-thiophen-2-yl, 5-methyl-[1,3,4]-oxadiazol-2-yl, 4-methyl-isoxazol-3-yl, 3-trifluoromethyl-pyrazol-1-yl, 1-methyl-pyrazol-3-yl, 3-methyl-pyrazol-1-yl, 5-methyl-3-trifluoromethyl-pyrazol-1-yl, 5-cyclopropyl-3-trifluoromethyl-pyrazol-1-yl, imidazo[2,1-b]-thiazol-6-yl, thiazol-4-yl, 2-propyl-pyrazol-3-yl, 2-ethyl-pyrazol-3-yl, 5-amino-pyridazin-2-yl, 3-amino-pyridazin-2-yl, 3-chloro-pyridazin-2-yl, 2-amino-pyrimidin-5-yl, 1-methyl-imidazol-4-yl, 6-amino-pyridin-3-yl, 6-amino-pyridazin-2-yl, 2-amino-pyridin-4-yl, 2-dimethylaminopyrimidin-5-yl, 6-amino-pyridin-2-yl, 2-methylamino-pyridin-4-yl, 2-dimethylamino-pyridin-4-yl, 3-methyl-2-dimethylamino-pyridin-4-yl, pyrimidin-5-yl, 2-methyl-pyridin-4-yl, 6-methylamino-pyridin-3-yl, 6-dimethylamino-pyridin-3-yl, 6-methylamino-pyrimidin-4-yl, 6-dimethylamino-pyridin-3-yl, 6-methylamino-pyridin-3-yl, 2-methylamino-pyrimidin-5-yl, 6-methyl-pyridin-3-yl, 4-methyl-thiazol-2-yl, 2,6-dimethyl-pyridin-3-yl, imidazo[1,2-a]pyridin-2-yl, 6-methyl-pyridin-2-yl, 1-ethyl-pyrazol-3-yl, 3-methyl-pyridin-2-yl, 4-methyl-thiazol-5-yl, 1-ethyl-imidazol-2-yl, 1-methyl-pyrazol-4-yl, imidazo[4,5-b]pyridin-2-yl, 3,5-difluoro-pyridin-2-yl, 6-fluoro-pyridin-2-yl, 1,5-dimethyl-pyrazol-3-yl, 5-methyl-pyridin-2-yl, 6-trifluoromethyl-pyridin-3-yl, 5-methyl-isoxazol-3-yl, 5-methyl-imidazol-2-yl, 5-methoxy-benzimidazol-2-yl, [1,2,4]triazol-3-yl, and 8-methyl-imidazo[1,2-a]pyridin-2-yl.

In certain embodiments of formula I, $R^5$ is heterocyclyl-$C_{1-6}$alkyl.

In embodiments where $R^5$ is heterocyclyl-$C_{1-6}$alkyl, such heterocyclyl-$C_{1-6}$alkyl may be heterocyclyl-methyl such as morpholinomethyl, piperidinyl-methyl, piperazinyl-methyl, thiomorpholinylmethyl, pyrrolidinylmethyl, or azetidinylmethyl, the heterocyclyl portion of each of which may be optionally substituted once or twice with a group or groups independently selected from methyl, methoxy, halo, methanesulfonyl, oxo or acetyl.

In embodiments where $R^5$ is heterocyclyl-methyl, such heterocyclylmethyl may be morpholin-4-yl-methyl, 4-methanesulfonyl-piperazin-1-yl-methyl, 4-acetyl-piperazin-1-yl-methyl, piperidin-1-yl, thiomorpholin-4-yl-methyl, 4-methyl-piperazin-1-yl-methyl, 3-oxo-piperazin-1-yl-methyl, 3-methoxy-piperidin-1-yl-methyl, 4-methoxy-piperidin-1-yl-methyl, 4-hydroxy-piperidin-1-yl-methyl, 1-oxo-thiomorpholin-4-yl-methyl, 3-hydroxy-pyrrolidin-1-yl-methyl, azetidin-3-yl-methyl, 4-methanesulfonyl-piperidin-1-yl-methyl, 4-fluoro-piperidin1-yl-methyl, 4-acetyl-3-methyl-piperazin-1-yl-methyl, 4-acetyl-3,5-dimethyl-piperazin-1-yl-methyl, 2,6-dimethyl-morpholin-4-yl-methyl, 4,4-difluoro-piperidin-1-yl-methyl, 3-fluoro-piperidin1-yl-methyl, 4-methyl-4-hydroxy-piperidin1-yl-methyl, or 3-fluoro-4-methoxy-piperidin1-yl-methyl.

In certain embodiments of formula I, $R^5$ is hydroxymethyl, methoxymethyl, pyrazin-2-yl or 5-methyl-pyrazin-2-yl.

In certain embodiments of formula I, $R^5$ is hydroxymethyl.

In certain embodiments of formula I, $R^5$ is methoxymethyl.

In certain embodiments of formula I, $R^5$ is pyrazin-2-yl.

In certain embodiments of formula I, $R^5$ is 5-methyl-pyrazin-2-yl.

In certain embodiments of formula I:
$R^1$ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, N,N-di-($C_{1-6}$alkyl)-amino-$C_{1-6}$alkyl, $C_{3-6}$-cycloalkyl, or $C_{3-6}$cycloalkyl-$C_{1-6}$alkyl;
$R^2$ is: 4-methyl-phenyl; 2-fluoro-4-methyl-phenyl; 2-chloro-4-fluoro-phenyl; 4-chloro-2-fluoro-phenyl; 2,4-dichloro-phenyl; 2,4-difluoro-phenyl; or 2-chloro-4-methyl-phenyl;
$R^3$ is hydrogen;
$R^4$ is: hydrogen; or methyl; and
$R^5$ is: $C_{1-6}$alkyl; $C_{1-6}$alkyloxy-$C_{1-6}$alkyl; hydroxy-$C_{1-6}$alkyl; $C_{1-6}$alkylsulfanyl-$C_{1-6}$alkyl; $C_{1-6}$alkylsulfonyl-$C_{1-6}$alkyl; amino-$C_{1-6}$alkyl; N—$C_{1-6}$alkyl-amino-$C_{1-6}$alkyl; N,N-di-$C_{1-6}$alkyl-amino-$C_{1-6}$alkyl; $C_{3-7}$cycloalkyl; optionally substituted phenyl; heteroaryl, or heterocyclyl-$C_{1-6}$alkyl.

In certain embodiments of formula I:
$R^1$ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, N,N-di-($C_{1-6}$alkyl)-amino-$C_{1-6}$alkyl, $C_{3-6}$-cycloalkyl, or $C_{3-6}$cycloalkyl-$C_{1-6}$alkyl;
$R^2$ is: 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-ppyridin-2-yl;
$R^3$ is hydrogen;
$R^4$ is: hydrogen; or methyl; and
$R^5$ is: $C_{1-6}$alkyl; $C_{1-6}$alkyloxy-$C_{1-6}$alkyl; hydroxy-$C_{1-6}$alkyl; $C_{1-6}$alkylsulfanyl-$C_{1-6}$alkyl; $C_{1-6}$alkylsulfonyl-$C_{1-6}$alkyl; amino-$C_{1-6}$alkyl; N—$C_{1-6}$alkyl-amino-$C_{1-6}$alkyl; N,N-di-$C_{1-6}$alkyl-amino-$C_{1-6}$alkyl; $C_{3-7}$cycloalkyl; optionally substituted phenyl; heteroaryl, or heterocyclyl-$C_{1-6}$alkyl.

In certain embodiments of formula I:
$R^1$ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{3-6}$-cycloalkyl, or $C_{3-6}$cycloalkyl-$C_{1-6}$alkyl;
$R^2$ is: 4-methyl-phenyl; 2-fluoro-4-methyl-phenyl; 2-chloro-4-fluoro-phenyl; 4-chloro-2-fluoro-phenyl; 2,4-dichloro-phenyl; 2,4-difluoro-phenyl; or 2-chloro-4-methyl-phenyl;
$R^3$ is hydrogen;
$R^4$ is: hydrogen; or methyl; and
$R^5$ is: hydroxymethyl; methoxymethyl; morpholin-4-ylmethyl; piperidin-1-yl methyl optionally substituted at the 4-position with methyl, methanesulfonyl or acetyl; 1,1,-dioxo-thiomorpholin-1-yl; piperidin-1-yl-methyl optionally substituted once or twice with a group or groups selected independently from methyl, methoxy or halo; pyridinyl; pyrimidinyl; pyrazinyl; pyridazinyl; pyrazolyl; or thiazolyl; wherein the pyridinyl, pyrimidinyl, pyrazinyl, pyridazinyl, pyrazolyl and thiazolyl each may be optionally substituted once or twice with a group or groups selected independently from methyl, methylamino, dimethylamino and halo.

In certain embodiments of formula I:
$R^1$ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, $C_{3-6}$-cycloalkyl, or $C_{3-6}$cycloalkyl-$C_{1-6}$alkyl;
$R^2$ is: 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-ppyridin-2-yl;
$R^3$ is hydrogen;
$R^4$ is: hydrogen; or methyl; and
$R^5$ is: hydroxymethyl; methoxymethyl; morpholin-4-ylmethyl; piperidin-1-yl methyl optionally substituted at the 4-position with methyl, methanesulfonyl or acetyl; 1,1,-dioxo-thiomorpholin-1-yl; piperidin-1-yl optionally substituted once or twice with a group or groups selected independently from methyl, methoxy or halo; pyridinyl; pyrimidinyl; pyrazinyl; pyridazinyl; pyrazolyl; or thiazolyl; wherein the pyridinyl, pyrimidinyl, pyrazinyl, pyridazinyl, pyrazolyl and thiazolyl each may be optionally substituted once or twice with a group or groups selected independently from methyl, methylamino, dimethylamino and halo.

In certain embodiments of formula I:
$R^1$ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{3-6}$-cycloalkyl, or $C_{3-6}$cycloalkyl-$C_{1-6}$alkyl;

R² is: 4-methyl-phenyl; 2-fluoro-4-methyl-phenyl; 2-chloro-4-fluoro-phenyl; 4-chloro-2-fluoro-phenyl; 2,4-dichloro-phenyl; 2,4-difluoro-phenyl; or 2-chloro-4-methyl-phenyl;

R³ is hydrogen; and

R⁴ and R⁵ together form a cyclopropyl group.

In certain embodiments of formula I:

R¹ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, $C_{3-6}$-cycloalkyl, or $C_{3-6}$cycloalkyl-$C_{1-6}$alkyl;

R² is: 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-ppyridin-2-yl;

R³ is hydrogen; and

R⁴ and R⁵ together form a cyclopropyl group.

In certain embodiments of formula I:

R¹ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, N,N-di-($C_{1-6}$alkyl)-amino-$C_{1-6}$alkyl, $C_{3-6}$-cycloalkyl, or $C_{3-6}$cycloalkyl-$C_{1-6}$alkyl;

R² is: 4-methyl-phenyl; 2-fluoro-4-methyl-phenyl; 2-chloro-4-fluoro-phenyl; 4-chloro-2-fluoro-phenyl; 2,4-dichloro-phenyl; 2,4-difluoro-phenyl; or 2-chloro-4-methyl-phenyl;

R³ is hydrogen;

R⁴ is methyl; and

R⁵ is methoxymethyl, hydroxymethyl, or pyridazin-2-yl.

In certain embodiments of formula I:

R¹ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, N,N-di-($C_{1-6}$alkyl)-amino-$C_{1-6}$alkyl, $C_{3-6}$-cycloalkyl, or $C_{3-6}$cycloalkyl-$C_{1-6}$alkyl;

R² is: 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-ppyridin-2-yl;

R³ is hydrogen;

R⁴ is methyl; and

R⁵ is methoxymethyl, hydroxymethyl, or pyridazin-2-yl.

In certain embodiments of formula I:

R¹ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, N,N-di-($C_{1-6}$alkyl)-amino-$C_{1-6}$alkyl, $C_{3-6}$-cycloalkyl, or $C_{3-6}$cycloalkyl-$C_{1-6}$alkyl;

R² is: 4-methyl-phenyl; 2-fluoro-4-methyl-phenyl; 2-chloro-4-fluoro-phenyl; 4-chloro-2-fluoro-phenyl; 2,4-dichloro-phenyl; 2,4-difluoro-phenyl; or 2-chloro-4-methyl-phenyl;

R³ and R⁴ are hydrogen; and

R⁵ is 5-methyl-pyridazin-2-yl.

In certain embodiments of formula I:

R¹ is tetrazol-1-yl optionally substituted at the 5-position with $C_{1-6}$alkyl, halo-$C_{1-6}$alkyl, $C_{1-6}$alkoxy-$C_{1-6}$alkyl, hydroxy-$C_{1-6}$alkyl, $C_{1-6}$alkylamino-$C_{1-6}$alkyl, N,N-di-($C_{1-6}$alkyl)-amino-$C_{1-4}$alkyl, $C_{3-6}$-cycloalkyl, or $C_{3-6}$cycloalkyl-$C_{1-6}$alkyl;

R² is: 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-ppyridin-2-yl;

R³ and R⁴ are hydrogen; and

R⁵ is 5-methyl-pyridazin-2-yl.

In certain embodiments of the invention where R² is optionally substituted phenyl, R³ is hydrogen and R⁴ is methyl, the subject compounds may be represented by formula IIa or formula IIb:

IIa

IIb or a pharmaceutically acceptable salt thereof, wherein:

R¹¹ and R¹² each independently is hydrogen, $C_{1-6}$alkyl, $C_{1-6}$alkyloxy, halo, $C_{1-6}$haloalkyl, hetero-$C_{1-6}$alkyl, $C_{1-6}$alkylsulfonyl or cyano;

R¹³ is hydrogen, $C_{1-6}$alkyl, halo-$C_{1-6}$alkyl, hetero-$C_{1-6}$alkyl, $C_{3-6}$-cycloalkyl or $C_{3-6}$cycloalkyl-$C_{1-6}$alkyl or cyano; and R⁵ is as defined herein.

In certain embodiments of the invention where R² is optionally substituted phenyl, and R³ and R⁴ are hydrogen, the subject compounds may be represented by formula IIc:

IIc or a pharmaceutically acceptable salt thereof, wherein R⁵, R¹¹, R¹² and R¹³ are as defined herein.

In certain embodiments of the invention the subject compounds are of formula IIIa or IIIb:

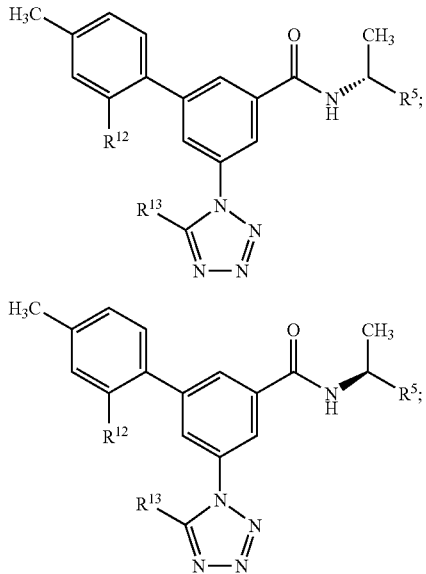

IIIa

IIIb or a pharmaceutically acceptable salt thereof, wherein $R^5$, $R^{12}$ and $R^{13}$ are as defined herein;

In certain embodiments of the invention the subject compounds are of formula IIIc:

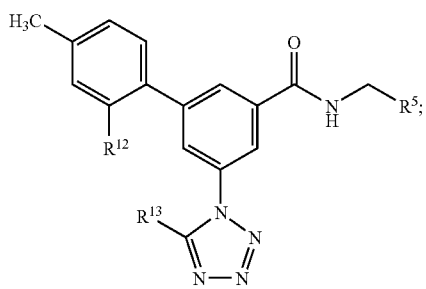

IIIc or a pharmaceutically acceptable salt thereof, wherein $R^5$, $R^{12}$ and $R^{13}$ are as defined herein;

In certain embodiments of the invention where $R^2$ is optionally substituted pyridinyl, $R^3$ is hydrogen and $R^4$ is methyl, the subject compounds may be represented by formula IVa or formula IVb:

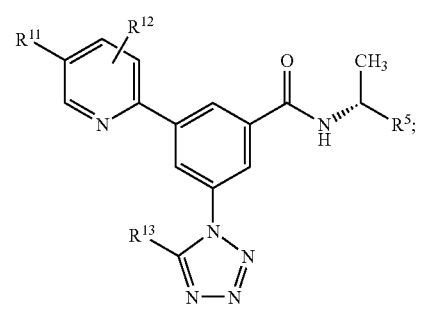

IVa

IVb or a pharmaceutically acceptable salt thereof, wherein $R^5$, $R^{11}$, $R^{12}$ and $R^{13}$ are as defined herein.

In certain embodiments of the invention where $R^2$ is optionally substituted pyridinyl, and $R^3$ and $R^4$ are hydrogen, the subject compounds may be represented by formula IVc:

IVc or a pharmaceutically acceptable salt thereof, wherein $R^5$, $R^{11}$, $R^{12}$ and $R^{13}$ are as defined herein.

In certain embodiments of any of formulas I, IIa, IIb, IIc, IIIa, IIIb, IIIc, IVa, IVb, IVc, $R^{11}$ is halo or methyl, and $R^{12}$ is hydrogen, halo or methyl.

In certain embodiments of any of formulas I, IIa, IIb, IIc, IIIa, IIIb, IIIc, IVa, IVb or IVc, $R^5$ is:

$C_{1-6}$alkyl selected from methyl, ethyl, propyl, isopropyl, n-butyl, isobutyl, tert-butyl, n-pentyl and isopentyl;

hetero-$C_{1-6}$alkyl selected from $C_{1-6}$alkyloxy-$C_{1-6}$alkyl, hydroxy-$C_{1-6}$alkyl, $C_{1-6}$alkylsulfanyl-$C_{1-6}$alkyl, $C_{1-6}$alkylsulfinyl-$C_{1-6}$alkyl, $C_{1-6}$alkyl-sulfonyl-$C_{1-6}$alkyl, amino-$C_{1-6}$alkyl, N—$C_{1-6}$alkylamino-$C_{1-6}$alkyl, and N,N-di-$C_{1-6}$alkylamino-$C_{1-6}$alkyl, the alkyl portions of which may be optionally substituted with halo;

$C_{3-7}$cycloalkyl selected from cyclopropyl, cyclobutyl, cyclopentyl and cyclohexyl, each optionally substituted;

aryl selected from optionally substituted phenyl and optionally substituted naphthyl;

heteroaryl selected from pyridinyl, pyrimidinyl, pyridazinyl, pyrazinyl, thienyl, pyrrolyl, oxazolyl, thiazolyl, imidazolyl, pyrazolyl, triazolyl, oxadiazolyl, 3-oxo-2,3-dihydro-isoxazolyl, tetrazolyl, imidazo[2,1-b]thiazolyl, imidazo[1,2-a]pyridinyl, imidazo[4,5-b]pyridinyl, benzimidazolyl, isoxazolyl and isothiazolyl, each optionally substituted;

heterocyclyl selected from piperidinyl, piperazinyl, morpholinyl, thiomorpholinyl, 1-oxo-thiomorpholinyl, 1,1-dioxo-thiomorpholinyl, pyranyl, pyrrolidinyl, tetrahydrofuranyl, 2-oxa-8-aza-spiro[4,5]decan-8-yl, 2-oxa-5-aza-bicyclo

[2.2.1]heptan-5-yl, and 3-oxa-8-aza-bicyclo[3.2.1]octan-8-yl, and azetidinyl, each optionally substituted;

$C_{3-7}$cycloalkyl-$C_{1-6}$alkyl selected from cyclopropyl-$C_{1-6}$-alkyl, cyclobutyl-$C_{1-6}$alkyl, cyclopentyl-$C_{1-6}$alkyl and cyclohexyl-$C_{1-6}$alkyl, the cycloalkyl portion of each being optionally substituted;

heteroaryl-$C_{1-6}$alkyl selected from pyridinyl-$C_{1-6}$alkyl, pyrimidinyl-$C_{1-6}$alkyl, pyridazinyl-$C_{1-6}$alkyl, pyrazinyl-$C_{1-6}$alkyl, furanyl-$C_{1-6}$alkyl, thienyl-$C_{1-6}$alkyl, pyrrolyl-$C_{1-6}$alkyl, oxazolyl-$C_{1-6}$alkyl, thiazolyl-$C_{1-6}$alkyl, imidazolyl-$C_{1-6}$alkyl, pyrazolyl-$C_{1-6}$alkyl, triazolyl-$C_{1-6}$alkyl, oxadiazolyl-$C_{1-6}$alkyl, 3-oxo-2,3-dihydro-isoxazolyl-$C_{1-6}$alkyl, imidazo[2,1-b]thiazolyl-$C_{1-6}$alkyl, imidazo[1,2-a]pyridinyl-$C_{1-6}$alkyl, imidazo[4,5-b]pyridinyl-$C_{1-6}$alkyl, benzimidazolyl-$C_{1-6}$alkyl, isoxazolyl-$C_{1-6}$alkyl and isothiazolyl-$C_{1-6}$alkyl, the heteroaryl portion of each being optionally substituted;

heterocyclyl-$C_{1-6}$alkyl selected from piperidinyl-$C_{1-6}$alkyl, piperazinyl-$C_{1-6}$alkyl, morpholinyl-$C_{1-6}$alkyl, thiomorpholinyl-$C_{1-6}$alkyl, 1-oxo-thiomorpholinyl-$C_{1-6}$alkyl, 1,1-dioxo-thiomorpholinyl-$C_{1-6}$alkyl, pyranyl-$C_{1-6}$alkyl, pyrrolidinyl-$C_{1-6}$alkyl, tetrahydrofuranyl-$C_{1-6}$alkyl, 2-oxa-8-aza-spiro[4,5]decan-8-yl-$C_{1-6}$alkyl, 2-oxa-5-aza-bicyclo[2.2.1]heptan-5-yl-$C_{1-6}$alkyl, 3-oxa-8-aza-bicyclo[3.2.1]octan-8-yl-$C_{1-6}$alkyl, and azetidin-$C_{1-6}$alkyl, the heterocyclyl portion of each being optionally substituted;

aryloxy-$C_{1-6}$alkyl selected from phenoxy-$C_{1-6}$alkyl and naphthyloxy-$C_{1-6}$alkyl, the aryl portion of each being optionally substituted; or —C(O)—$R^8$ or —$CH_2$—C(O)—$R^8$ wherein $R^8$ is as defined herein.

In certain embodiments of any of formulas I, IIa, IIb, IIc, IIIa, IIIb, IIIc, IVa, IVb or IVc, $R^5$ is:

$C_{1-6}$alkyl selected from methyl, ethyl, propyl, isopropyl, n-butyl, isobutyl, tert-butyl, n-pentyl and isopentyl;

hetero-$C_{1-6}$alkyl selected from $C_{1-6}$alkyloxy-$C_{1-6}$alkyl, hydroxy-$C_{1-6}$alkyl, $C_{1-6}$alkylsulfanyl-$C_{1-6}$alkyl, $C_{1-6}$alkyl-sulfinyl-$C_{1-6}$alkyl, $C_{1-6}$alkyl-sulfonyl-$C_{1-6}$alkyl, amino-$C_{1-6}$alkyl, N—$C_{1-6}$alkylamino-$C_{1-6}$alkyl, and N,N-di-$C_{1-6}$alkylamino-$C_{1-6}$alkyl, the alkyl portions of which may be optionally substituted with halo;

$C_{3-7}$cycloalkyl selected from cyclopropyl, cyclobutyl, cyclopentyl and cyclohexyl, each optionally substituted;

aryl selected from optionally substituted phenyl and optionally substituted naphthyl; heteroaryl selected from pyridinyl, pyrimidinyl, pyridazinyl, pyrazinyl, thienyl, pyrrolyl, oxazolyl, thiazolyl, imidazolyl, pyrazolyl, triazolyl, oxadiazolyl, 3-oxo-2,3-dihydro-isoxazolyl, tetrazolyl, imidazo[2,1-b]thiazolyl, imidazo[1,2-a]pyridinyl, imidazo[4,5-b]pyridinyl, benzimidazolyl, isoxazolyl and isothiazolyl, each optionally substituted;

heterocyclyl selected from piperidinyl, piperazinyl, morpholinyl, thiomorpholinyl, 1-oxo-thiomorpholinyl, 1,1-dioxo-thiomorpholinyl, pyranyl, pyrrolidinyl tetrahydrofuranyl and azetidinyl, each optionally substituted;

$C_{3-7}$cycloalkyl-$C_{1-6}$alkyl selected from cyclopropyl-$C_{1-6}$alkyl, cyclobutyl-$C_{1-6}$alkyl, cyclopentyl-$C_{1-6}$alkyl and cyclohexyl-$C_{1-6}$alkyl, the cycloalkyl portion of each being optionally substituted;

heteroaryl-$C_{1-6}$alkyl selected from pyridinyl-$C_{1-6}$alkyl, pyrimidinyl-$C_{1-6}$alkyl, pyridazinyl-$C_{1-6}$alkyl, pyrazinyl-$C_{1-6}$alkyl, furanyl-$C_{1-6}$alkyl, thienyl-$C_{1-6}$alkyl, pyrrolyl-$C_{1-6}$alkyl, oxazolyl-$C_{1-6}$alkyl, thiazolyl-$C_{1-6}$alkyl, imidazolyl-$C_{1-6}$alkyl, isoxazolyl-$C_{1-6}$alkyl and isothiazolyl-$C_{1-6}$alkyl, the heteroaryl portion of each being optionally substituted;

heterocyclyl-$C_{1-6}$alkyl selected from piperidinyl-$C_{1-6}$alkyl, piperazinyl-$C_{1-6}$alkyl, morpholinyl-$C_{1-6}$alkyl, thiomorpholinyl-$C_{1-6}$alkyl, 1-oxo-thiomorpholinyl-$C_{1-6}$alkyl, 1,1-dioxo-thiomorpholinyl-$C_{1-6}$alkyl, pyranyl-$C_{1-4}$alkyl, pyrrolidinyl-$C_{1-6}$alkyl tetrahydrofuranyl-$C_{1-6}$alkyl, and azetidin-$C_{1-6}$alkyl, the heterocyclyl portion of each being optionally substituted;

aryloxy-$C_{1-6}$alkyl selected from phenoxy-$C_{1-6}$alkyl and naphthyloxy-$C_{1-6}$alkyl, the aryl portion of each being optionally substituted; or —C(O)—$R^8$ or —$CH_2$—C(O)—$R^8$ wherein $R^8$ is as defined herein.

In certain embodiments of any of formulas I, IIa, IIb, IIc, IIIa, IIIb, IIIc, IVa, IVb or IVc, $R^5$ is $C_{1-6}$alkyl selected from methyl, ethyl, propyl, isopropyl, n-butyl, isobutyl, tert-butyl, n-pentyl and isopentyl.

In certain embodiments of any of formulas I, IIa, IIb, IIc, IIIa, IIIb, IIIc, IVa, IVb or IVc, $R^5$ is hetero-$C_{1-6}$alkyl selected from $C_{1-6}$alkyloxy-$C_{1-6}$alkyl, hydroxy-$C_{1-6}$alkyl, $C_{1-6}$alkyl-sulfanyl-$C_{1-6}$alkyl, $C_{1-6}$alkyl-sulfinyl-$C_{1-6}$alkyl, $C_{1-6}$alkyl-sulfonyl-$C_{1-6}$alkyl, amino-$C_{1-6}$alkyl, N—$C_{1-6}$alkylamino-$C_{1-6}$alkyl, and N,N-di-$C_{1-6}$alkylamino-$C_{1-6}$alkyl.

In certain embodiments of any of formulas I, IIa, IIb, IIc, IIIa, IIIb, IIIc, IVa, IVb or IVc, $R^5$ is $C_{3-7}$cycloalkyl selected from cyclopropyl, cyclobutyl, cyclopentyl and cyclohexyl, each optionally substituted.

In certain embodiments of any of formulas I, IIa, IIb, IIc, IIIa, IIIb, IIIc, IVa, IVb or IVc, $R^5$ is aryl selected from optionally substituted phenyl and optionally substituted naphthyl.

In certain embodiments of any of formulas I, IIa, IIb, IIc, IIIa, IIIb, IIIc, IVa, IVb or IVc, $R^5$ is heteroaryl selected from pyridinyl, pyrimidinyl, pyridazinyl, pyrazinyl, thienyl, pyrrolyl, oxazolyl, thiazolyl, imidazolyl, isoxazolyl and isothiazolyl, each optionally substituted.

In certain embodiments of any of formulas I, IIa, IIb, IIc, IIIa, IIIb, IIIc, IVa, IVb or IVc, $R^5$ is heterocyclyl selected from piperidinyl, piperazinyl, morpholinyl, thiomorpholinyl, 1-oxo-thiomorpholinyl, 1,1-dioxo-thiomorpholinyl, pyranyl, pyrrolidinyl and tetrahydrofuranyl, each optionally substituted.

In certain embodiments of any of formulas I, IIa, IIb, IIc, IIIa, IIIb, IIIc, IVa, IVb or IVc, $R^5$ is $C_{3-7}$cycloalkyl-$C_{1-6}$alkyl selected from cyclopropyl-$C_{1-6}$alkyl, cyclobutyl-$C_{1-6}$alkyl, cyclopentyl-$C_{1-6}$alkyl and cyclohexyl-$C_{1-6}$alkyl, the cycloalkyl portion of each being optionally substituted.

In certain embodiments of any of formulas I, IIa, IIb, IIc, IIIa, IIIb, IIIc, IVa, IVb or IVc, $R^5$ is heteroaryl-$C_{1-6}$alkyl selected from pyridinyl-$C_{1-6}$alkyl, pyrimidinyl-$C_{1-6}$alkyl, pyridazinyl-$C_{1-6}$alkyl, pyrazinyl-$C_{1-6}$alkyl, furanyl-$C_{1-6}$alkyl, thienyl-$C_{1-6}$alkyl, pyrrolyl-$C_{1-6}$alkyl, oxazolyl-$C_{1-6}$alkyl, thiazolyl-$C_{1-6}$alkyl, imidazolyl-$C_{1-6}$alkyl, isoxazolyl-$C_{1-6}$alkyl and isothiazolyl-$C_{1-6}$alkyl, the heteroaryl portion of each being optionally substituted.

In certain embodiments of any of formulas I, IIa, IIb, IIc, IIIa, IIIb, IIIc, IVa, IVb or IVc, $R^5$ is heterocyclyl-$C_{1-6}$alkyl selected from piperidinyl-$C_{1-6}$alkyl, piperazinyl-$C_{1-6}$alkyl, morpholinyl-$C_{1-6}$alkyl, thiomorpholinyl-$C_{1-6}$alkyl, 1-oxo-thiomorpholinyl-$C_{1-6}$alkyl, 1,1-dioxo-thiomorpholinyl-$C_{1-6}$alkyl, pyranyl-$C_{1-6}$alkyl, pyrrolidinyl-$C_{1-6}$alkyl and tetrahydrofuranyl-$C_{1-6}$alkyl, the heterocyclyl portion of each being optionally substituted.

In certain embodiments of any of formulas I, IIa, IIb, IIc, IIIa, IIIb, IIIc, IVa, IVb or IVc, $R^5$ is aryloxy-$C_{1-6}$alkyl selected from phenoxy-$C_{1-6}$alkyl and naphthyloxy-$C_{1-6}$alkyl, the aryl portion of each being optionally substituted.

In certain embodiments of any of formulas I, IIa, IIb, IIc, IIIa, IIIb, IIIc, IVa, IVb or IVc, $R^5$ is —C(O)—$R^8$ and $R^8$ is as defined herein.

In certain embodiments of any of formulas I, IIa, IIb, IIc, IIIa, IIIb, IIIc, IVa, IVb or IVc, $R^5$ is —CH$_2$—C(O)—$R^8$ wherein $R^8$ is as defined herein.

In certain embodiments of any of formulas I, IIa, IIb, IIc, IIIa, IIIb, IIIc, IVa, IVb or IVc, $R^5$ is:

$C_{1-6}$alkyl selected from methyl, ethyl, propyl, isopropyl, n-butyl, isobutyl, tert-butyl, n-pentyl and isopentyl;

$C_{1-6}$alkoxy-$C_{1-6}$alkyl selected from methoxymethyl, ethoxymethyl, 2-(methoxy)-ethyl, 2-(ethoxy)-ethyl, 3-(methoxy)-propyl, 3-(ethoxy)-propyl, 3-methoxy-3-methyl-butyl, 4-methoxy-butyl, or 4-methoxy-4-methyl-pentyl;

$C_{1-6}$alkylsulfanyl-$C_{1-6}$alkyl selected from methylsulfanyl-methyl, ethylsulfanylmethyl, 2-(methylsulfanyl)-ethyl, 2-(ethylsulfanyl)-ethyl, 3-(methylsulfanyl)-propyl, 3-(ethanyl)-propyl, 3-methanesulfanyl-3-methyl-butyl, 4-methanesulfanyl-butyl, and 4-methylsulfanyl-4-methyl-pentyl;

$C_{1-6}$alkylsulfonyl-$C_{1-6}$alkyl selected from methylsulfonyl-methyl, ethylsulfanylmethyl, 2-(methylsulfonyl)-ethyl, 2-(ethylsulfonyl)-ethyl, 3-(methylsulfonyl)-propyl, 3-(ethanyl)-propyl, 3-methanesulfonyl-3-methyl-butyl, 4-methanesulfonyl-butyl, and 4-methylsulfonyl-4-methyl-pentyl;

hydroxy-$C_{1-6}$alkyl selected from hydroxymethyl, 2-hydroxy-ethyl, 3-hydroxy-propyl, 2-hydroxy-propyl, 2-hydroxy-2-methyl-propyl, 3-hydroxy-3-methylbutyl, 4-hydroxy-4-methylpentyl, 2-hydroxy-2-ethyl-propyl, 3-hydroxy-3-ethylbutyl and 4-hydroxy-4-ethylpentyl;

amino-$C_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl;

N—$C_{1-6}$alkyl-amino-$C_{1-6}$alkyl selected from N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-ethylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl;

N,N-di-$C_{1-6}$alkyl-amino-$C_{1-6}$alkyl selected from N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methylbutyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl;

$C_{3-7}$cycloalkyl selected from cyclopropyl, cyclobutyl, cyclopentyl and cyclohexyl, each optionally substituted;

aryl selected from optionally substituted phenyl, optionally substituted naphth-1-yl and optionally substituted naphth-2-yl;

heteroaryl selected from pyridin-2-yl, pyridin-3-yl, pyridin-4-yl, pyrimidin-2-yl, pyridazin-3-yl, pyridazin-4-yl, pyrazin-2-yl, thien-2-yl, thien-3-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, isoxazol-3-yl, isoxazol-4-yl, isoxazol-5-yl, isothiazol-3-yl, isothiazol-4-yl, and isothiazol-5-yl, each optionally substituted;

heterocyclyl selected from piperidin-1-yl, piperidin-4-yl, piperazin-1-yl, morpholin-4-yl, thiomorpholin-4-yl, 1-oxo-thiomorpholin-4-yl, 1,1-dioxo-thiomorpholin-4-yl, pyran-4-yl, pyrrolidin-1-yl, pyrrolidin-3-yl, tetrahydrofuran-2-yl, tetrahydrofuran-3-yl, 2-oxa-8-aza-spiro[4,5]decan-8-yl, 2-oxa-5-aza-bicyclo[2.2.1]heptan-5-yl, and 3-oxa-8-aza-bicyclo[3.2.1]octan-8-yl, each optionally substituted;

$C_{3-7}$cycloalkyl-$C_{1-6}$alkyl selected from cyclopropyl-methyl, cyclobutyl-methyl, cyclopentyl-methyl, cyclohexyl-methyl, cyclopropyl-ethyl, cyclobutyl-ethyl, cyclopentyl-ethyl, cyclohexyl-ethyl, 3-(cyclopropyl)-propyl, 3-(cyclobutyl)-propyl, 3-(cyclopentyl)-propyl, and 3-(cyclohexyl)-propyl, the cycloalkyl portion of each being optionally substituted;

heteroaryl-$C_{1-6}$alkyl selected from pyridin-2-ylmethyl, pyridin-3-ylmethyl, pyridin-4-ylmethyl, pyrimidin-2-ylmethyl, pyridazin-3-ylmethyl, pyridazin-4-ylmethyl, pyrazin-2-ylmethyl, furan-2-ylmethyl, furan-3-ylmethyl, thien-2-ylmethyl, thien-3-ylmethyl, pyrrol-1-ylmethyl, pyrrol-2-ylmethyl, pyrrol-3-ylmethyl, oxazol-2-ylmethyl, oxazol-4-ylmethyl, oxazol-5-ylmethyl, thiazol-2-ylmethyl, thiazol-4-ylmethyl, thiazol-5-ylmethyl, imidazol-1-ylmethyl, imidazol-2-ylmethyl, imidazol-4-ylmethyl, isoxazol-3-ylmethyl, isoxazol-4-ylmethyl, isoxazol-5-ylmethyl, isothiazol-3-ylmethyl, isothiazol-4-ylmethyl, isothiazol-5-ylmethyl, pyridin-2-ylethyl, pyridin-3-ylethyl, pyridin-4-ylethyl, pyrimidin-2-ylethyl, pyridazin-3-ylethyl, pyridazin-4-ylethyl, pyrazin-2-ylethyl, furan-2-ylethyl, furan-3-ylethyl, thien-2-ylethyl, thien-3-ylethyl, pyrrol-1-ylethyl, pyrrol-2-ylethyl, pyrrol-3-ylethyl, oxazol-2-ylethyl, oxazol-4-ylethyl, oxazol-5-ylethyl, thiazol-2-ylethyl, thiazol-4-ylethyl, thiazol-5-ylethyl, imidazol-1-ylethyl, imidazol-2-ylethyl, imidazol-4-ylethyl, isoxazol-3-ylethyl, isoxazol-4-ylethyl, isoxazol-5-ylethyl, isothiazol-3-ylethyl, isothiazol-4-ylethyl, isothiazol-5-ylethyl, 3-(pyridin-2-yl)-propyl, 3-(pyridin-3-yl)-propyl, 3-(pyridin-4-yl)-propyl, 3-(pyrimidin-2-yl)-propyl, 3-(pyridazin-3-yl)-propyl, 3-(pyridazin-4-yl)-propyl, 3-(pyrazin-2-yl)-propyl, 3-(furan-2-yl)-propyl, 3-(furan-3-yl)-propyl, 3-(thien-2-yl)-propyl, 3-(thien-3-yl)-propyl, 3-(pyrrol-1-yl)-propyl, 3-(pyrrol-2-yl)-propyl, 3-(pyrrol-3-yl)-propyl, 3-(oxazol-2-yl)-propyl, 3-(oxazol-4-yl)-propyl, 3-(oxazol-5-yl)-propyl, 3-(thiazol-2-yl)-propyl, 3-(thiazol-4-yl)-propyl, 3-(thiazol-5-yl)-propyl, 3-(imidazol-1-yl)-propyl, 3-(imidazol-2-yl)-propyl, 3-(imidazol-4-yl)-propyl, 3-(isoxazol-3-yl)-propyl, 3-(isoxazol-4-yl)-propyl, 3-(isoxazol-5-yl)-propyl, 3-(isothiazol-3-yl)-propyl, 3-(isothiazol-4-yl)-propyl, and 3-(isothiazol-5-yl)-propyl, the heteroaryl portion of each being optionally substituted;

heterocyclyl-$C_{1-6}$alkyl selected from piperidin-1-ylmethyl, piperidin-4-ylmethyl, piperazin-1-ylmethyl, morpholin-4-ylmethyl, thiomorpholin-4-ylmethyl, 1-oxo-thiomorpholin-4-ylmethyl, 1,1-dioxo-thiomorpholin-4-ylmethyl, pyran-4-ylmethyl, pyrrolidin-1-ylmethyl, pyrrolidin-3-ylmethyl, tetrahydrofuran-2-ylmethyl, tetrahydrofuran-3-ylmethyl, piperidin-1-ylethyl, piperidin-4-ylethyl, piperazin-1-ylethyl, morpholin-4-ylethyl, thiomorpholin-4-ylethyl, 1-oxo-thiomorpholin-4-ylethyl, 1,1-dioxo-thiomorpholin-4-ylethyl, pyran-4-ylethyl, pyrrolidin-1-ylethyl, pyrrolidin-3-ylethyl, tetrahydrofuran-2-ylethyl, tetrahydrofuran-3-ylethyl, 3-(piperidin-1-yl)-propyl, 3-(piperidin-4-yl)-propyl, 3-(piperazin-1-yl)-propyl, 3-(morpholin-4-yl)-propyl, 3-(thiomorpholin-4-yl)-propyl, 3-(1-oxo-thiomorpholin-4-yl)-propyl, 3-(1,1-dioxo-thiomorpholin-4-yl)-propyl, 3-(pyran-4-yl)-propyl, pyrrolidin-1-yl)-propyl, 3-(pyrrolidin-3-yl)-propyl, 3-(tetrahydrofuran-2-yl)-propyl, 3-(tetrahydrofuran-3-yl)-propyl, 2-oxa-8-aza-spiro[4,5]decan-8-ylmethyl, 2-oxa-5-aza-bicyclo[2.2.1]heptan-5-ylmethyl, 3-oxa-8-aza-bicyclo[3.2.1]octan-8-ylmethyl, the heterocyclyl portion of each being optionally substituted; or —C(O)—$R^8$ or —$CH_2$—C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy. Preferably in such embodiments $R^8$ is $C_{1-6}$alkyloxy, N—$C_{1-6}$alkyl-amino, or N,N-di-$C_{1-6}$alkyl-amino.

In certain embodiments of any of formulas I, IIa, IIb, IIc, IIIa, IIIb, IIIc, IVa, IVb or IVc, $R^5$ is $C_{1-6}$alkyl selected from methyl, ethyl, propyl, isopropyl, n-butyl, isobutyl, tert-butyl, n-pentyl and isopentyl.

In certain embodiments of any of formulas I, IIa, IIb, IIc, IIIa, IIIb, IIIc, IVa, IVb or IVc, $R^5$ is $C_{1-6}$alkoxy-$C_{1-6}$alkyl selected from methoxymethyl, ethoxymethyl, 2-(methoxy)-ethyl, 2-(ethoxy)-ethyl, 3-(methoxy)-propyl, 3-(ethoxy)-propyl, 3-methoxy-3-methyl-butyl, 4-methoxy-butyl, or 4-methoxy-4-methyl-pentyl.

In certain embodiments of any of formulas I, IIa, IIb, IIc, IIIa, IIIb, IIIc, IVa, IVb or IVc, $R^5$ is $C_{1-6}$alkylsulfanyl-$C_{1-6}$alkyl selected from methylsulfanylmethyl, ethylsulfanylmethyl, 2-(methylsulfanyl)-ethyl, 2-(ethylsulfanyl)-ethyl, 3-(methylsulfanyl)-propyl, 3-(ethanyl)-propyl, 3-methanesulfanyl-3-methyl-butyl, 4-methanesulfanyl-butyl, and 4-methylsulfanyl-4-methyl-pentyl.

In certain embodiments of any of formulas I, IIa, IIb, IIc, IIIa, IIIb, IIIc, IVa, IVb or IVc, $R^5$ is $C_{1-6}$alkylsulfonyl-$C_{1-6}$alkyl selected from methylsulfonylmethyl, ethylsulfanylmethyl, 2-(methylsulfonyl)-ethyl, 2-(ethylsulfonyl)-ethyl, 3-(methylsulfonyl)-propyl, 3-(ethanyl)-propyl, 3-methanesulfonyl-3-methyl-butyl, 4-methanesulfonyl-butyl, and 4-methylsulfonyl-4-methyl-pentyl.

In certain embodiments of any of formulas I, IIa, IIb, IIc, IIIa, IIIb, IIIc, IVa, IVb or IVc, $R^5$ is hydroxy-$C_{1-6}$alkyl selected from hydroxymethyl, 2-hydroxy-ethyl, 3-hydroxy-propyl, 2-hydroxy-propyl, 2-hydroxy-2-methyl-propyl, 3-hydroxy-3-methylbutyl, 4-hydroxy-4-methylpentyl, 2-hydroxy-2-ethyl-propyl, 3-hydroxy-3-ethylbutyl and 4-hydroxy-4-ethylpentyl.

In certain embodiments of any of formulas I, IIa, IIb, IIc, IIIa, IIIb, IIIc, IVa, IVb or IVc, $R^5$ is amino-$C_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl.

In certain embodiments of any of formulas I, IIa, IIb, IIc, IIIa, IIIb, IIIc, IVa, IVb or IVc, $R^5$ is N—$C_{1-6}$alkyl-amino-$C_{1-6}$alkyl selected from N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-ethylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl.

In certain embodiments of any of formulas I, IIa, IIb, IIc, IIIa, IIIb, IIIc, IVa, IVb or IVc, $R^5$ is N,N-di-$C_{1-6}$alkyl-amino-$C_{1-6}$alkyl selected from N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methylbutyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl.

In certain embodiments of any of formulas I, IIa, IIb, IIc, IIIa, IIIb, IIIc, IVa, IVb or IVc, $R^5$ is $C_{3-7}$cycloalkyl selected from cyclopropyl, cyclobutyl, cyclopentyl and cyclohexyl, each optionally substituted.

In certain embodiments of any of formulas I, IIa, IIb, IIc, IIIa, IIIb, IIIc, IVa, IVb or IVc, $R^5$ is aryl selected from optionally substituted phenyl, optionally substituted naphth-1-yl and optionally substituted naphth-2-yl.

In certain embodiments of any of formulas I, IIa, IIb, IIc, IIIa, IIIb, IIIc, IVa, IVb or IVc, $R^5$ is heteroaryl selected from pyridin-2-yl, pyridin-3-yl, pyridin-4-yl, pyrimidin-2-yl, pyridazin-3-yl, pyridazin-4-yl, pyrazin-2-yl, thien-2-yl, thien-3-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, isoxazol-3-yl, isoxazol-4-yl, isoxazol-5-yl, isothiazol-3-yl, isothiazol-4-yl, and isothiazol-5-yl, each optionally substituted.

In certain embodiments of any of formulas I, IIa, IIb, IIc, IIIa, IIIb, IIIc, IVa, IVb or IVc, $R^5$ is heterocyclyl selected from piperidin-1-yl, piperidin-4-yl, piperazin-1-yl, morpholin-4-yl, thiomorpholin-4-yl, 1-oxo-thiomorpholin-4-yl, 1,1-dioxo-thiomorpholin-4-yl, pyran-4-yl, pyrrolidin-1-yl, pyrrolidin-3-yl, tetrahydrofuran-2-yl and tetrahydrofuran-3-yl, each optionally substituted.

In certain embodiments of any of formulas I, IIa, IIb, IIc, IIIa, IIIb, IIIc, IVa, IVb or IVc, $R^5$ is $C_{3-7}$cycloalkyl-$C_{1-6}$alkyl selected from cyclopropyl-methyl, cyclobutyl-methyl, cyclopentyl-methyl, cyclohexyl-methyl, cyclopropyl-ethyl, cyclobutyl-ethyl, cyclopentyl-ethyl, cyclohexyl-ethyl, 3-(cyclopropyl)-propyl, 3-(cyclobutyl)-propyl, 3-(cyclopentyl)-propyl, and 3-(cyclohexyl)-propyl, the cycloalkyl portion of each being optionally substituted.

In certain embodiments of any of formulas I, IIa, IIb, IIc, IIIa, IIIb, IIIc, IVa, IVb or IVc, $R^5$ is heteroaryl-$C_{1-6}$alkyl selected from pyridin-2-ylmethyl, pyridin-3-ylmethyl, pyridin-4-ylmethyl, pyrimidin-2-ylmethyl, pyridazin-3-ylmethyl, pyridazin-4-ylmethyl, pyrazin-2-ylmethyl, furan-2-ylmethyl, furan-3-ylmethyl, thien-2-ylmethyl, thien-3-ylmethyl, pyrrol-1-ylmethyl, pyrrol-2-ylmethyl, pyrrol-3-ylmethyl, oxazol-2-ylmethyl, oxazol-4-ylmethyl, oxazol-5-ylmethyl, thiazol-2-ylmethyl, thiazol-4-ylmethyl, thiazol-5-ylmethyl, imidazol-1-ylmethyl, imidazol-2-ylmethyl, imidazol-4-ylmethyl, isoxazol-3-ylmethyl, isoxazol-4-ylmethyl, isoxazol-5-ylmethyl, isothiazol-3-ylmethyl, isothiazol-4-ylmethyl, isothiazol-5-ylmethyl, pyridin-2-ylethyl, pyridin-3-ylethyl, pyridin-4-ylethyl, pyrimidin-2-ylethyl, pyridazin-3-ylethyl, pyridazin-4-ylethyl, pyrazin-2-ylethyl, furan-2-ylethyl, furan-3-ylethyl, thien-2-ylethyl, thien-3-ylethyl, pyrrol-1-ylethyl, pyrrol-2-ylethyl, pyrrol-3-ylethyl, oxazol-2-ylethyl, oxazol-4-ylethyl, oxazol-5-ylethyl, thiazol-2-ylethyl, thiazol-4-ylethyl, thiazol-5-ylethyl, imidazol-1-ylethyl, imidazol-2-ylethyl, imidazol-4-ylethyl, isoxazol- 3-ylethyl, isoxazol-4-ylethyl, isoxazol-5-ylethyl, isothiazol-3-ylethyl, isothiazol-4-ylethyl, isothiazol-5-ylethyl, 3-(pyridin-2-yl)-propyl, 3-(pyridin-3-yl)-propyl, 3-(pyridin-4-yl)-propyl, 3-(pyrimidin-2-yl)-propyl, 3-(pyridazin-3-yl)-propyl, 3-(pyridazin-4-yl)-propyl, 3-(pyrazin-2-yl)-propyl, 3-(furan-2-yl)-propyl, 3-(furan-3-yl)-propyl, 3-(thien-2-yl)-propyl, 3-(thien-3-yl)-propyl, 3-(pyrrol-1-yl)-propyl, 3-(pyrrol-2-yl)-propyl, 3-(pyrrol-3-yl)-propyl, 3-(oxazol-2-yl)-propyl, 3-(oxazol-4-yl)-propyl, 3-(oxazol-5-yl)-propyl, 3-(thiazol-2-yl)-propyl, 3-(thiazol-4-yl)-propyl, 3-(thiazol-5-yl)-propyl, 3-(imidazol-1-yl)-propyl, 3-(imidazol-2-yl)-propyl, 3-(imidazol-4-yl)-propyl, 3-(isoxazol-3-yl)-propyl, 3-(isoxazol-4-yl)-propyl, 3-(isoxazol-5-yl)-propyl, 3-(isothiazol-3-yl)-propyl, 3-(isothiazol-4-yl)-propyl, and 3-(isothiazol-5-yl)-propyl, the heteroaryl portion of each being optionally substituted.

In certain embodiments of any of formulas I, IIa, IIb, IIc, IIIa, IIIb, IIIc, IVa, IVb or IVc, $R^5$ is heterocyclyl-$C_{1-6}$alkyl selected from piperidin-1-ylmethyl, piperidin-4-ylmethyl, piperazin-1-ylmethyl, morpholin-4-ylmethyl, thiomorpholin-4-ylmethyl, 1-oxo-thiomorpholin-4-ylmethyl, 1,1-dioxo-thiomorpholin-4-ylmethyl, pyran-4-ylmethyl, pyrrolidin-1-ylmethyl, pyrrolidin-3-ylmethyl, tetrahydrofuran-2-ylmethyl, tetrahydrofuran-3-ylmethyl, piperidin-1-ylethyl, piperidin-4-ylethyl, piperazin-1-ylethyl, morpholin-4-ylethyl, thiomorpholin-4-ylethyl, 1-oxo-thiomorpholin-4-ylethyl, 1,1-dioxo-thiomorpholin-4-ylethyl, pyran-4-ylethyl, pyrrolidin-1-ylethyl, pyrrolidin-3-ylethyl, tetrahydrofuran-2-ylethyl, tetrahydrofuran-3-ylethyl, 3-(piperidin-1-yl)-propyl, 3-(piperidin-4-yl)-propyl, 3-(piperazin-1-yl)-propyl, 3-(morpholin-4-yl)-propyl, 3-(thiomorpholin-4-yl)-propyl, 3-(1-oxo-thiomorpholin-4-yl)-propyl, 3-(1,1-dioxo-thiomorpholin-4-yl)-propyl, 3-(pyran-4-yl)-propyl, pyrrolidin-1-yl)-propyl, 3-(pyrrolidin-3-yl)-propyl, 3-(tetrahydrofuran-2-yl)-propyl, 3-(tetrahydrofuran-3-yl)-propyl, 2-oxa-8-aza-spiro[4.5]decan-8-ylmethyl, 2-oxa-5-aza-bicyclo[2.2.1]heptan-5-ylmethyl, 3-oxa-8-aza-bicyclo[3.2.1]octan-8-ylmethyl, the heterocyclyl portion of each being optionally substituted.

In certain embodiments of any of formulas I, IIa, IIb, IIc, IIIa, IIIb, IIIc, IVa, IVb or IVc, $R^5$ is —C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy.

In certain embodiments of any of formulas I, IIa, IIb, IIc, IIIa, IIIb, IIIc, IVa, IVb or IVc, $R^5$ is $CH_2$—C(O)—$R^8$ wherein $R^8$ is $C_{1-6}$alkyl, $C_{1-6}$alkyloxy, N—$C_{1-6}$-alkyl-amino, N,N-di-$C_{1-6}$alkyl-amino, heterocyclyl, N—$C_{3-6}$cycloalkyl-amino or $C_{3-6}$cycloalkyloxy.

In certain embodiments of any of formulas I, IIa, IIb, IIc, IIIa, IIIb, IIIc, IVa, IVb or IVc, $R^5$ is:

hetero-$C_{1-6}$alkyl selected from hydroxymethyl, 2-hydroxy-2-methyl-pentan-1-yl and methoxymethyl;

heterocyclyl-$C_{1-6}$alkyl selected from morpholin-4-ylmethyl, piperidin-1-ylmethyl, piperazin-1-ylmethyl, thiomorpholin-1-ylmethyl, 4-methanesulfonyl-piperazin-1-ylmethyl, 4-acetyl-piperazin-1-ylmethyl, 4-acetyl-3-methyl-piperazin-1-ylmethyl, 3-oxy-piperazin-1-ylmethyl, 4-methanesulfonyl-piperidin-1-ylmethyl, 4-fluoropiperidin-1-ylmethyl, 4,4-difluoropiperidin-1-ylmethyl, 3-fluoro-piperidin-1-ylmethyl, 4-methoxy-piperidin-1-ylmethyl, 3-methoxy-piperidin-1-ylmethyl, 4-hydroxy-piperidin-1-ylmethyl, 3-hydroxypiperidin-1-ylmethyl, 4-methoxy-3-fluoro-piperidin-1-ylmethyl, 2,6-dimethyl-morpholin-4-ylmethyl, 1-oxy-thiomorpholin-4-ylmethyl and 1,1-dioxy-thiomorpholin-4-ylmethyl; or heteroaryl selected from pyrazin-2-yl, pyridazin-3-yl and thiazol-2-yl.

In certain embodiments of any of formulas I, IIa, IIb, IIc, IIIa, IIIb, IIIc, IVa, IVb or IVc, $R^5$ is hetero-$C_{1-6}$alkyl selected from hydroxymethyl, 2-hydroxy-2-methyl-pentan-1-yl and methoxymethyl.

In certain embodiments of any of formulas I, IIa, IIb, IIc, IIIa, IIIb, IIIc, IVa, IVb or IVc, $R^5$ is heterocyclyl-$C_{1-6}$-alkyl selected from morpholin-4-ylmethyl, piperidin-1-ylmethyl, piperazin-1-ylmethyl, thiomorpholin-1-ylmethyl, 4-methanesulfonyl-piperazin-1-ylmethyl, 4-acetyl-piperazin-1-ylmethyl, 4-acetyl-3-methyl-piperazin-1-ylmethyl, 3-oxy-piperazin-1-ylmethyl, 4-methanesulfonyl-piperidin-1-ylmethyl, 4-fluoropiperidin-1-ylmethyl, 4,4-difluoropiperidin-1-ylmethyl, 3-fluoro-piperidin-1-ylmethyl, 4-methoxy-piperidin-1-ylmethyl, 3-methoxy-piperidin-1-ylmethyl, 4-hydroxy-piperidin-1-ylmethyl, 3-hydroxypiperidin-1-ylmethyl, 4-methoxy-3-fluoro-piperidin-1-ylmethyl, 2,6-dimethyl-morpholin-4-ylmethyl, 1-oxy-thiomorpholin-4-ylmethyl and 1,1-dioxy-thiomorpholin-4-ylmethyl.

In certain embodiments of any of formulas I, IIa, IIb, IIc, IIIa, IIIb, IIIc, IVa, IVb or IVc, $R^5$ is heteroaryl selected from pyrazin-2-yl, pyridazin-3-yl and thiazol-2-yl.

In certain embodiments of formula I, $R^1$ is: tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is:

$C_{1-6}$alkyl;

$C_{1-6}$alkyloxy-$C_{1-6}$alkyl;

hydroxy-$C_{1-6}$alkyl;

$C_{1-6}$alkylsulfanyl-$C_{1-6}$alkyl;

$C_{1-6}$alkylsulfonyl-$C_{1-6}$alkyl;

amino-$C_{1-6}$alkyl;

N—$C_{1-6}$alkyl-amino-$C_{1-6}$alkyl;

N,N-di-$C_{1-6}$alkyl-amino-$C_{1-6}$alkyl;

$C_{3-7}$cycloalkyl;

optionally substituted phenyl;

optionally substituted naphthyl;

optionally substituted pyridinyl;

optionally substituted pyrazinyl;

optionally substituted pyradizinyl;

optionally substituted thiazolyl;

optionally substituted piperidinyl-$C_{1-6}$alkyl;

optionally substituted piperazinyl-$C_{1-6}$alkyl;

optionally substituted morpholinyl-$C_{1-6}$alkyl;

optionally substituted thiomorpholinyl-$C_{1-6}$alkyl;

optionally substituted pyrrolidinyl-$C_{1-6}$alkyl; or

—C(O)—$R^8$ or —$CH_2$—C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy. When $R^8$ is heterocyclyl, preferred heterocyclyl include morpholinyl and piperidinyl, each optionally substituted.

In certain embodiments of formula I: $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is $C_{1-6}$alkyl. In such embodiments $R^5$ may be $C_{1-6}$alkyl selected from methyl, ethyl, propyl, isopropyl, n-butyl, isobutyl, tert-butyl, n-pentyl and isopentyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is $C_{1-6}$alkyloxy-$C_{1-6}$alkyl. In such embodiments $R^5$ may be $C_{1-6}$alkyloxy-$C_{1-6}$alkyl selected from methoxymethyl, ethoxymethyl, 2-(methoxy)-ethyl, 2-(ethoxy)-ethyl, 3-(methoxy)-propyl, 3-(ethoxy)-propyl, 3-methoxy-3-methyl-butyl, 4-methoxy-butyl, and 4-methoxy-4-methyl-pentyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-4}$-cycloalkyl; $R^2$ is phenyl substituted once or twice with fluoro, chloro or methyl; $R^3$ and $R^6$ are hydrogen; $R^4$ is methyl; and $R^5$ is $C_{1-6}$alkylsulfanyl-$C_{1-6}$alkyl. In such embodiments $R^5$ may be $C_{1-6}$alkylsulfanyl-$C_{1-6}$-alkyl selected from methylsulfanylmethyl, ethylsulfanylmethyl, 2-(methylsulfanyl)-ethyl, 2-(ethylsulfanyl)-ethyl, 3-(methylsulfanyl)-propyl, 3-(ethanyl)-propyl, 3-methanesulfanyl-3-methyl-butyl, 4-methanesulfanyl-butyl, and 4-methylsulfanyl-4-methyl-pentyl.

In certain embodiments of formula I, $R^1$ is; tetrazol-1-yl optionally substituted at the 5-position with $C_{1-6}$alkyl, halo-$C_{1-6}$-alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is $C_{1-6}$alkylsulfonyl-$C_{1-6}$alkyl. In such embodiments $R^5$ may be $C_{1-6}$alkylsulfonyl-$C_{1-6}$alkyl selected from methylsulfonylmethyl, ethylsulfanylmethyl, 2-(methylsulfonyl)-ethyl, 2-(ethylsulfonyl)-ethyl, 3-(methylsulfonyl)-propyl, 3-(ethanyl)-propyl, 3-methanesulfonyl-3-methyl-butyl, 4-methanesulfonyl-butyl, and 4-methylsulfonyl-4-methyl-pentyl.

In certain embodiments of formula I, $R^1$ is; tetrazol-1-yl optionally substituted at the 5-position with $C_{1-6}$alkyl, halo-$C_{1-6}$-alkyl, $C_{1-6}$alkoxy-$C_{1-6}$-alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is hydroxy-$C_{1-6}$alkyl. In such embodiments $R^5$ may be hydroxy-$C_{1-6}$alkyl selected from hydroxymethyl, 2-hydroxy-ethyl, 3-hydroxy-propyl, 2-hydroxy-propyl, 2-hydroxy-2-methyl-propyl, 3-hydroxy-3-methylbutyl, 4-hydroxy-4-methylpentyl, 2-hydroxy-2-ethyl-propyl, 3-hydroxy-3-ethylbutyl and 4-hydroxy-4-ethylpentyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is $R^5$ is amino-$C_{1-6}$alkyl. In such embodiments, $R^5$ may be amino-$C_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is $R^5$ is N—$C_{1-6}$alkyl-amino-$C_{1-6}$alkyl. In such embodiments $R^5$ may be N—$C_{1-6}$alkyl-amino-$C_{1-6}$alkyl selected from N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-methylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is N,N-di-$C_{1-6}$alkyl-amino-$C_{1-6}$alkyl. In such embodiments $R^5$ may be N,N-di-$C_{1-6}$alkyl-amino-$C_{1-6}$alkyl selected from N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methylbutyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted phenyl. In such embodiments $R^5$ may be phenyl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is phenyl substituted once or twice with halo, cyano, trifluoromethyl, methanesulfonyl, methoxy, or methyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted pyridinyl. In such embodiments $R^5$ may be pyridin-2-yl, pyridin-3-yl or pyridin-4-yl each optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyridin-2-yl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted pyrazinyl. In certain embodiments $R^5$ may be pyrazin-2-yl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyrazin-2-yl In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted pyrimidinyl. In certain embodiments $R^5$ may be pyrimidin-2-yl optionally substituted once, twice or three times with $C_{1-6}$alkyl, $C_{1-6}$alkyloxy, halo, $C_{1-4}$haloalkyl, hetero-$C_{1-6}$alkyl, $C_{1-6}$alkylsulfonyl or cyano. In certain embodiments $R^5$ is pyrimidin-2-yl In certain embodiments of formula I, $R^1$ is; tetrazol-1-yl optionally substituted at the 5-position with $C_{1-6}$alkyl, halo- $C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted pyridazinyl. In certain embodiments $R^5$ may be pyridazin-3-yl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyridazdin-3-yl In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted thiazolyl. In certain embodiments $R^5$ may be thiazolyl-2-yl optionally substituted once or twice with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted piperidinyl-$C_{1-6}$alkyl. In such embodiments $R^5$ may be piperidin-1-ylmethyl, 4-hydroxy-piperidiny-1-ylmethyl, 4-methoxy-piperidin-1-ylmethyl, 4-methanesulfonyl-piperidin-1-ylmethyl, 4-fluoro-piperidin-1-ylmethyl or 4,4-difluoropiperidin-1-ylmethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted piperazinyl-$C_{1-6}$alkyl. In such embodiments $R^5$ may be piperazin-1-ylmethyl, 4-methyl-piperazin-1-ylmethyl, 4-methanesulfonyl-piperazin-1-ylmethyl, 4-acetyl-piperazin-1-ylmethyl, 3-methyl-piperazin-1-ylmethyl, 3,4-dimethyl-piperazin-1-ylmethyl, 3-methyl-4-methanesulfonyl-piperazin-1-ylmethyl, 3-methyl-4-acetyl-piperazin-1-ylmethyl, 3,5-dimethyl-piperazin-1-ylmethyl, 3,4,5-trimethyl-piperazin-1-ylmethyl, 3,5-dimethyl-4-methanesulfonyl-piperazin-1-ylmethyl, 3,5-dimethyl-4-acetyl-piperazin-1-ylmethyl, 4-(pyrimidn-2-yl)-piperazin-1-ylmethyl or 3-methoxy-piperazin-1-ylmethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted morpholinyl-$C_{1-6}$alkyl. In such embodiments $R^5$ may be morpholin-4-ylmethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted thiomorpholinyl-$C_{1-6}$alkyl. In such embodiments $R^5$ may be thiomorpholin-4-ylmethyl, 1-oxothiomorpholin-4-ylmethyl or 1,1,-dioxo-thiomorpholin-4-ylmethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is optionally substituted pyrrolidinyl-$C_{1-6}$alkyl. In such embodiments $R^5$ may be pyrrolidin-1-ylmethyl or 3-hydroxypyrrolidin-1-ylmethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is —C(O)—$R^8$ wherein $R^8$ is $C_{1-6}$alkyl, $C_{1-6}$alkyloxy, N—$C_{1-6}$-alkyl-amino, N,N-di-$C_{1-6}$alkyl-amino, heterocyclyl, N—$C_{3-6}$cycloalkyl-amino or $C_{3-6}$cycloalkyloxy.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is —$CH_2$—C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy.

In certain embodiments of formula I, $R^1$ is: tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is:

hetero-$C_{1-6}$alkyl selected from hydroxymethyl, 2-hydroxy-2-methyl-pentan-1-yl and methoxymethyl;

heterocyclyl-$C_{1-6}$alkyl selected from morpholin-4-ylmethyl, piperidin-1-ylmethyl, piperazin-1-ylmethyl, thiomorpholin-1-ylmethyl, 4-methanesulfonyl-piperazin-1-ylmethyl, 4-acetyl-piperazin-1-ylmethyl, 4-acetyl-3-methyl-piperazin-1-ylmethyl, 3-oxy-piperazin-1-ylmethyl, 4-methanesulfonyl-piperidin-1-ylmethyl, 4-fluoropiperidin-1-ylmethyl, 4,4-difluoropiperidin-1-ylmethyl, 3-fluoro-piperidin-1-ylmethyl, 4-methoxy-piperidin-1-ylmethyl, 3-methoxy-piperidin-1-ylmethyl, 4-hydroxy-piperidin-1-ylmethyl, 3-hydroxypiperidin-1-ylmethyl, 4-methoxy-3-fluoro-piperidin-1-ylmethyl, 2,6-dimethyl-morpholin-4-ylmethyl, 1-oxy-thiomorpholin-4-ylmethyl and 1,1-dioxythiomorpholin-4-ylmethyl; or heteroaryl selected from pyrazin-2-yl, pyridazin-3-yl and thiazol-2-yl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is hetero-$C_{1-6}$alkyl selected from hydroxymethyl, 2-hydroxy-2-methyl-pentan-1-yl and methoxymethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is heterocyclyl-$C_{1-6}$alkyl selected from morpholin-4-ylmethyl, piperidin-1-ylmethyl, piperazin-1-ylmethyl, thiomorpholin-1-ylmethyl, 4-methanesulfonyl-piperazin-1-ylmethyl, 4-acetyl-piperazin-1-ylmethyl, 4-acetyl-3-methyl-piperazin-1-ylmethyl, 3-oxy-piperazin-1-ylmethyl, 4-methanesulfonyl-piperidin-1-ylmethyl, 4-fluoropiperidin-1-ylmethyl, 4,4-difluoropiperidin-1-ylmethyl, 3-fluoro-piperidin-1-ylmethyl, 4-methoxy-piperidin-1-ylmethyl, 3-methoxy-piperidin-1-ylmethyl, 4-hydroxy-piperidin-1-ylmethyl, 3-hydroxypiperidin-1-ylmethyl, 4-methoxy-3-fluoro-piperidin-1-ylmethyl, 2,6-dimethyl-morpholin-4-ylmethyl, 1-oxy-thiomorpholin-4-ylmethyl and 1,1-dioxy-thiomorpholin-4-ylmethyl.

In certain embodiments of formula I, $R^1$ is; tetrazol-1-yl optionally substituted at the 5-position with $C_{1-6}$alkyl, halo-$C_{1-6}$alkyl, $C_{1-6}$alkoxy-$C_{1-6}$alkyl or $C_{3-6}$-cycloalkyl; $R^2$ is phenyl substituted once or twice with fluoro, chloro or methyl; $R^3$ and $R^6$ are hydrogen; $R^4$ is methyl; and $R^5$ is heteroaryl selected from pyrazin-2-yl, pyridazin-3-yl and thiazol-2-yl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl; and $R^5$ is:
$C_{1-6}$alkyl;
$C_{1-6}$alkyloxy-$C_{1-6}$alkyl;
hydroxy-$C_{1-6}$alkyl;
$C_{1-6}$alkylsulfanyl-$C_{1-6}$alkyl;
$C_{1-6}$alkylsulfonyl-$C_{1-6}$alkyl;
amino-$C_{1-6}$alkyl;
N—$C_{1-6}$alkyl-amino-$C_{1-6}$alkyl;
N,N-di-$C_{1-6}$alkyl-amino-$C_{1-6}$alkyl;
$C_{3-7}$cycloalkyl;
optionally substituted phenyl;
optionally substituted naphthyl;
optionally substituted pyridinyl;
optionally substituted pyrazinyl;
optionally substituted pyradizinyl;
optionally substituted thiazolyl;
optionally substituted piperidinyl-$C_{1-6}$alkyl;
optionally substituted piperazinyl-$C_{1-6}$alkyl;
optionally substituted morpholinyl-$C_{1-4}$alkyl;
optionally substituted thiomorpholinyl-$C_{1-6}$alkyl;
optionally substituted pyrrolidinyl-$C_{1-6}$alkyl; or
—C(O)—$R^8$ or —CH$_2$—C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is $C_{1-6}$alkyl. In such embodiments $R^5$ may be $C_{1-6}$alkyl selected from methyl, ethyl, propyl, isopropyl, n-butyl, isobutyl, tert-butyl, n-pentyl and isopentyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is $C_{1-6}$alkyloxy-$C_{1-6}$alkyl. In such embodiments $R^5$ may be $C_{1-6}$alkyloxy-$C_{1-6}$alkyl selected from methoxymethyl, ethoxymethyl, 2-(methoxy)-ethyl, 2-(ethoxy)-ethyl, 3-(methoxy)-propyl, 3-(ethoxy)-propyl, 3-methoxy-3-methyl-butyl, 4-methoxy-butyl, and 4-methoxy-4-methyl-pentyl.

In certain embodiments of formula IIa or IIb, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is $C_{1-6}$alkylsulfanyl-$C_{1-6}$alkyl. In such embodiments $R^5$ may be $C_{1-6}$alkylsulfanyl-$C_{1-6}$alkyl selected from methylsulfanylmethyl, ethylsulfanylmethyl, 2-(methylsulfanyl)-ethyl, 2-(ethylsulfanyl)-ethyl, 3-(methylsulfanyl)-propyl, 3-(ethanyl)-propyl, 3-methanesulfanyl-3-methyl-butyl, 4-methanesulfanyl-butyl, and 4-methylsulfanyl-4-methyl-pentyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is $C_{1-6}$alkylsulfonyl-$C_{1-6}$alkyl. In such embodiments $R^5$ may be $C_{1-6}$alkylsulfonyl-$C_{1-6}$alkyl selected from methylsulfonylmethyl, ethylsulfanylmethyl, 2-(methylsulfonyl)-ethyl, 2-(ethylsulfonyl)-ethyl, 3-(methylsulfonyl)-propyl, 3-(ethanyl)-propyl, 3-methanesulfonyl-3-methyl-butyl, 4-methanesulfonyl-butyl, and 4-methylsulfonyl-4-methyl-pentyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is hydroxy-$C_{1-6}$alkyl. In such embodiments $R^5$ may be hydroxy-$C_{1-6}$alkyl selected from hydroxymethyl, 2-hydroxy-ethyl, 3-hydroxy-propyl, 2-hydroxy-propyl, 2-hydroxy-2-methyl-propyl, 3-hydroxy-3-methylbutyl, 4-hydroxy-4-methylpentyl, 2-hydroxy-2-ethyl-propyl, 3-hydroxy-3-ethylbutyl and 4-hydroxy-4-ethylpentyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is amino-$C_{1-6}$alkyl. In such embodiments, $R^5$ may be amino-$C_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is N—$C_{1-6}$alkyl-amino-$C_{1-6}$alkyl. In such embodiments $R^5$ may be N—$C_{1-4}$alkyl-amino-$C_{1-6}$alkyl selected from N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-ethylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is N,N-di-$C_{1-6}$alkyl-amino-$C_{1-6}$alkyl. In such embodiments $R^5$ may be N,N-di-$C_{1-6}$alkyl-amino-$C_{1-6}$alkyl selected from N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methyl butyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl.

In certain embodiments of formula IIa or IIb, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted phenyl. In such embodiments $R^5$ may be phenyl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is phenyl substituted once or twice with halo, cyano, trifluoromethyl, methanesulfonyl, methoxy, or methyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted pyridinyl. In such embodiments $R^5$ may be pyridin-2-yl, pyridin-3-yl or pyridin-4-yl each optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyridin-2-yl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted pyrazinyl. In certain embodiments $R^5$ may be pyrazin-2-yl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyrazin-2-yl In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted pyrimidinyl. In certain embodiments $R^5$ may be pyrimidin-2-yl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyrimidin-2-yl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted pyridazinyl. In certain embodiments $R^5$ may be pyridazin-3-yl optionally substituted once, twice or three times with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano. In certain embodiments $R^5$ is pyridazdin-3-yl In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted thiazolyl. In certain embodiments $R^5$ may be thiazolyl-2-yl optionally substituted once or twice with $C_{1-6}$alkyl, $C_{1-6}$alkyloxy, halo, $C_{1-6}$haloalkyl, hetero-$C_{1-6}$alkyl, $C_{1-6}$alkylsulfonyl or cyano.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted piperidinyl-$C_{1-6}$alkyl. In such embodiments $R^5$ may be piperidin-1-ylmethyl, 4-hydroxy-piperidiny-1-ylmethyl, 4-methoxy-piperidin-1-ylmethyl, 4-methanesulfonyl-piperidin-1-ylmethyl, 4-fluoro-piperidin-1-ylmethyl or 4,4-difluoropiperidin-1-ylmethyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted piperazinyl-$C_{1-6}$alkyl. In such embodiments $R^5$ may be piperazin-1-ylmethyl, 4-methyl-piperazin-1-ylmethyl, 4-methanesulfonyl-piperazin-1-ylmethyl, 4-acetyl-piperazin-1-ylmethyl, 3-methyl-piperazin-1-ylmethyl, 3,4-dimethyl-piperazin-1-ylmethyl, 3-methyl-4-methanesulfonyl-piperazin-1-ylmethyl, 3-methyl-4-acetyl-piperazin-1-ylmethyl, 3,5-dimethyl-piperazin-1-ylmethyl, 3,4,5-trimethyl-piperazin-1-ylmethyl, 3,5-dimethyl-4-methanesulfonyl-piperazin-1-ylmethyl, 3,5-dimethyl-4-acetyl-piperazin-1-ylmethyl, 4-(pyrimidn-2-yl)-piperazin-1-ylmethyl or 3-methoxy-piperazin-1-ylmethyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted morpholinyl-$C_{1-6}$alkyl. In such embodiments $R^5$ may be morpholin-4-ylmethyl.

In certain embodiments of formula IIa, IIb or IIc, $R^{11}$ is fluoro, chloro or methyl, $R^{12}$ is hydrogen, fluoro or chloro, $R^{13}$ is hydrogen or $C_{1-6}$alkyl, and $R^5$ is optionally substituted thiomorpholinyl-$C_{1-6}$alkyl. In such embodiments $R^5$ may be thiomorpholin-4-ylmethyl, 1-oxo-thiomorpholin-4-ylmethyl or 1,1,-dioxo-thiomorpholin-4-ylmethyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is optionally substituted pyrrolidinyl-$C_{1-6}$alkyl. In such embodiments $R^5$ may be pyrrolidin-1-ylmethyl or 3-hydroxypyrrolidin-1-ylmethyl.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is —C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is —CH$_2$—C(O)—$R^8$ wherein $R^8$ is $C_{1-6}$alkyl, $C_{1-6}$alkyloxy, N—$C_{1-6}$alkyl-amino, N,N-di-$C_{1-6}$alkyl-amino, heterocyclyl, N—$C_{3-6}$cycloalkyl-amino or $C_{3-6}$cycloalkyloxy.

In certain embodiments of formula IIa, IIb or IIc, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is:

hetero-$C_{1-6}$alkyl selected from hydroxymethyl, 2-hydroxy-2-methyl-pentan-1-yl and methoxymethyl;

heterocyclyl-$C_{1-6}$alkyl selected from morpholin-4-ylmethyl, piperidin-1-ylmethyl, piperazin-1-ylmethyl, thiomorpholin-1-ylmethyl, 4-methanesulfonyl-piperazin-1-ylmethyl, 4-acetyl-piperazin-1-ylmethyl, 4-acetyl-3-methyl-piperazin-1-ylmethyl, 3-oxy-piperazin-1-ylmethyl, 4-methanesulfonyl-piperidin-1-ylmethyl, 4-fluoropiperidin-1-ylmethyl, 4,4-difluoropiperidin-1-ylmethyl, 3-fluoro-piperidin-1-ylmethyl, 4-methoxy-piperidin-1-ylmethyl, 3-methoxy-piperidin-1-ylmethyl, 4-hydroxy-piperidin-1-ylmethyl, 3-hydroxypiperidin-1-ylmethyl, 4-methoxy-3-fluoro-piperidin-1-ylmethyl, 2,6-dimethyl-morpholin-4-ylmethyl, 1-oxy-thiomorpholin-4-ylmethyl and 1,1-dioxy-thiomorpholin-4-ylmethyl; or heteroaryl selected from pyrazin-2-yl, pyridazin-3-yl and thiazol-2-yl.

In certain embodiments of formula IIa or IIb, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is hetero-$C_{1-6}$alkyl selected from hydroxymethyl, 2-hydroxy-2-methyl-pentan-1-yl and methoxymethyl.

In certain embodiments of formula IIa or IIb, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is heterocyclyl-$C_{1-6}$alkyl selected from morpholin-4-ylmethyl, piperidin-1-ylmethyl, piperazin-1-ylmethyl, thiomorpholin-1-ylmethyl, 4-methanesulfonyl-piperazin-1-ylmethyl, 4-acetyl-piperazin-1-ylmethyl, 4-acetyl-3-methyl-piperazin-1-ylmethyl, 3-oxy-piperazin-1-ylmethyl, 4-methanesulfonyl-piperidin-1-ylmethyl, 4-fluoropiperidin-1-ylmethyl, 4,4-difluoropiperidin-1-ylmethyl, 3-fluoro-piperidin-1-ylmethyl, 4-methoxy-piperidin-1-ylmethyl, 3-methoxy-piperidin-1-ylmethyl, 4-hydroxy-piperidin-1-ylmethyl, 3-hydroxypiperidin-1-ylmethyl, 4-methoxy-3-fluoro-piperidin-1-ylmethyl, 2,6-dimethyl-morpholin-4-ylmethyl, 1-oxy-thiomorpholin-4-ylmethyl and 1,1-dioxy-thiomorpholin-4-ylmethyl.

In certain embodiments of formula IIa or IIb, $R^{11}$ is fluoro, chloro or methyl, $R^{12}$ is hydrogen, fluoro or chloro, $R^{13}$ is hydrogen, $C_{1-6}$alkyl, $C_{1-6}$alkoxy-$C_{1-6}$alkyl or cyclopropyl, and $R^5$ is heteroaryl selected from pyrazin-2-yl, pyridazin-3-yl and thiazol-2-yl.

In certain embodiments of any of formulas I, IIa, IIb, IIc, IIIa, IIIb, IIIc, IVa, IVb or IVc, $R^5$ is:

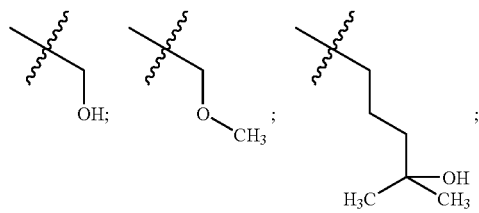

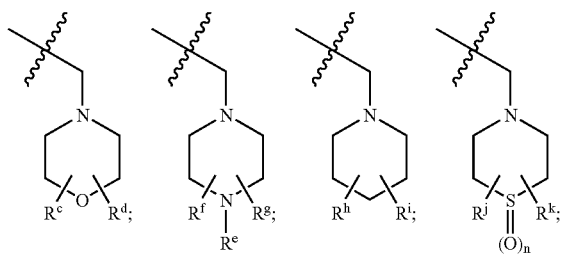

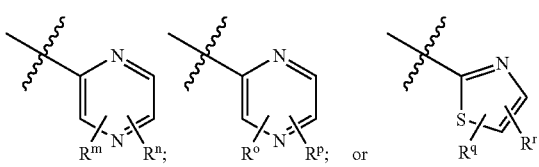

wherein:
n is 0, 1 or 2;
$R^c$ and $R^d$ each independently is hydrogen or $C_{1-6}$alkyl;
$R^e$ is hydrogen, $C_{1-6}$alkyl, acetyl or $C_{1-6}$alkyl-sulfonyl;
$R^f$ and $R^g$ each independently is hydrogen or $C_{1-6}$alkyl;
$R^h$ and $R^i$ each independently is hydrogen, $C_{1-6}$alkyl, fluoro, hydroxy or $C_{1-6}$alkyloxy;
$R^j$ and $R^k$ each independently is hydrogen or $C_{1-6}$alkyl; and
$R^m$, $R^n$, $R^o$, $R^p$, $R^q$ and $R^r$, each independently is hydrogen, $C_{1-6}$alkyl, halo, $C_{1-6}$alkoxy, $C_{1-6}$alkyl-sulfonyl halo-$C_{1-6}$alkyl, or cyano.

In certain embodiments of any of formulas I, IIa, IIb, IIc, IIIa, IIIb, IIIc, IVa, IVb or IVc, $R^5$ is

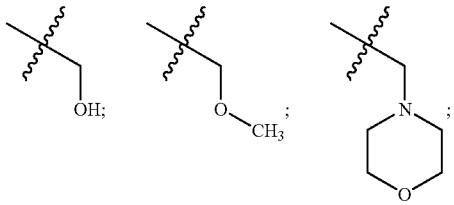

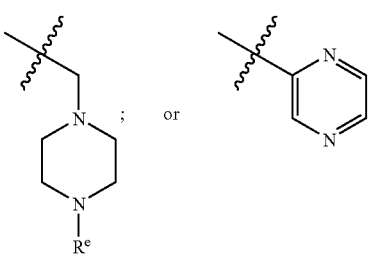

wherein $R^e$ is as defined herein.

Where any of $R^1$, $R^2$, $R^3$, $R^4$, $R^5$, $R^6$, $R^7$, $R^8$, $R^9$, $R^{10}$, $R^{11}$, $R^{12}$, $R^{13}$, Ra, $R^b$, $R^c$, $R^d$, $R^e$, $R^f$, $R^g$, $R^h$, $R^i$, $R^j$, $R^k$, $R^m$, $R^n$, $R^o$, $R^p$, $R^q$ or $R^r$ is alkyl or contains an alkyl moiety, such alkyl is preferably lower alkyl, i.e. $C_1$-$C_6$alkyl, and more preferably $C_1$-$C_4$alkyl.

The invention also provides methods for treating a disease mediated by a $P2X_3$ receptor antagonist, a $P2X_{2/3}$ receptor antagonist, or both, the method comprising administering to a subject in need thereof an effective amount of a compound of any of formulas (I) through (VIII). The disease may be genitourinary disease or urinary tract disease. In other instances the disease may be a disease is associated with pain. The urinary tract disease may be: reduced bladder capacity; frequent micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits; pelvic pain syndrome; prostatodynia; cystitis; or idiophatic bladder hypersensitivity. The disease associated with pain may be: inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome. The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

Representative compounds in accordance with the methods of the invention are shown in Table 1.

TABLE 1

| # | Structure | Name (Autonom ™) | Mp or M + H |
|---|---|---|---|
| 1 | 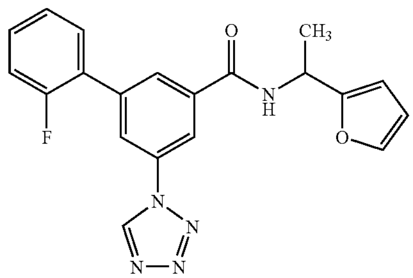 | 2'-Fluoro-5-tetrazol-1-yl-biphenyl-3-carboxylic acid (1-furan-2-yl-ethyl)-amide | 378 |
| 2 | 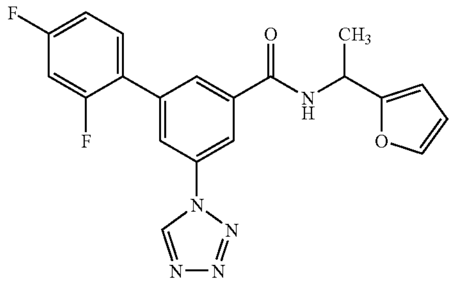 | 2',4'-Difluoro-5-tetrazol-1-yl-biphenyl-3-carboxylic acid (1-furan-2-yl-ethyl)-amide | 161.9-163.4° C. |
| 3 | 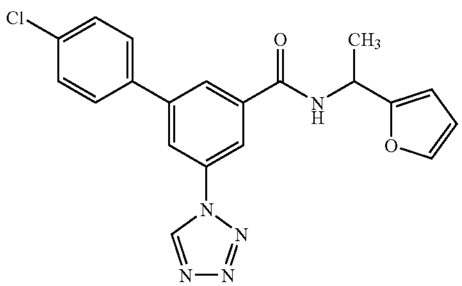 | 4'-Chloro-5-tetrazol-1-yl-biphenyl-3-carboxylic acid (1-furan-2-yl-ethyl)-amide | 152.9-155.0° C. |
| 4 | 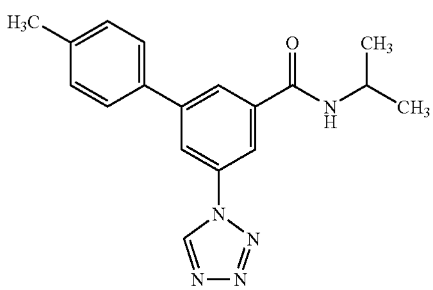 | 4'-Methyl-5-tetrazol-1-yl-biphenyl-3-carboxylic acid isopropylamide | 200.8-202.0° C. |
| 5 | 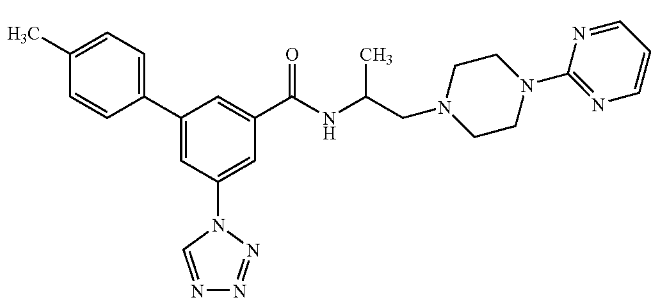 | 4'-Methyl-5-tetrazol-1-yl-biphenyl-3-carboxylic acid [1-methyl-2-(4-pyrimidin-2-yl-piperazin-1-yl)-ethyl]-amide | 106.5-110.7° C. |

TABLE 1-continued

| # | Structure | Name (Autonom ™) | Mp or M + H |
|---|---|---|---|
| 6 | 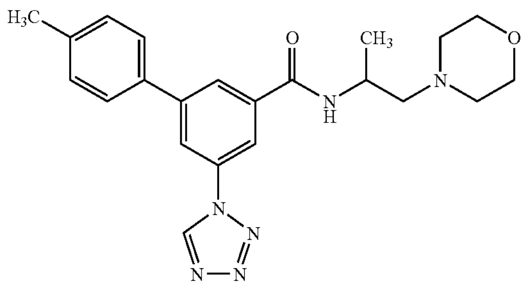 | 4'-Methyl-5-tetrazol-1-yl-biphenyl-3-carboxylic acid (1-methyl-2-morpholin-4-yl-ethyl)-amide | 122.0-125.0° C. |
| 7 | 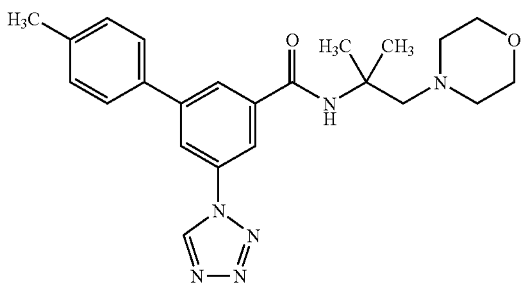 | 4'-Methyl-5-tetrazol-1-yl-biphenyl-3-carboxylic acid (1,1-dimethyl-2-morpholin-4-yl-ethyl)-amide | 85.5-87.0° C. |
| 8 | 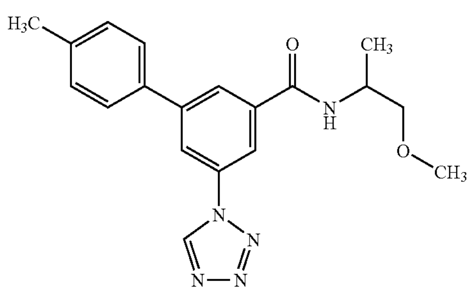 | 4'-Methyl-5-tetrazol-1-yl-biphenyl-3-carboxylic acid (2-methoxy-1-methyl-ethyl)-amide | 352 |
| 9 | 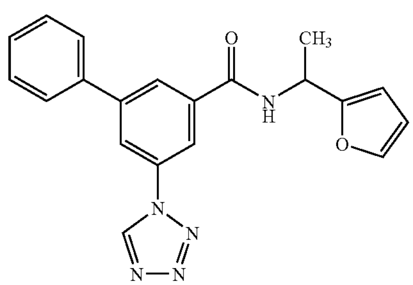 | 5-Tetrazol-1-yl-biphenyl-3-carboxylic acid (1-furan-2-yl-ethyl)-amide | 360 |
| 10 | 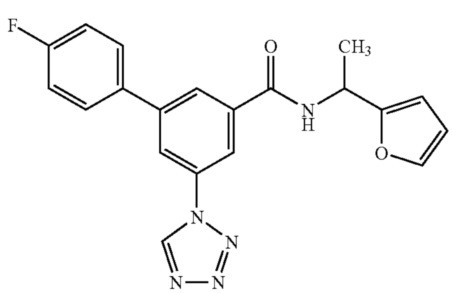 | 4'-Fluoro-5-tetrazol-1-yl-biphenyl-3-carboxylic acid (1-furan-2-yl-ethyl)-amide | 92.3-93.2° C. |

TABLE 1-continued

| # | Structure | Name (Autonom ™) | Mp or M + H |
|---|---|---|---|
| 11 | 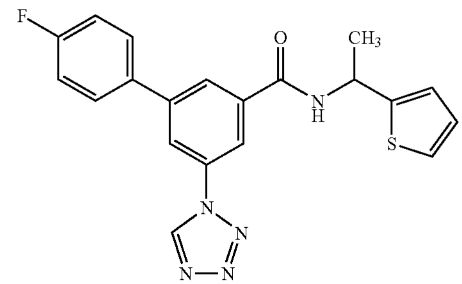 | 4'-Methyl-5-tetrazol-1-yl-biphenyl-3-carboxylic acid (1-thiophen-2-yl-ethyl)-amide | 143.2-136.1° C. |
| 12 | 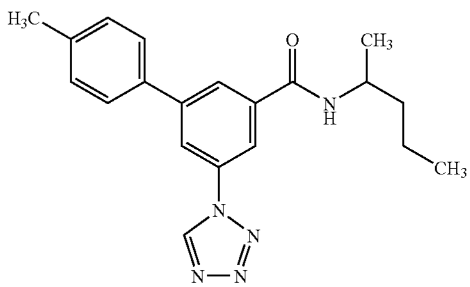 | 4'-Methyl-5-tetrazol-1-yl-biphenyl-3-carboxylic acid (1-methyl-butyl)-amide | 128.3-130.1° C. |
| 13 | 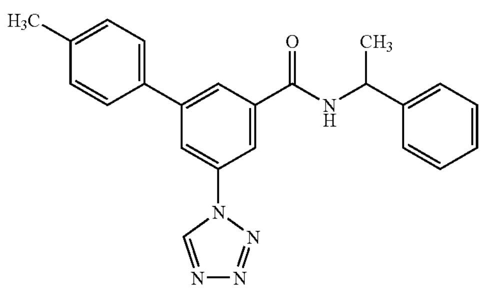 | 4'-Methyl-5-tetrazol-1-yl-biphenyl-3-carboxylic acid (1-phenyl-ethyl)-amide | 114.1-115.2° C. |
| 14 | 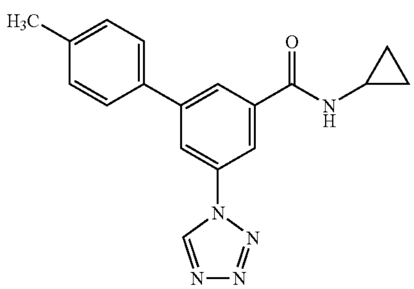 | 4'-Methyl-5-tetrazol-1-yl-biphenyl-3-carboxylic acid cycloproplamide | 320 |
| 15 | 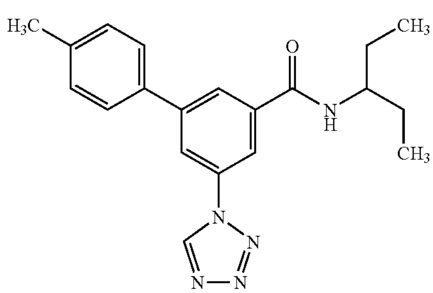 | 4'-Methyl-5-tetrazol-1-yl-biphenyl-3-carboxylic acid (1-ethyl-propyl)-amide | 350 |

TABLE 1-continued

| # | Structure | Name (Autonom ™) | Mp or M + H |
|---|---|---|---|
| 16 | 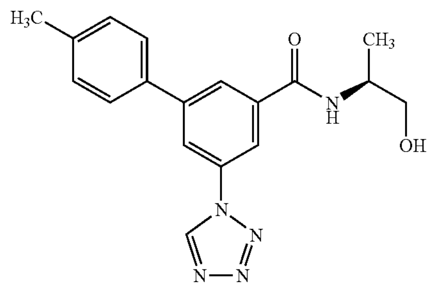 | 4'-Methyl-5-tetrazol-1-yl-biphenyl-3-carboxylic acid (2-hydroxy-1-methyl-ethyl)-amide | 338 |
| 17 | 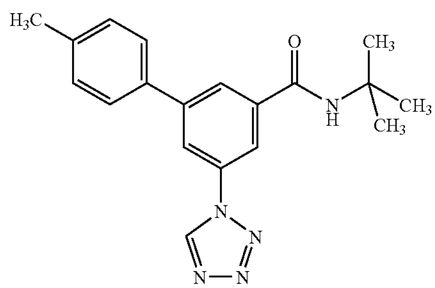 | 4'-Methyl-5-tetrazol-1-yl-biphenyl-3-carboxylic acid tert-butylamide | 336 |
| 18 | 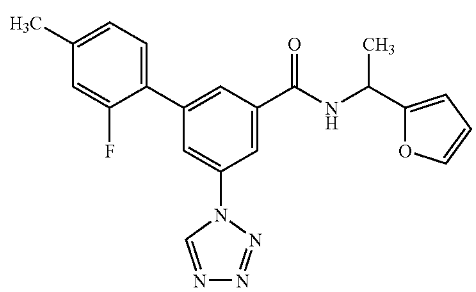 | 2'-Fluoro-4'-methyl-5-tetrazol-1-yl-biphenyl-3-carboxylic acid (1-furan-2-yl-ethyl)-amide | 392 |
| 19 | 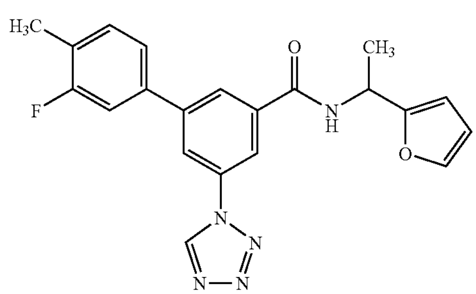 | 3'-Fluoro-4'-methyl-5-tetrazol-1-yl-biphenyl-3-carboxylic acid (1-furan-2-yl-ethyl)-amide | 392 |
| 20 | 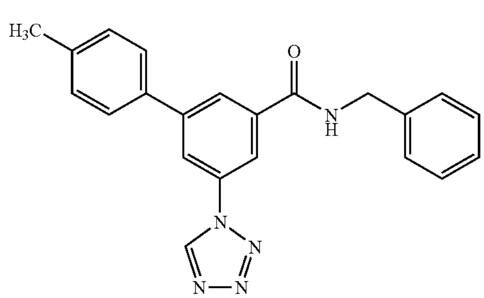 | 4'-Methyl-5-tetrazol-1-yl-biphenyl-3-carboxylic acid benzylamide | 370 |

TABLE 1-continued

| # | Structure | Name (Autonom ™) | Mp or M + H |
|---|---|---|---|
| 21 | 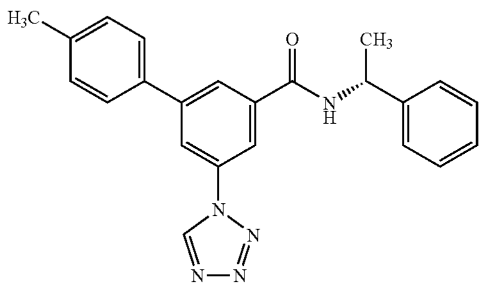 | 4'-Methyl-5-tetrazol-1-yl-biphenyl-3-carboxylic acid (1-phenyl-ethyl)-amide | 384 |
| 22 | 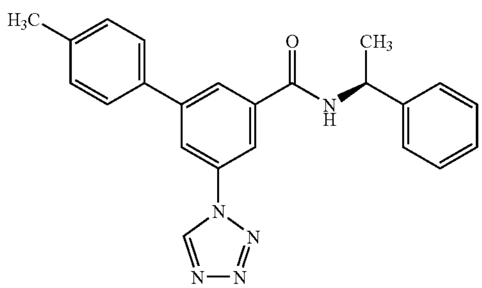 | 4'-Methyl-5-tetrazol-1-yl-biphenyl-3-carboxylic acid (1-phenyl-ethyl)-amide | 384 |
| 23 | 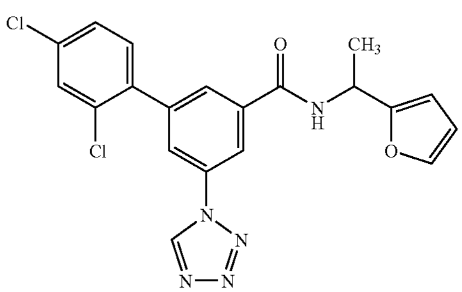 | 2',4'-Dichloro-5-tetrazol-1-yl-biphenyl-3-carboxylic acid (1-furan-2-yl-ethyl)-amide | 428 |
| 24 | 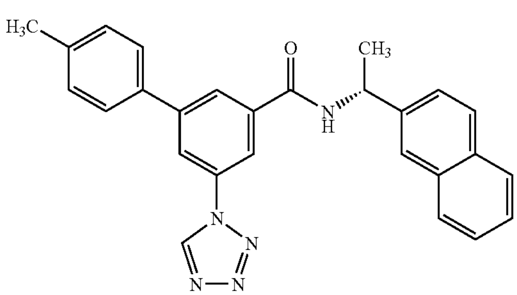 | 4'-Methyl-5-tetrazol-1-yl-biphenyl-3-carboxylic acid (1-naphthalen-2-yl-ethyl)-amide | 434 |
| 25 | 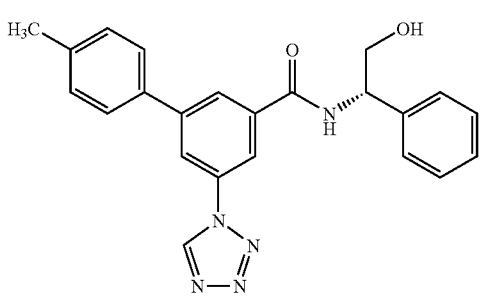 | 4'-Methyl-5-tetrazol-1-yl-biphenyl-3-carboxylic acid (2-hydroxy-1-phenyl-ethyl)-amide | 400 |

TABLE 1-continued

| # | Structure | Name (Autonom ™) | Mp or M + H |
|---|---|---|---|
| 26 | 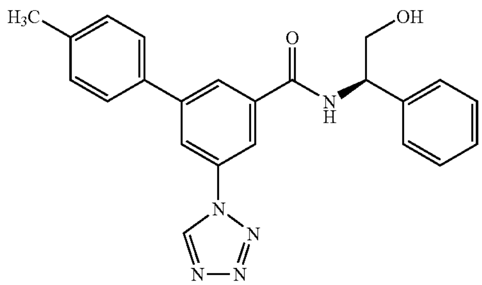 | 4'-Methyl-5-tetrazol-1-yl-biphenyl-3-carboxylic acid (2-hydroxy-1-phenyl-ethyl)-amide | 400 |
| 27 | 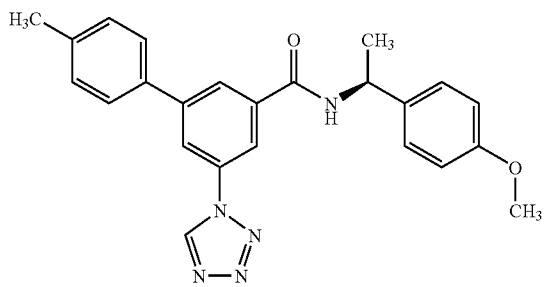 | 4'-Methyl-5-tetrazol-1-yl-biphenyl-3-carboxylic acid [1-(4-methoxy-phenyl)-ethyl]-amide | 414 |
| 28 | 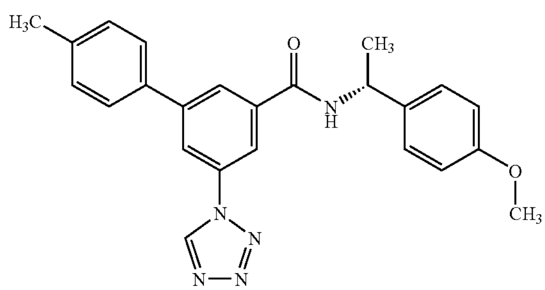 | 4'-Methyl-5-tetrazol-1-yl-biphenyl-3-carboxylic acid [1-(4-methoxy-phenyl)-ethyl]-amide | 414 |
| 29 | 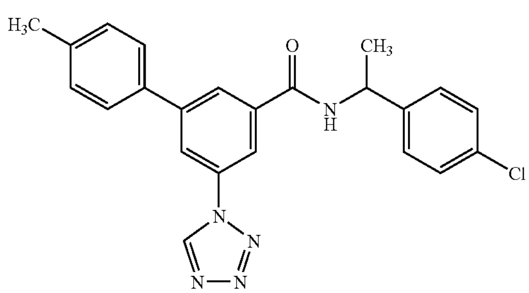 | 4'-Methyl-5-tetrazol-1-yl-biphenyl-3-carboxylic acid [1-(4-chloro-phenyl)-ethyl]-amide | 418 |
| 30 | 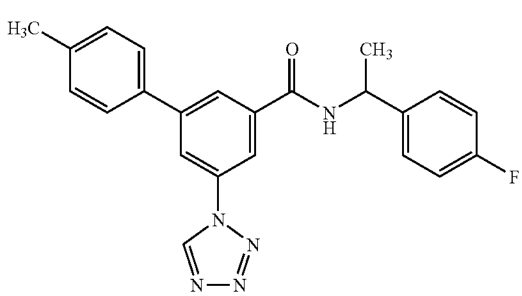 | 4'-Methyl-5-tetrazol-1-yl-biphenyl-3-carboxylic acid [1-(4-fluoro-phenyl)-ethyl]-amide | 402 |

TABLE 1-continued

| # | Structure | Name (Autonom ™) | Mp or M + H |
|---|---|---|---|
| 31 | 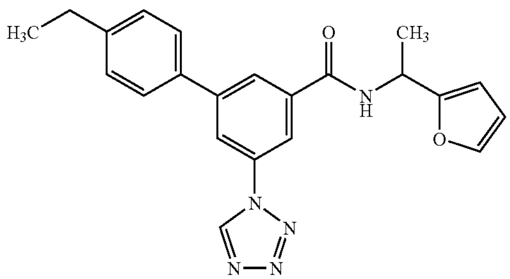 | 4'-Ethyl-5-tetrazol-1-yl-biphenyl-3-carboxylic acid (1-furan-2-yl-ethyl)-amide | 388 |
| 32 | 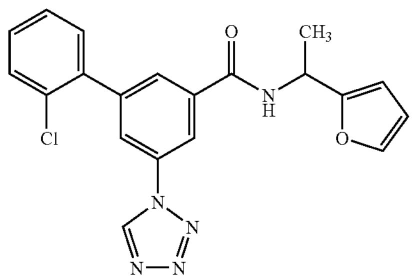 | 2'-Chloro-5-tetrazol-1-yl-biphenyl-3-carboxylic acid (1-furan-2-yl-ethyl)-amide | 394 |
| 33 | 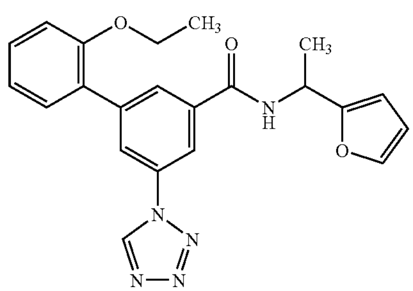 | 2'-Ethoxy-5-tetrazol-1-yl-biphenyl-3-carboxylic acid (1-furan-2-yl-ethyl)-amide | 404 |
| 34 | 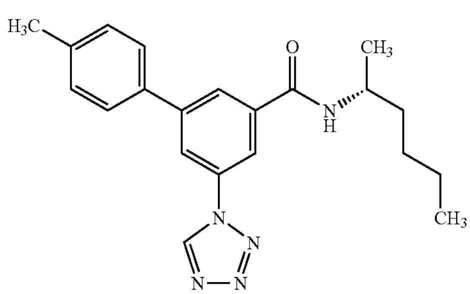 | 4'-Methyl-5-tetrazol-1-yl-biphenyl-3-carboxylic acid (1-methyl-pentyl)-amide | 364 |
| 35 | 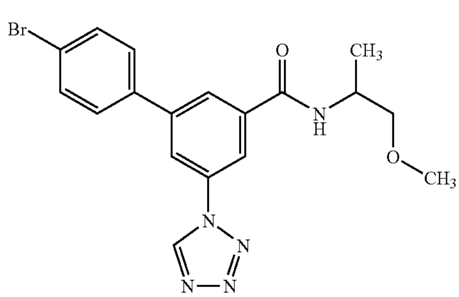 | 4'-Bromo-5-tetrazol-1-yl-biphenyl-3-carboxylic acid (2-methoxy-1-methyl-ethyl)-amide | 417 |

TABLE 1-continued

| # | Structure | Name (Autonom ™) | Mp or M + H |
|---|---|---|---|
| 36 | 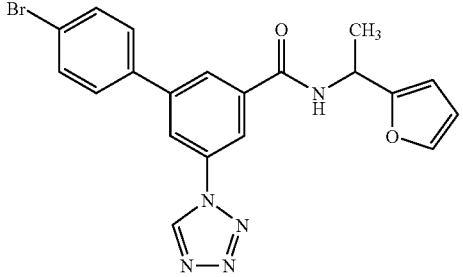 | 4'-Bromo-5-tetrazol-1-yl-biphenyl-3-carboxylic acid (1-furan-2-yl-ethyl)-amide | 439 |
| 37 | 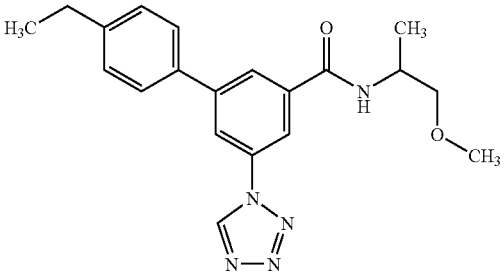 | 4'-Ethyl-5-tetrazol-1-yl-biphenyl-3-carboxylic acid (2-methoxy-1-methyl-ethyl)-amide | 366 |
| 38 | 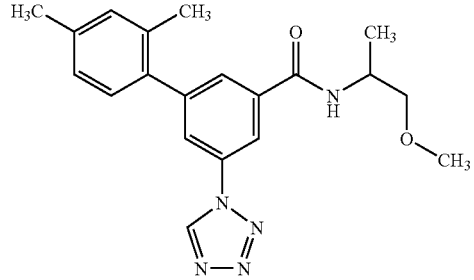 | 2',4'-Dimethyl-5-tetrazol-1-yl-biphenyl-3-carboxylic acid (2-methoxy-1-methyl-ethyl)-amide | 366 |
| 39 | 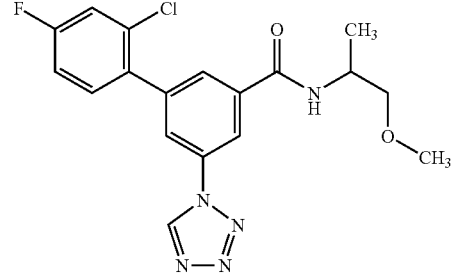 | 2'-Chloro-4'-fluoro-5-tetrazol-1-yl-biphenyl-3-carboxylic acid (2-methoxy-1-methyl-ethyl)-amide | 390 |
| 40 | 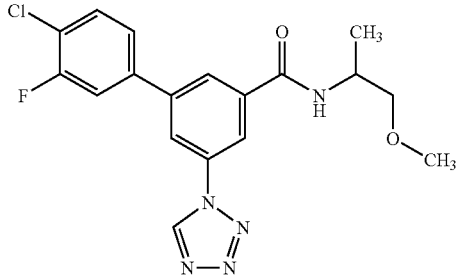 | 4'-Chloro-3'-fluoro-5-tetrazol-1-yl-biphenyl-3-carboxylic acid (2-methoxy-1-methyl-ethyl)-amide | 390 |

TABLE 1-continued

| # | Structure | Name (Autonom ™) | Mp or M + H |
|---|---|---|---|
| 41 | 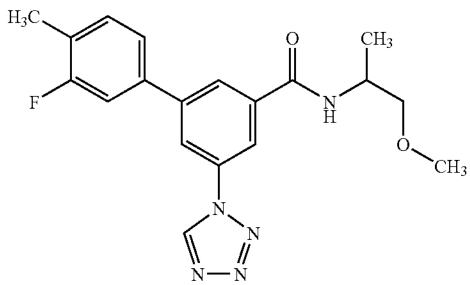 | 3'-Fluoro-4'-methyl-5-tetrazol-1-yl-biphenyl-3-carboxylic acid (2-methoxy-1-methyl-ethyl)-amide | 370 |
| 42 | 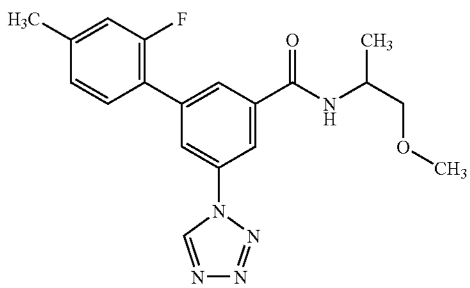 | 2'-Fluoro-4'-methyl-5-tetrazol-1-yl-biphenyl-3-carboxylic acid (2-methoxy-1-methyl-ethyl)-amide | 370 |
| 43 | 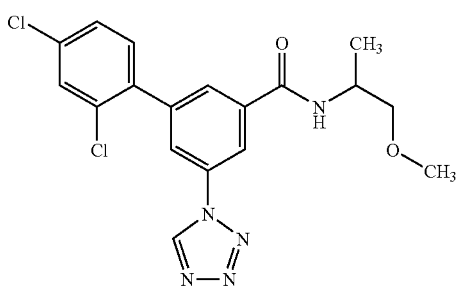 | 2',4'-Dichloro-5-tetrazol-1-yl-biphenyl-3-carboxylic acid (2-methoxy-1-methyl-ethyl)-amide | 406 |
| 44 | 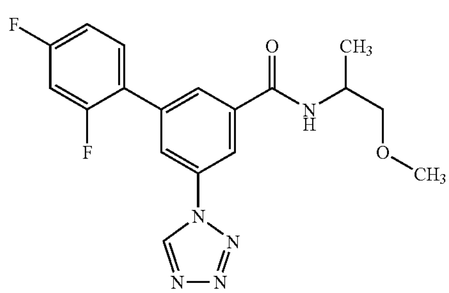 | 2',4'-Difluoro-5-tetrazol-1-yl-biphenyl-3-carboxylic acid (2-methoxy-1-methyl-ethyl)-amide | 374 |
| 45 | 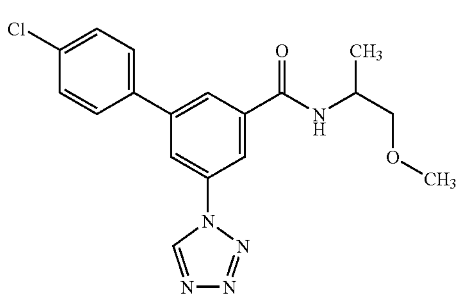 | 4'-Chloro-5-tetrazol-1-yl-biphenyl-3-carboxylic acid (2-methoxy-1-methyl-ethyl)-amide | 372 |

TABLE 1-continued

| # | Structure | Name (Autonom ™) | Mp or M + H |
|---|-----------|------------------|-------------|
| 46 | 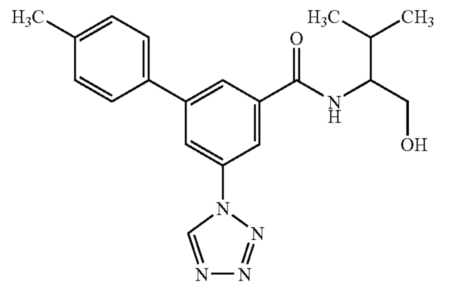 | 4'-Methyl-5-tetrazol-1-yl-biphenyl-3-carboxylic acid (1-hydroxymethyl-2-methyl-propyl)-amide | 366 |
| 47 | 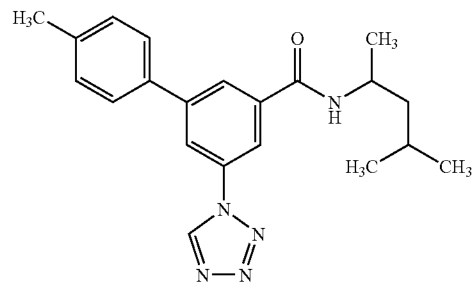 | 4'-Methyl-5-tetrazol-1-yl-biphenyl-3-carboxylic acid (1,3-dimethyl-butyl)-amide | 364 |
| 48 | 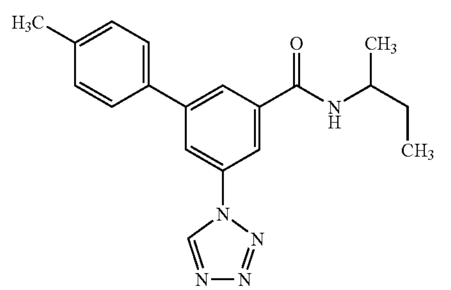 | 4'-Methyl-5-tetrazol-1-yl-biphenyl-3-carboxylic acid sec-butylamide | 336 |
| 49 | 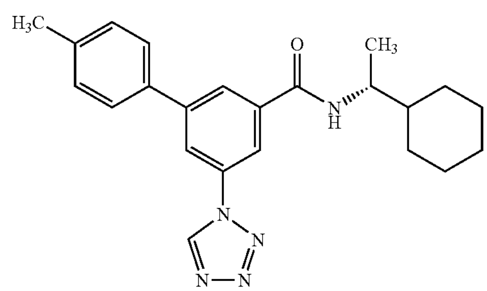 | 4'-Methyl-5-tetrazol-1-yl-biphenyl-3-carboxylic acid (1-cyclohexyl-ethyl)-amide | 390 |
| 50 | 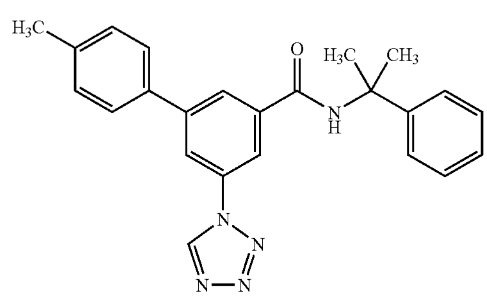 | 4'-Methyl-5-tetrazol-1-yl-biphenyl-3-carboxylic acid (1-methyl-1-phenyl-ethyl)-amide | 398 |

TABLE 1-continued

| # | Structure | Name (Autonom ™) | Mp or M + H |
|---|---|---|---|
| 51 | 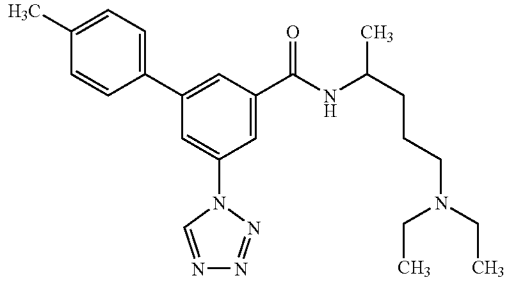 | 4'-Methyl-5-tetrazol-1-yl-biphenyl-3-carboxylic acid (4-diethylamino-1-methyl-butyl)-amide | 421 |
| 52 | 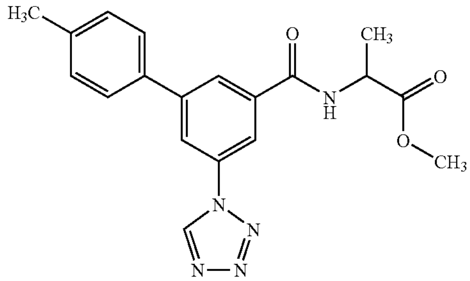 | 2-[(4'-Methyl-5-tetrazol-1-yl-biphenyl-3-carbonyl)-amino]-propionic acid methyl ester | 366 |
| 53 | 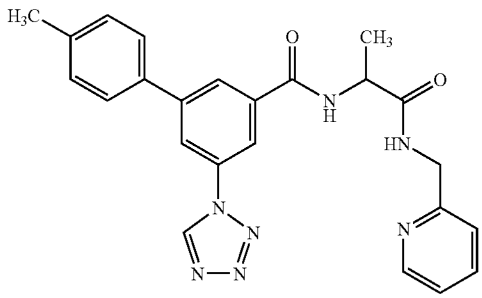 | 4'-Methyl-5-tetrazol-1-yl-biphenyl-3-carboxylic acid {1-[(pyridin-2-ylmethyl)-carbamoyl]-ethyl}-amide | 442 |
| 54 | 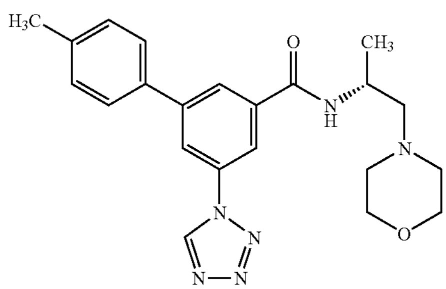 | 4'-Methyl-5-tetrazol-1-yl-biphenyl-3-carboxylic acid (1-methyl-2-morpholin-4-yl-ethyl)-amide | 407 |
| 55 | 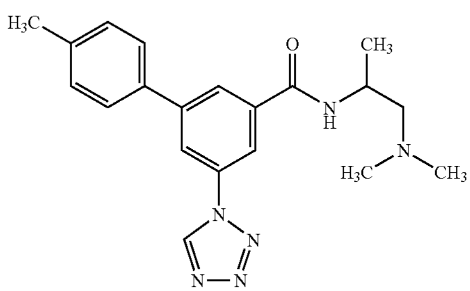 | 4'-Methyl-5-tetrazol-1-yl-biphenyl-3-carboxylic acid (2-dimethylamino-1-methyl-ethyl)-amide | 365 |

TABLE 1-continued

| # | Structure | Name (Autonom ™) | Mp or M + H |
|---|---|---|---|
| 56 | 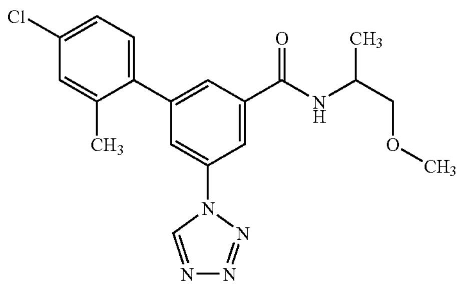 | 4'-Chloro-2'-methyl-5-tetrazol-1-yl-biphenyl-3-carboxylic acid (2-methoxy-1-methyl-ethyl)-amide | 386 |
| 57 | 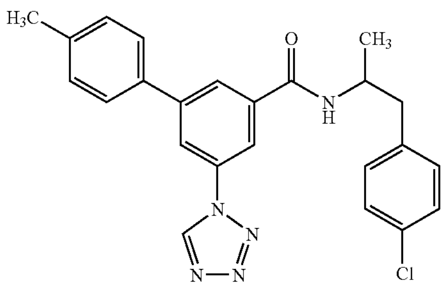 | 4'-Methyl-5-tetrazol-1-yl-biphenyl-3-carboxylic acid [2-(4-chloro-phenyl)-1-methyl-ethyl]-amide | 432 |
| 58 | 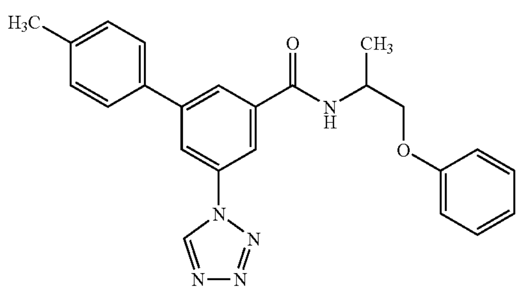 | 4'-Methyl-5-tetrazol-1-yl-biphenyl-3-carboxylic acid (1-methyl-2-phenoxy-ethyl)-amide | 414 |
| 59 | 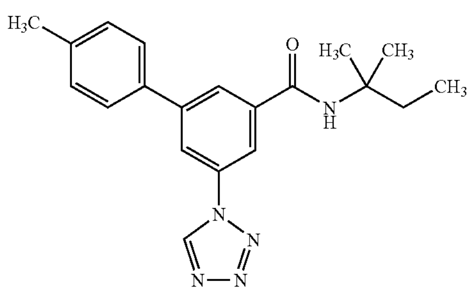 | 4'-Methyl-5-tetrazol-1-yl-biphenyl-3-carboxylic acid (1,1-dimethyl-propyl)-amide | 350 |
| 60 | 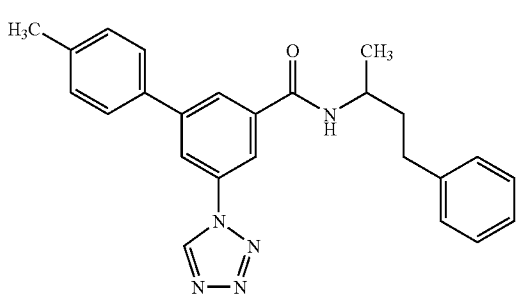 | 4'-Methyl-5-tetrazol-1-yl-biphenyl-3-carboxylic acid (1-methyl-3-phenyl-propyl)-amide | 412 |

TABLE 1-continued

| # | Structure | Name (Autonom ™) | Mp or M + H |
|---|---|---|---|
| 61 | 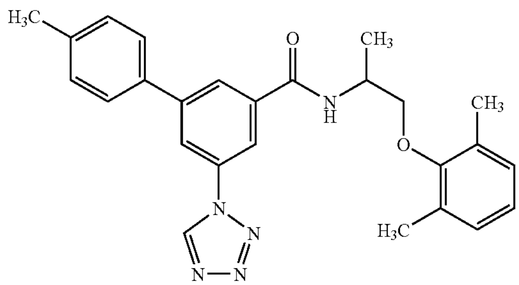 | 4'-Methyl-5-tetrazol-1-yl-biphenyl-3-carboxylic acid [2-(2,6-dimethyl-phenoxy)-1-methyl-ethyl]-amide | 442 |
| 62 | 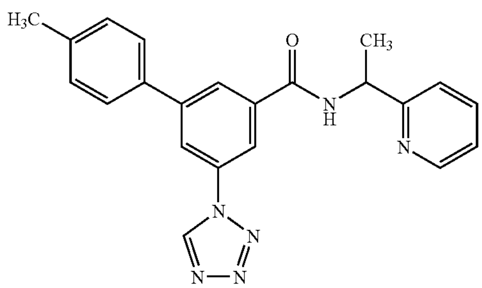 | 4'-Methyl-5-tetrazol-1-yl-biphenyl-3-carboxylic acid (1-pyridin-2-yl-ethyl)-amide | 385 |
| 63 | 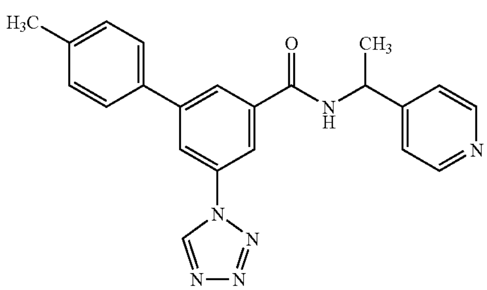 | 4'-Methyl-5-tetrazol-1-yl-biphenyl-3-carboxylic acid (1-pyridin-4-yl-ethyl)-amide | 385 |
| 64 | 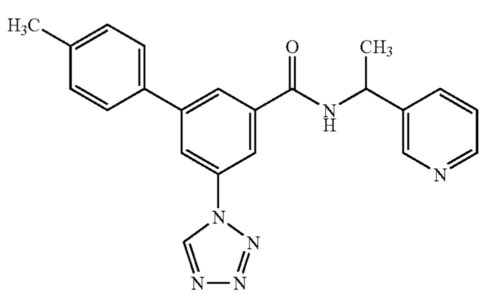 | 4'-Methyl-5-tetrazol-1-yl-biphenyl-3-carboxylic acid (1-pyridin-3-yl-ethyl)-amide | 385 |
| 65 | 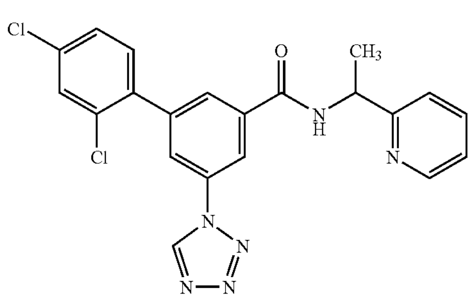 | 2',4'-Dichloro-5-tetrazol-1-yl-biphenyl-3-carboxylic acid (1-pyridin-2-yl-ethyl)-amide | 439 |

TABLE 1-continued

| # | Structure | Name (Autonom ™) | Mp or M + H |
|---|---|---|---|
| 66 | 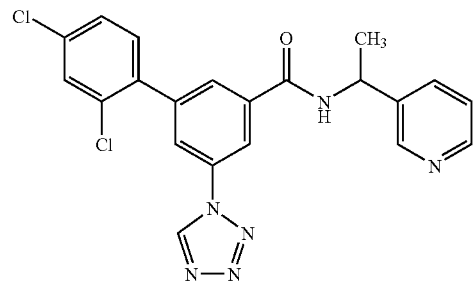 | 2',4'-Dichloro-5-tetrazol-1-yl-biphenyl-3-carboxylic acid (1-pyridin-3-yl-ethyl)-amide | 439 |
| 67 | 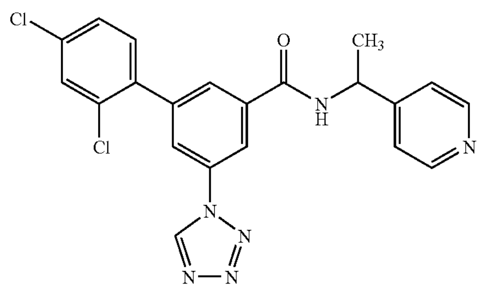 | 2',4'-Dichloro-5-tetrazol-1-yl-biphenyl-3-carboxylic acid (1-pyridin-4-yl-ethyl)-amide | 439 |
| 68 | 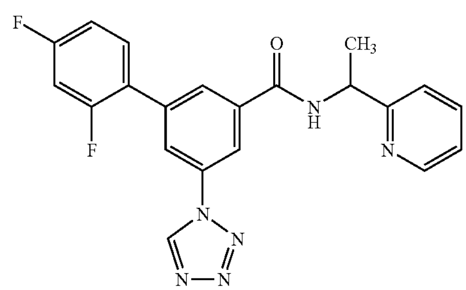 | 2',4'-Difluoro-5-tetrazol-1-yl-biphenyl-3-carboxylic acid (1-pyridin-2-yl-ethyl)-amide | 407 |
| 69 | 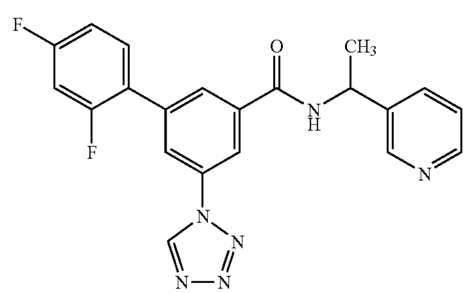 | 2',4'-Difluoro-5-tetrazol-1-yl-biphenyl-3-carboxylic acid (1-pyridin-3-yl-ethyl)-amide | 407 |
| 70 | 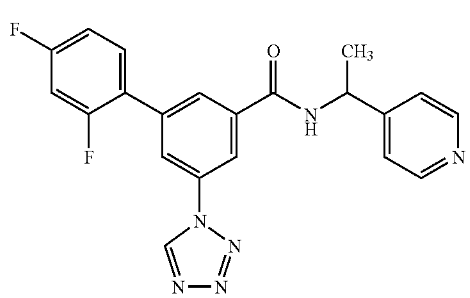 | 2',4'-Difluoro-5-tetrazol-1-yl-biphenyl-3-carboxylic acid (1-pyridin-4-yl-ethyl)-amide | 407 |

TABLE 1-continued

| # | Structure | Name (Autonom ™) | Mp or M + H |
|---|---|---|---|
| 71 | 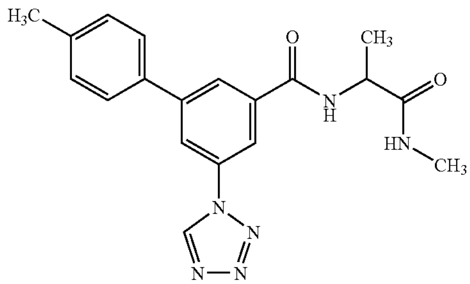 | 4'-Methyl-5-tetrazol-1-yl-biphenyl-3-carboxylic acid (1-methylcarbamoyl-ethyl)-amide | 365 |
| 72 | 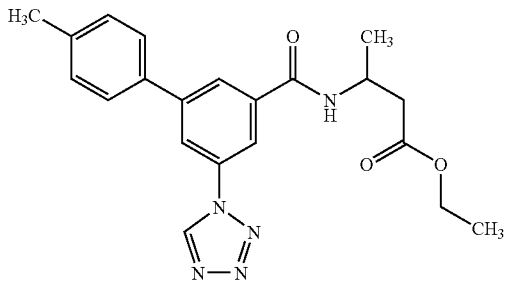 | 3-[(4'-Methyl-5-tetrazol-1-yl-biphenyl-3-carbonyl)-amino]-butyric acid ethyl ester | 394 |
| 73 | 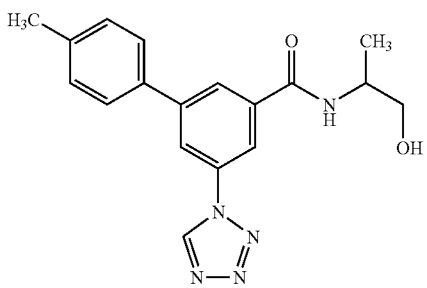 | 4'-Methyl-5-tetrazol-1-yl-biphenyl-3-carboxylic acid (2-hydroxy-1-methyl-ethyl)-amide | 338 |
| 74 | 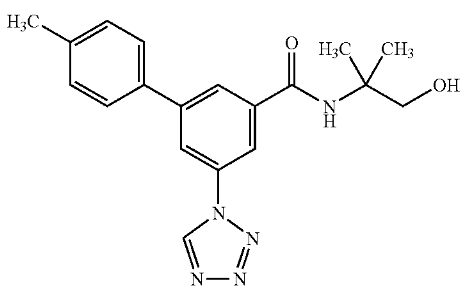 | 4'-Methyl-5-tetrazol-1-yl-biphenyl-3-carboxylic acid (2-hydroxy-1,1-dimethyl-ethyl)-amide | 352 |
| 75 | 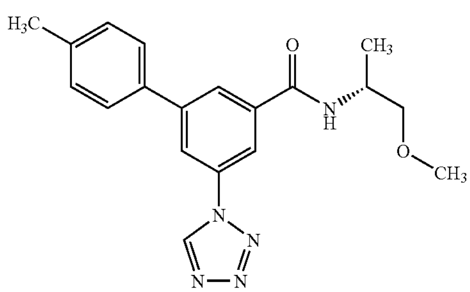 | 4'-Methyl-5-tetrazol-1-yl-biphenyl-3-carboxylic acid (2-methoxy-1-methyl-ethyl)-amide | 352 |

TABLE 1-continued

| # | Structure | Name (Autonom ™) | Mp or M + H |
|---|---|---|---|
| 76 | 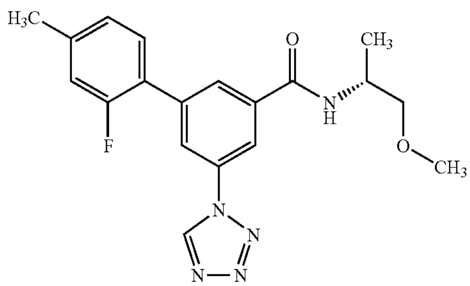 | 2'-Fluoro-4'-methyl-5-tetrazol-1-yl-biphenyl-3-carboxylic acid (2-methoxy-1-methyl-ethyl)-amide | 370 |
| 77 | 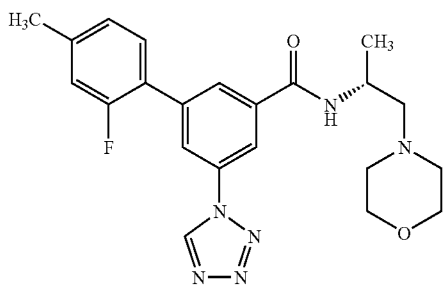 | 2'-Fluoro-4'-methyl-5-tetrazol-1-yl-biphenyl-3-carboxylic acid (1-methyl-2-morpholin-4-yl-ethyl)-amide | 425 |
| 78 | 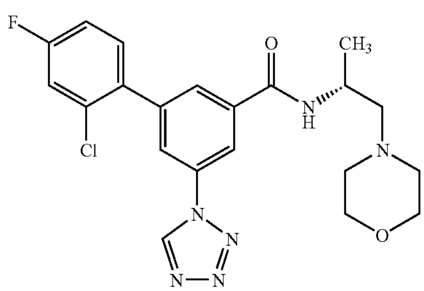 | 2'-Chloro-4'-fluoro-5-tetrazol-1-yl-biphenyl-3-carboxylic acid (1-methyl-2-morpholin-4-yl-ethyl)-amide | 445 |
| 79 | 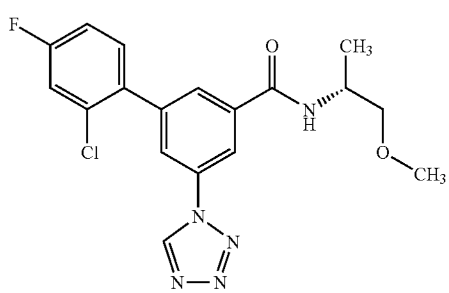 | 2'-Chloro-4'-fluoro-5-tetrazol-1-yl-biphenyl-3-carboxylic acid (2-methoxy-1-methyl-ethyl)-amide | 390 |
| 80 | 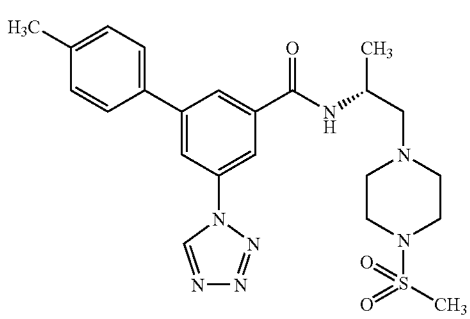 | 4'-Methyl-5-tetrazol-1-yl-biphenyl-3-carboxylic acid [2-(4-methanesulfonyl-piperazin-1-yl)-1-methyl-ethyl]-amide | 484 |

TABLE 1-continued

| # | Structure | Name (Autonom ™) | Mp or M + H |
|---|---|---|---|
| 81 | 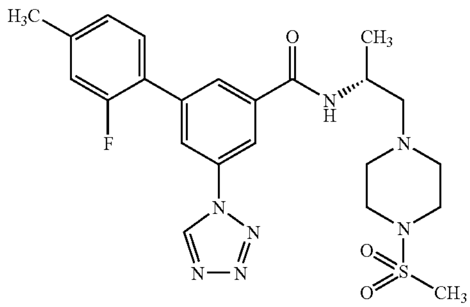 | 2'-Fluoro-4'-methyl-5-tetrazol-1-yl-biphenyl-3-carboxylic acid [2-(4-methanesulfonyl-piperazin-1-yl)-1-methyl-ethyl]-amide | 502 |
| 82 | 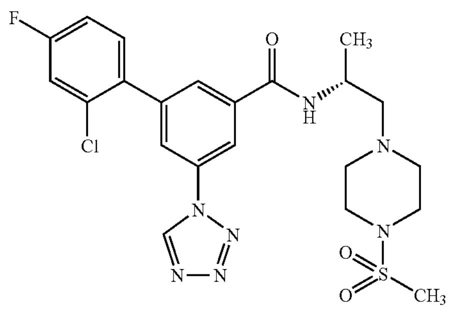 | 2'-Chloro-4'-fluoro-5-tetrazol-1-yl-biphenyl-3-carboxylic acid [2-(4-methanesulfonyl-piperazin-1-yl)-1-methyl-ethyl]-amide | 522 |
| 83 | 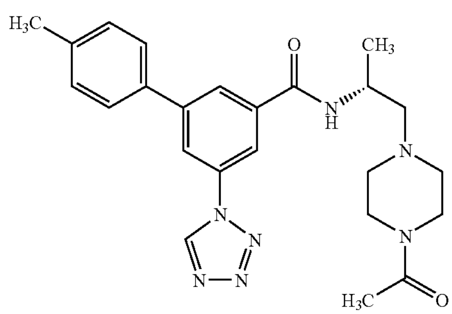 | 4'-Methyl-5-tetrazol-1-yl-biphenyl-3-carboxylic acid [2-(4-acetyl-piperazin-1-yl)-1-methyl-ethyl]-amide | 448 |
| 84 | 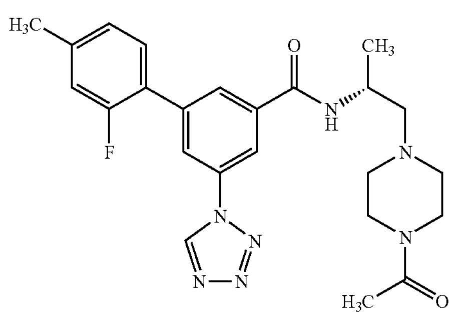 | 2'-Fluoro-4'-methyl-5-tetrazol-1-yl-biphenyl-3-carboxylic acid [2-(4-acetyl-piperazin-1-yl)-1-methyl-ethyl]-amide | 466 |
| 85 | 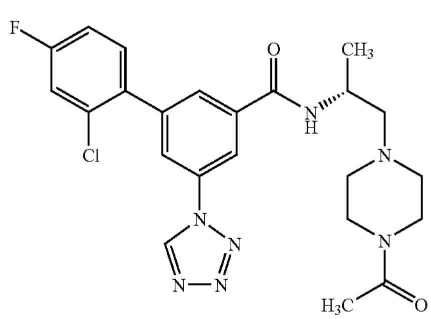 | 2'-Chloro-4'-fluoro-5-tetrazol-1-yl-biphenyl-3-carboxylic acid [2-(4-acetyl-piperazin-1-yl)-1-methyl-ethyl]-amide | 486 |

TABLE 1-continued

| # | Structure | Name (Autonom ™) | Mp or M + H |
|---|---|---|---|
| 86 | 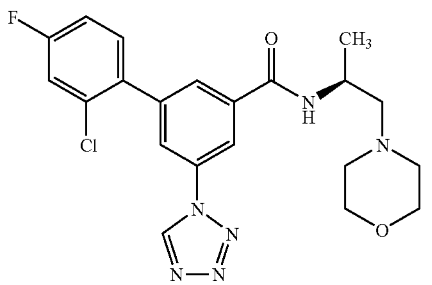 | 2'-Chloro-4'-fluoro-5-tetrazol-1-yl-biphenyl-3-carboxylic acid (1-methyl-2-morpholin-4-yl-ethyl)-amide | 445 |
| 87 | 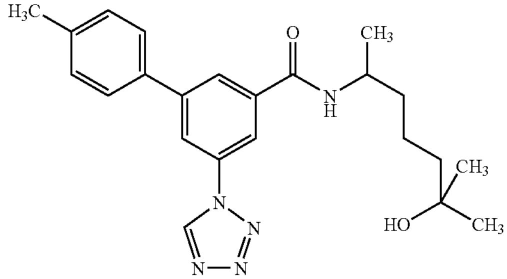 | 4'-Methyl-5-tetrazol-1-yl-biphenyl-3-carboxylic acid (5-hydroxy-1,5-dimethyl-hexyl)-amide | 408 |
| 88 | 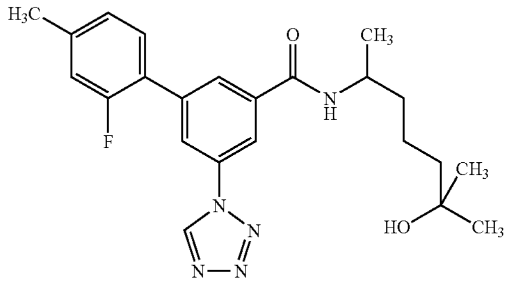 | 2'-Fluoro-4'-methyl-5-tetrazol-1-yl-biphenyl-3-carboxylic acid (5-hydroxy-1,5-dimethyl-hexyl)-amide | 426 |
| 89 | 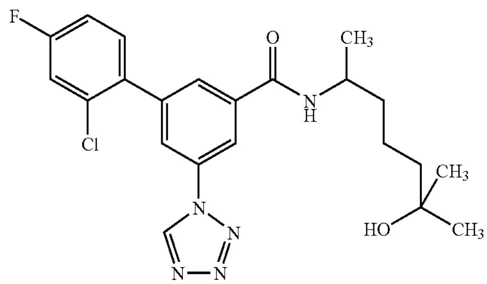 | 2'-Chloro-4'-fluoro-5-tetrazol-1-yl-biphenyl-3-carboxylic acid (5-hydroxy-1,5-dimethyl-hexyl)-amide | 446 |
| 90 | 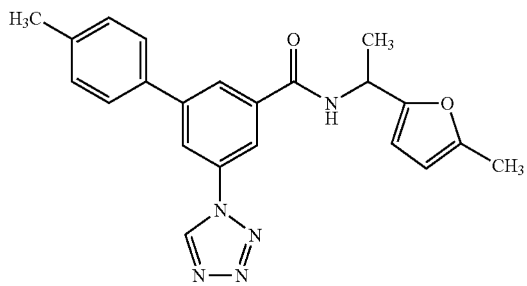 | 4'-Methyl-5-tetrazol-1-yl-biphenyl-3-carboxylic acid [1-(5-methyl-furan-2-yl)-ethyl]-amide | 388 |

TABLE 1-continued

| # | Structure | Name (Autonom ™) | Mp or M + H |
|---|---|---|---|
| 91 | 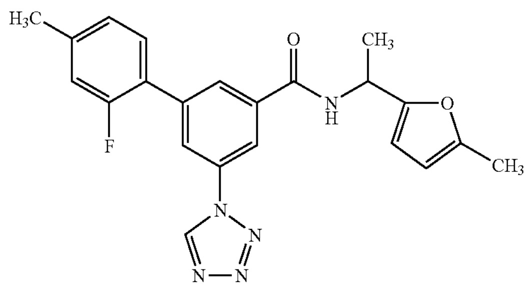 | 2'-Fluoro-4'-methyl-5-tetrazol-1-yl-biphenyl-3-carboxylic acid [1-(5-methyl-furan-2-yl)-ethyl]-amide | 406 |
| 92 | 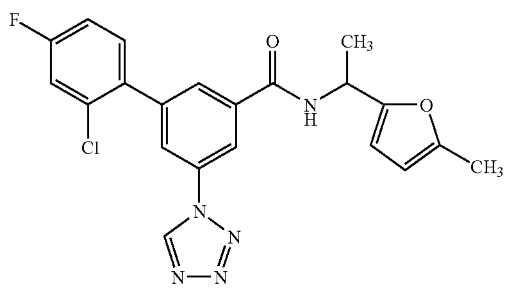 | 2'-Chloro-4'-fluoro-5-tetrazol-1-yl-biphenyl-3-carboxylic acid [1-(5-methyl-furan-2-yl)-ethyl]-amide | 426 |
| 93 | 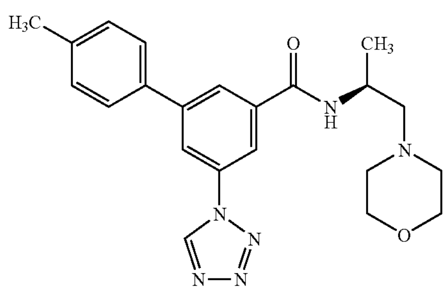 | 4'-Methyl-5-tetrazol-1-yl-biphenyl-3-carboxylic acid (1-methyl-2-morpholin-4-yl-ethyl)-amide | 407 |
| 94 | 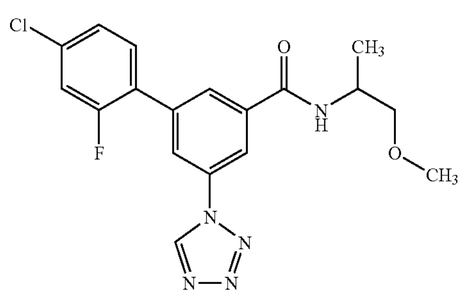 | 4'-Chloro-2'-fluoro-5-tetrazol-1-yl-biphenyl-3-carboxylic acid (2-methoxy-1-methyl-ethyl)-amide | 390 |
| 95 | 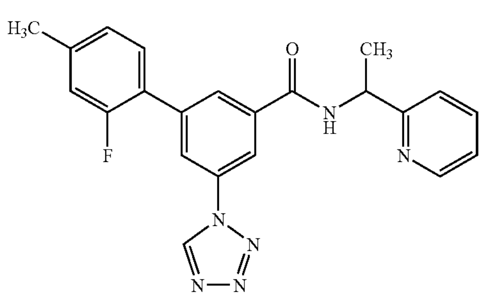 | 2'-Fluoro-4'-methyl-5-tetrazol-1-yl-biphenyl-3-carboxylic acid (1-pyridin-2-yl-ethyl)-amide | 403 |

TABLE 1-continued

| # | Structure | Name (Autonom ™) | Mp or M + H |
|---|---|---|---|
| 96 | 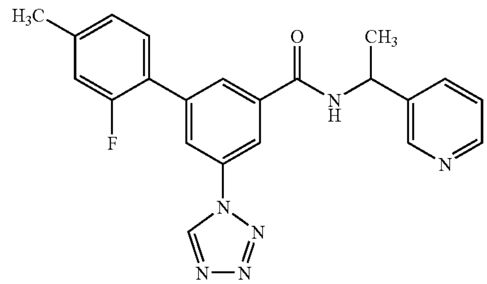 | 2'-Fluoro-4'-methyl-5-tetrazol-1-yl-biphenyl-3-carboxylic acid (1-pyridin-3-yl-ethyl)-amide | 403 |
| 97 | 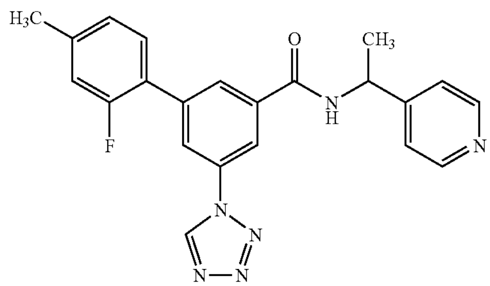 | 2'-Fluoro-4'-methyl-5-tetrazol-1-yl-biphenyl-3-carboxylic acid (1-pyridin-4-yl-ethyl)-amide | 403 |
| 98 | 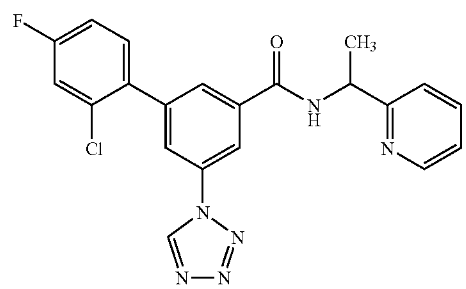 | 2'-Chloro-4'-fluoro-5-tetrazol-1-yl-biphenyl-3-carboxylic acid (1-pyridin-2-yl-ethyl)-amide | 423 |
| 99 | 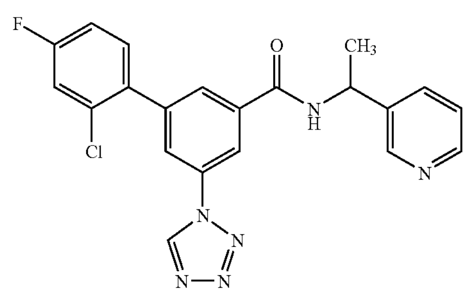 | 2'-Chloro-4'-fluoro-5-tetrazol-1-yl-biphenyl-3-carboxylic acid (1-pyridin-3-yl-ethyl)-amide | 423 |
| 100 | 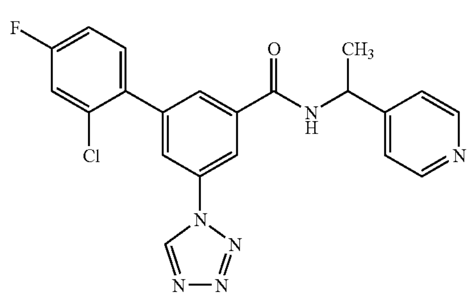 | 2'-Chloro-4'-fluoro-5-tetrazol-1-yl-biphenyl-3-carboxylic acid (1-pyridin-4-yl-ethyl)-amide | 423 |

TABLE 1-continued

| # | Structure | Name (Autonom ™) | Mp or M + H |
|---|---|---|---|
| 101 | 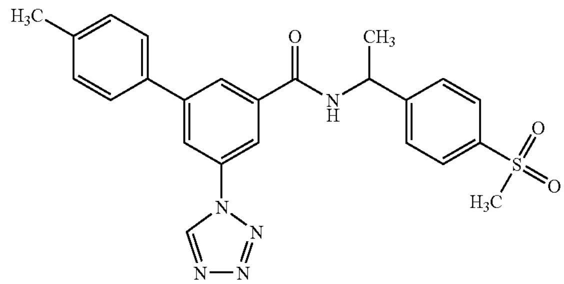 | 4'-Methyl-5-tetrazol-1-yl-biphenyl-3-carboxylic acid [1-(4-methanesulfonyl-phenyl)-ethyl]-amide | 462 |
| 102 | 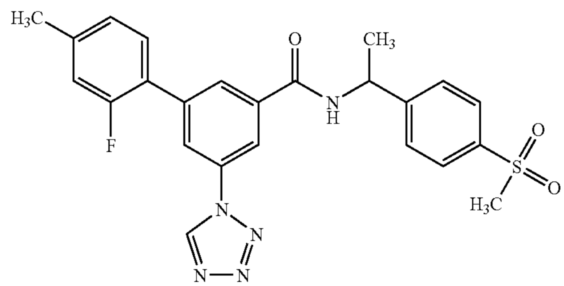 | 2'-Fluoro-4'-methyl-5-tetrazol-1-yl-biphenyl-3-carboxylic acid [1-(4-methanesulfonyl-phenyl)-ethyl]-amide | 480 |
| 103 | 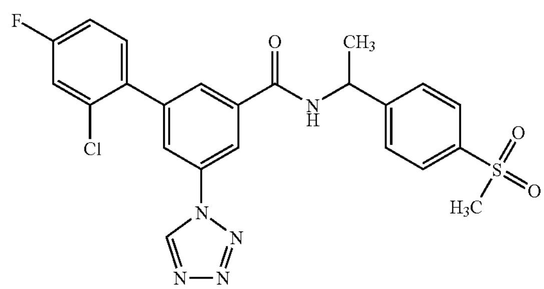 | 2'-Chloro-4'-fluoro-5-tetrazol-1-yl-biphenyl-3-carboxylic acid [1-(4-methanesulfonyl-phenyl)-ethyl]-amide | 500 |
| 104 | 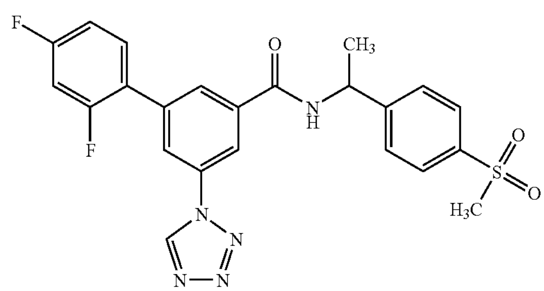 | 2',4'-Difluoro-5-tetrazol-1-yl-biphenyl-3-carboxylic acid [1-(4-methanesulfonyl-phenyl)-ethyl]-amide | 484 |
| 105 | 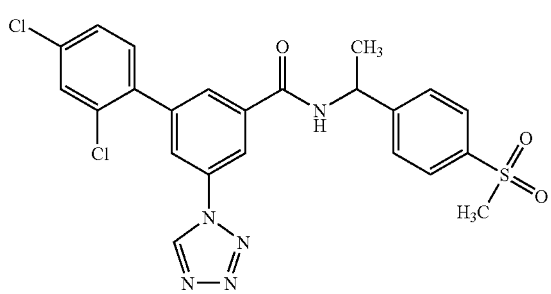 | 2,',4'-Dichloro-5-tetrazol-1-yl-biphenyl-3-carboxylic acid [1-(4-methanesulfonyl-phenyl)-ethyl]-amide | 516 |

TABLE 1-continued

| # | Structure | Name (Autonom ™) | Mp or M + H |
|---|---|---|---|
| 106 | 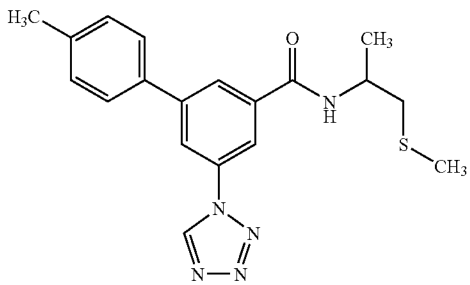 | 4'-Methyl-5-tetrazol-1-yl-biphenyl-3-carboxylic acid (1-methyl-2-methylsulfanyl-ethyl)-amide | 368 |
| 107 | 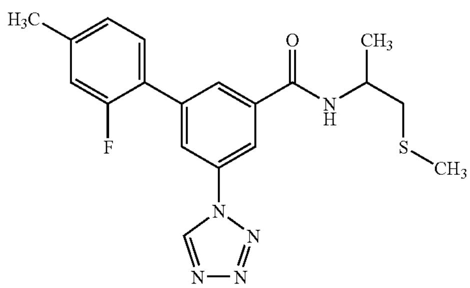 | 2'-Fluoro-4'-methyl-5-tetrazol-1-yl-biphenyl-3-carboxylic acid (1-methyl-2-methylsulfanyl-ethyl)-amide | 386 |
| 108 | 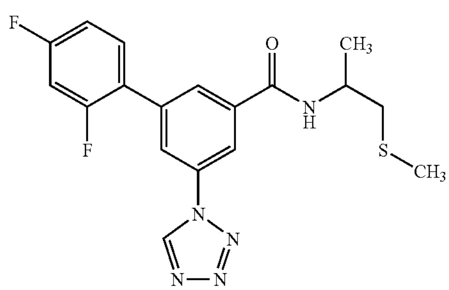 | 2',4'-Difluoro-5-tetrazol-1-yl-biphenyl-3-carboxylic acid (1-methyl-2-methylsulfanyl-ethyl)-amide | 390 |
| 109 | 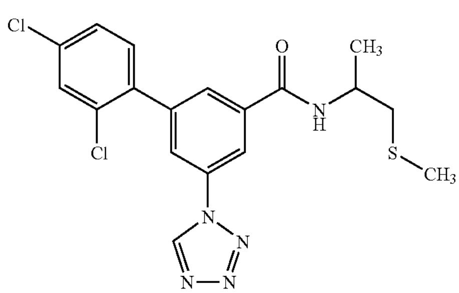 | 2',4'-Dichloro-5-tetrazol-1-yl-biphenyl-3-carboxylic acid (1-methyl-2-methylsulfanyl-ethyl)-amide | 422 |
| 110 | 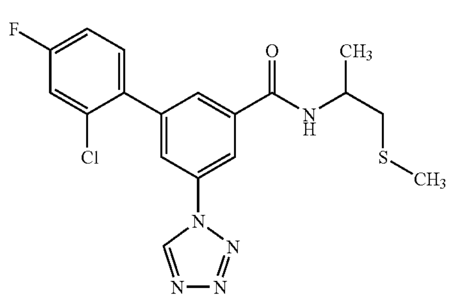 | 2'-Chloro-4'-fluoro-5-tetrazol-1-yl-biphenyl-3-carboxylic acid (1-methyl-2-methylsulfanyl-ethyl)-amide | 406 |

TABLE 1-continued

| # | Structure | Name (Autonom ™) | Mp or M + H |
|---|---|---|---|
| 111 | 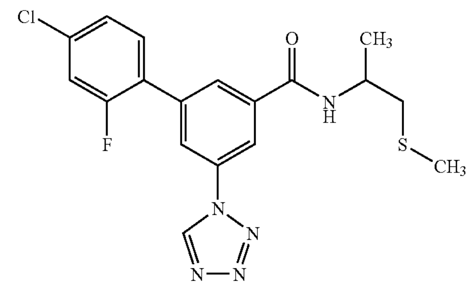 | 4'-Chloro-2'-fluoro-5-tetrazol-1-yl-biphenyl-3-carboxylic acid (1-methyl-2-methylsulfanyl-ethyl)-amide | 406 |
| 112 | 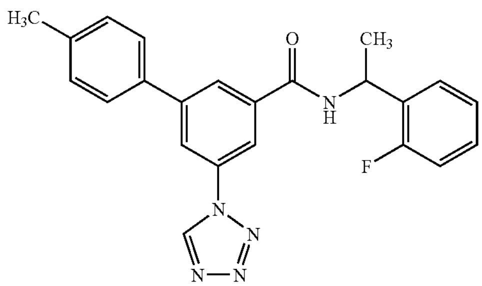 | 4'-Methyl-5-tetrazol-1-yl-biphenyl-3-carboxylic acid [1-(2-fluoro-phenyl)-ethyl]-amide | 402 |
| 113 | 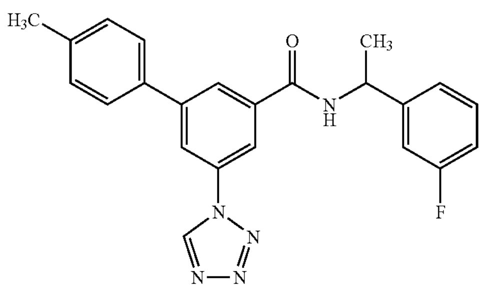 | 4'-Methyl-5-tetrazol-1-yl-biphenyl-3-carboxylic acid [1-(3-fluoro-phenyl)-ethyl]-amide | 402 |
| 114 | 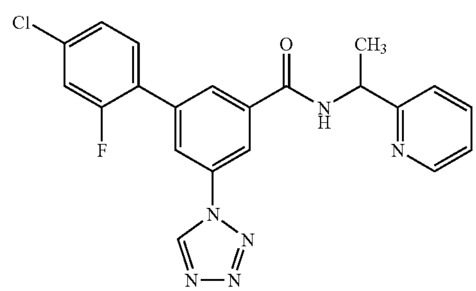 | 4'-Chloro-2'-fluoro-5-tetrazol-1-yl-biphenyl-3-carboxylic acid (1-pyridin-2-yl-ethyl)-amide | 423 |
| 115 | 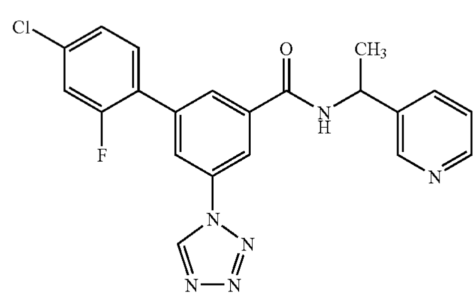 | 4'-Chloro-2'-fluoro-5-tetrazol-1-yl-biphenyl-3-carboxylic acid (1-pyridin-3-yl-ethyl)-amide | 423 |

TABLE 1-continued

| # | Structure | Name (Autonom ™) | Mp or M + H |
|---|---|---|---|
| 116 | 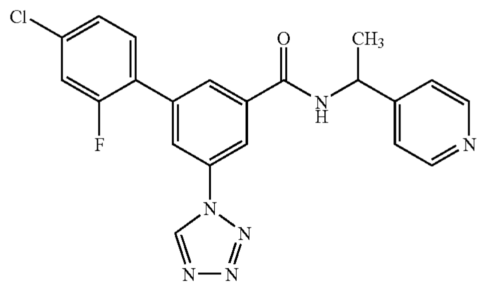 | 4'-Chloro-2'-fluoro-5-tetrazol-1-yl-biphenyl-3-carboxylic acid (1-pyridin-4-yl-ethyl)-amide | 423 |
| 117 | 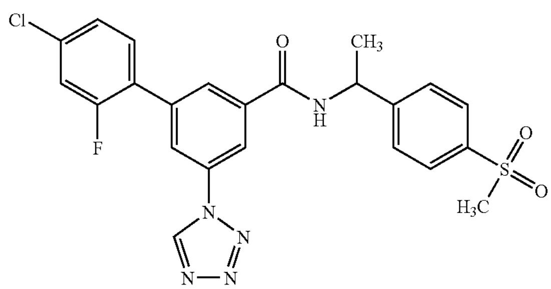 | 4'-Chloro-2'-fluoro-5-tetrazol-1-yl-biphenyl-3-carboxylic acid [1-(4-methanesulfonyl-phenyl)-ethyl]-amide | 500 |
| 118 | 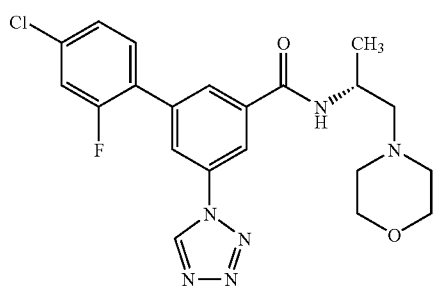 | 4'-Chloro-2'-fluoro-5-tetrazol-1-yl-biphenyl-3-carboxylic acid (1-methyl-2-morpholin-4-yl-ethyl)-amide | 445 |
| 119 | 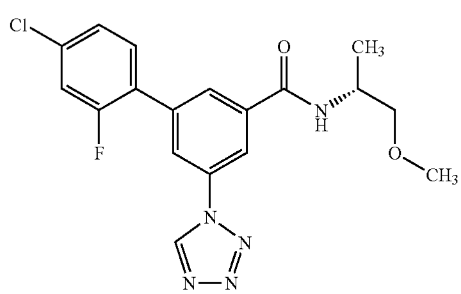 | 4'-Chloro-2'-fluoro-5-tetrazol-1-yl-biphenyl-3-carboxylic acid (2-methoxy-1-methyl-ethyl)-amide | 390 |
| 120 | 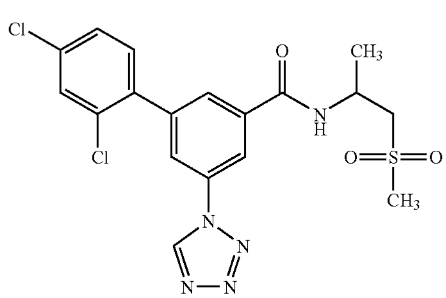 | 2',4'-Dichloro-5-tetrazol-1-yl-biphenyl-3-carboxylic acid (2-methanesulfonyl-1-methyl-ethyl)-amide | 450 |

TABLE 1-continued

| # | Structure | Name (Autonom ™) | Mp or M + H |
|---|---|---|---|
| 121 | 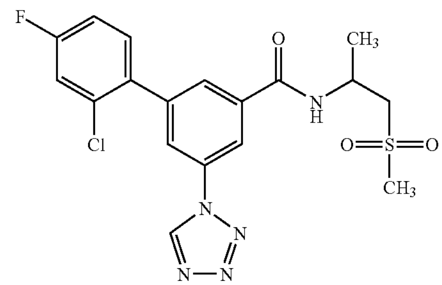 | 2'-Chloro-4'-fluoro-5-tetrazol-1-yl-biphenyl-3-carboxylic acid (2-methanesulfonyl-1-methyl-ethyl)-amide | 438 |
| 122 | 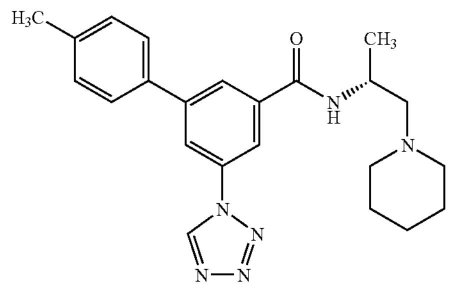 | 4'-Methyl-5-tetrazol-1-yl-biphenyl-3-carboxylic acid (1-methyl-2-piperidin-1-yl-ethyl)-amide | 405 |
| 123 | 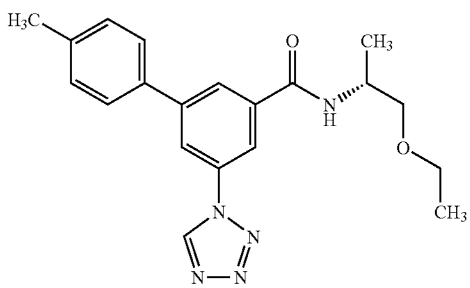 | 4'-Methyl-5-tetrazol-1-yl-biphenyl-3-carboxylic acid (2-ethoxy-1-methyl-ethyl)-amide | 366 |
| 124 | 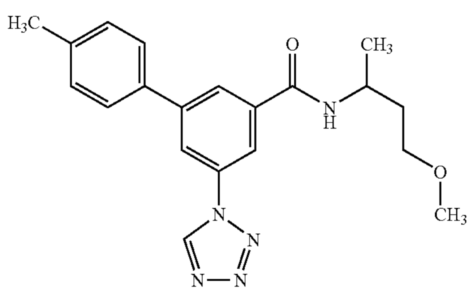 | 4'-Methyl-5-tetrazol-1-yl-biphenyl-3-carboxylic acid (3-methoxy-1-methyl-propyl)-amide | 366 |
| 125 | 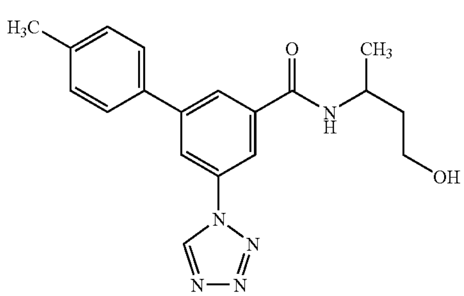 | 4'-Methyl-5-tetrazol-1-yl-biphenyl-3-carboxylic acid (3-hydroxy-1-methyl-propyl)-amide | 352 |

TABLE 1-continued

| # | Structure | Name (Autonom ™) | Mp or M + H |
|---|---|---|---|
| 126 | 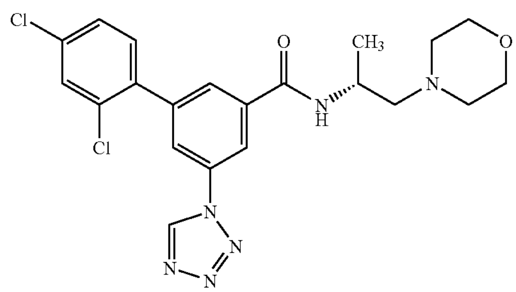 | 2',4'-Dichloro-5-tetrazol-1-yl-biphenyl-3-carboxylic acid (1-methyl-2-morpholin-4-yl-ethyl)-amide | 461 |
| 127 | 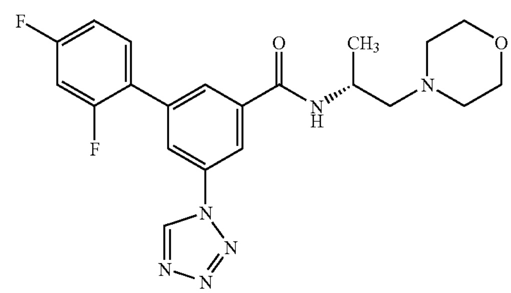 | 2',4'-Difluoro-5-tetrazol-1-yl-biphenyl-3-carboxylic acid (1-methyl-2-morpholin-4-yl-ethyl)-amide | 429 |
| 128 | 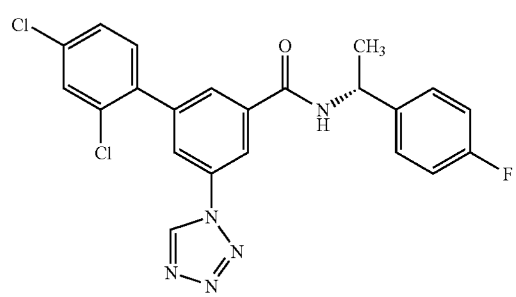 | 2',4'-Dichloro-5-tetrazol-1-yl-biphenyl-3-carboxylic acid [1-(4-fluoro-phenyl)-ethyl]-amide | 456 |
| 129 | 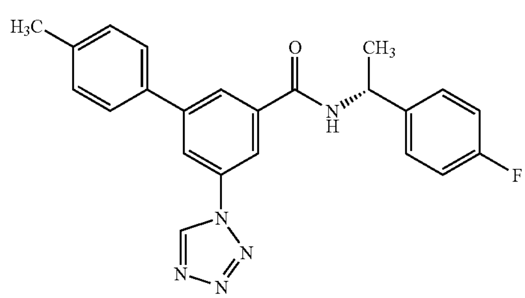 | 4'-Methyl-5-tetrazol-1-yl-biphenyl-3-carboxylic acid [1-(4-fluoro-phenyl)-ethyl]-amide | 402 |
| 130 | 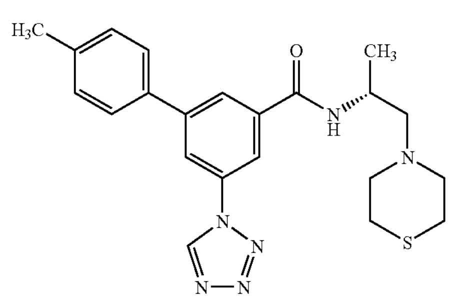 | 4'-Methyl-5-tetrazol-1-yl-biphenyl-3-carboxylic acid (1-methyl-2-thiomorpholin-4-yl-ethyl)-amide | 423 |

TABLE 1-continued

| # | Structure | Name (Autonom ™) | Mp or M + H |
|---|---|---|---|
| 131 | 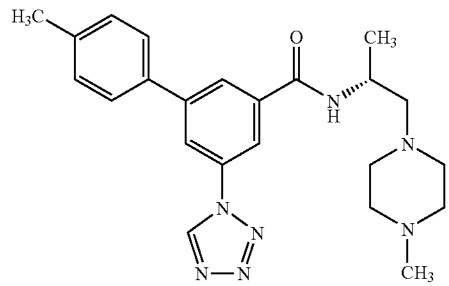 | 4'-Methyl-5-tetrazol-1-yl-biphenyl-3-carboxylic acid [1-methyl-2-(4-methyl-piperazin-1-yl)-ethyl]-amide | 420 |
| 132 | 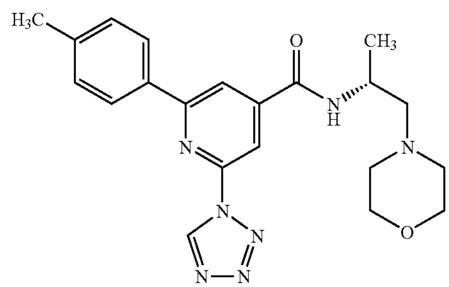 | N-(1-Methyl-2-morpholin-4-yl-ethyl)-2-tetrazol-1-yl-6-p-tolyl-isonicotinamide | 408 |
| 133 | 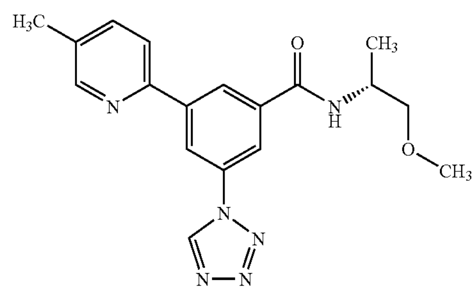 | N-(2-Methoxy-1-methyl-ethyl)-3-(5-methyl-pyridin-2-yl)-5-tetrazol-1-yl-benzamide | 353 |
| 134 | 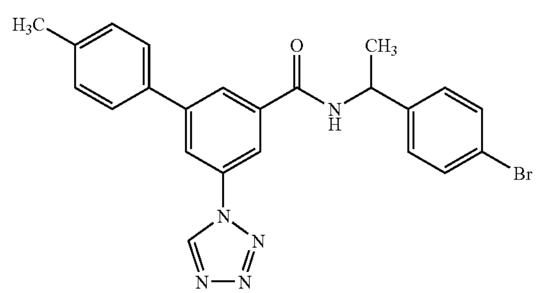 | 4'-Methyl-5-tetrazol-1-yl-biphenyl-3-carboxylic acid [1-(4-bromo-phenyl)-ethyl]-amide | 463 |
| 135 | 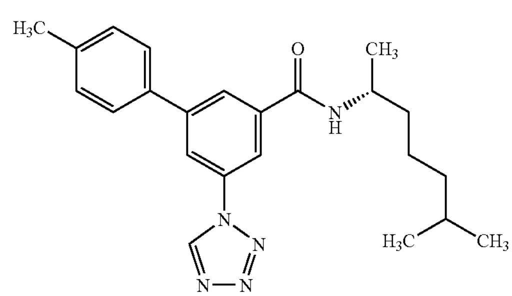 | 4'-Methyl-5-tetrazol-1-yl-biphenyl-3-carboxylic acid (1,5-dimethyl-hexyl)-amide | 392 |

TABLE 1-continued

| # | Structure | Name (Autonom ™) | Mp or M + H |
|---|---|---|---|
| 136 | 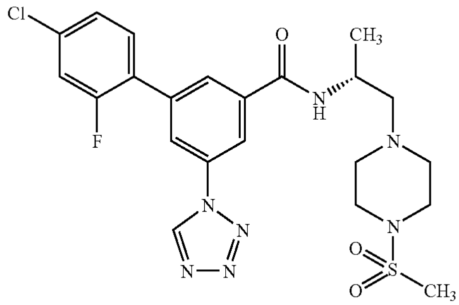 | 4'-Chloro-2'-fluoro-5-tetrazol-1-yl-biphenyl-3-carboxylic acid [2-(4-methanesulfonyl-piperazin-1-yl)-1-methyl-ethyl]-amide | 522 |
| 137 | 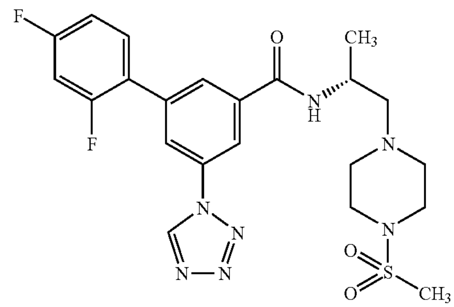 | 2',4'-Difluoro-5-tetrazol-1-yl-biphenyl-3-carboxylic acid [2-(4-methanesulfonyl-piperazin-1-yl)-1-methyl-ethyl]-amide | 506 |
| 138 | 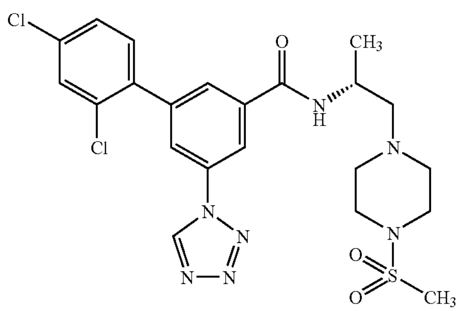 | 2',4'-Dichloro-5-tetrazol-1-yl-biphenyl-3-carboxylic acid [2-(4-methanesulfonyl-piperazin-1-yl)-1-methyl-ethyl]-amide | 538 |
| 139 | 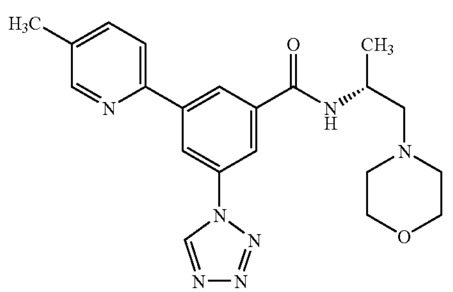 | N-(1-Methyl-2-morpholin-4-yl-ethyl)-3-(5-methyl-pyridin-2-yl)-5-tetrazol-1-yl-benzamide | 408 |
| 140 | 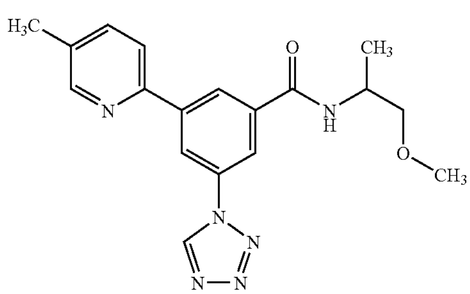 | N-(2-Methoxy-1-methyl-ethyl)-3-(5-methyl-pyridin-2-yl)-5-tetrazol-1-yl-benzamide | 353 |

TABLE 1-continued

| # | Structure | Name (Autonom ™) | Mp or M + H |
|---|---|---|---|
| 141 | 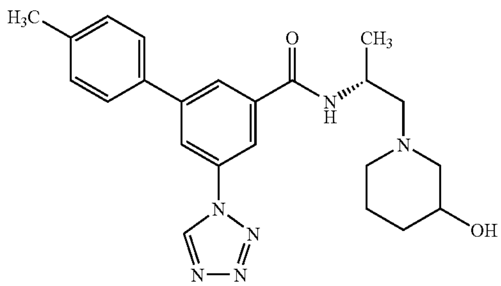 | 4'-Methyl-5-tetrazol-1-yl-biphenyl-3-carboxylic acid [2-(3-hydroxy-piperidin-1-yl)-1-methyl-ethyl]-amide | 421 |
| 142 | 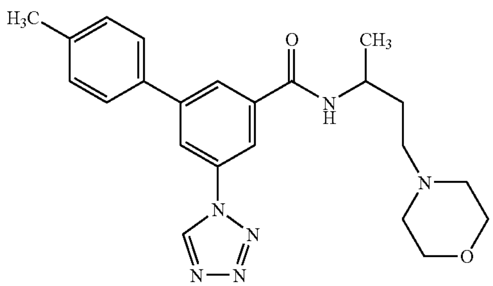 | 4'-Methyl-5-tetrazol-1-yl-biphenyl-3-carboxylic acid (1-methyl-3-morpholin-4-yl-propyl)-amide | 421 |
| 143 | 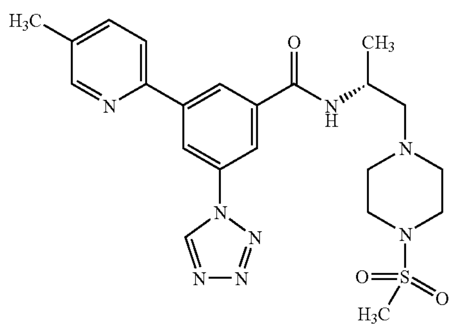 | N-[2-(4-Methanesulfonyl-piperazin-1-yl)-1-methyl-ethyl]-3-(5-methyl-pyridin-2-yl)-5-tetrazol-1-yl-benzamide | 485 |
| 144 | 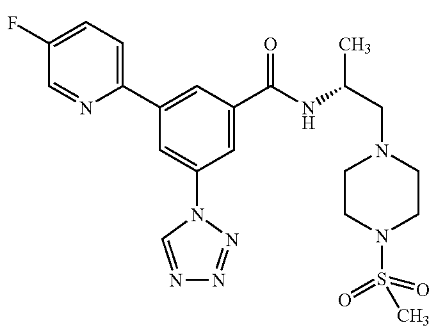 | 3-(5-Fluoro-pyridin-2-yl)-N-[2-(4-methanesulfonyl-piperazin-1-yl)-1-methyl-ethyl]-5-tetrazol-1-yl-benzamide | 489 |
| 145 | 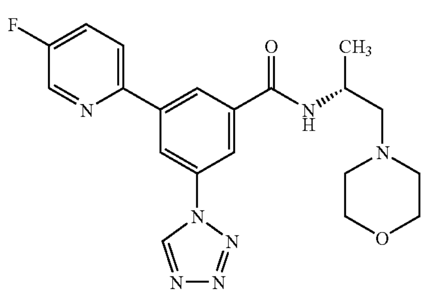 | 3-(5-Fluoro-pyridin-2-yl)-N-(1-methyl-2-morpholin-4-yl-ethyl)-5-tetrazol-1-yl-benzamide | 412 |

TABLE 1-continued

| # | Structure | Name (Autonom ™) | Mp or M + H |
|---|---|---|---|
| 146 | 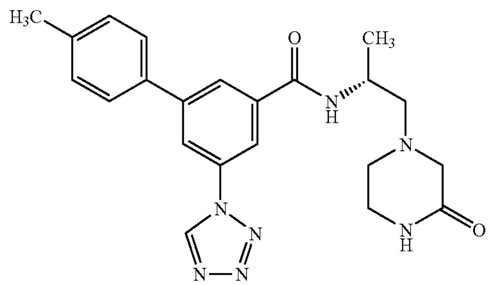 | 4'-Methyl-5-tetrazol-1-yl-biphenyl-3-carboxylic acid [1-methyl-2-(3-oxo-piperazin-1-yl)-ethyl]-amide | 420 |
| 147 | 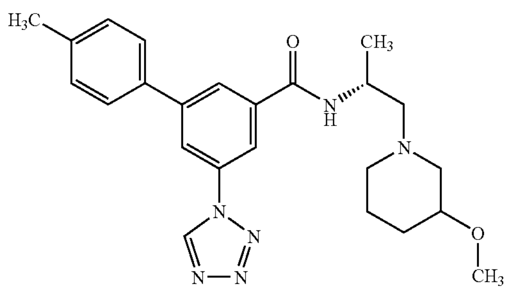 | 4'-Methyl-5-tetrazol-1-yl-biphenyl-3-carboxylic acid [2-(3-methoxy-piperidin-1-yl)-1-methyl-ethyl]-amide | 435 |
| 148 | 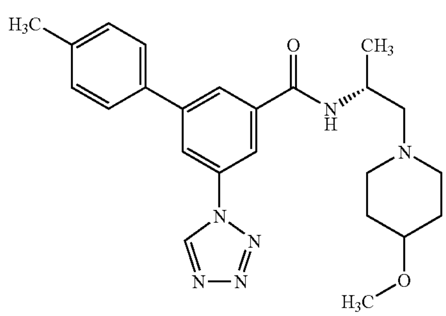 | 4'-Methyl-5-tetrazol-1-yl-biphenyl-3-carboxylic acid [2-(4-methoxy-piperidin-1-yl)-1-methyl-ethyl]-amide | 435 |
| 149 | 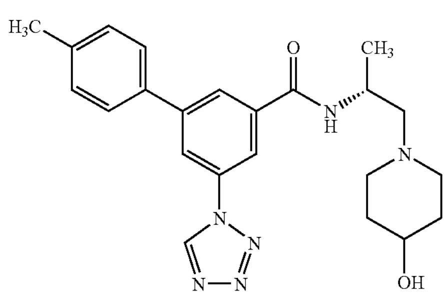 | 4'-Methyl-5-tetrazol-1-yl-biphenyl-3-carboxylic acid [2-(4-hydroxy-piperidin-1-yl)-1-methyl-ethyl]-amide | 421 |
| 150 | 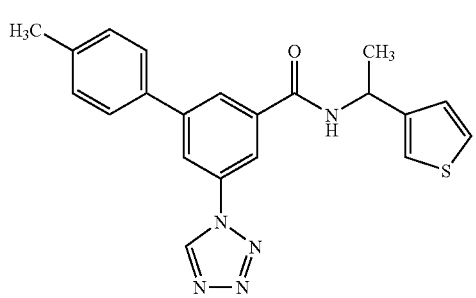 | 4'-Methyl-5-tetrazol-1-yl-biphenyl-3-carboxylic acid (1-thiophen-3-yl-ethyl)-amide | 390 |

TABLE 1-continued

| # | Structure | Name (Autonom ™) | Mp or M + H |
|---|---|---|---|
| 151 | 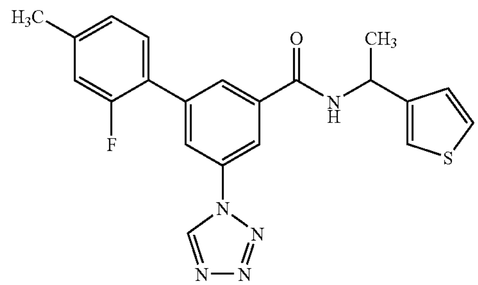 | 2'-Fluoro-4'-methyl-5-tetrazol-1-yl-biphenyl-3-carboxylic acid (1-thiophen-3-yl-ethyl)-amide | 408 |
| 152 | 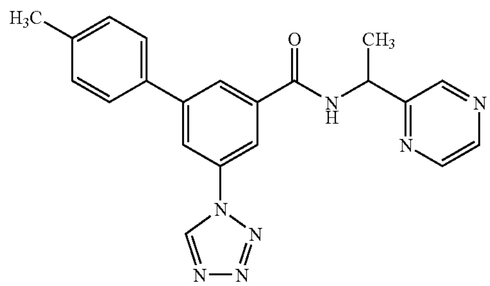 | 4'-Methyl-5-tetrazol-1-yl-biphenyl-3-carboxylic acid (1-pyrazin-2-yl-ethyl)-amide | 386 |
| 153 | 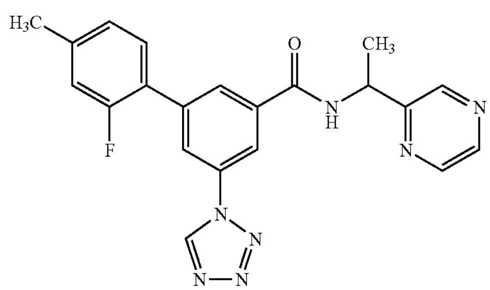 | 2'-Fluoro-4'-methyl-5-tetrazol-1-yl-biphenyl-3-carboxylic acid (1-pyrazin-2-yl-ethyl)-amide | 404 |
| 154 | 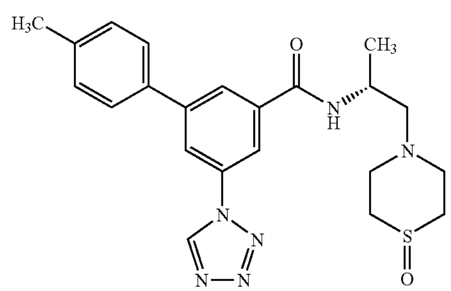 | 4'-Methyl-5-tetrazol-1-yl-biphenyl-3-carboxylic acid [1-methyl-2-(1-oxo-1lambda*4*-thiomorpholin-4-yl)-ethyl]-amide | 439 |
| 155 | 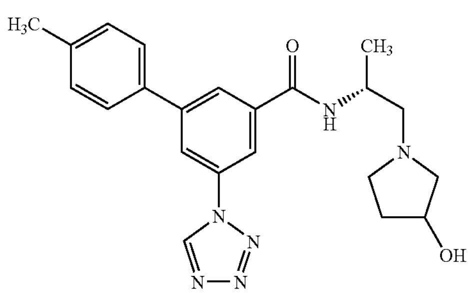 | 4'-Methyl-5-tetrazol-1-yl-biphenyl-3-carboxylic acid [2-(3-hydroxy-pyrrolidin-1-yl)-1-methyl-ethyl]-amide | 407 |

TABLE 1-continued

| # | Structure | Name (Autonom ™) | Mp or M + H |
|---|---|---|---|
| 156 | 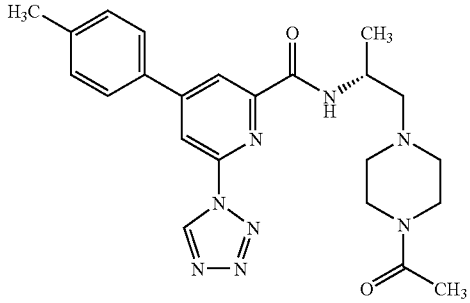 | 6-Tetrazol-1-yl-4-p-tolyl-pyridin-2-carboxylic acid [2-(4-acetyl-piperazin-1-yl)-1-methyl-ethyl]-amide | 449 |
| 157 | 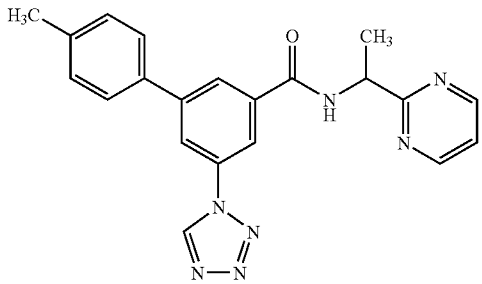 | 4'-Methyl-5-tetrazol-1-yl-biphenyl-3-carboxylic acid (1-pyrimidin-2-yl-ethyl)-amide | 386 |
| 158 | 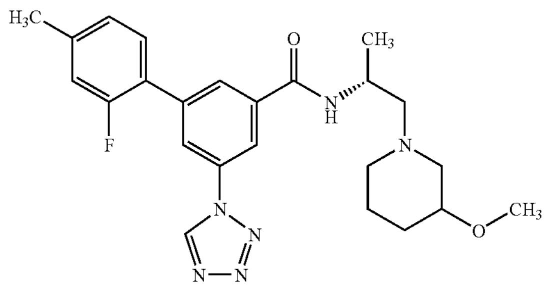 | 2'-Fluoro-4'-methyl-5-tetrazol-1-yl-biphenyl-3-carboxylic acid [2-(3-methoxy-piperidin-1-yl)-1-methyl-ethyl]-amide | 453 |
| 159 | 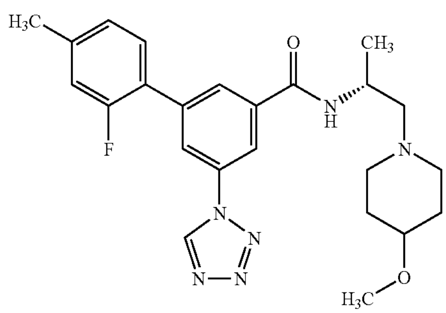 | 2'-Fluoro-4'-methyl-5-tetrazol-1-yl-biphenyl-3-carboxylic acid [2-(4-methoxy-piperidin-1-yl)-1-methyl-ethyl]-amide | 453 |
| 160 | 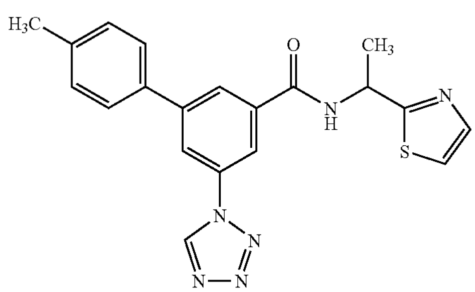 | 4'-Methyl-5-tetrazol-1-yl-biphenyl-3-carboxylic acid (1-thiazol-2-yl-ethyl)-amide | 391 |

TABLE 1-continued

| # | Structure | Name (Autonom ™) | Mp or M + H |
|---|---|---|---|
| 161 | 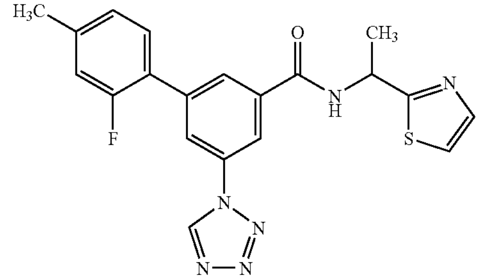 | 2'-Fluoro-4'-methyl-5-tetrazol-1-yl-biphenyl-3-carboxylic acid (1-thiazol-2-yl-ethyl)-amide | 409 |
| 162 | 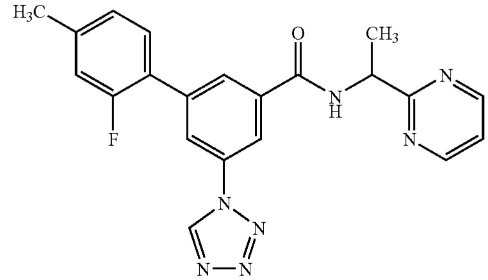 | 2'-Fluoro-4'-methyl-5-tetrazol-1-yl-biphenyl-3-carboxylic acid (1-pyrimidin-2-yl-ethyl)-amide | 404 |
| 163 | 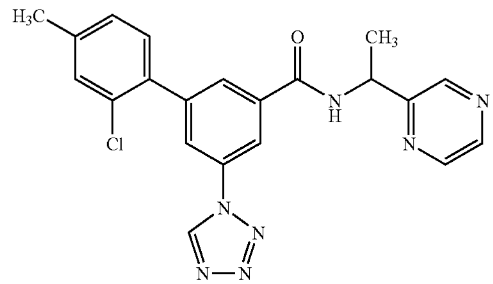 | 2'-Chloro-4'-methyl-5-tetrazol-1-yl-biphenyl-3-carboxylic acid (1-pyrazin-2-yl-ethyl)-amide | 420 |
| 164 | 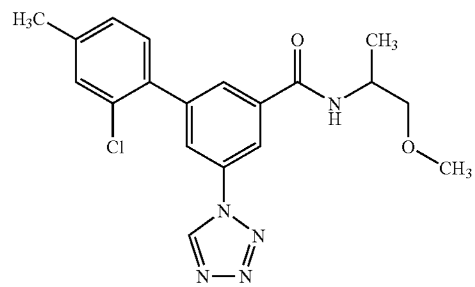 | 2'-Chloro-4'-methyl-5-tetrazol-1-yl-biphenyl-3-carboxylic acid (2-methoxy-1-methyl-ethyl)-amide | 386 |
| 165 | 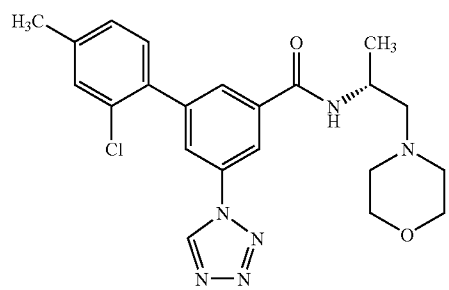 | 2'-Chloro-4'-methyl-5-tetrazol-1-yl-biphenyl-3-carboxylic acid (1-methyl-2-morpholin-4-yl-ethyl)-amide | 441 |

TABLE 1-continued

| # | Structure | Name (Autonom ™) | Mp or M + H |
|---|---|---|---|
| 166 | 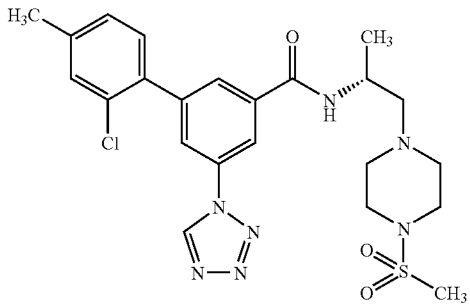 | 2'-Chloro-4'-methyl-5-tetrazol-1-yl-biphenyl-3-carboxylic acid [2-(4-methanesulfonyl-piperazin-1-yl)-1-methyl-ethyl]-amide | 518 |
| 167 | 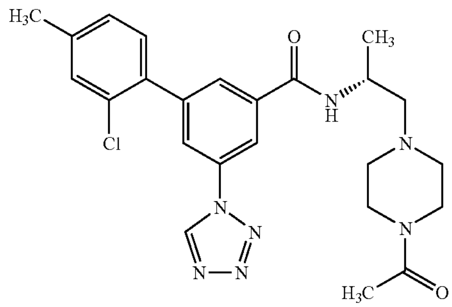 | 2'-Chloro-4'-methyl-5-tetrazol-1-yl-biphenyl-3-carboxylic acid [2-(4-acetyl-piperazin-1-yl)-1-methyl-ethyl]-amide | 482 |
| 168 | 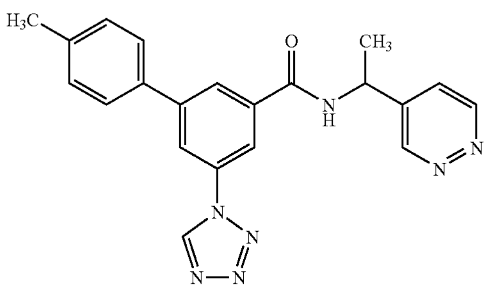 | 4'-Methyl-5-tetrazol-1-yl-biphenyl-3-carboxylic acid (1-pyridazin-4-yl-ethyl)-amide | 386 |
| 169 | 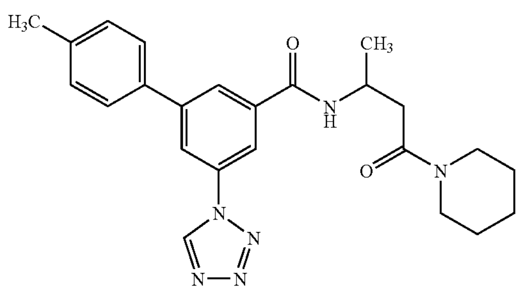 | 4'-Methyl-5-tetrazol-1-yl-biphenyl-3-carboxylic acid (1-methyl-3-oxo-3-piperidin-1-yl-propyl)-amide | 433 |
| 170 | 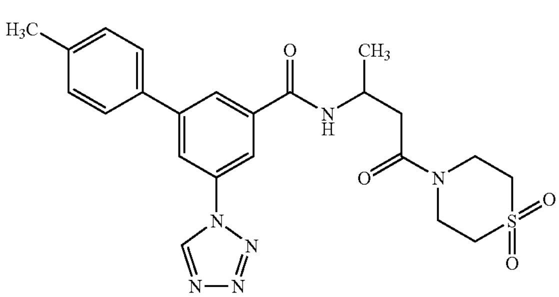 | 4'-Methyl-5-tetrazol-1-yl-biphenyl-3-carboxylic acid [3-(1,1-dioxo-1lambda*6*-thiomorpholin-4-yl)-1-methyl-3-oxo-propyl]-amide | 483 |

TABLE 1-continued

| # | Structure | Name (Autonom ™) | Mp or M + H |
|---|---|---|---|
| 171 | 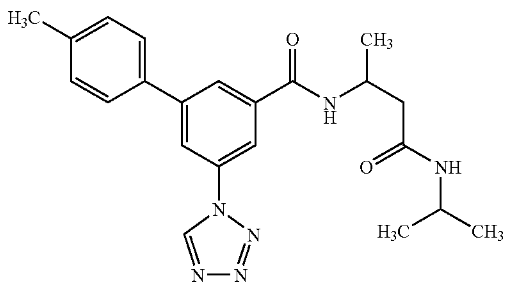 | 4'-Methyl-5-tetrazol-1-yl-biphenyl-3-carboxylic acid (2-isopropylcarbamoyl-1-methyl-ethyl)-amide | 407 |
| 172 | 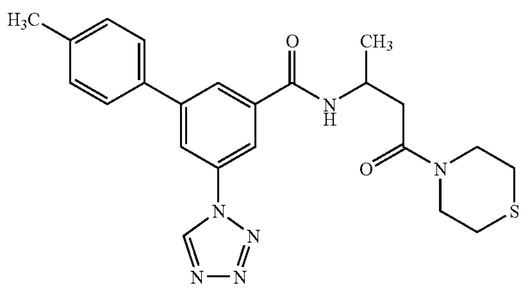 | 4'-Methyl-5-tetrazol-1-yl-biphenyl-3-carboxylic acid (1-methyl-3-oxo-3-thiomorpholin-4-yl-propyl)-amide | 451 |
| 173 | 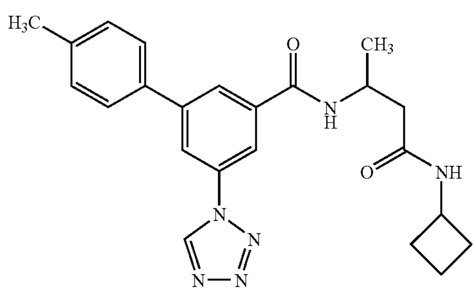 | 4'-Methyl-5-tetrazol-1-yl-biphenyl-3-carboxylic acid (2-cyclobutylcarbamoyl-1-methyl-ethyl)-amide | 419 |
| 174 | 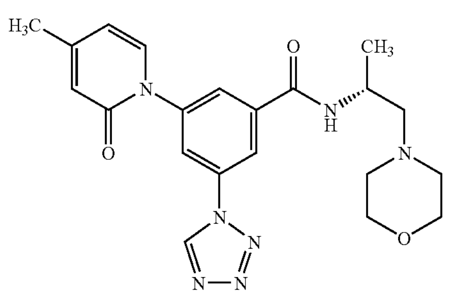 | N-(1-Methyl-2-morpholin-4-yl-ethyl)-3-(4-methyl-2-oxo-2H-pyridin-1-yl)-5-tetrazol-1-yl-benzamide | 424 |
| 175 | 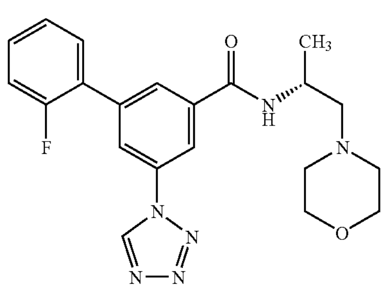 | 2'-Fluoro-5-tetrazol-1-yl-biphenyl-3-carboxylic acid (1-methyl-2-morpholin-4-yl-ethyl)-amide | 411 |

TABLE 1-continued

| # | Structure | Name (Autonom ™) | Mp or M + H |
|---|---|---|---|
| 176 | 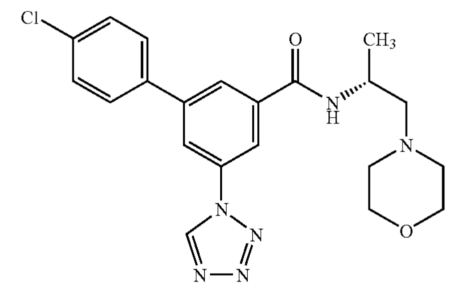 | 4'-Chloro-5-tetrazol-1-yl-biphenyl-3-carboxylic acid (1-methyl-2-morpholin-4-yl-ethyl)-amide | 427 |
| 177 | 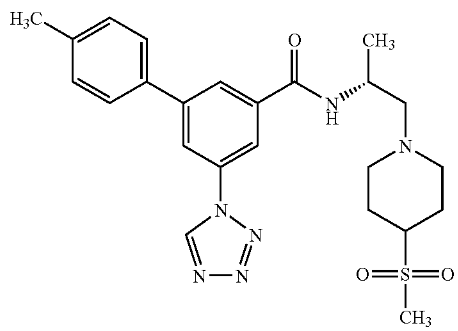 | 4'-Methyl-5-tetrazol-1-yl-biphenyl-3-carboxylic acid [(R)-2-(4-methanesulfonyl-piperidin-1-yl)-1-methyl-ethyl]-amide | 483 |
| 178 | 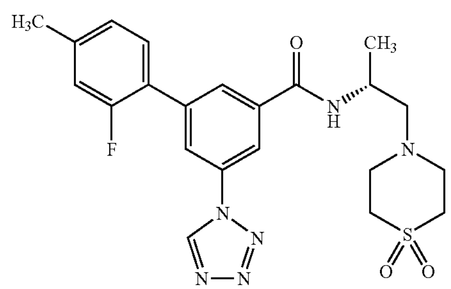 | 2'-Fluoro-4'-methyl-5-tetrazol-1-yl-biphenyl-3-carboxylic acid [(R)-2-(1,1-dioxo-1lambda*6*-thiomorpholin-4-yl)-1-methyl-ethyl]-amide | 473 |
| 179 | 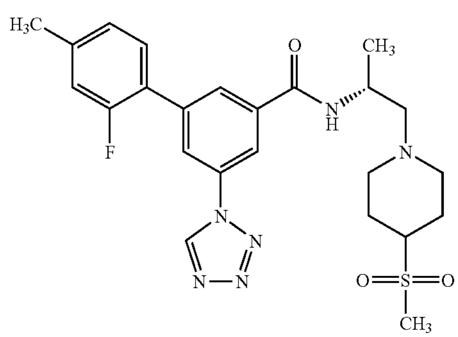 | 2'-Fluoro-4'-methyl-5-tetrazol-1-yl-biphenyl-3-carboxylic acid [(R)-2-(4-methanesulfonyl-piperidin-1-yl)-1-methyl-ethyl]-amide | 501 |
| 180 | 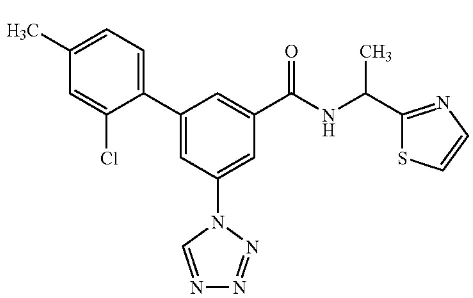 | 2'-Chloro-4'-methyl-5-tetrazol-1-yl-biphenyl-3-carboxylic acid (1-thiazol-2-yl-ethyl)-amide | 425 |

TABLE 1-continued

| # | Structure | Name (Autonom ™) | Mp or M + H |
|---|---|---|---|
| 181 | 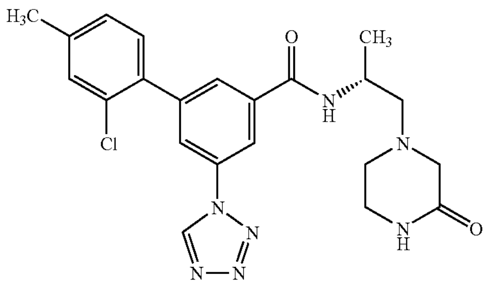 | 2'-Chloro-4'-methyl-5-tetrazol-1-yl-biphenyl-3-carboxylic acid [(R)-1-methyl-2-(3-oxo-piperazin-1-yl)-ethyl]-amide | 454 |
| 182 | 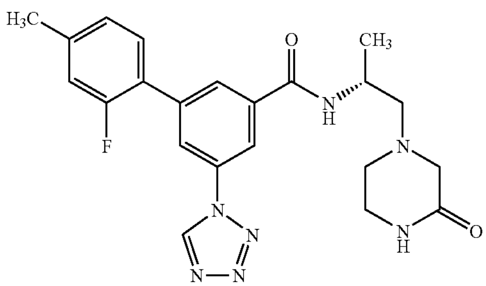 | 2'-Fluoro-4'-methyl-5-tetrazol-1-yl-biphenyl-3-carboxylic acid [(R)-1-methyl-2-(3-oxo-piperazin-1-yl)-ethyl]-amide | 438 |
| 183 | 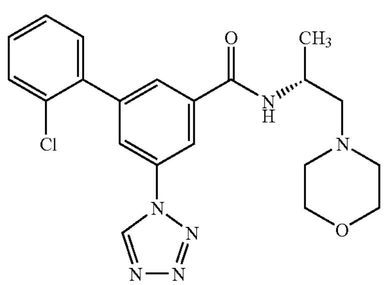 | 2'-Chloro-5-tetrazol-1-yl-biphenyl-3-carboxylic acid ((R)-1-methyl-2-morpholin-4-yl-ethyl)-amide | 427 |
| 184 | 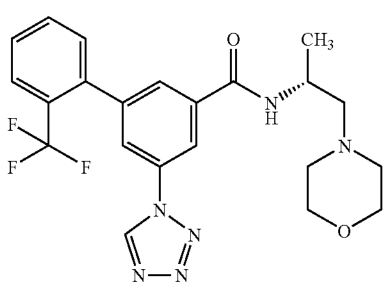 | 5-Tetrazol-1-yl-2'-trifluoromethyl-biphenyl-3-carboxylic acid ((R)-1-methyl-2-morpholin-4-yl-ethyl)-amide | 461 |
| 185 | 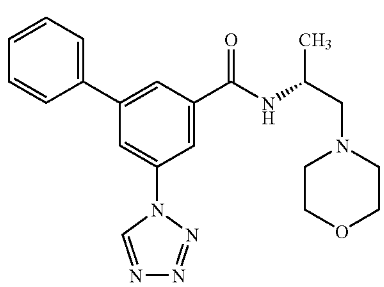 | 5-Tetrazol-1-yl-biphenyl-3-carboxylic acid ((R)-1-methyl-2-morpholin-4-yl-ethyl)-amide | 393 |

TABLE 1-continued

| # | Structure | Name (Autonom ™) | Mp or M + H |
|---|---|---|---|
| 186 | 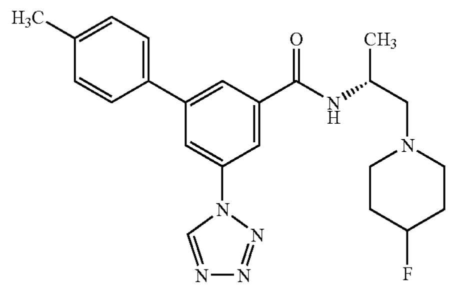 | 4'-Methyl-5-tetrazol-1-yl-biphenyl-3-carboxylic acid [(R)-2-(4-fluoro-piperidin-1-yl)-1-methyl-ethyl]-amide | 423 |
| 187 | 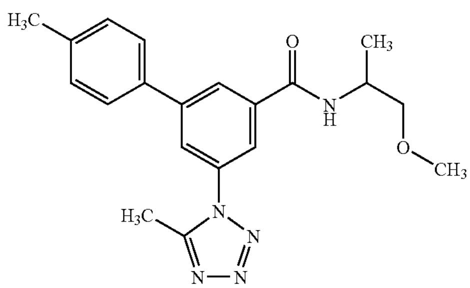 | 4'-Methyl-5-(5-methyl-tetrazol-1-yl)-biphenyl-3-carboxylic acid (2-methoxy-1-methyl-ethyl)-amide | 366 |
| 188 | 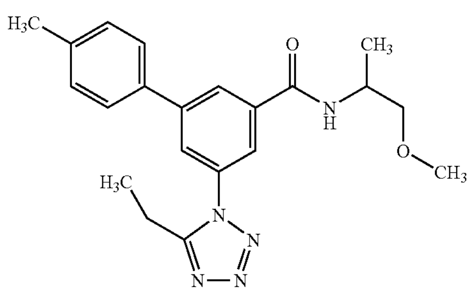 | 5-(5-Ethyl-tetrazol-1-yl)-4'-methyl-biphenyl-3-carboxylic acid (2-methoxy-1-methyl-ethyl)-amide | 380 |
| 189 | 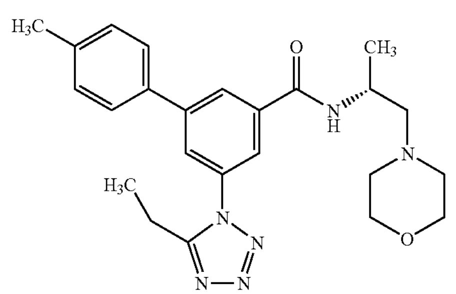 | 5-(5-Ethyl-tetrazol-1-yl)-4'-methyl-biphenyl-3-carboxylic acid ((R)-1-methyl-2-morpholin-4-yl-ethyl)-amide | 435 |
| 190 | 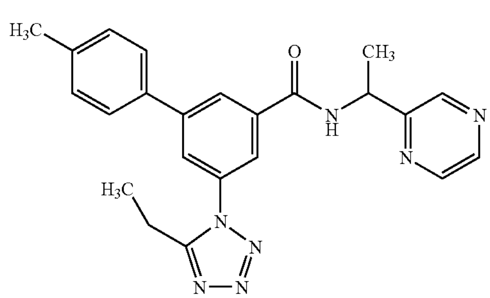 | 5-(5-Ethyl-tetrazol-1-yl)-4'-methyl-biphenyl-3-carboxylic acid (1-pyrazin-2-yl-ethyl)-amide | 164.5-166.2° C. |

TABLE 1-continued

| # | Structure | Name (Autonom ™) | Mp or M + H |
|---|---|---|---|
| 191 | 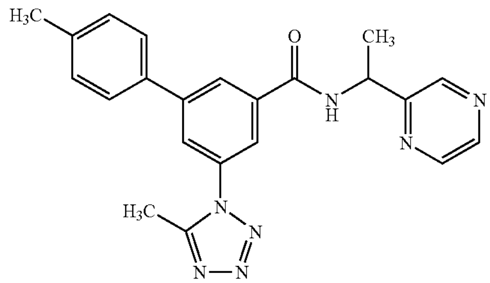 | 4'-Methyl-5-(5-methyl-tetrazol-1-yl)-biphenyl-3-carboxylic acid (1-pyrazin-2-yl-ethyl)-amide | 400 |
| 192 | 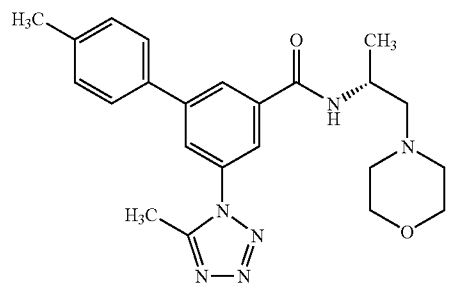 | 4'-Methyl-5-(5-methyl-tetrazol-1-yl)-biphenyl-3-carboxylic acid ((R)-1-methyl-2-morpholin-4-yl-ethyl)-amide | 421 |
| 193 | 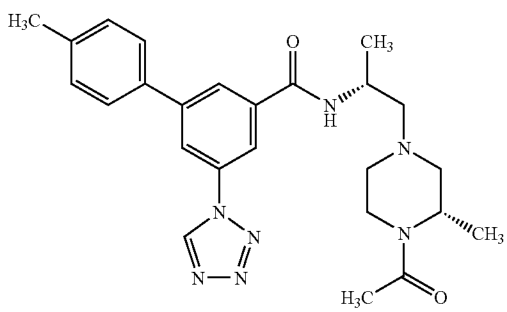 | 4'-Methyl-5-tetrazol-1-yl-biphenyl-3-carboxylic acid [(R)-2-((S)-4-acetyl-3-methyl-piperazin-1-yl)-1-methyl-ethyl]-amide | 462 |
| 194 | 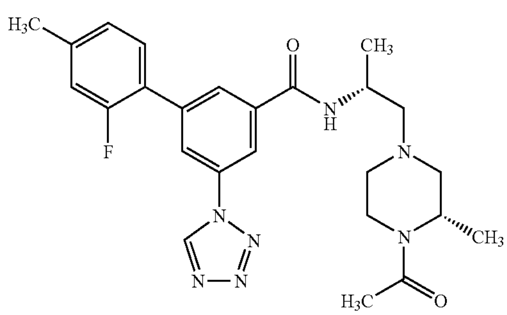 | 2'-Fluoro-4'-methyl-5-tetrazol-1-yl-biphenyl-3-carboxylic acid [(R)-2-((S)-4-acetyl-3-methyl-piperazin-1-yl)-1-methyl-ethyl]-amide | 480 |
| 195 | 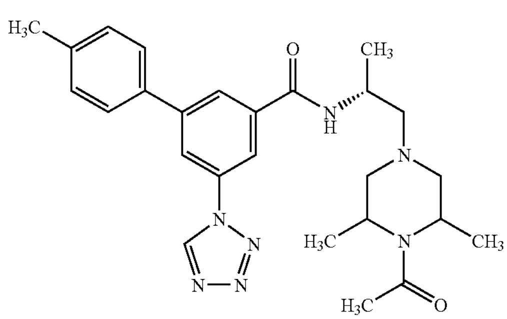 | 4'-Methyl-5-tetrazol-1-yl-biphenyl-3-carboxylic acid [(R)-2-(4-acetyl-3,5-dimethyl-piperazin-1-yl)-1-methyl-ethyl]-amide | 476 |

| # | Structure | Name (Autonom™) | Mp or M + H |
|---|---|---|---|
| 196 | 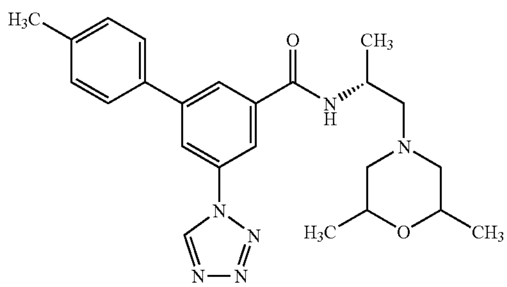 | 4'-Methyl-5-tetrazol-1-yl-biphenyl-3-carboxylic aid [(R)-2-(2,6-dimethyl-morpholin-4-yl)-1-methyl-ethyl]-amide | 435 |
| 197 | 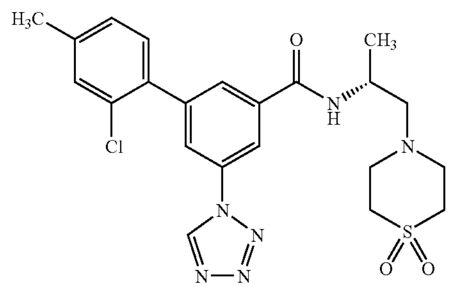 | 2'-Chloro-4'-methyl-5-tetrazol-1-yl-biphenyl-3-carboxylic acid [(R)-2-(1,1-dioxo-1lambda*6*-thiomorpholin-4-yl)-1-methyl-ethyl]-amide | 489 |
| 198 | 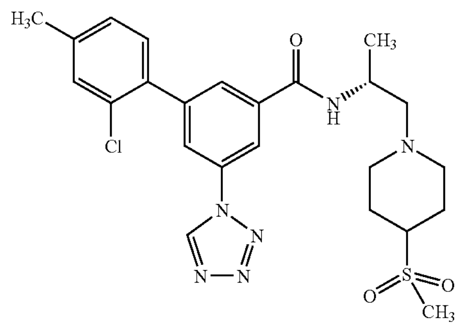 | 2'-Chloro-4'-methyl-5-tetrazol-1-yl-biphenyl-3-carboxylic acid [(R)-2-(4-methanesulfonyl-piperidin-1-yl)-1-methyl-ethyl]-amide | 517 |
| 199 | 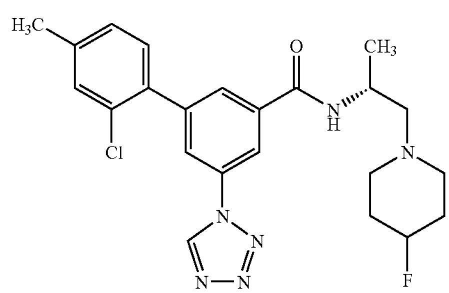 | 2'-Chloro-4'-methyl-5-tetrazol-1-yl-biphenyl-3-carboxylic acid [(R)-2-(4-fluoro-piperidin-1-yl)-1-methyl-ethyl]-amide | 457 |
| 200 | 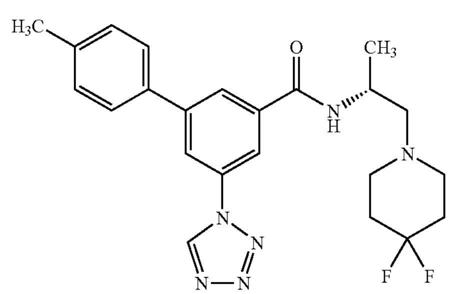 | 4'-Methyl-5-tetrazol-1-yl-biphenyl-3-carboxylic acid [(R)-2-(4,4-difluoro-piperidin-1-yl)-1-methyl-ethyl]-amide | 441 |

TABLE 1-continued

| # | Structure | Name (Autonom ™) | Mp or M + H |
|---|-----------|------------------|-------------|
| 201 | 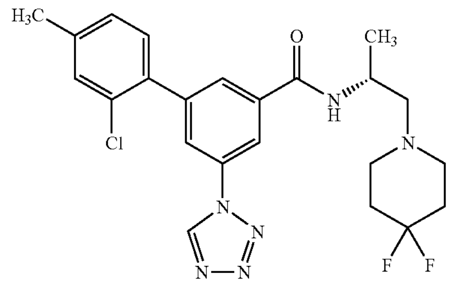 | 2'-Chloro-4'-methyl-5-tetrazol-1-yl-biphenyl-3-carboxylic acid [(R)-2-(4,4-difluoro-piperidin-1-yl)-1-methyl-ethyl]-amide | 475 |
| 202 | 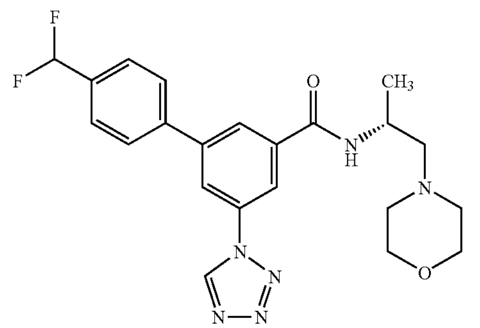 | 4'-Difluoromethyl-5-tetrazol-1-yl-biphenyl-3-carboxylic acid (1-methyl-2-morpholin-4-yl-ethyl)-amide | 443 |
| 203 | 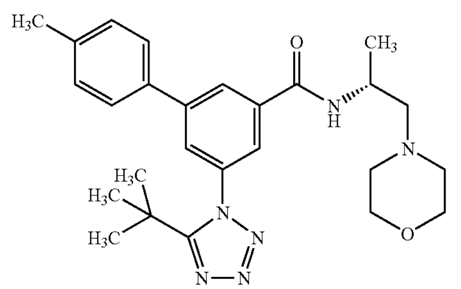 | 5-(5-tert-Butyl-tetrazol-1-yl)-4'-methyl-biphenyl-3-carboxylic acid (1-methyl-2-morpholin-4-yl-ethyl)-amide | 463 |
| 204 | 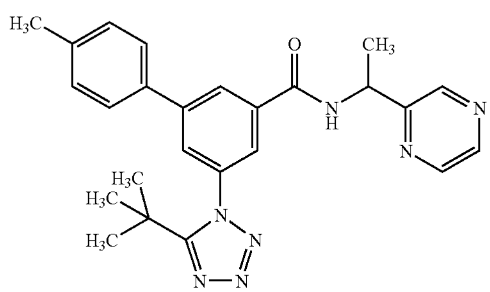 | 5-(5-tert-Butyl-tetrazol-1-yl)-4'-methyl-biphenyl-3-carboxylic acid (1-pyrazin-2-yl-ethyl)-amide | 442 |
| 205 | 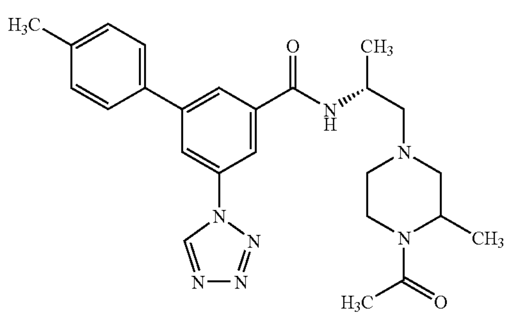 | 4'-Methyl-5-tetrazol-1-yl-biphenyl-3-carboxylic acid [2-(4-acetyl-3-methyl-piperazin-1-yl)-1-methyl-ethyl]-amide | 462 |

| # | Structure | Name (Autonom ™) | Mp or M + H |
|---|---|---|---|
| 206 | 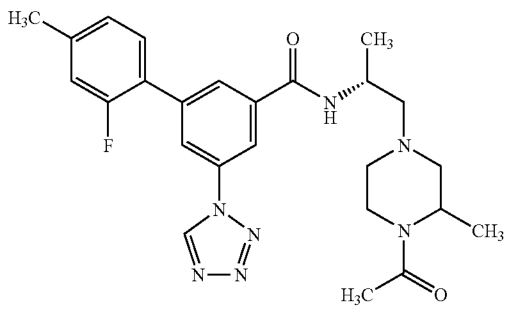 | 2'-Fluoro-4'-methyl-5-tetrazol-1-yl-biphenyl-3-carboxylic acid [2-(4-acetyl-3-methyl-piperazin-1-yl)-1-methyl-ethyl]-amide | 480 |
| 207 | 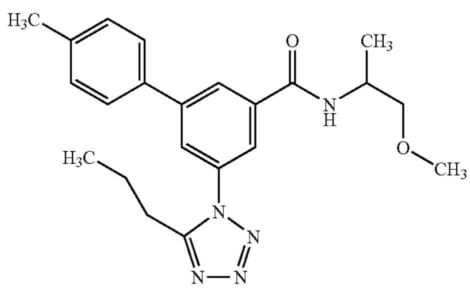 | 4'-Methyl-5-(5-propyl-tetrazol-1-yl)-biphenyl-3-carboxylic acid (2-methoxy-1-methyl-ethyl)-amide | 394 |
| 208 | 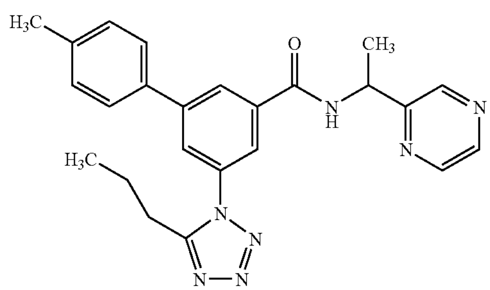 | 4'-Methyl-5-(5-propyl-tetrazol-1-yl)-biphenyl-3-carboxylic acid (1-pyrazin-2-yl-ethyl)-amide | 177.2-178.0° C. |
| 209 | 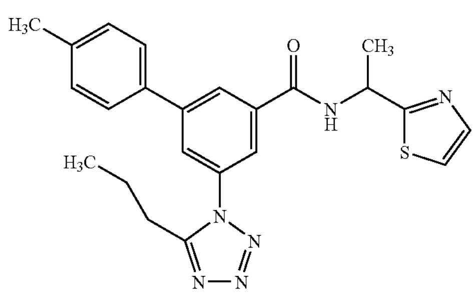 | 4'-Methyl-5-(5-propyl-tetrazol-1-yl)-biphenyl-3-carboxylic acid (1-thiazol-2-yl-ethyl)-amide | 433 |
| 210 | 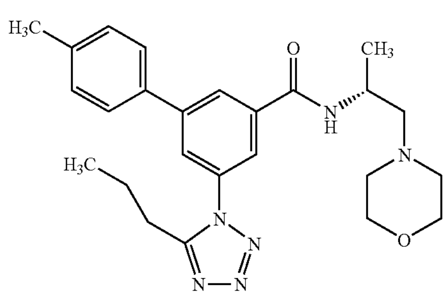 | 4'-Methyl-5-(5-propyl-tetrazol-1-yl)-biphenyl-3-carboxylic acid (1-methyl-2-morpholin-4-yl-ethyl)-amide | 449 |

TABLE 1-continued

| # | Structure | Name (Autonom ™) | Mp or M + H |
|---|---|---|---|
| 211 | 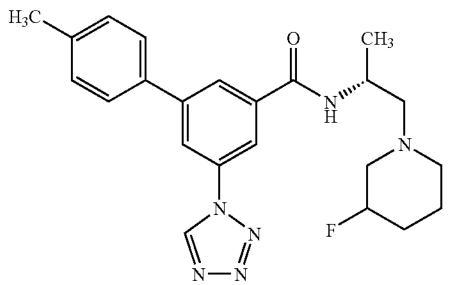 | 4'-Methyl-5-tetrazol-1-yl-biphenyl-3-carboxylic acid [2-(3-fluoro-piperidin-1-yl)-1-methyl-ethyl]-amide | 423 |
| 212 | 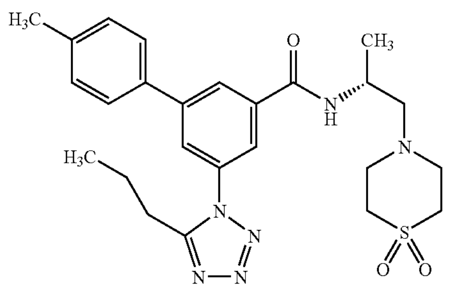 | 4'-Methyl-5-(5-propyl-tetrazol-1-yl)-biphenyl-3-carboxylic acid [2-(1,1-dioxo-1lambda*6*-thiomorpholin-4-yl)-1-methyl-ethyl]-amide | 497 |
| 213 | 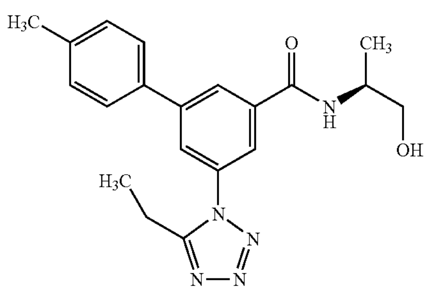 | 5-(5-Ethyl-tetrazol-1-yl)-4'-methyl-biphenyl-3-carboxylic acid (2-hydroxy-1-methyl-ethyl)-amide | 366 |
| 214 | 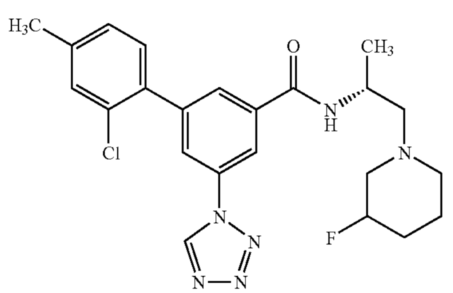 | 2'-Chloro-4'-methyl-5-tetrazol-1-yl-biphenyl-3-carboxylic acid [2-(3-fluoro-piperidin-1-yl)-1-methyl-ethyl]-amide | 457 |
| 215 | 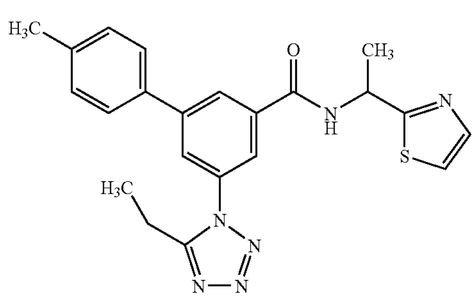 | 5-(5-Ethyl-tetrazol-1-yl)-4'-methyl-biphenyl-3-carboxylic acid (1-thiazol-2-yl-ethyl)-amide | 419 |

TABLE 1-continued

| # | Structure | Name (Autonom ™) | Mp or M + H |
|---|---|---|---|
| 216 | 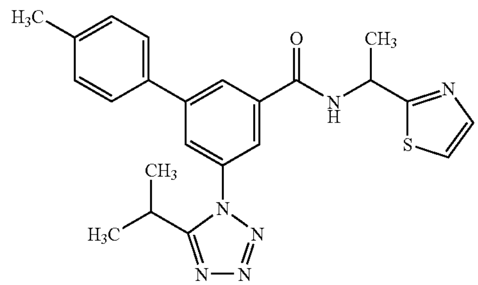 | 5-(5-Isopropyl-tetrazol-1-yl)-4'-methyl-biphenyl-3-carboxylic acid (1-thiazol-2-yl-ethyl)-amide | 433 |
| 217 | 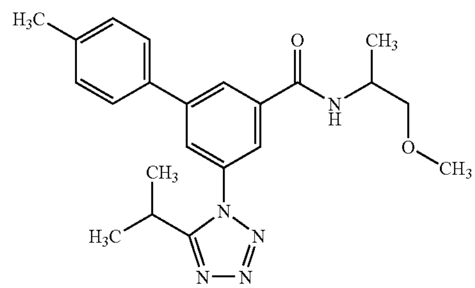 | 5-(5-Isopropyl-tetrazol-1-yl)-4'-methyl-biphenyl-3-carboxylic acid (2-methoxy-1-methyl-ethyl)-amide | 394 |
| 218 | 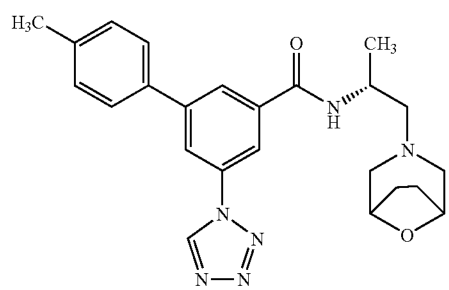 | 4'-Methyl-5-tetrazol-1-yl-biphenyl-3-carboxylic acid [1-methyl-2-(8-oxa-3-aza-bicyclo[3.2.1]oct-3-yl)-ethyl]-amide | 433 |
| 219 | 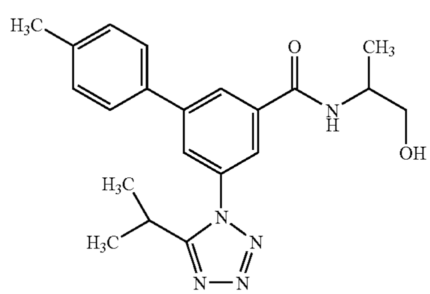 | 5-(5-Isopropyl-tetrazol-1-yl)-4'-methyl-biphenyl-3-carboxylic acid (2-hydroxy-1-methyl-ethyl)-amide | 380 |
| 220 | 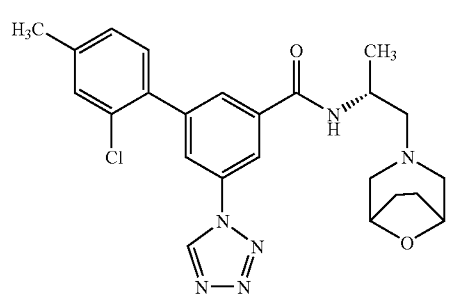 | 2'-Chloro-4'-methyl-5-tetrazol-1-yl-biphenyl-3-carboxylic acid [1-methyl-2-(8-oxa-3-aza-bicyclo[3.2.1]oct-3-yl)-ethyl]-amide | 467 |

TABLE 1-continued

| # | Structure | Name (Autonom ™) | Mp or M + H |
|---|---|---|---|
| 221 | 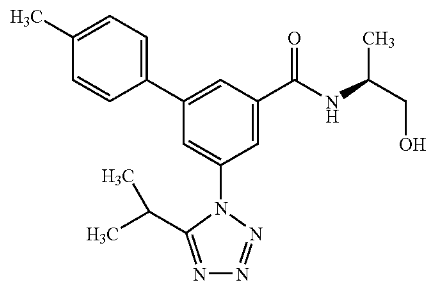 | 5-(5-Isopropyl-tetrazol-1-yl)-4'-methyl-biphenyl-3-carboxylic acid (2-hydroxy-1-methyl-ethyl)-amide | 85.5-88.5° C. |
| 222 | 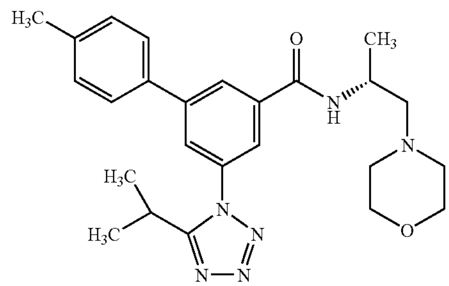 | 5-(5-Isopropyl-tetrazol-1-yl)-4'-methyl-biphenyl-3-carboxylic acid (1-methyl-2-morpholin-4-yl-ethyl)-amide | 449 |
| 223 | 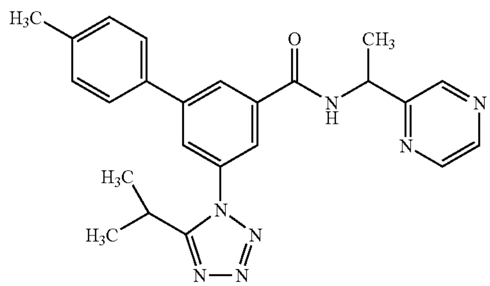 | 5-(5-Isopropyl-tetrazol-1-yl)-4'-methyl-biphenyl-3-carboxylic acid (1-pyrazin-2-yl-ethyl)-amide | 174.6-175.5° C. |
| 224 | 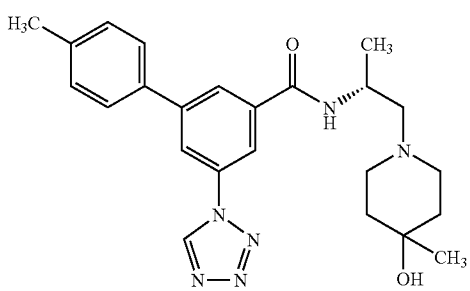 | 4'-Methyl-5-tetrazol-1-yl-biphenyl-3-carboxylic acid [2-(4-hydroxy-4-methyl-piperdin-1-yl)-1-methyl-ethyl]-amide | 435 |
| 225 | 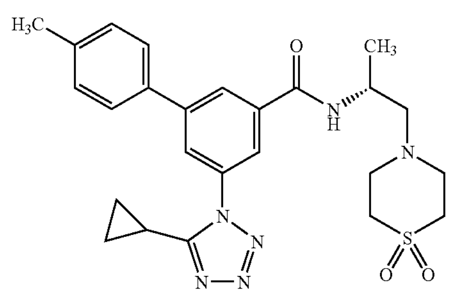 | 5-(5-Cyclopropyl-tetrazol-1-yl)-4'-methyl-biphenyl-3-carboxylic acid [2-(1,1-dioxo-1lambda*6*-thiomorpholin-4-yl)-1-methyl-ethyl]-amide | 495 |

TABLE 1-continued

| # | Structure | Name (Autonom ™) | Mp or M + H |
|---|---|---|---|
| 226 | 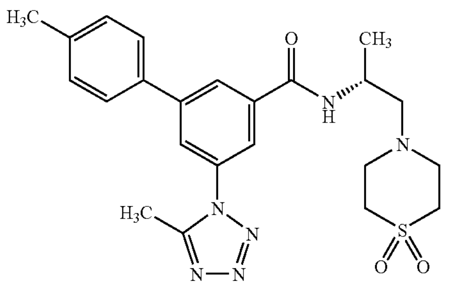 | 4'-Methyl-5-(5-methyl-tetrazol-1-yl)-biphenyl-3-carboxylic acid [2-(1,1,-dioxo-1lambda*6*-thiomorpholin-4-yl)-1-methyl-ethyl]-amide | 469 |
| 227 | 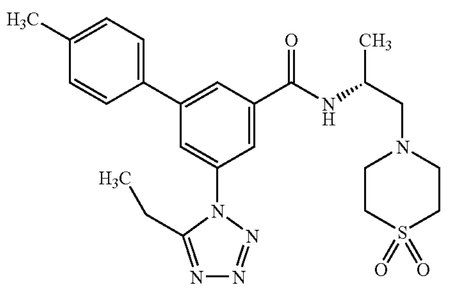 | 5-(5-Ethyl-tetrazol-1-yl)-4'-methyl-biphenyl-3-carboxylic acid [2-(1,1-dioxo-1lambda*6*-thiomorpholin-4-yl)-1-methyl-ethyl]-amide | 483 |
| 228 | 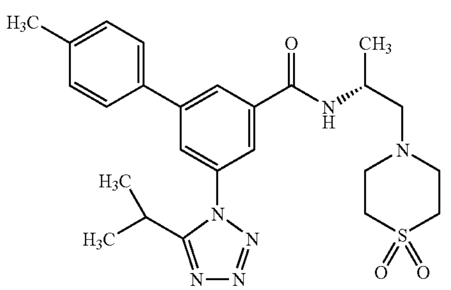 | 5-(5-Isopropyl-tetrazol-1-yl)-4'-methyl-biphenyl-3-carboxylic acid [2-(1,1-dioxo-1lambda*6*-thiomorpholin-4-yl)-1-methyl-ethyl]-amide | 497 |
| 229 | 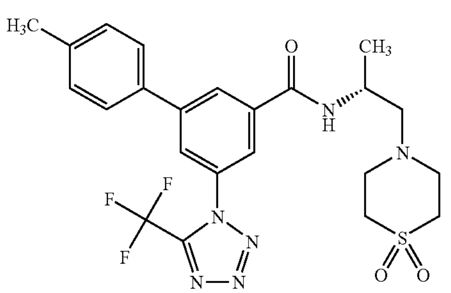 | 4'-Methyl-5-(5-trifluoromethyl-tetrazol-1-yl)-biphenyl-3-carboxylic acid [2-(1,1-dioxo-1lambda*6*-thiomorpholin-4-yl)-1-methyl-ethyl]-amide | 523 |
| 230 | 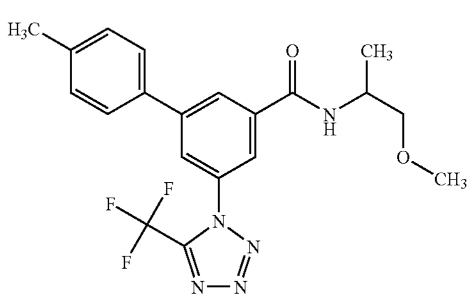 | 4'-Methyl-5-(5-trifluoromethyl-tetrazol-1-yl)-biphenyl-3-carboxylic acid (2-methoxy-1-methyl-ethyl)-amide | 420 |

TABLE 1-continued

| # | Structure | Name (Autonom ™) | Mp or M + H |
|---|---|---|---|
| 231 | 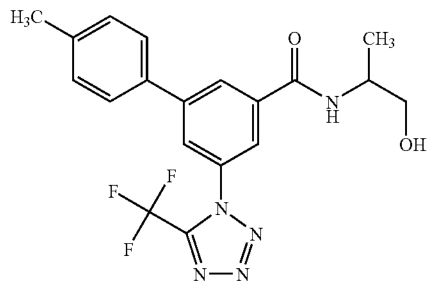 | 4'-Methyl-5-(5-trifluoromethyl-tetrazol-1-yl)-biphenyl-3-carboxylic acid (2-hydroxy-1-methyl-ethyl)-amide | 406 |
| 232 | 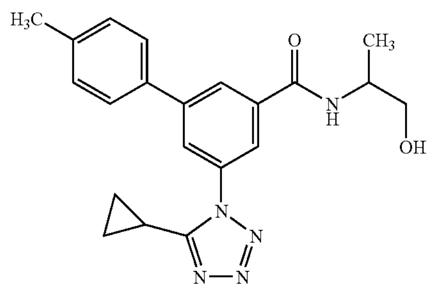 | 5-(5-Cyclopropyl-tetrazol-1-yl)-4'-methyl-biphenyl-3-carboxylic acid (2-hydroxy-1-methyl-ethyl)-amide | 378 |
| 233 | 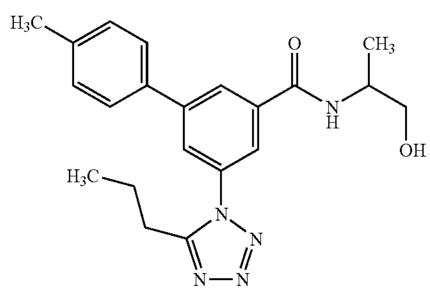 | 4'-Methyl-5-(5-propyl-tetrazol-1-yl)-biphenyl-3-carboxylic acid (2-hydroxy-1-methyl-ethyl)-amide | 380 |
| 234 | 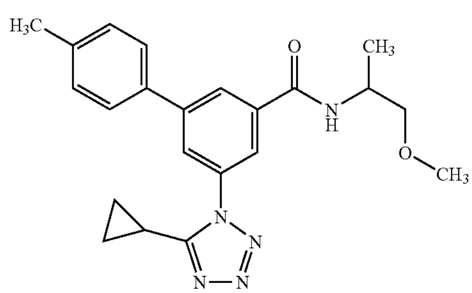 | 5-(5-Cyclopropyl-tetrazol-1-yl)-4'-methyl-biphenyl-3-carboxylic acid (2-methoxy-1-methyl-ethyl)-amide | 392 |
| 235 | 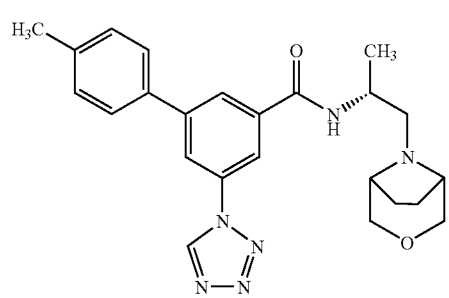 | 4'-Methyl-5-tetrazol-1-yl-biphenyl-3-carboxylic acid [1-methyl-2-(3-oxa-8-aza-bicyclo[3.2.1]oct-8-yl)-ethyl]-amide | 433 |

TABLE 1-continued

| # | Structure | Name (Autonom ™) | Mp or M + H |
|---|---|---|---|
| 236 | 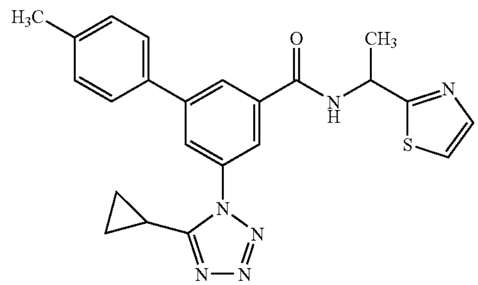 | 5-(5-Cyclopropyl-tetrazol-1-yl)-4'-methyl-biphenyl-3-carboxylic acid (1-thiazol-2-yl-ethyl)-amide | 431 |
| 237 | 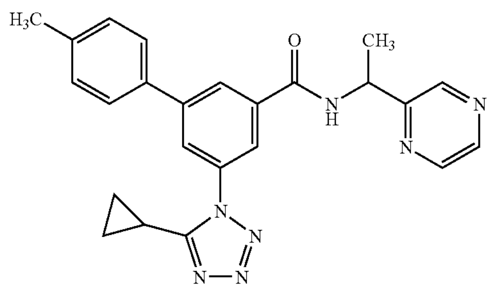 | 5-(5-Cyclopropyl-tetrazol-1-yl)-4'-methyl-biphenyl-3-carboxylic acid (1-pyrazin-2-yl-ethyl)-amide | 426 |
| 238 | 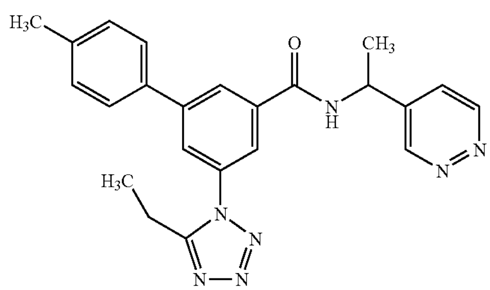 | 5-(5-Ethyl-tetrazol-1-yl)-4'-methyl-biphenyl-3-carboxylic acid (1-pyridazin-4-yl-ethyl)-amide | 414 |
| 239 | 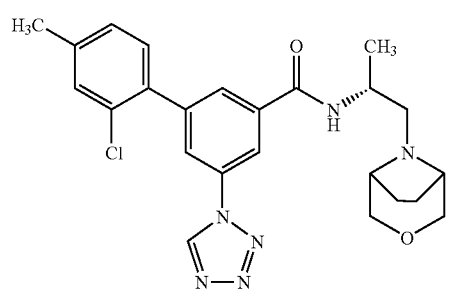 | 2'-Chloro-4'-methyl-5-tetrazol-1-yl-biphenyl-3-carboxylic acid [1-methyl-2-(3-oxa-8-aza-bicyclo[3.2.1]oct-8-yl)-ethyl]-amide | 467 |
| 240 | 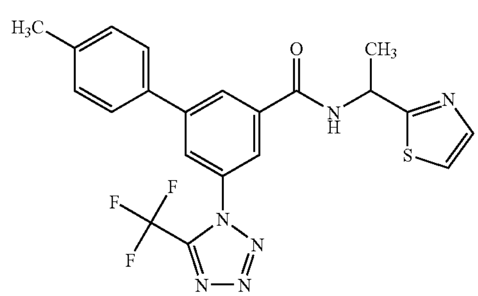 | 4'-Methyl-5-(5-trifluoromethyl-tetrazol-1-yl)-biphenyl-3-carboxylic acid (1-thiazol-2-yl-ethyl)-amide | 458 |

TABLE 1-continued

| # | Structure | Name (Autonom ™) | Mp or M + H |
|---|---|---|---|
| 241 | 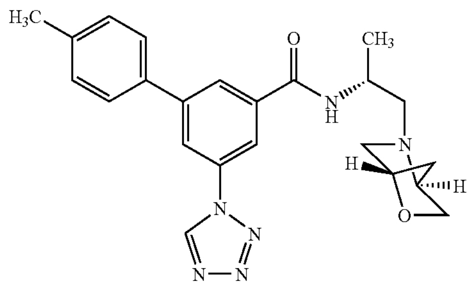 | 4'-Methyl-5-tetrazol-1-yl-biphenyl-3-carboxylic acid [1-methyl-2-(2-oxa-5-aza-bicyclo[2.2.1]hept-5-yl)-ethyl]-amide | 419 |
| 242 | 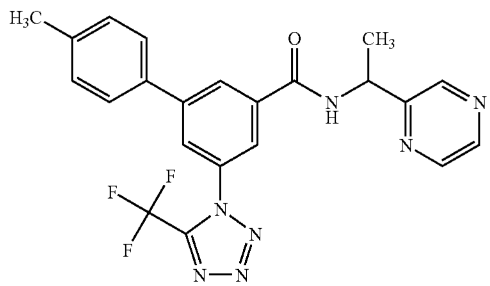 | 4'-Methyl-5-(5-trifluoromethyl-tetrazol-1-yl)-biphenyl-3-carboxylic acid (1-pyrazin-2-yl-ethyl)-amide | 454 |
| 243 | 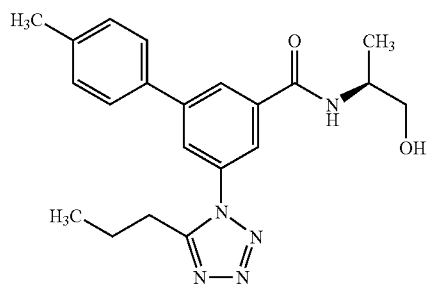 | 4'-Methyl-5-(5-propyl-tetrazol-1-yl)-biphenyl-3-carboxylic acid (2-hydroxy-1-methyl-ethyl)-amide | 380 |
| 244 | 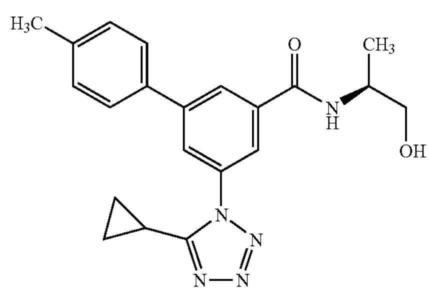 | 5-(5-Cyclopropyl-tetrazol-1-yl)-4'-methyl-biphenyl-3-carboxylic acid (2-hydroxy-1-methyl-ethyl)-amide | 378 |
| 245 | 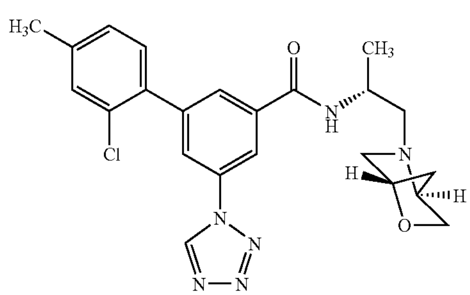 | 2'-Chloro-4'-methyl-5-tetrazol-1-yl-biphenyl-3-carboxylic acid [1-methyl-2-(2-oxa-5-aza-bicyclo[2.2.1]hept-5-yl)-ethyl]-amide | 453 |

TABLE 1-continued

| # | Structure | Name (Autonom ™) | Mp or M + H |
|---|---|---|---|
| 246 | 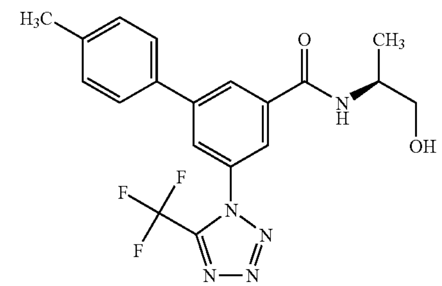 | 4'-Methyl-5-(5-trifluoromethyl-tetrazol-1-yl)-biphenyl-3-carboxylic acid (2-hydroxy-1-methyl-ethyl)-amide | 406 |
| 247 | 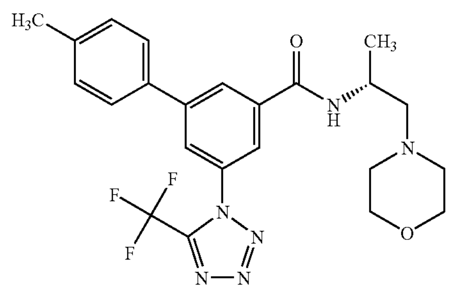 | 4'-Methyl-5-(5-trifluoromethyl-tetrazol-1-yl)-biphenyl-3-carboxylic acid (1-methyl-2-morpholin-4-yl-ethyl)-amide | 475 |
| 248 | 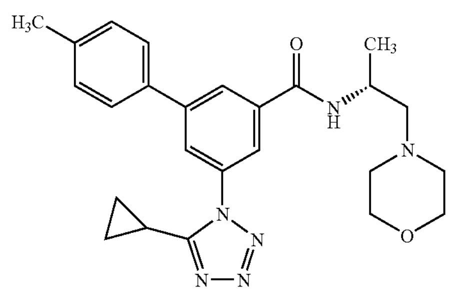 | 5-(5-Cyclopropyl-tetrazol-1-yl)-4'-methyl-biphenyl-3-carboxylic acid (1-methyl-2-morpholin-4-yl-ethyl)-amide | 447 |
| 249 | 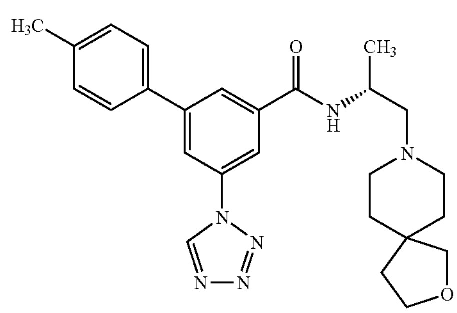 | 4'-Methyl-5-tetrazol-1-yl-biphenyl-3-carboxylic acid [1-methyl-2-(2-oxa-8-aza-spiro[4.5]dec-8-yl)-ethyl]-amide | 461 |
| 250 | 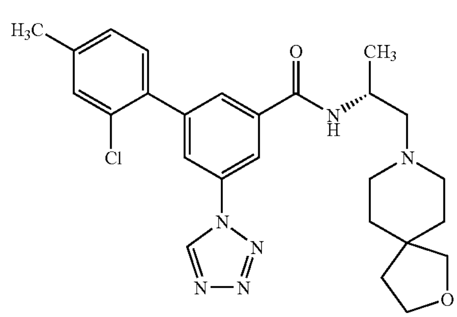 | 2'-Chloro-4'-methyl-5-tetrazol-1-yl-biphenyl-3-carboxylic acid [1-methyl-2-(2-oxa-8-aza-spiro[4.5]dec-8-yl)-ethyl]-amide | 495 |

TABLE 1-continued

| # | Structure | Name (Autonom ™) | Mp or M + H |
|---|---|---|---|
| 251 | 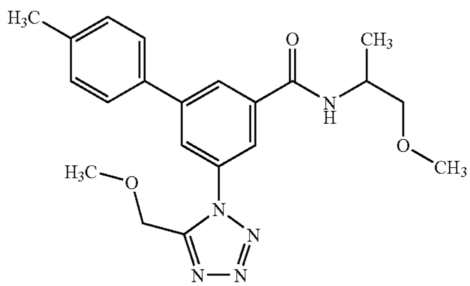 | 5-(5-Methoxymethyl-tetrazol-1-yl)-4'-methyl-biphenyl-3-carboxylic acid (2-methoxy-1-methyl-ethyl)-amide | 396 |
| 252 | 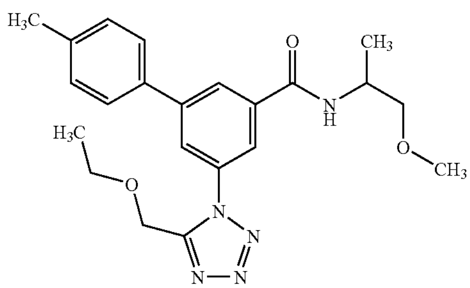 | 5-(5-Ethoxymethyl-tetrazol-1-yl)-4'-methyl-biphenyl-3-carboxylic acid (2-methoxy-1-methyl-ethyl)-amide | 410 |
| 253 | 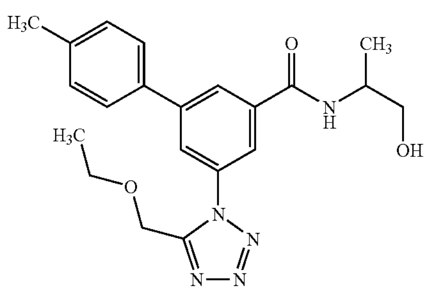 | 5-(5-Ethoxymethyl-tetrazol-1-yl)-4'-methyl-biphenyl-3-carboxylic acid (2-hydroxy-1-methyl-ethyl)-amide | 396 |
| 254 | 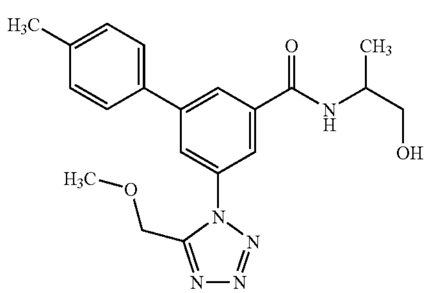 | 5-(5-Methoxymethyl-tetrazol-1-yl)-4'-methyl-biphenyl-3-carboxylic acid (2-hydroxy-1-methyl-ethyl)-amide | 382 |
| 255 | 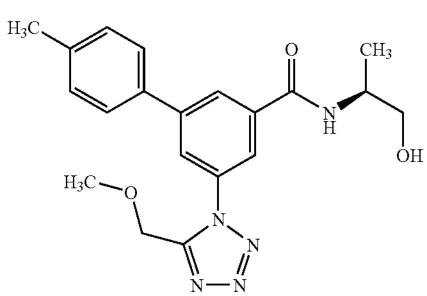 | 5-(5-Methoxymethyl-tetrazol-1-yl)-4'-methyl-biphenyl-3-carboxylic acid (2-hydroxy-1-methyl-ethyl)-amide | 382 |

TABLE 1-continued

| # | Structure | Name (Autonom ™) | Mp or M + H |
|---|---|---|---|
| 256 | 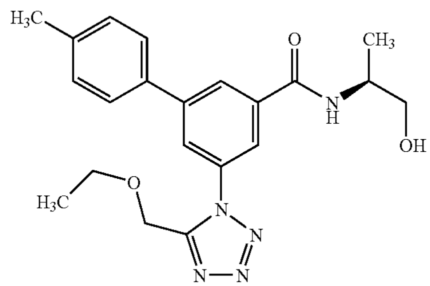 | 5-(5-Ethoxymethyl-tetrazol-1-yl)-4'-methyl-biphenyl-3-carboxylic acid (2-hydroxy-1-methyl-ethyl)-amide | 396 |
| 257 | 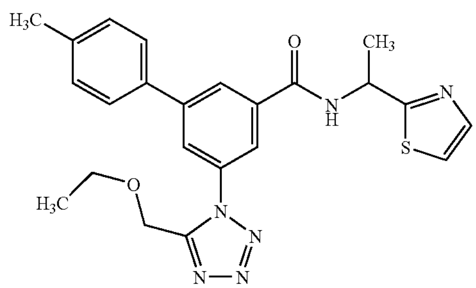 | 5-(5-Ethoxymethyl-tetrazol-1-yl)-4'-methyl-biphenyl-3-carboxylic acid (1-thiazol-2-yl-ethyl)-amide | 449 |
| 258 | 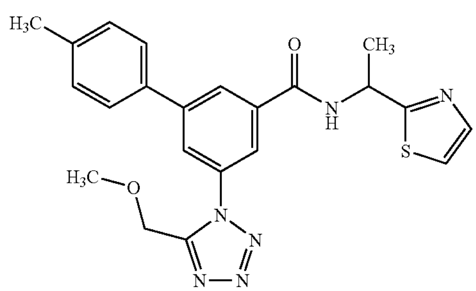 | 5-(5-Methoxymethyl-tetrazol-1-yl)-4'-methyl-biphenyl-3-carboxylic acid (1-thiazol-2-yl-ethyl)-amide | 435 |
| 259 | 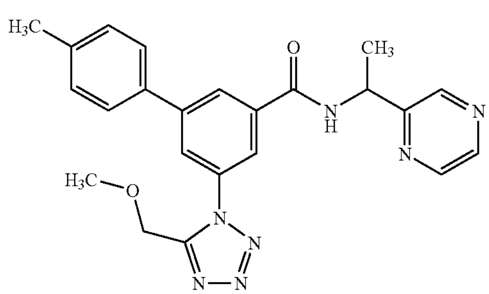 | 5-(5-Methoxymethyl-tetrazol-1-yl)-4'-methyl-biphenyl-3-carboxylic acid (1-pyrazin-2-yl-ethyl)-amide | 430 |
| 260 | 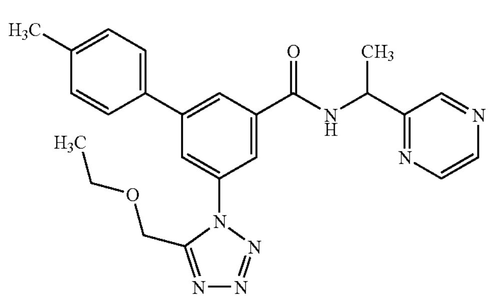 | 5-(5-Ethoxymethyl-tetrazol-1-yl)-4'-methyl-biphenyl-3-carboxylic acid (1-pyrazin-2-yl-ethyl)-amide | 444 |

TABLE 1-continued

| # | Structure | Name (Autonom ™) | Mp or M + H |
|---|---|---|---|
| 261 | 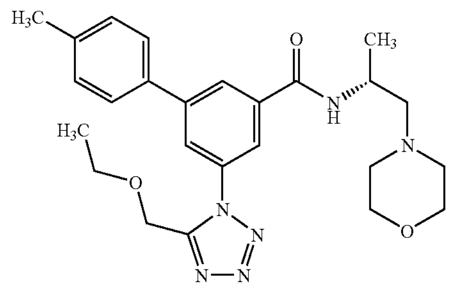 | 5-(5-Ethoxymethyl-tetrazol-1-yl)-4'-methyl-biphenyl-3-carboxylic acid (1-methyl-2-morpholin-4-yl-ethyl)-amide | 465 |
| 262 | 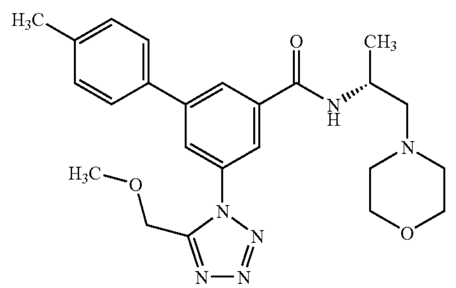 | 5-(5-Methoxymethyl-tetrazol-1-yl)-4'-methyl-biphenyl-3-carboxylic acid (1-methyl-2-morpholin-4-yl-ethyl)-amide | 451 |
| 263 | 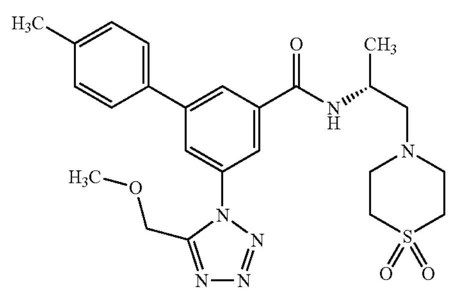 | 5-(5-Methoxymethyl-tetrazol-1-yl)-4'-methyl-biphenyl-3-carboxylic acid [2-(1,1-dioxo-1lambda*6*-thiomorpholin-4-yl)-1-methyl-ethyl]-amide | 499 |
| 264 | 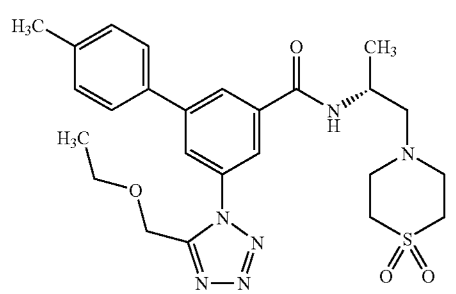 | 5-(5-Ethoxymethyl-tetrazol-1-yl)-4'-methyl-biphenyl-3-carboxylic acid [2-(1,1-dioxo-1lambda*6*-thiomorpholin-4-yl)-1-methyl-ethyl]-amide | 513 |
| 265 | 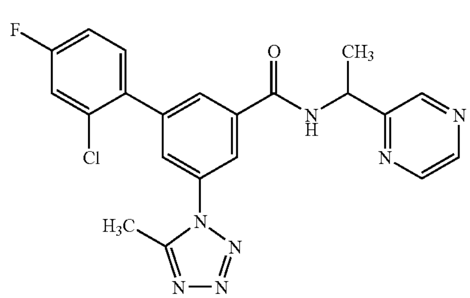 | 2'-Chloro-4'-fluoro-5-(5-methyl-tetrazol-1-yl)-biphenyl-3-carboxylic acid (1-pyrazin-2-yl-ethyl)-amide | 438 |

TABLE 1-continued

| # | Structure | Name (Autonom ™) | Mp or M + H |
|---|---|---|---|
| 266 | 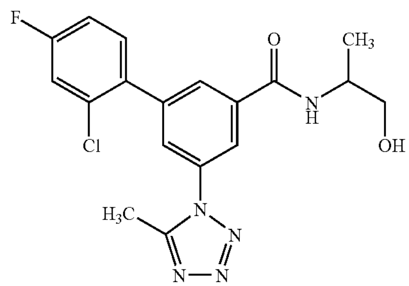 | 2'-Chloro-4'-fluoro-5-(5-methyl-tetrazol-1-yl)-biphenyl-3-carboxylic acid (2-hydroxy-1-methyl-ethyl)-amide | 390 |
| 267 | 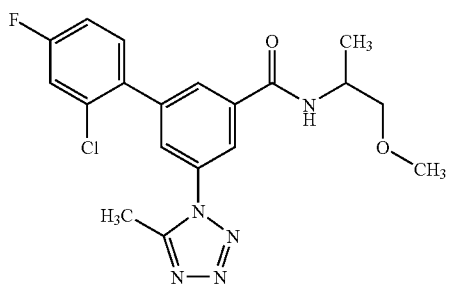 | 2'-Chloro-4'-fluoro-5-(5-methyl-tetrazol-1-yl)-biphenyl-3-carboxylic acid (2-methoxy-1-methyl-ethyl)-amide | 404 |
| 268 | 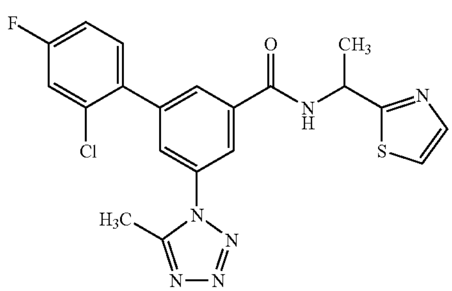 | 2'-Chloro-4'-fluoro-5-(5-methyl-tetrazol-1-yl)-biphenyl-3-carboxylic acid (1-thiazol-2-yl-ethyl)-amide | 443 |
| 269 | 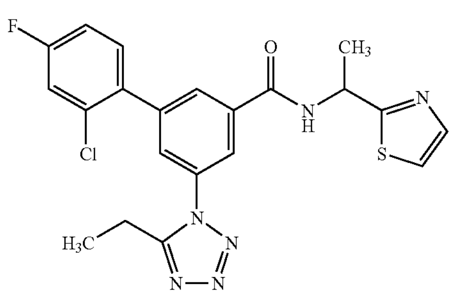 | 2'-Chloro-5-(5-ethyl-tetrazol-1-yl)-4'-fluoro-biphenyl-3-carboxylic acid (1-thiazol-2-yl-ethyl)-amide | 457 |
| 270 | 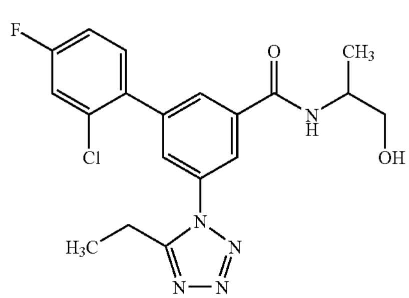 | 2'-Chloro-5-(5-ethyl-tetrazol-1-yl)-4'-fluoro-biphenyl-3-carboxylic acid (2-hydroxy-1-methyl-ethyl)-amide | 404 |

TABLE 1-continued

| # | Structure | Name (Autonom ™) | Mp or M + H |
|---|---|---|---|
| 271 | 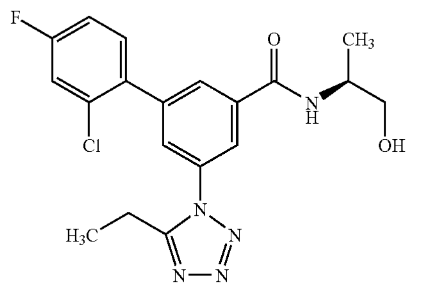 | 2'-Chloro-5-(5-ethyl-tetrazol-1-yl)-4'-fluoro-biphenyl-3-carboxylic acid (2-hydroxy-1-methyl-ethyl)-amide | 404 |
| 272 | 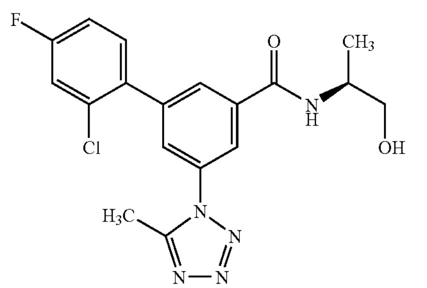 | 2'-Chloro-4'-fluoro-5-(5-methyl-tetrazol-1-yl)-biphenyl-3-carboxylic acid (2-hydroxy-1-methyl-ethyl)-amide | 390 |
| 273 | 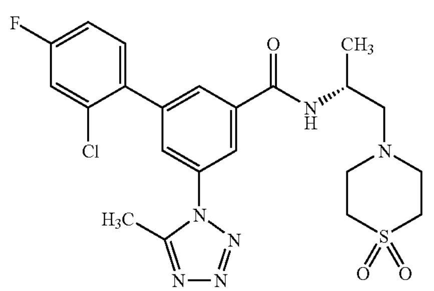 | 2'-Chloro-4'-5-(5-methyl-tetrazol-1-yl)-biphenyl-3-carboxylic acid [2-(1,1-dioxo-1lambda*6*-thiomorpholin-4-yl)-1-methyl-ethyl]-amide | 507 |
| 274 | 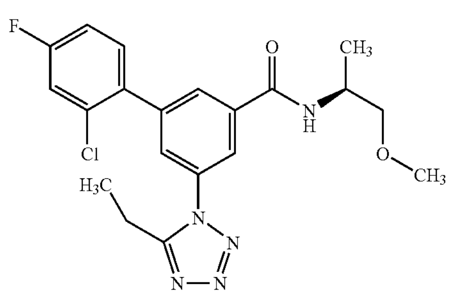 | 2'-Chloro-5-(5-ethyl-tetrazol-1-yl)-4'-fluoro-biphenyl-3-carboxylic acid (2-methoxy-1-methyl-ethyl)-amide | 418 |
| 275 | 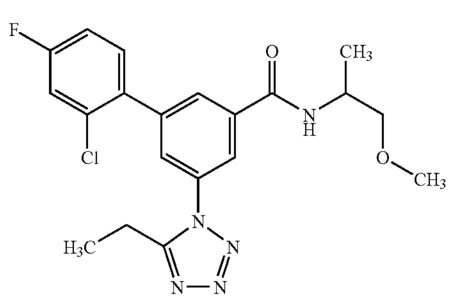 | 2'-Chloro-5-(5-ethyl-tetrazol-1-yl)-4'-fluoro-biphenyl-3-carboxylic acid (2-methoxy-1-methyl-ethyl)-amide | 418 |

TABLE 1-continued

| # | Structure | Name (Autonom ™) | Mp or M + H |
|---|---|---|---|
| 276 | 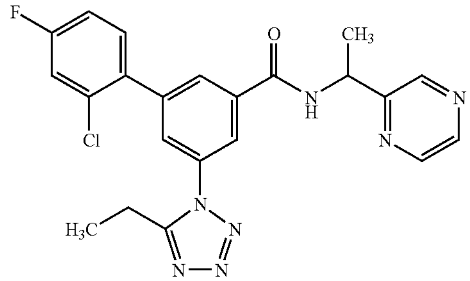 | 2'-Chloro-5-(5-ethyl-tetrazol-1-yl)-4'-fluoro-biphenyl-3-carboxylic acid (1-pyrazin-2-yl-ethyl)-amide | 452 |
| 277 | 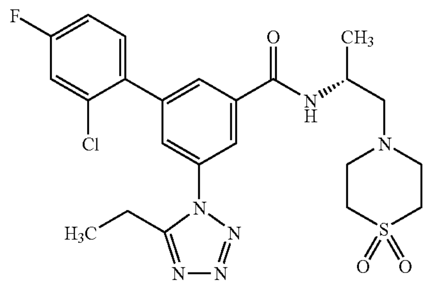 | 2'-Chloro-5-(5-ethyl-tetrazol-1-yl)-4'-fluoro-biphenyl-3-carboxylic acid [2-(1,1-dioxo-1lambda*6*-thiomorpholin-4-yl)-1-methyl-ethyl]-amide | 521 |
| 278 | 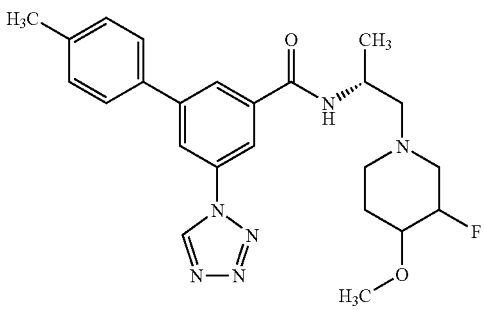 | 4'-Methyl-5-tetrazol-1-yl-biphenyl-3-carboxylic acid [2-(3-fluoro-4-methoxy-piperidin-1-yl)-1-methyl-ethyl]-amide | 453 |
| 279 | 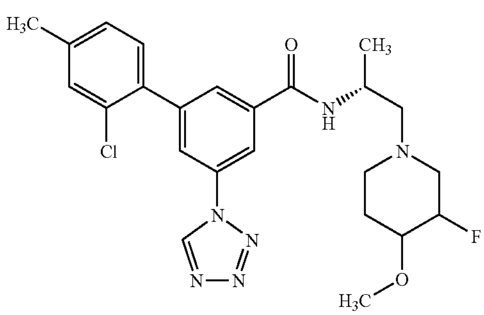 | 2'-Chloro-4'-methyl-5-tetrazol-1-yl-biphenyl-3-carboxylic acid [2-(3-fluoro-4-methoxy-piperidin-1-yl)-1-methyl-ethyl]-amide | 487 |
| 280 | 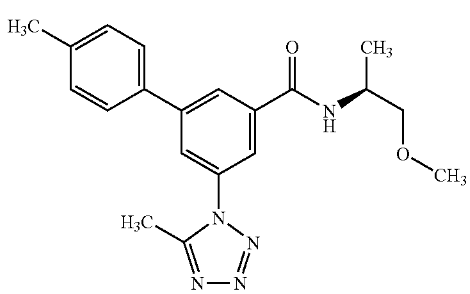 | 4'-Methyl-5-(5-methyl-tetrazol-1-yl)-biphenyl-3-carboxylic acid (2-methoxy-1-methyl-ethyl)-amide | 366 |

TABLE 1-continued

| # | Structure | Name (Autonom ™) | Mp or M + H |
|---|-----------|------------------|-------------|
| 281 | 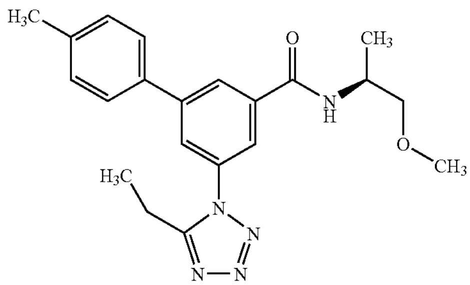 | 5-(5-Ethyl-tetrazol-1-yl)-4'-methyl-biphenyl-3-carboxylic acid (2-methoxy-1-methyl-ethyl)-amide | 380 |
| 282 | 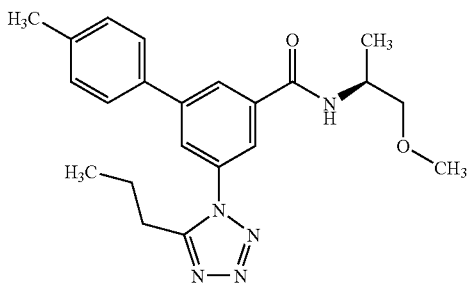 | 4'-Methyl-5-(5-propyl-tetrazol-1-yl)-biphenyl-3-carboxylic acid (2-methoxy-1-methyl-ethyl)-amide | 394 |
| 283 | 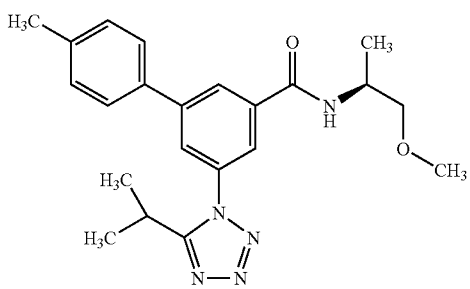 | 5-(5-Isopropyl-tetrazol-1-yl)-4'-methyl-biphenyl-3-carboxylic acid (2-methoxy-1-methyl-ethyl)-amide | 394 |
| 284 | 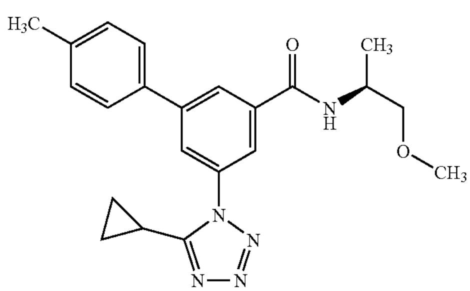 | 5-(5-Cyclopropyl-tetrazol-1-yl)-4'-methyl-biphenyl-3-carboxylic acid (2-methoxy-1-methyl-ethyl)-amide | 392 |
| 285 | 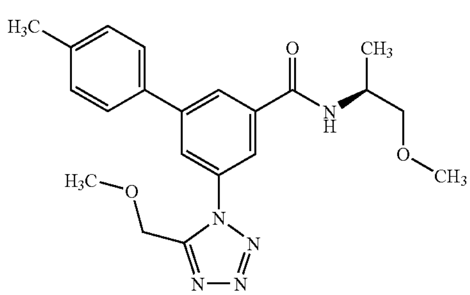 | 5-(5-Methoxymethyl-tetrazol-1-yl)-4'-methyl biphenyl-3-carboxylic acid (2-methoxy-1-methyl-ethyl)-amide | 396 |

TABLE 1-continued

| # | Structure | Name (Autonom ™) | Mp or M + H |
|---|---|---|---|
| 286 | 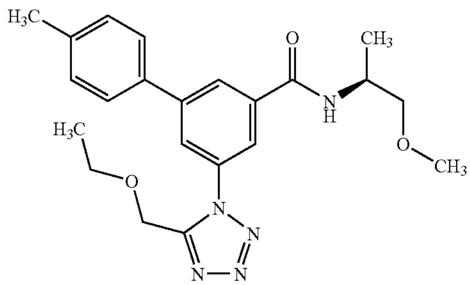 | 5-(5-Ethoxymethyl-tetrazol-1-yl)-4'-methyl-biphenyl-3-carboxylic acid (2-methoxy-1-methyl-ethyl)-amide | 410 |
| 287 | 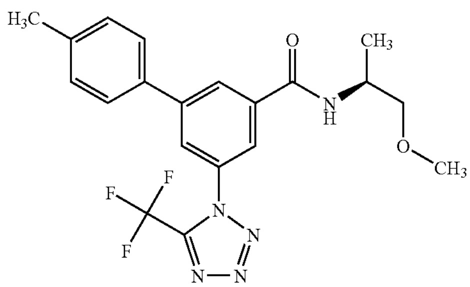 | 4'-Methyl-5-(5-trifluoromethyl-tetrazol-1-yl)-biphenyl-3-carboxylic acid (2-methoxy-1-methyl-ethyl)-amide | 420 |
| 288 | 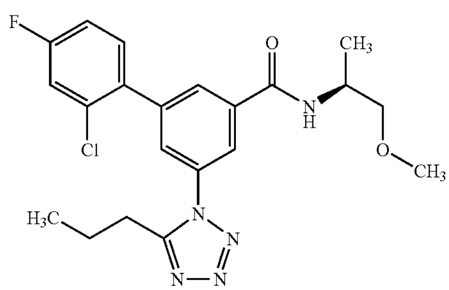 | 2'-Chloro-4'-fluoro-5-(5-propyl-tetrazol-1-yl)-biphenyl-3-carboxylic acid (2-methoxy-1-methyl-ethyl)-amide | 432 |
| 289 | 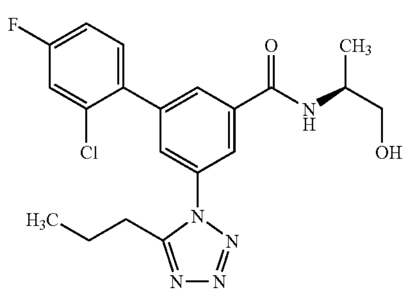 | 2'-Chloro-4'-fluoro-5-(5-propyl-tetrazol-1-yl)-biphenyl-3-carboxylic acid (2-hydroxy-1-methyl-ethyl)-amide | 418 |
| 290 | 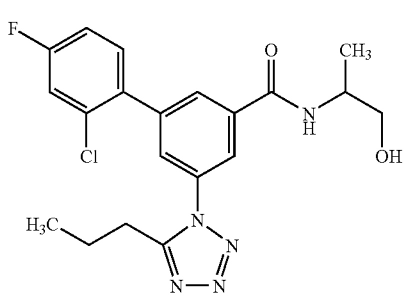 | 2'-Chloro-4'-fluoro-5-(5-propyl-tetrazol-1-yl)-biphenyl-3-carboxylic acid (2-hydroxy-1-methyl-ethyl)-amide | 418 |

TABLE 1-continued

| # | Structure | Name (Autonom ™) | Mp or M + H |
|---|---|---|---|
| 291 | 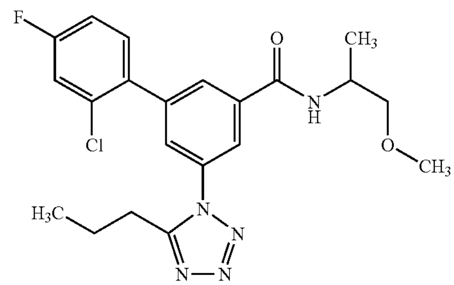 | 2'-Chloro-4'-fluoro-5-(5-propyl-tetrazol-1-yl)-biphenyl-3-carboxylic acid (2-methoxy-1-methyl-ethyl)-amide | 432 |
| 292 | 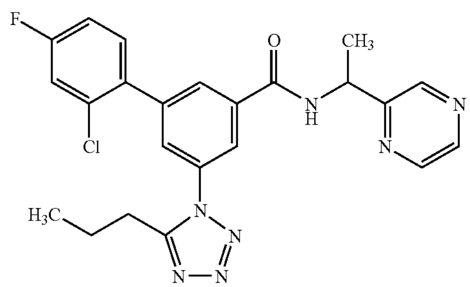 | 2'-Chloro-4'-fluoro-5-(5-propyl-tetrazol-1-yl)-biphenyl-3-carboxylic acid (1-pyrazin-2-yl-ethyl)-amide | 466 |
| 293 | 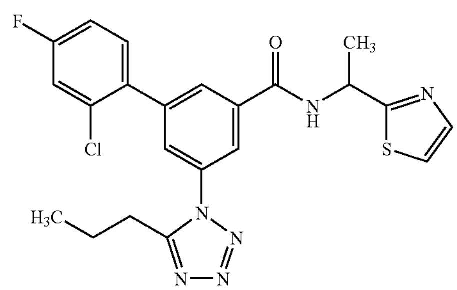 | 2'-Chloro-4'-fluoro-5-(5-propyl-tetrazol-1-yl)-biphenyl-3-carboxylic acid (1-thiazol-2-yl-ethyl)-amide | 471 |
| 294 | 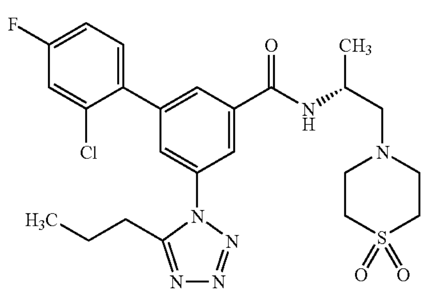 | 2'-Chloro-4'-fluoro-5-(5-propyl-tetrazol-1-yl)-biphenyl-3-carboxylic acid [2-(1,1-dioxo-1lambda*6*-thiomorpholin-4-yl)-1-methyl-ethyl]-amide | 535 |
| 295 | 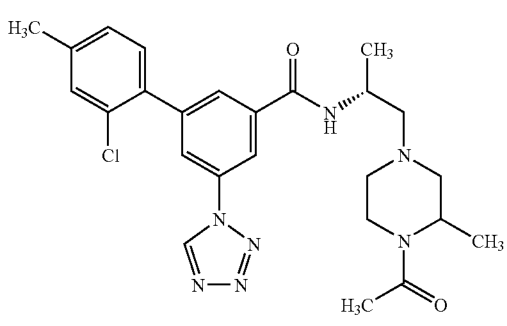 | 2'-Chloro-4'-methyl-5-tetrazol-1-yl-biphenyl-3-carboxylic acid [2-(4-acetyl-3-methyl-piperazin-1-yl)-1-methyl-ethyl]-amide | 497 |

| # | Structure | Name (Autonom ™) | Mp or M + H |
|---|---|---|---|
| 296 | 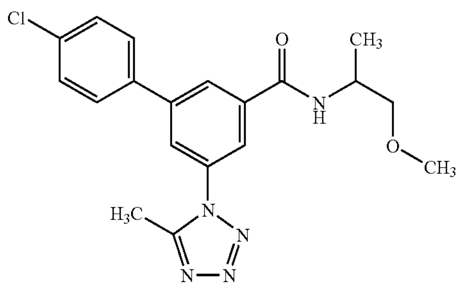 | 4'-Chloro-5-(5-methyl-tetrazol-1-yl)-biphenyl-3-carboxylic acid (2-methoxy-1-methyl-ethyl)-amide | 386 |
| 297 | 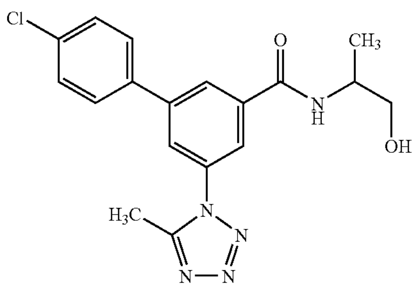 | 4'-Chloro-5-(5-methyl-tetrazol-1-yl)-biphenyl-3-carboxylic acid (2-hydroxy-1-methyl-ethyl)-amide | 372 |
| 298 | 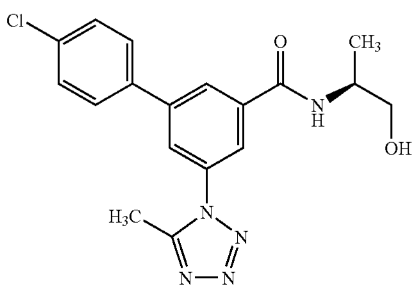 | 4'-Chloro-5-(5-methyl-tetrazol-1-yl)-biphenyl-3-carboxylic acid (2-hydroxy-1-methyl-ethyl)-amide | 372 |
| 299 | 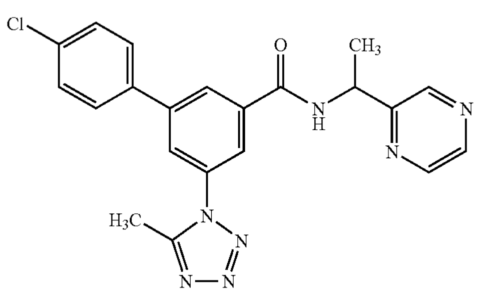 | 4'-Chloro-5-(5-methyl-tetrazol-1-yl)-biphenyl-3-carboxylic acid (1-pyrazin-2-yl-ethyl)-amide | 420 |
| 300 | 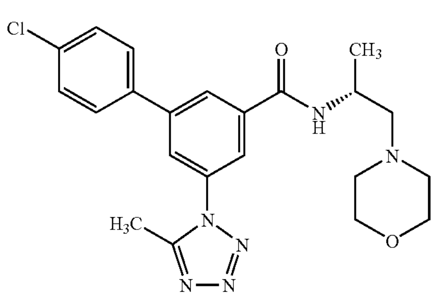 | 4'-Chloro-5-(5-methyl-tetrazol-1-yl)-biphenyl-3-carboxylic acid (1-methyl-2-morpholin-4-yl-ethyl)-amide | 441 |

TABLE 1-continued

| # | Structure | Name (Autonom ™) | Mp or M + H |
|---|---|---|---|
| 301 | 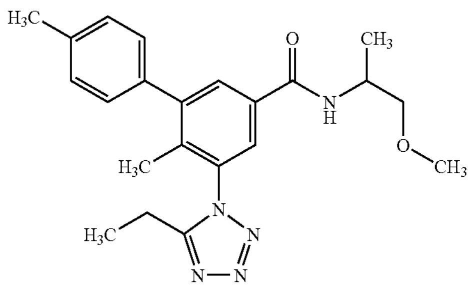 | 5-(5-Ethyl-tetrazol-1-yl)-6,4'-dimethyl-biphenyl-3-carboxylic acid (2-methoxy-1-methyl-ethyl)-amide | 394 |
| 302 | 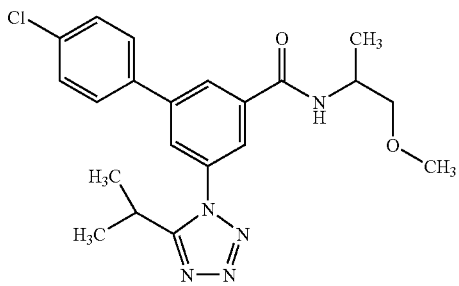 | 4'-Chloro-5-(5-isopropyl-tetrazol-1-yl)-biphenyl-3-carboxylic acid (2-methoxy-1-methyl-ethyl)-amide | 414 |
| 303 | 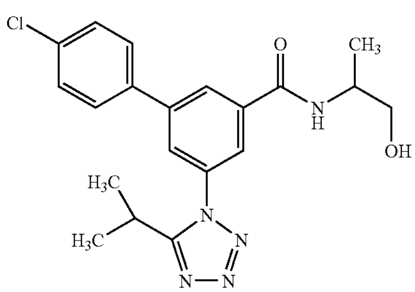 | 4'-Chloro-5-(5-isopropyl-tetrazol-1-yl)-biphenyl-3-carboxylic acid (2-hydroxy-1-methyl-ethyl)-amide | 400 |
| 304 | 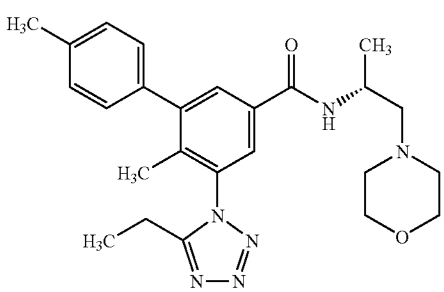 | 5-(5-Ethyl-tetrazol-1-yl)-6,4'-dimethyl-biphenyl-3-carboxylic acid (1-methyl-2-morpholin-4-yl-ethyl)-amide | 448 |
| 305 | 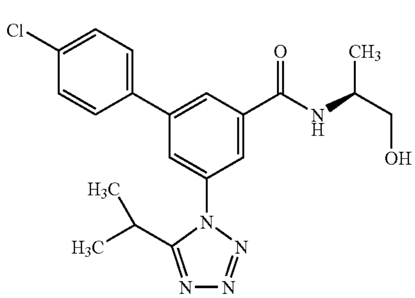 | 4'-Chloro-5-(5-isopropyl-tetrazol-1-yl)-biphenyl-3-carboxylic acid (2-hydroxy-1-methyl-ethyl)-amide | 400 |

TABLE 1-continued

| # | Structure | Name (Autonom ™) | Mp or M + H |
|---|---|---|---|
| 306 | 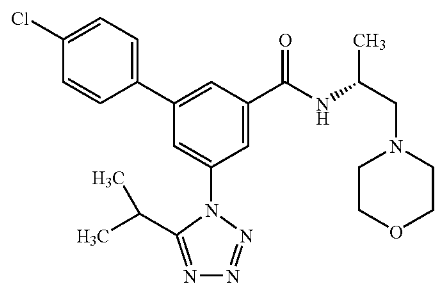 | 4'-Chloro-5-(5-isopropyl-tetrazol-1-yl)-biphenyl-3-carboxylic acid (1-methyl-2-morpholin-4-yl-ethyl)-amide | 469 |
| 307 | 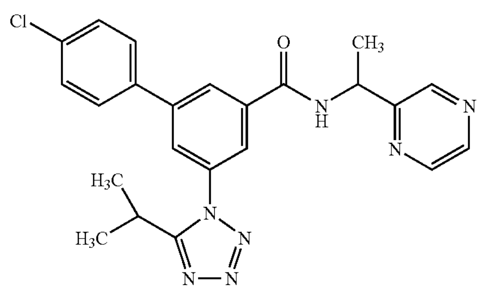 | 4'-Chloro-5-(5-isopropyl-tetrazol-1-yl)-biphenyl-3-carboxylic acid (1-pyrazin-2-yl-ethyl)-amide | 448 |
| 308 | 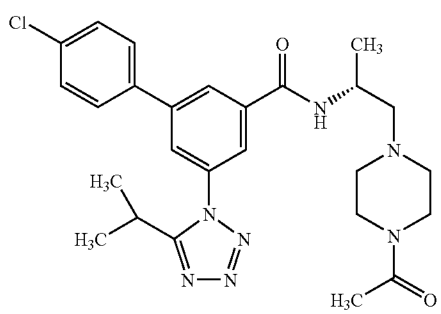 | 4'-Chloro-5-(5-isopropyl-tetrazol-1-yl)-biphenyl-3-carboxylic acid [2-(4-acetyl-piperazin-1-yl)-1-methyl-ethyl]-amide | 510 |
| 309 | 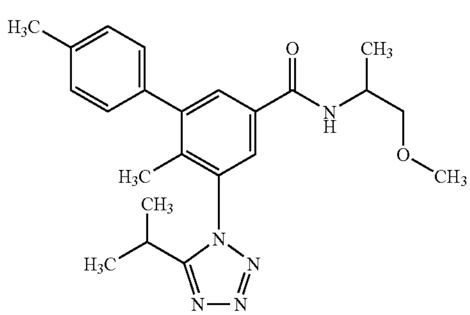 | 5-(5-Isopropyl-tetrazol-1-yl)-6,4'-dimethyl-biphenyl-3-carboxylic acid (2-methoxy-1-methyl-ethyl)-amide | 408 |
| 310 | 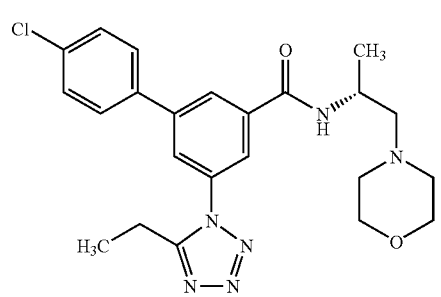 | 4'-Chloro-5-(5-ethyl-tetrazol-1-yl)-biphenyl-3-carboxylic acid (1-methyl-2-morpholin-4-yl-ethyl)-amide | 455 |

TABLE 1-continued

| # | Structure | Name (Autonom ™) | Mp or M + H |
|---|---|---|---|
| 311 | 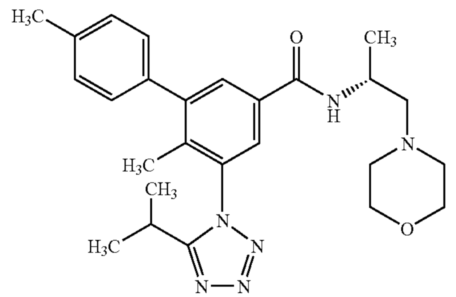 | 5-(5-Isopropyl-tetrazol-1-yl)-6,4'-dimethyl-biphenyl-3-carboxylic acid (1-methyl-2-morpholin-4-yl-ethyl)-amide | 463 |
| 312 | 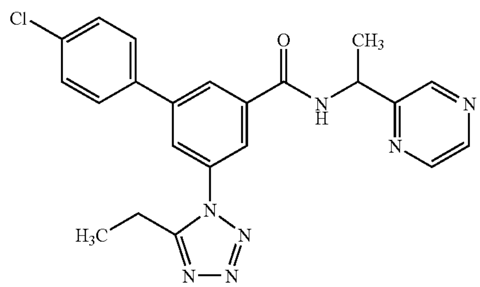 | 4'-Chloro-5-(5-ethyl-tetrazol-1-yl)-biphenyl-3-carboxylic acid (1-pyrazin-2-yl-ethyl)-amide | 434 |
| 313 | 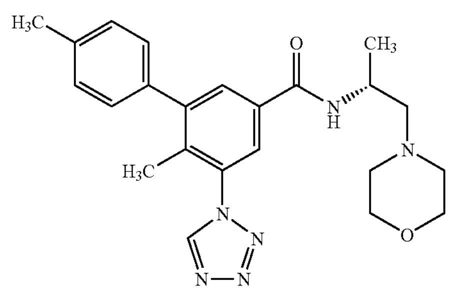 | 6,4'-Dimethyl-5-tetrazol-1-yl-biphenyl-3-carboxylic acid (1-methyl-2-morpholin-4-yl-ethyl)-amide | 421 |
| 314 | 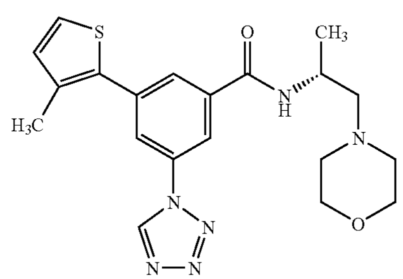 | N-((R)-1-Methyl-2-morpholin-4-yl-ethyl)-3-(3-methyl-thiophen-2-yl)-5-tetrazol-1-yl-benzamide | 413 |
| 315 | 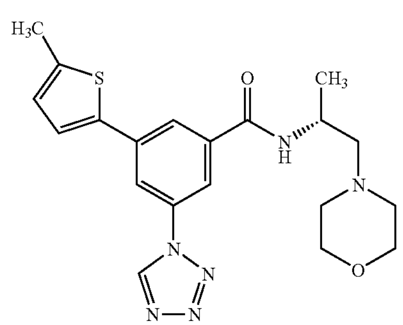 | N-((R)-1-Methyl-2-morpholin-4-yl-ethyl)-3-(5-methyl-thiophen-2-yl)-5-tetrazol-1-yl-benzamide | 413 |

TABLE 1-continued

| # | Structure | Name (Autonom ™) | Mp or M + H |
|---|---|---|---|
| 316 | 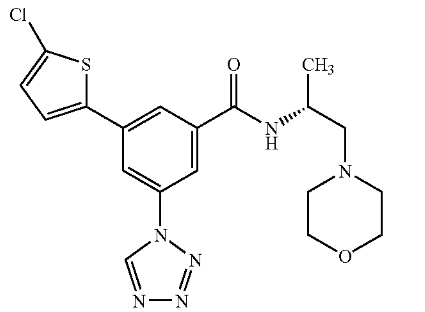 | 3-(5-Chloro-thiophen-2-yl)-N-((R)-1-methyl-2-morpholin-4-yl-ethyl)-5-tetrazol-1-yl-benzamide | 433 |
| 317 | 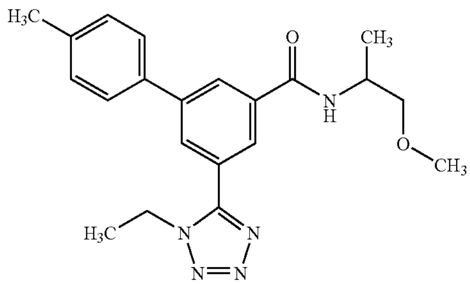 | 5-(1-Ethyl-1 H-tetrazol-5-yl)-4'-methyl-biphenyl-3-carboxylic acid (2-methoxy-1-methyl-ethyl)-amide | 380 |
| 318 | 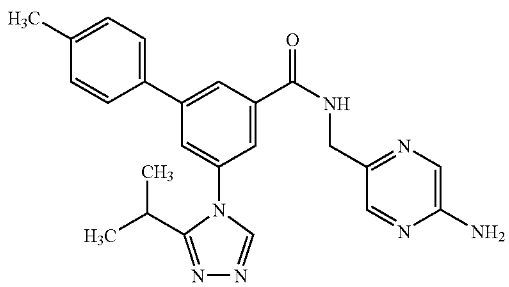 | 5-(5-Ethyl-tetrazol-1-yl)-4'-methyl-biphenyl-3-carboxylic acid (5-amino-pyrazin-2-ylmethyl)-amide | 429 |
| 319 | 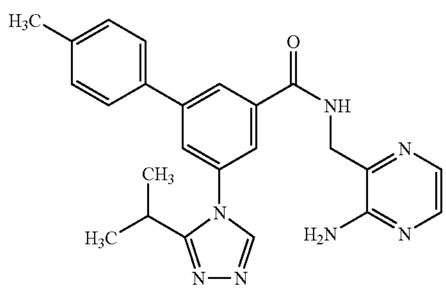 | 5-(5-Ethyl-tetrazol-1-yl)-4'-methyl-biphenyl-3-carboxylic acid (3-amino-pyrazin-2-ylmethyl)-amide | 429 |
| 320 | 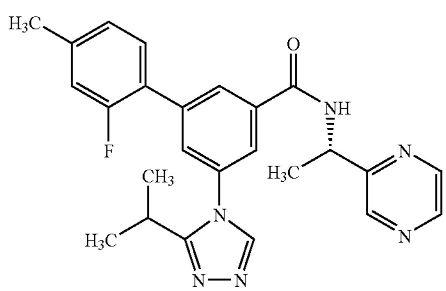 | 2'-Fluoro-5-(5-isopropyl-tetrazol-1-yl)-4'-methyl-biphenyl-3-carboxylic acid ((S)-1-pyrazin-2-yl-ethyl)-amide | 79.5-87.9° C. |

TABLE 1-continued

| # | Structure | Name (Autonom ™) | Mp or M + H |
|---|---|---|---|
| 321 | 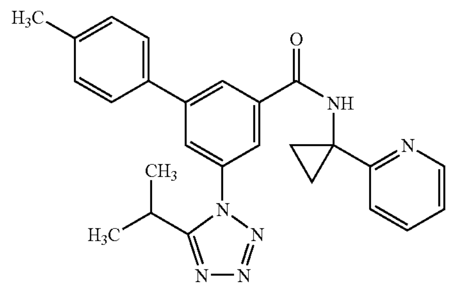 | 5-(5-Isopropyl-tetrazol-1-yl)-4'-methyl-biphenyl-3-carboxylic acid (1-pyridin-2-yl-cyclopropyl)-amide | 110.0-114.0° C. |
| 322 | 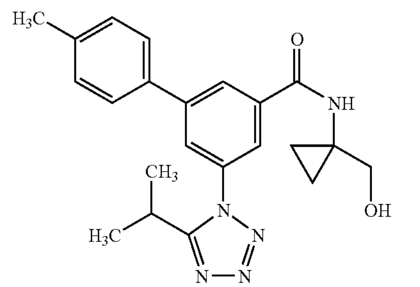 | 5-(5-Isopropyl-tetrazol-1-yl)-4'-methyl-biphenyl-3-carboxylic acid (1-hydroxymethyl-cylcopropyl)-amide | 392 |
| 323 | 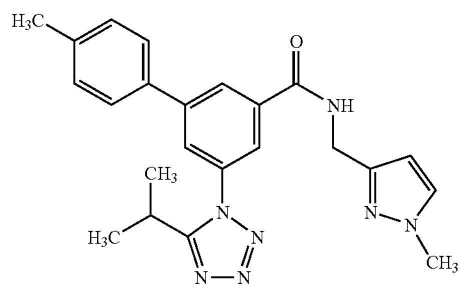 | 5-(5-Isopropyl-tetrazol-1-yl)-4'-methyl-biphenyl-3-carboxylic acid (1-methyl-1 H-pyrazol-3-ylmethyl)-amide | 416 |
| 324 | 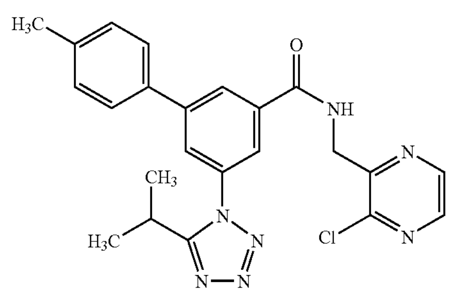 | 5-(5-Isopropyl-tetrazol-1-yl)-4'-methyl-biphenyl-3-carboxylic acid (3-chloro-pyrazin-2-ylmethyl)-amide | 198.5-200.5° C. |
| 325 | 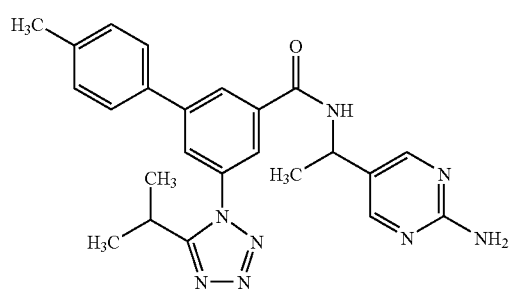 | 5-(5-Isopropyl-tetrazol-1-yl)-4'-methyl-biphenyl-3-carboxylic acid [1-(2-amino-pyrimidin-5-yl)-ethyl]-amide | 184.0-185.0° C. |

TABLE 1-continued

| # | Structure | Name (Autonom ™) | Mp or M + H |
|---|---|---|---|
| 326 | 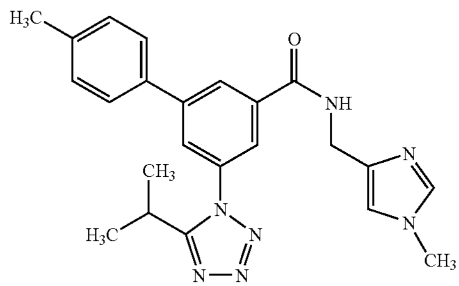 | 5-(5-Isopropyl-tetrazol-1-yl)-4'-methyl-biphenyl-3-carboxylic acid (1-methyl-1H-imidazol-4-ylmethyl)-amide | 218.0-220.3° C. |
| 327 | 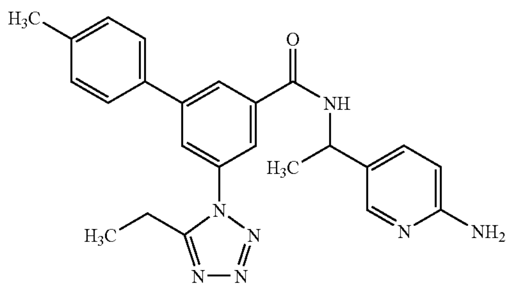 | 5-(5-Ethyl-tetrazol-1-yl)-4'-methyl-biphenyl-3-carboxylic acid [1-(6-amino-pyridin-3-yl)-ethyl]-amide | 428 |
| 328 | 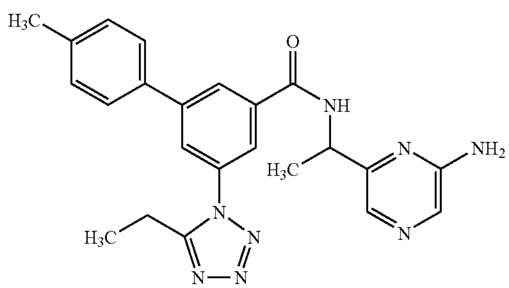 | 5-(5-Ethyl-tetrazol-1-yl)-4'-methyl-biphenyl-3-carboxylic acid [1-(6-amino-pyridin-2-yl)-ethyl]-amide | 429 |
| 329 | 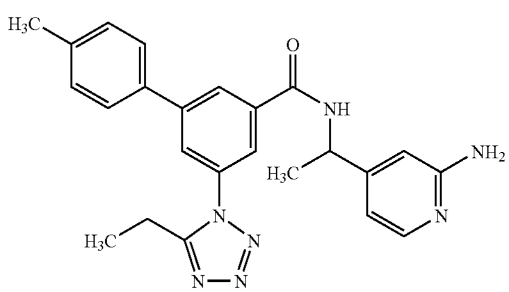 | 5-(5-Ethyl-tetrazol-1-yl)-4'-methyl-biphenyl-3-carboxylic acid [1-(2-amino-pyridin-4-yl)-ethyl]-amide | 428 |
| 330 | 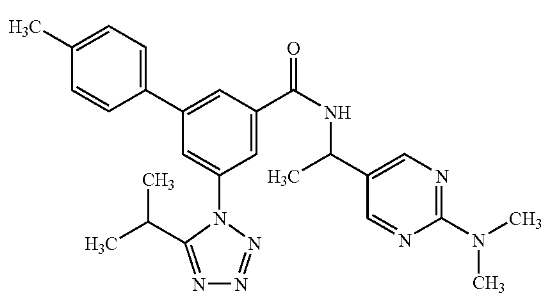 | 5-(5-Isopropyl-tetrazol-1-yl)-4'-methyl-biphenyl-3-carboxylic acid [1-(2-dimethylamino-pyrimidin-5-yl)-ethyl]-amide | 471 |

TABLE 1-continued

| # | Structure | Name (Autonom ™) | Mp or M + H |
|---|---|---|---|
| 331 | 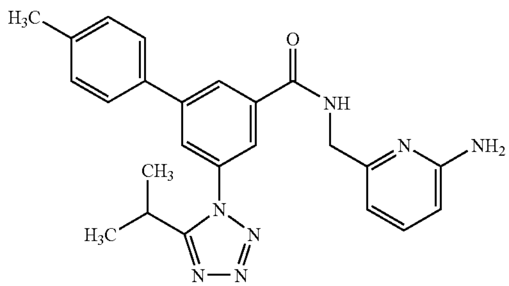 | 5-(5-Isopropyl-tetrazol-1-yl)-4'-methyl-biphenyl-3-carboxylic acid (6-amino-pyridin-2-ylmethyl)-amide | 428 |
| 332 | 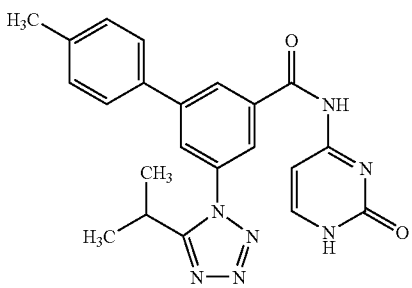 | 2'-Fluoro-5-(5-isopropyl-tetrazol-1-yl)-4'-methyl-biphenyl-3-carboxylic acid (2-oxo-1,2-dihydro-pyrimidin-4-yl)-amide | 416 |
| 333 | 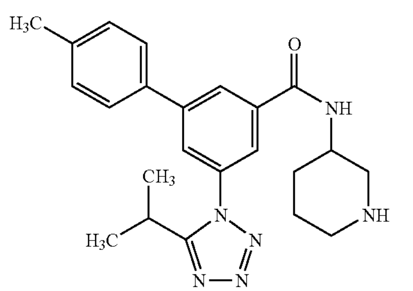 | 5-(5-Isopropyl-tetrazol-1-yl)-4'-methyl-biphenyl-3-carboxylic acid piperidin-3-ylamide | 405 |
| 334 | 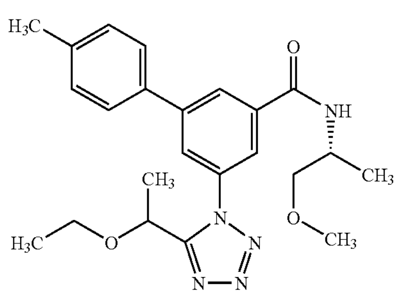 | 5-[5-(1-Ethoxy-ethyl)-tetrazol-1-yl]-4'-methyl-biphenyl-3-carboxylic acid ((R)-2-methoxy-1-methyl-ethyl)-amide | 424 |
| 335 | 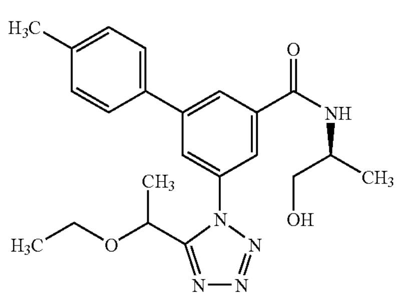 | 5-[5-(1-Ethoxy-ethyl)-tetrazol-1-yl]-4'-methyl-biphenyl-3-carboxylic acid ((S)-2-hydroxy-1-methyl-ethyl)-amide | 410 |

TABLE 1-continued

| # | Structure | Name (Autonom ™) | Mp or M + H |
|---|---|---|---|
| 336 | 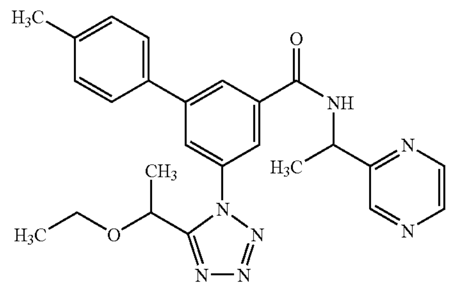 | 5-[5-(1-Ethoxy-ethyl)-tetrazol-1-yl]-4'-methyl-biphenyl-3-carboxylic acid (1-pyrazin-2-yl-ethyl)-amide | 474 |
| 337 | 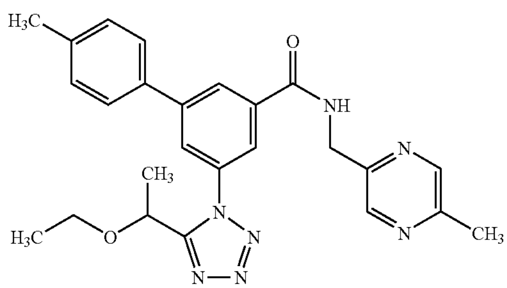 | 5-[5-(1-Ethoxy-ethyl)-tetrazol-1-yl]-4'-methyl-biphenyl-3-carboxylic acid (5-methyl-pyrazin-2-ylmethyl)-amide | 474 |
| 338 | 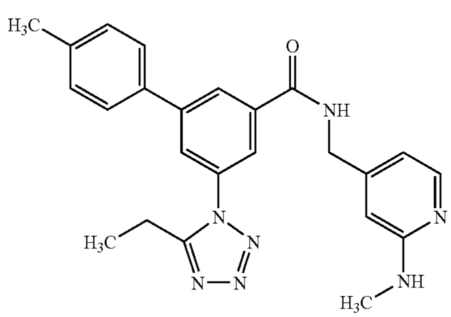 | 5-(5-Ethyl-tetrazol-1-yl)-4'-methyl-biphenyl-3-carboxylic acid (2-methylamino-pyridin-4-ylmethyl)-amide | 444 |
| 339 | 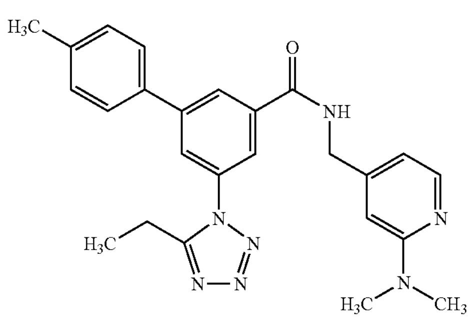 | 5-(5-Ethyl-tetrazol-1-yl)-4'-methyl-biphenyl-3-carboxylic acid (2-dimethylamino-pyridin-4-ylmethyl)-amide | 458 |
| 340 | 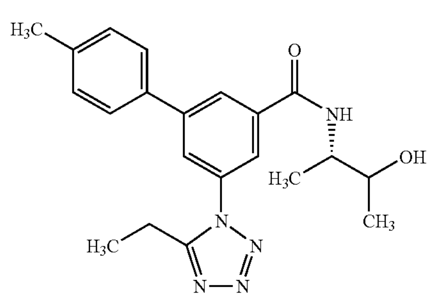 | 5-(5-Isopropyl-tetrazol-1-yl)-4'-methyl-biphenyl-3-carboxylic acid ((S)-2-hydroxy-1-methyl-propyl)-amide | 380 |

TABLE 1-continued

| # | Structure | Name (Autonom ™) | Mp or M + H |
|---|---|---|---|
| 341 | 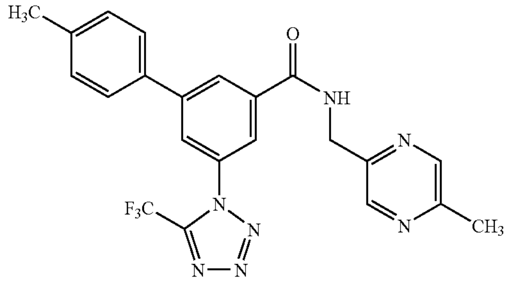 | 4'-Methyl-5-(5-trifluoromethyl-tetrazol-1-yl)-biphenyl-3-carboxylic acid (5-methyl-pyrazin-2-ylmethyl)-amide | 470 |
| 342 | 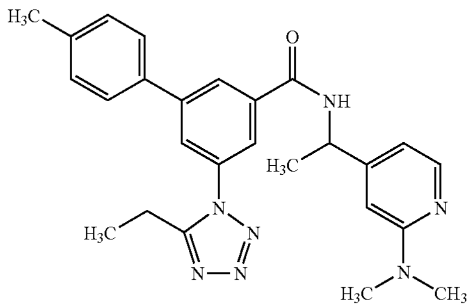 | 5-(5-Ethyl-tetrazol-1-yl)-4'-methyl-biphenyl-3-carboxylic acid [1-(2-dimethylamino-pyridin-4-yl)-ethyl]-amide | 472 |
| 343 | 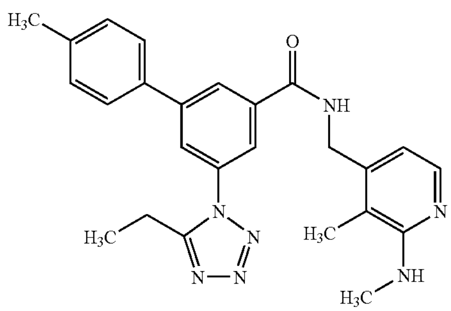 | 5-(5-Ethyl-tetrazol-1-yl)-4'-methyl-biphenyl-3-carboxylic acid [1-(2-methylamino-pyridin-4-yl)-ethyl]-amide | 458 |
| 344 | 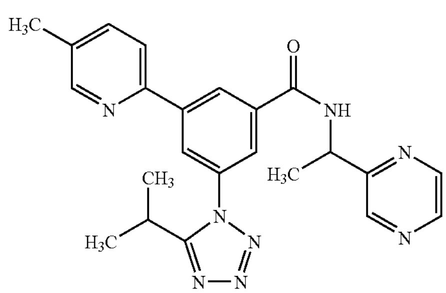 | 3-(5-Isopropyl-tetrazol-1-yl)-5-(5-methyl-pyridin-2-yl)-N-(1-pyrazin-2-yl-ethyl)-benzamide | 429 |
| 345 | 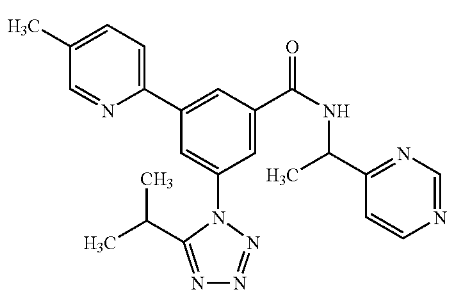 | 3-(5-Isopropyl-tetrazol-1-yl)-5-(5-methyl-pyridin-2-yl)-N-(1-pyrimidin-5-yl-ethyl)-benzamide | 429 |

TABLE 1-continued

| # | Structure | Name (Autonom ™) | Mp or M + H |
|---|---|---|---|
| 346 | 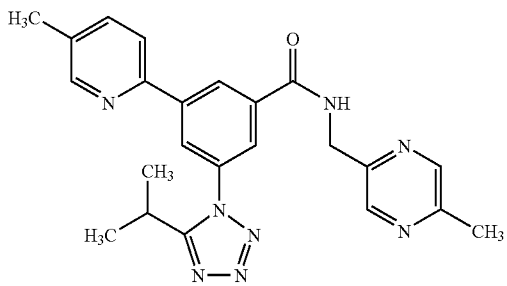 | 3-(5-Isopropyl-tetrazol-1-yl)-N-(5-methyl-pyrazin-2-ylmethyl)-5-(5-methyl-pyridin-2-yl)-benzamide | 165.0-168.0° C. |
| 347 | 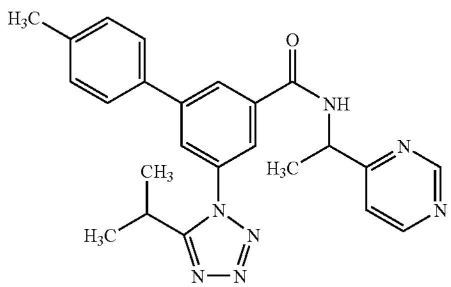 | 5-(5-Isopropyl-tetrazol-1-yl)-4'-methyl-biphenyl-3-carboxylic acid (1-pyrimidin-5-yl-ethyl)-amide | 428 |
| 348 | 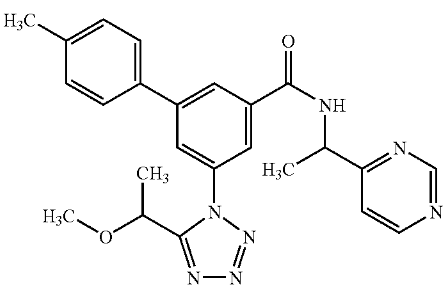 | 5-[5-(1-Methoxy-ethyl)-tetrazol-1-yl]-4'-methyl-biphenyl-3-carboxylic acid (1-pyrimidin-5-yl-ethyl)-amide | 444 |
| 349 | 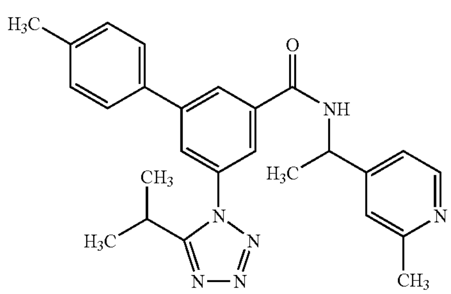 | 5-(5-Isopropyl-tetrazol-1-yl)-4'-methyl-biphenyl-3-carboxylic acid [1-(2-methyl-pyridin-4-yl)-ethyl]-amide | 441 |
| 350 | 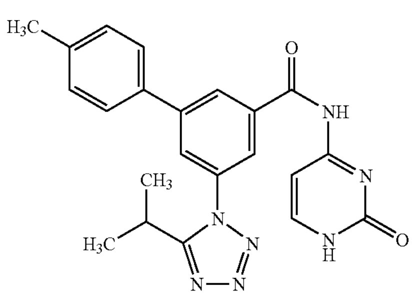 | 5-(5-Isopropyl-tetrazol-1-yl)-4'-methyl-biphenyl-3-carboxylic acid (2-oxo-1,2-dihydro-pyrimidin-4-yl)-amide | 416 |

TABLE 1-continued

| # | Structure | Name (Autonom ™) | Mp or M + H |
|---|---|---|---|
| 351 | 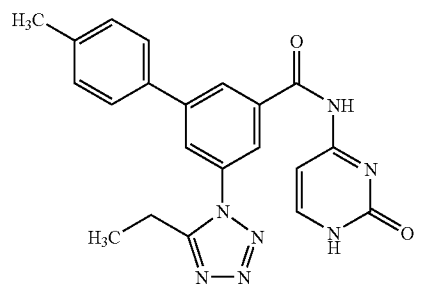 | 5-(5-Ethyl-tetrazol-1-yl)-4'-methyl-biphenyl-3-carboxylic acid (2-oxo-1,2-dihydro-pyrimidin-4-yl)-amide | 402 |
| 352 | 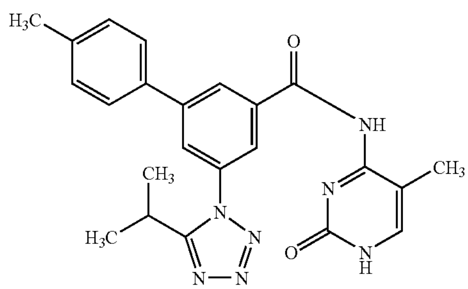 | 5-(5-Isopropyl-tetrazol-1-yl)-4'-methyl-biphenyl-3-carboxylic acid (5-methyl-2-oxo-1,2-dihydro-pyrimidin-4-yl)-amide | 430 |
| 353 | 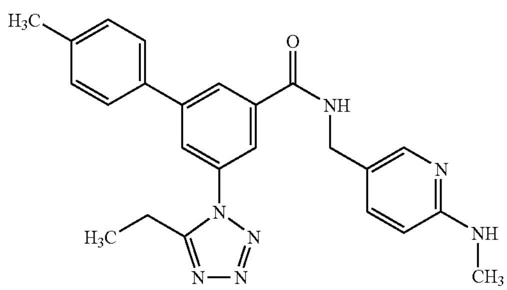 | 5-(5-Ethyl-tetrazol-1-yl)-4'-methyl-biphenyl-3-carboxylic acid (6-methylamino-pyridin-3-ylmethyl)-amide | 428 |
| 354 | 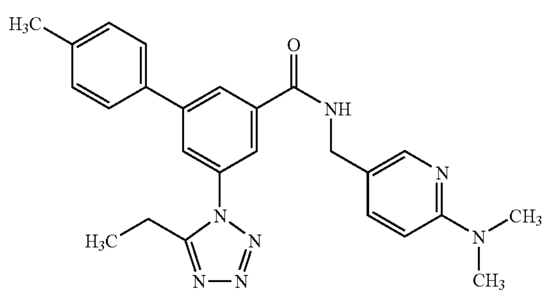 | 5-(5-Ethyl-tetrazol-1-yl)-4'-methyl-biphenyl-3-carboxylic acid (6-dimethylamino-pyridin-3-ylmethyl)-amide | 442 |
| 355 | 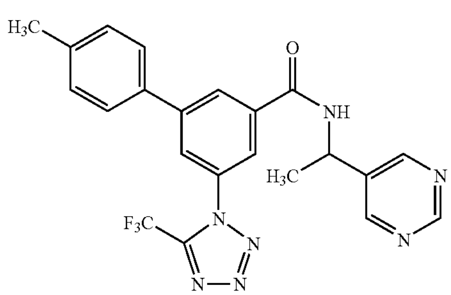 | 4'-Methyl-5-(5-trifluoromethyl-tetrazol-1-yl)-biphenyl-3-carboxylic acid (1-pyrimidin-5-yl-ethyl)-amide | 454 |

TABLE 1-continued

| # | Structure | Name (Autonom ™) | Mp or M + H |
|---|---|---|---|
| 356 | 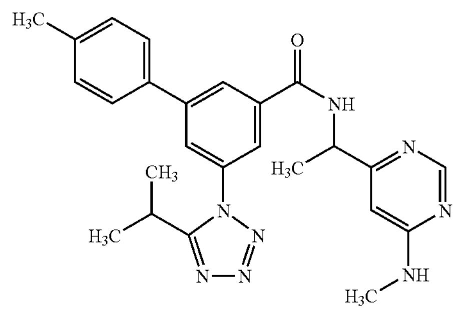 | 5-(5-Isopropyl-tetrazol-1-yl)-4'-methyl-biphenyl-3-carboxylic acid [(S)-1-(6-methylamino-pyrimidin-4-yl)-ethyl]-amide | 108.0-109.4° C. |
| 357 | 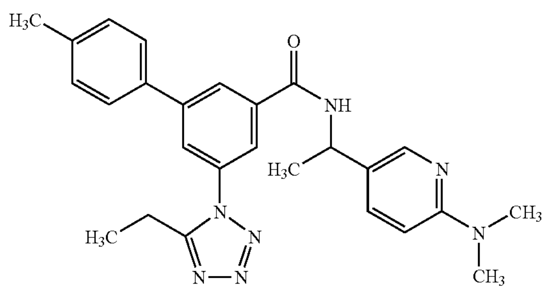 | 5-(5-Ethyl-tetrazol-1-yl)-4'-methyl-biphenyl-3-carboxylic acid [1-(6-dimethylamino-pyridin-3-yl)-ethyl]-amide | 456 |
| 358 | 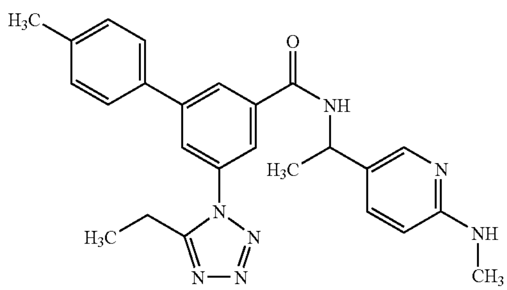 | 5-(5-Ethyl-tetrazol-1-yl)-4'-methyl-biphenyl-3-carboxylic acid [1-(6-methylamino-pyridin-3-yl)-ethyl]-amide | 442 |
| 359 | 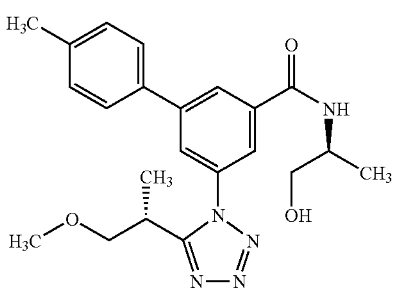 | 5-[5-((R)-2-Methoxy-1-methyl-ethyl)-tetrazol-1-yl]-4'methyl-biphenyl-3-carboxylic acid ((S)-2-hydroxy-1-methyl-ethyl)-amide | 410 |
| 360 | 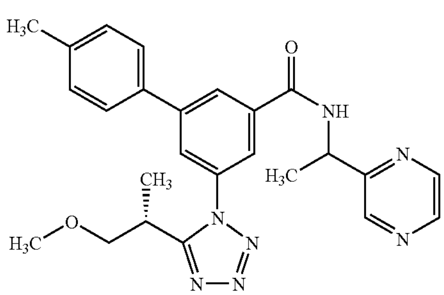 | 5-[5-((R)-2-Methoxy-1-methyl-ethyl)-tetrazol-1-yl]-4'methyl-biphenyl-3-carboxylic acid (1-pyrazin-2-yl-ethyl)-amide | 458 |

TABLE 1-continued

| # | Structure | Name (Autonom ™) | Mp or M + H |
|---|---|---|---|
| 361 | 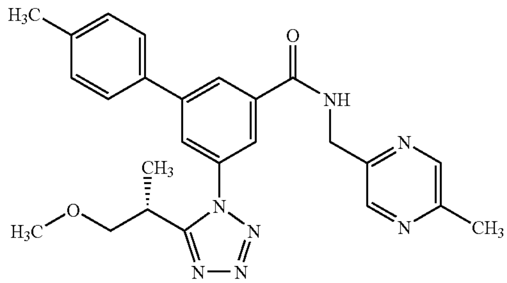 | 5-[5-((R)-2-Methoxy-1-methyl-ethyl)-tetrazol-1-yl]-4'methyl-biphenyl-3-carboxylic acid (5-methyl-pyrazin-2-ylmethyl)-amide | 458 |
| 362 | 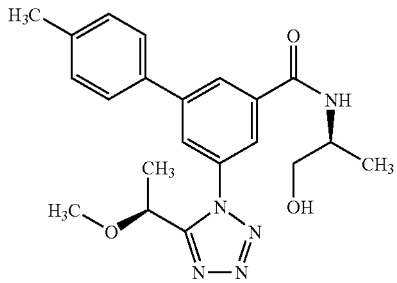 | 5-[3-((S)-1-Methoxy-ethyl)-tetrazol-1-yl]-4'-methyl-biphenyl-3-carboxylic acid ((S)-2-hydroxy-1-methyl-ethyl)-amide | 396 |
| 363 | 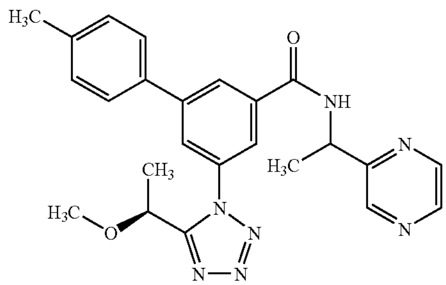 | 5-[5-((S)-1-Methoxy-ethyl)-tetrazol-1-yl]-4'-methyl-biphenyl-3-carboxylic acid (1-pyrazin-2-yl-ethyl)-amide | 444 |
| 364 | 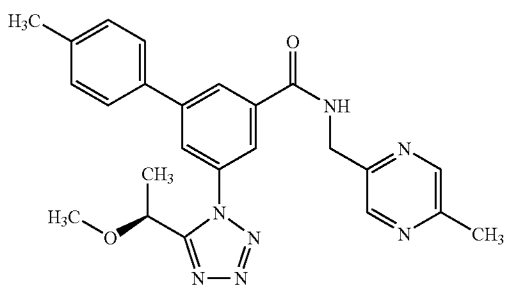 | 5-[5-((S)-1-Methoxy-ethyl)-tetrazol-1-yl]-4'-methyl-biphenyl-3-carboxylic acid (5-methyl-pyrazin-2-ylmethyl)-amide | 444 |
| 365 | 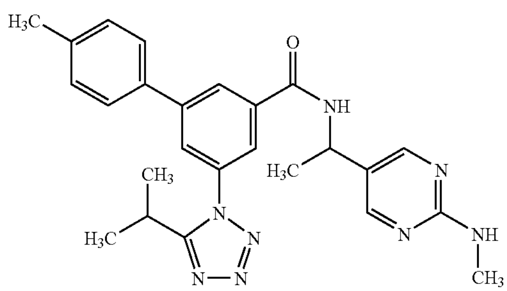 | 5-(5-Isopropyl-tetrazol-1-yl)-4'-methyl-biphenyl-3-carboxylic acid [1-(2-methylamino-pyrimidin-5-yl)-ethyl]-amide | 154.0-155.0° C. |

TABLE 1-continued

| # | Structure | Name (Autonom ™) | Mp or M + H |
|---|---|---|---|
| 366 | 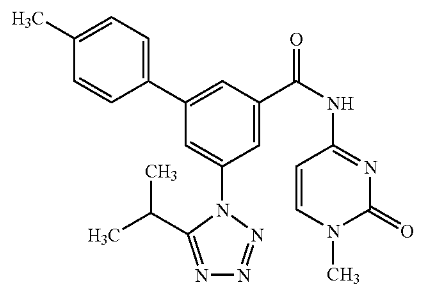 | 5-(5-Isopropyl-tetrazol-1-yl)-4'-methyl-biphenyl-3-carboxylic acid (1-methyl-2-oxo-1,2-dihydro-pyrimidin-4-yl)-amide | 430 |
| 367 | 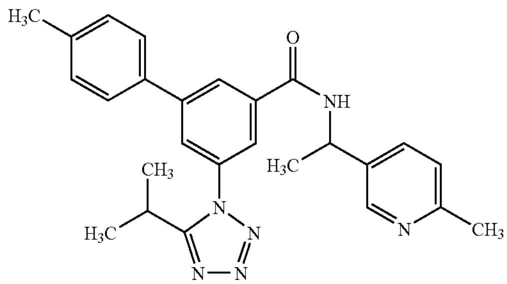 | 5-(5-Isopropyl-tetrazol-1-yl)-4'-methyl-biphenyl-3-carboxylic acid [1-(6-methyl-pyridin-3-yl)-ethyl]-amide | 441 |
| 368 | 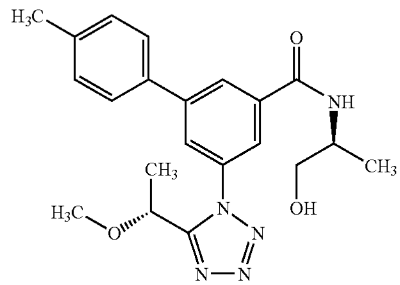 | 5-[5-((R)-1-Methoxy-ethyl)-tetrazol-1-yl]-4'-methyl-biphenyl-3-carboxylic acid ((S)-2-hydroxy-1-methyl-ethyl)-amide | 396 |
| 369 | 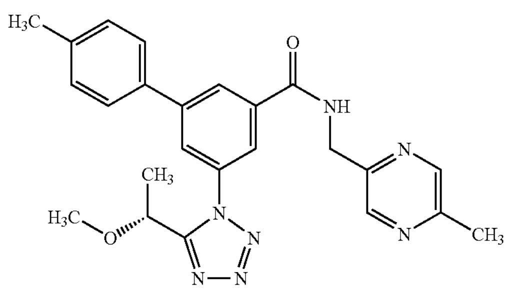 | 5-[5-((R)-1-Methoxy-ethyl)-tetrazol-1-yl]-4'-methyl-biphenyl-3-carboxylic acid (5-methyl-pyrazin-2-ylmethyl)-amide | 444 |
| 370 | 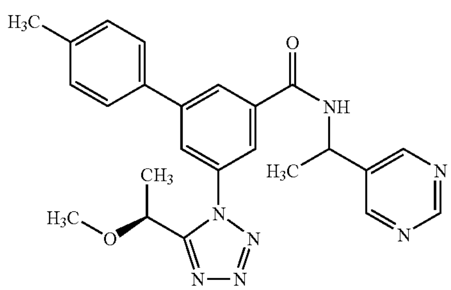 | 5-[5-((S)-1-Methoxy-ethyl)-tetrazol-1-yl]-4'-methyl-biphenyl-3-carboxylic acid (1-pyrimidin-5-yl-ethyl)-amide | 444 |

TABLE 1-continued

| # | Structure | Name (Autonom ™) | Mp or M + H |
|---|---|---|---|
| 371 | 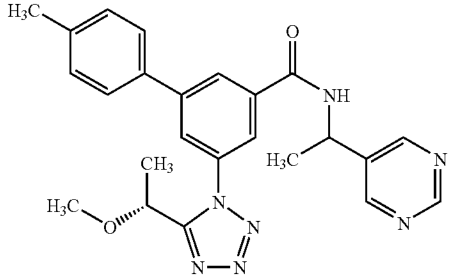 | 5-[5-((R)-1-Methoxy-ethyl)-tetrazol-1-yl]-4'-methyl-biphenyl-3-carboxylic acid (1-pyrimidin-5-yl-ethyl)-amide | 444 |
| 372 | 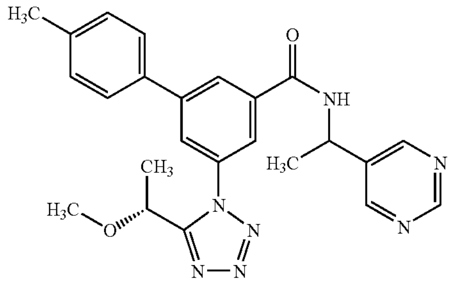 | 5-[5-(1-Methoxy-ethyl)-tetrazol-1-yl]-4'-methyl-biphenyl-3-carboxylic acid (1-pyrimidin-5-yl-ethyl)-amide | 444 |
| 373 | 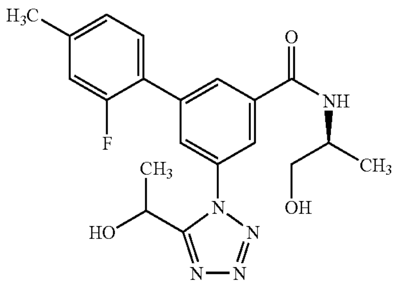 | 2'-Fluoro-5-[5-(1-hydroxy-ethyl)-tetrazol-1-yl]-4'-methyl-biphenyl-3-carboxylic acid ((S)-2-hydroxy-1-methyl-ethyl)-amide | 400 |
| 374 | 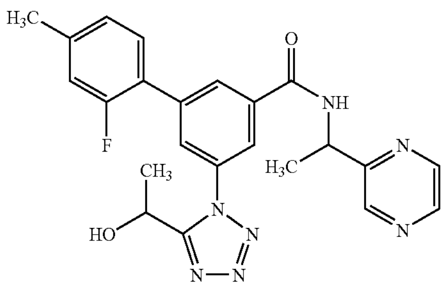 | 2'-Fluoro-5-[5-(1-hydroxy-ethyl)-tetrazol-1-yl]-4'-methyl-biphenyl-3-carboxylic acid (1-pyrazin-2-yl-ethyl)-amide | 448 |
| 375 | 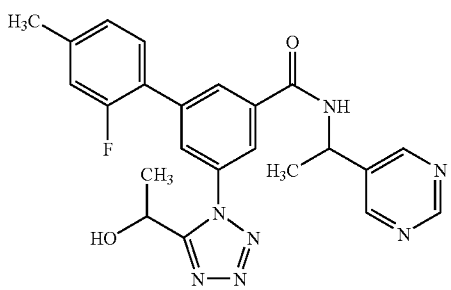 | 2'-Fluoro-5-[5-(1-hydroxy-ethyl)-tetrazol-1-yl]-4'-methyl-biphenyl-3-carboxylic acid (1-pyrimidin-5-yl-ethyl)-amide | 448 |

TABLE 1-continued

| # | Structure | Name (Autonom ™) | Mp or M + H |
|---|---|---|---|
| 376 | 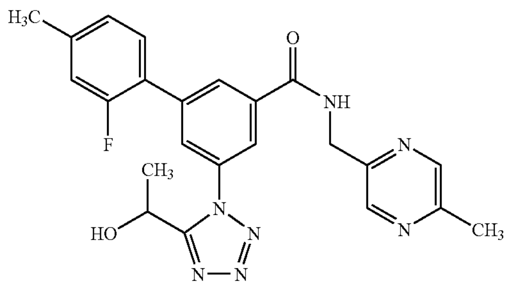 | 2'-Fluoro-5-[5-(1-hydroxy-ethyl)-tetrazol-1-yl]-4'-methyl-biphenyl-3-carboxylic acid (5-methyl-pyrazin-2-ylmethyl)-amide | 448 |
| 377 | 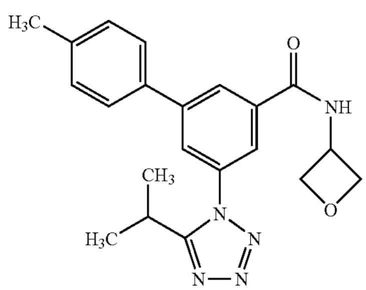 | 5-(5-Isopropyl-tetrazol-1-yl)-4'-methyl-biphenyl-3-carboxylic acid oxetan-3-ylamide | 378 |
| 378 | 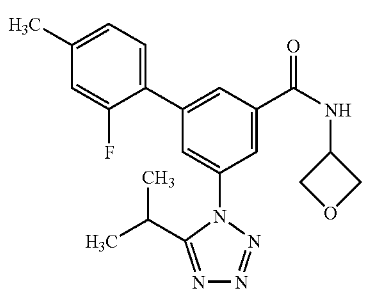 | 2'-Fluoro-5-(5-isopropyl-tetrazol-1-yl)-4'-methyl-biphenyl-3-carboxylic acid oxetan-3-ylamide | 396 |
| 379 | 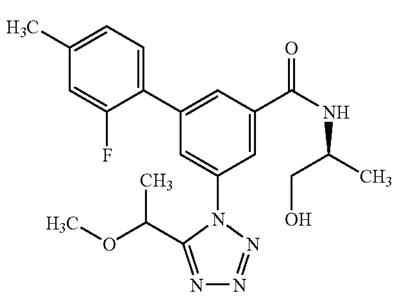 | 2'-Fluoro-5-[5-(1-methoxy-ethyl)-tetrazol-1-yl]-4'-methyl-biphenyl-3-carboxylic acid ((S)-2-hydroxy-1-methyl-ethyl)-amide | 414 |
| 380 | 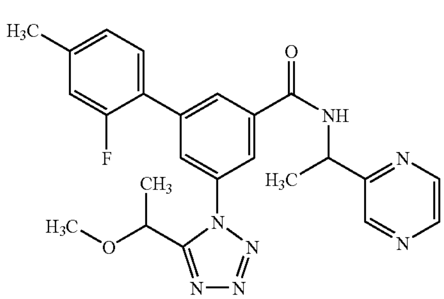 | 2'-Fluoro-5-[5-(1-methoxy-ethyl)-tetrazol-1-yl]-4'-methyl-biphenyl-3-carboxylic acid (1-pyrazin-2-yl-ethyl)-amide | 462 |

TABLE 1-continued

| # | Structure | Name (Autonom ™) | Mp or M + H |
|---|---|---|---|
| 381 | 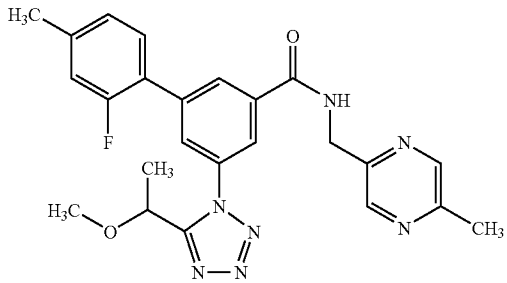 | 2'-Fluoro-5-[5-(1-methoxy-ethyl)-tetrazol-1-yl]-4'-methyl-biphenyl-3-carboxylic acid (5-methyl-pyrazin-2-ylmethyl)-amide | 462 |
| 382 | 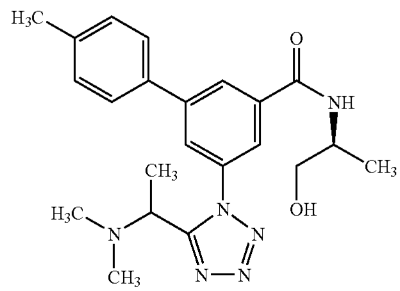 | 5-[5-(1-Dimethylamino-ethyl)-tetrazol-1-yl]-4'-methyl-biphenyl-3-carboxylic acid ((S)-2-hydroxy-1-methyl-ethyl)-amide | 409 |
| 383 | 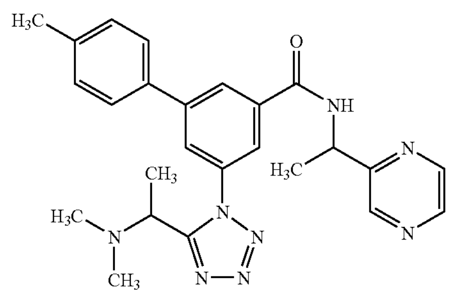 | 5-[5-(1-Dimethylamino-ethyl)-tetrazol-1-yl]-4'-methyl-biphenyl-3-carboxylic acid (1-pyrazin-2-yl-ethyl)-amide | 457 |
| 384 | 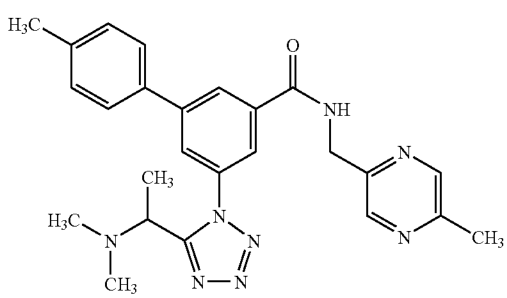 | 5-[5-(1-Dimethylamino-ethyl)-tetrazol-1-yl]-4'-methyl-biphenyl-3-carboxylic acid (5-methyl-pyrazin-2-ylmethyl)-amide | 457 |
| 385 | 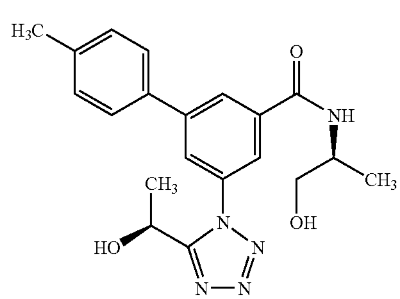 | 5-[5-((S)-1-Hydroxy-ethyl)-tetrazol-1-yl]4'-methyl-biphenyl-3-carboxylic acid ((S)-2-hydroxy-1-methyl-ethyl)-amide | 382 |

TABLE 1-continued

| # | Structure | Name (Autonom ™) | Mp or M + H |
|---|---|---|---|
| 386 | 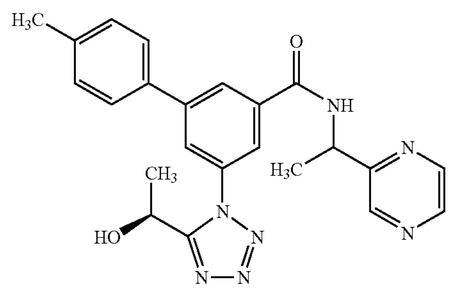 | 5-[5-((S)-1-Hydroxy-ethyl)-tetrazol-1-yl]4'-methyl-biphenyl-3-carboxylic acid (1-pyrazin-2-yl-ethyl)-amide | 430 |
| 387 | 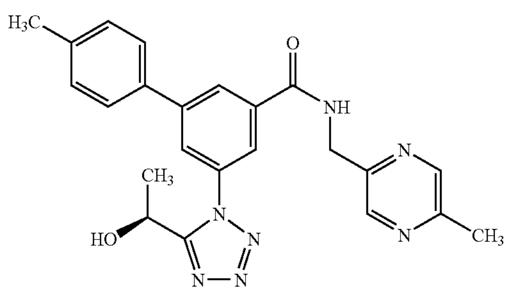 | 5-[5-((S)-1-Hydroxy-ethyl)-tetrazol-1-yl]4'-methyl-biphenyl-3-carboxylic acid (5-methyl-pyrazin-2-ylmethyl)-amide | 430 |
| 388 | 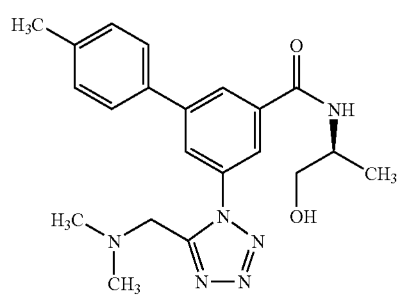 | 5-(5-Dimethylaminomethyl-tetrazol-1-yl)-4'-methyl-biphenyl-3-carboxylic acid ((S)-2-hydroxy-1-methyl-ethyl)-amide | 395 |
| 389 | 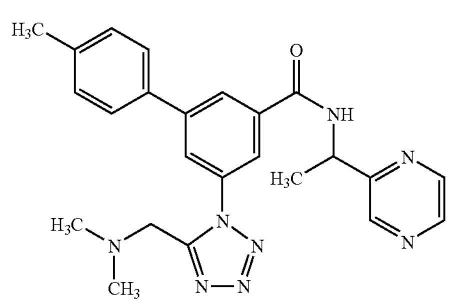 | 5-(5-Dimethylaminomethyl-tetrazol-1-yl)-4'-methyl-biphenyl-3-carboxylic acid (1-pyrazin-2-yl-ethyl)-amide | 443 |
| 390 | 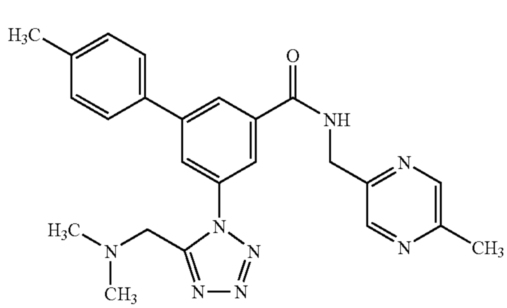 | 5-(5-Dimethylaminomethyl-tetrazol-1-yl)-4'-methyl-biphenyl-3-carboxylic acid (5-methyl-pyrazin-2-ylmethyl)-amide | 443 |

TABLE 1-continued

| # | Structure | Name (Autonom ™) | Mp or M + H |
|---|---|---|---|
| 391 | 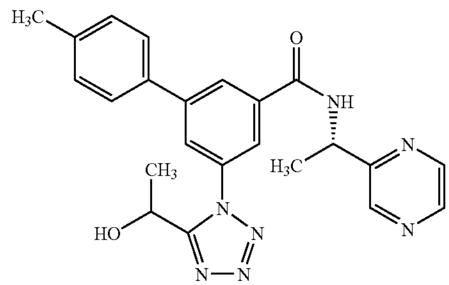 | 5-[5-(1-Hydroxy-ethyl)-tetrazol-1-yl]-4'-methyl-biphenyl-3-carboxylic acid ((S)-1-pyrazin-2-yl-ethyl)-amide | 90.0-92.0° C. |
| 492 | 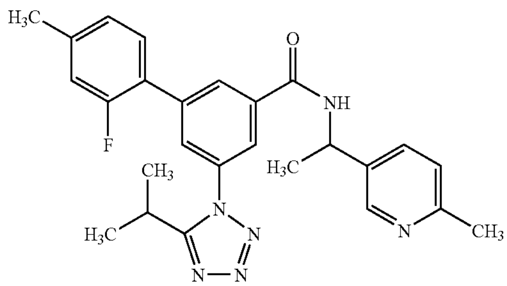 | 2'-Fluoro-5-(5-isopropyl-tetrazol-1-yl)-α'-methyl-biphenyl-3-carboxylic acid [1-(6-methyl-pyridin-3-yl)-ethyl]-amide | 459 |
| 393 | 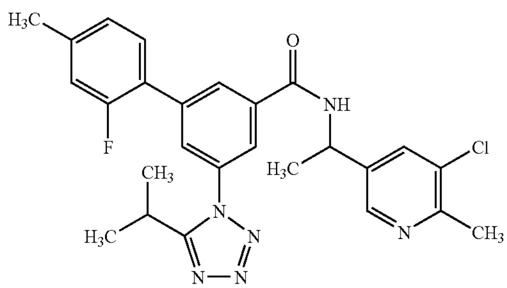 | 2'-Fluoro-5-(5-isopropyl-tetrazol-1-yl)-α'-methyl-biphenyl-3-carboxylic acid [1-(6-chloro-5-methyl-pyridin-2-yl)-ethyl]-amide | 493 |
| 394 | 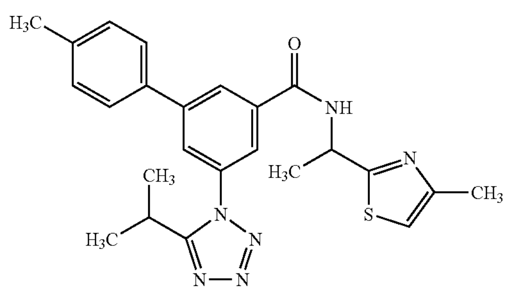 | 5-(5-Isopropyl-tetrazol-1-yl)-4'-methyl-biphenyl-3-carboxylic acid [1-(4-methyl-thiazol-2-yl)-ethyl]-amide | 447 |
| 396 | 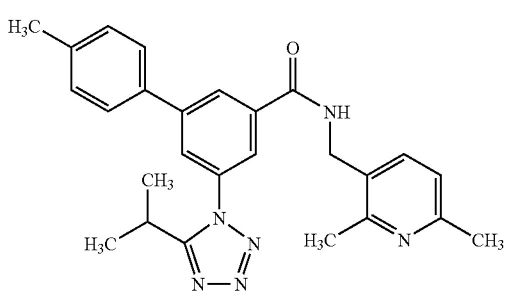 | 5-(5-Ethyl-tetrazol-1-yl)-4'-methyl-biphenyl-3-carboxylic acid (2,6-dimethyl-pyridin-3-ylmethyl)-amide | 441 |

TABLE 1-continued

| # | Structure | Name (Autonom ™) | Mp or M + H |
|---|---|---|---|
| 396 | 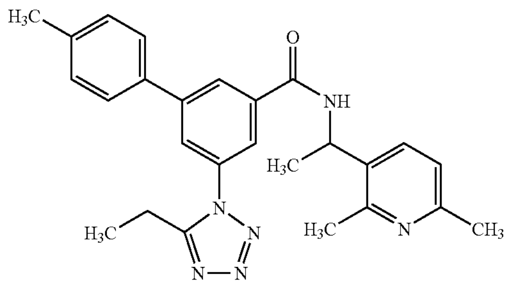 | 5-(5-Ethyl-tetrazol-1-yl)-4'-methyl-biphenyl-3-carboxylic acid [1-(2,6-dimethyl-pyridin-3-yl)-ethyl]-amide | 441 |
| 397 | 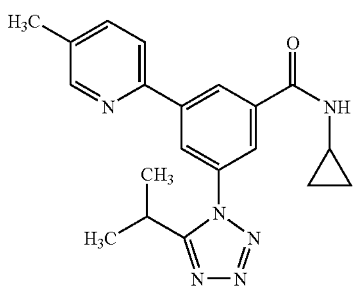 | N-Cyclopropyl-3-(5-isopropyl-tetrazol-1-yl)-5-(5-methyl-pyridin-2-yl)-benzamide | 363 |
| 398 | 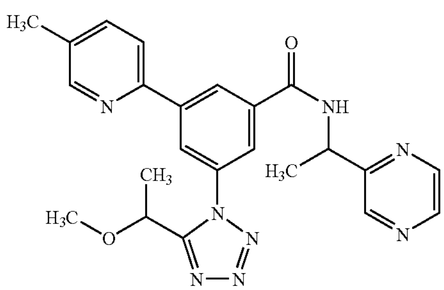 | 3-[5-(1-Methoxy-ethyl)-tetrazol-1-yl]-5-(5-methyl-pyridin-2-yl)-N-(1-pyrazin-2-yl-ethyl)-benzamide | 445 |
| 399 | 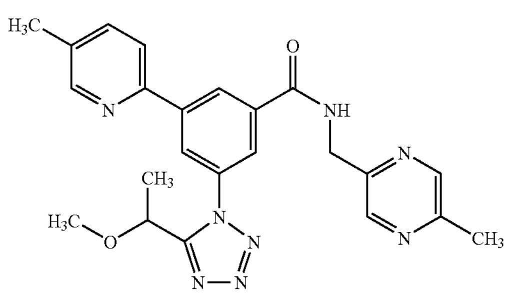 | 3-[5-(1-Methoxy-ethyl)-tetrazol-1-yl]-N-(5-methyl-pyrazin-2-ylmethyl)-5-(5-methyl-pyridin-2-yl)-benzamide | 445 |
| 400 | 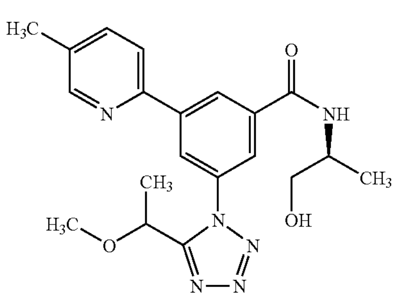 | N-((S)-2-Hydroxy-1-methyl-ethyl)-3-[5-(1-methoxy-ethyl)-tetrazol-1-yl]-5-(5-methyl-pyridin-2-yl)-benzamide | 397 |

TABLE 1-continued

| # | Structure | Name (Autonom ™) | Mp or M + H |
|---|---|---|---|
| 401 | 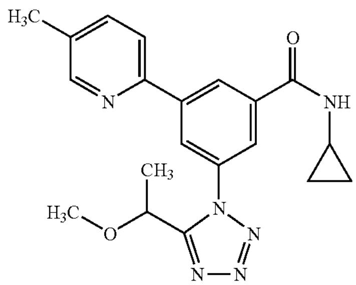 | N-Cyclopropyl-3-[5-(1-methoxy-ethyl)-tetrazol-1-yl]-5-(5-methyl-pyridin-2-yl)-benzamide | 379 |
| 402 | 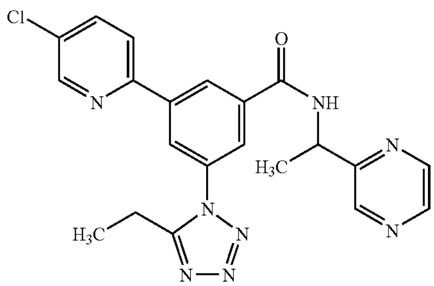 | 3-(5-Chloro-pyridin-2-yl)-5-(5-ethyl-tetrazol-1-yl)-N-(1-pyrazin-2-yl-ethyl)-benzamide | 70.9-73.3° C. |
| 403 | 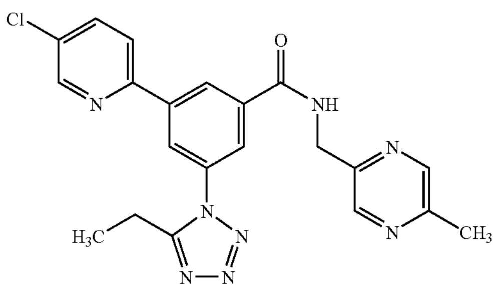 | 3-(5-Chloro-pyridin-2-yl)-5-(5-ethyl-tetrazol-1-yl)-N-(5-methyl-pyrazin-2-ylmethyl)-benzamide | 170.1-172.4° C. |
| 404 | 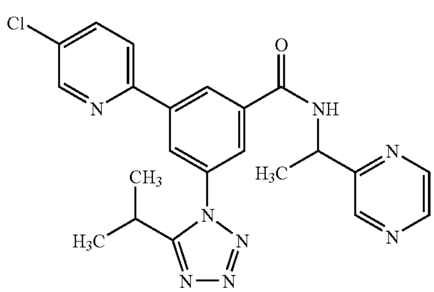 | 3-(5-Chloro-pyridin-2-yl)-5-(5-isopropyl-tetrazol-1-yl)-N-(1-pyrazin-2-yl-ethyl)-benzamide | 449 |
| 405 | 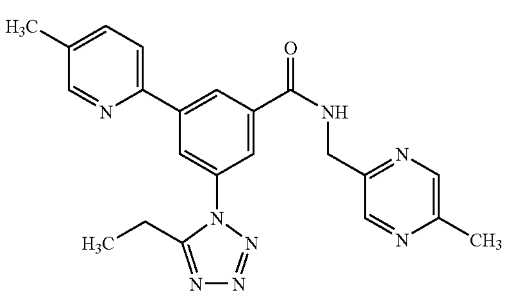 | 3-(5-Ethyl-tetrazol-1-yl)-N-(5-methyl-pyrazin-2-ylmethyl)-5-(5-methyl-pyridin-2-yl)-benzamide | 168.0-171.1° C. (HCl salt) |

TABLE 1-continued

| # | Structure | Name (Autonom ™) | Mp or M + H |
|---|---|---|---|
| 406 | 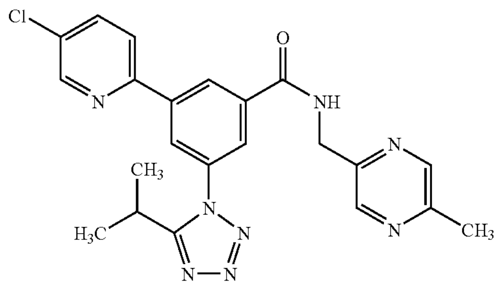 | 3-(5-Chloro-pyridin-2-yl)-5-(5-isopropyl-tetrazol-1-yl)-N-(5-methyl-pyrazin-2-ylmethyl)-benzamide | 179.5–181.2° C. |
| 407 | 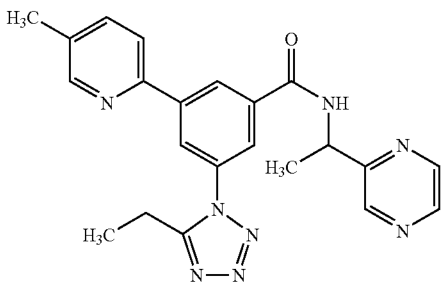 | 3-(5-Ethyl-tetrazol-1-yl)-5-(5-methyl-pyridin-2-yl)-N-(1-pyrazin-2-yl-ethyl)-benzamide | 168.0–169.3° C. |
| 408 | 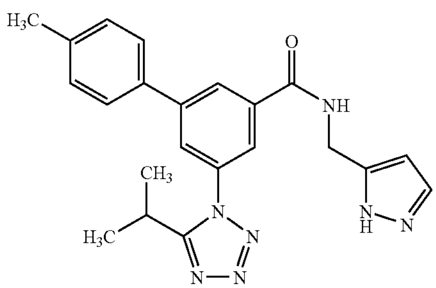 | 5-(5-Isopropyl-tetrazol-1-yl)-4'-methyl-biphenyl-3-carboxylic acid (2 H-pyrazol-3-ylmethyl)-amide | 402 |
| 409 | 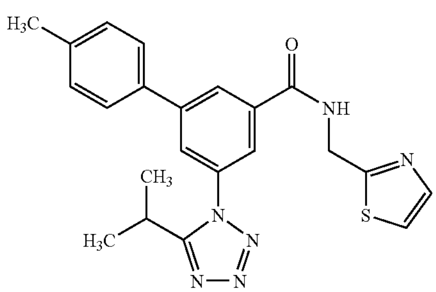 | 5-(5-Isopropyl-tetrazol-1-yl)-4'-methyl-biphenyl-3-carboxylic acid (thiazol-2-ylmethyl)-amide | 419 |
| 410 | 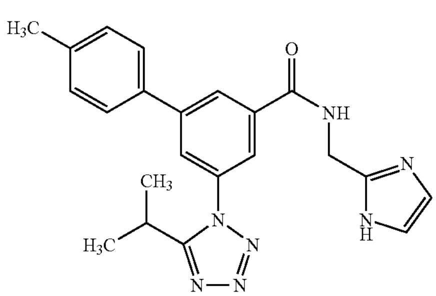 | 5-(5-Isopropyl-tetrazol-1-yl)-4'-methyl-biphenyl-3-carboxylic acid (1 H-imidazol-2-ylmethyl)-amide | 402 |

TABLE 1-continued

| # | Structure | Name (Autonom ™) | Mp or M + H |
|---|---|---|---|
| 411 | 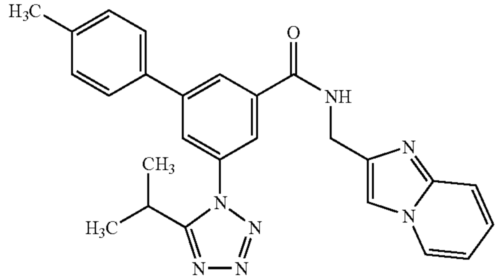 | 5-(5-Isopropyl-tetrazol-1-yl)-4'-methyl-biphenyl-3-carboxylic acid (imidazo[1,2-α]pyridin-2-ylmethyl)-amide | 452 |
| 412 | 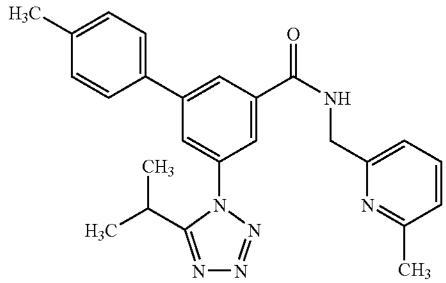 | 5-(5-Isopropyl-tetrazol-1-yl)-4'-methyl-biphenyl-3-carboxylic acid (6-methyl-pyridin-2-ylmethyl)-amide | 427 |
| 413 | 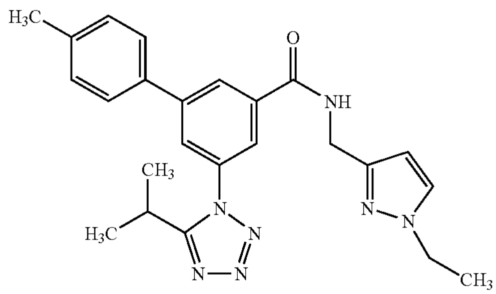 | 5-(5-Isopropyl-tetrazol-1-yl)-4'-methyl-biphenyl-3-carboxylic acid (1-ethyl-1H-pyrazol-3-ylmethyl)-amide | 430 |
| 414 | 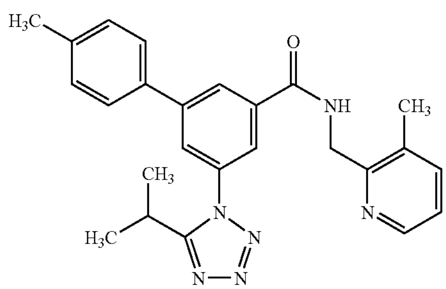 | 5-(5-Isopropyl-tetrazol-1-yl)-4'-methyl-biphenyl-3-carboxylic acid (3-methyl-pyridin-2-ylmethyl)-amide | 427 |
| 415 | 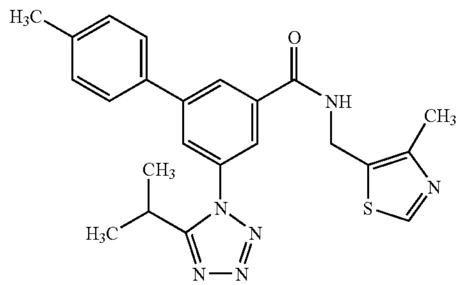 | 5-(5-Isopropyl-tetrazol-1-yl)-4'-methyl-biphenyl-3-carboxylic acid (4-methyl-thiazol-5-ylmethyl)-amide | 433 |

TABLE 1-continued

| # | Structure | Name (Autonom ™) | Mp or M + H |
|---|---|---|---|
| 416 | 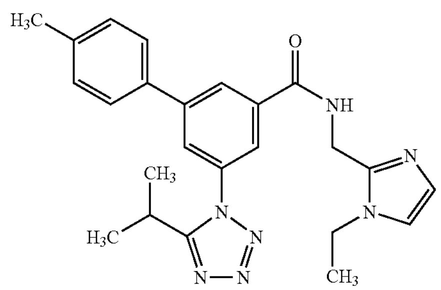 | 5-(5-Isopropyl-tetrazol-1-yl)-4'-methyl-biphenyl-3-carboxylic acid (1-ethyl-1 H-imidazol-2-ylmethyl)-amide | 430 |
| 417 | 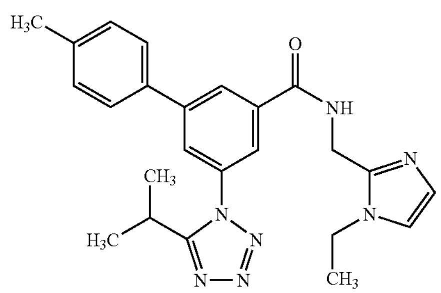 | 5-(5-Isopropyl-tetrazol-1-yl)-4'-methyl-biphenyl-3-carboxylic acid (1-ethyl-1 H-imidazol-2-ylmethyl)-amide | 430 |
| 418 | 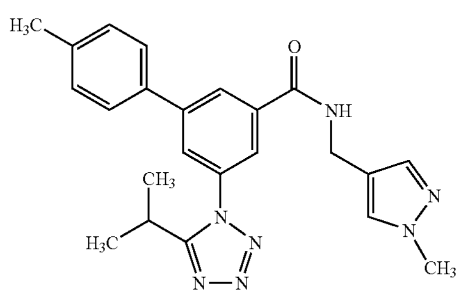 | 5-(5-Isopropyl-tetrazol-1-yl)-4'-methyl-biphenyl-3-carboxylic acid (1-methyl-1 H-pyrazol-4-ylmethyl)-amide | 416 |
| 419 | 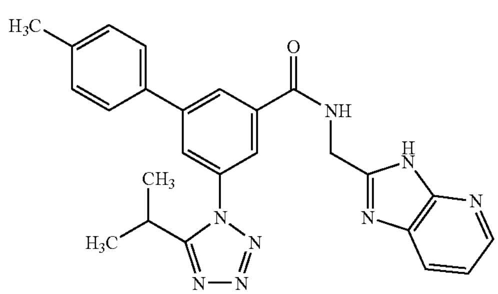 | 5-(5-Isopropyl-tetrazol-1-yl)-4'-methyl-biphenyl-3-carboxylic acid (3 H-imidazo[4,5-b]pyridin-2-ylmethyl)-amide | 453 |
| 420 | 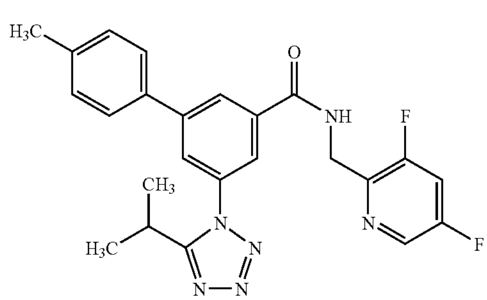 | 5-(5-Isopropyl-tetrazol-1-yl)-4'-methyl-biphenyl-3-carboxylic acid (3,5-difluoro-pyridin-2-ylmethyl)-amide | 449 |

TABLE 1-continued

| # | Structure | Name (Autonom ™) | Mp or M + H |
|---|---|---|---|
| 421 | 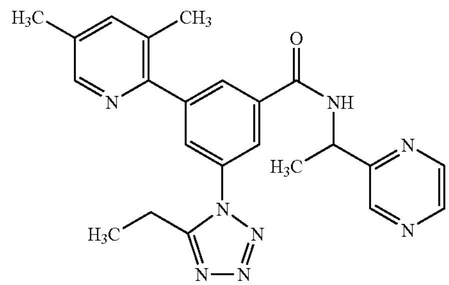 | 3-(3,5-Dimethyl-pyridin-2-yl)-5-(5-ethyl-tetrazol-y-yl)-N-(1-pyrazin-2-yl-ethyl)-benzamide | 429 |
| 422 | 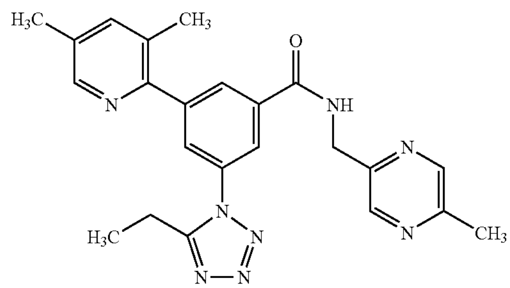 | 3-(3,5-Dimethyl-pyridin-2-yl)-5-(5-ethyl-tetrazol-y-yl)-N-(5-methyl-pyrazin-2-ylmethyl)-benzamide | 429 |
| 423 | 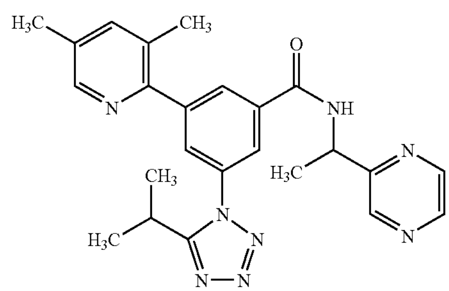 | 3-(3,5-Dimethyl-pyridin-2-yl)-5-(5-isopropyl-tetrazol-1-yl)-N-(1-pyrazin-2-yl-ethyl)-benzamide | 443 |
| 424 | 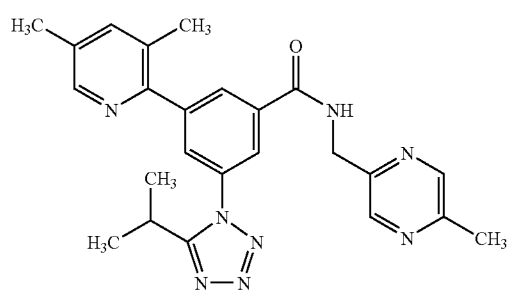 | 3-(3,5-Dimethyl-pyridin-2-yl)-5-(5-isopropyl-tetrazol-1-yl)-N-(5-methyl-pyrazin-2-ylmethyl)-benzamide | 443 |
| 425 | 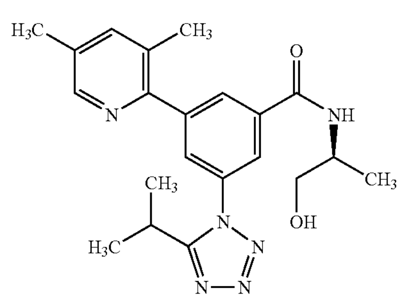 | 3-(3,5-Dimethyl-pyridin-2-yl)-N-((S)-2-hydroxy-1-methyl-ethyl)-5-(5-isopropyl-tetrazol-1-y)-benzamide | 395 |

TABLE 1-continued

| # | Structure | Name (Autonom ™) | Mp or M + H |
|---|---|---|---|
| 426 | 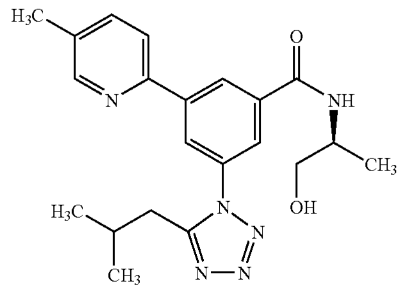 | N-((S)-2-Hydroxy-1-methyl-ethyl)-3-(5-isobutyl-tetrazol-1-yl)-5-(5-methyl-pyridin-2-yl)-benzamide | 395 |
| 427 | 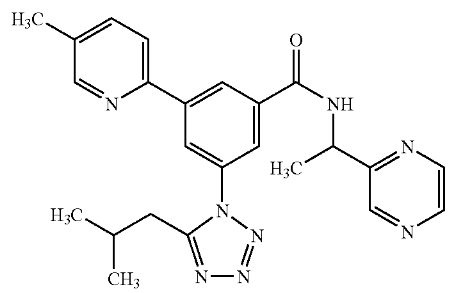 | 3-(5-Isobutyl-tetrazol-1-yl)-5-(5-methyl-pyridin-2-yl)-N-(1-pyrazin-2-yl-ethyl)-benzamide | 443 |
| 428 | 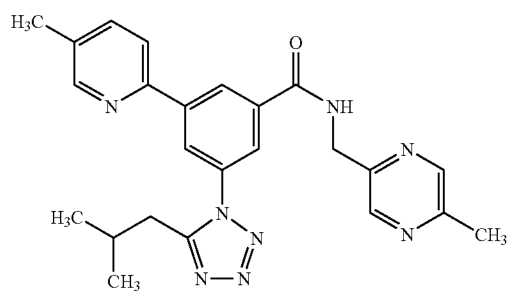 | 3-(5-Isobutyl-tetrazol-1-yl)-N-(5-methyl-pyrazin-2-ylmethyl)-5-(5-methyl-pyridin-2-yl)-benzamide | 443 |
| 429 | 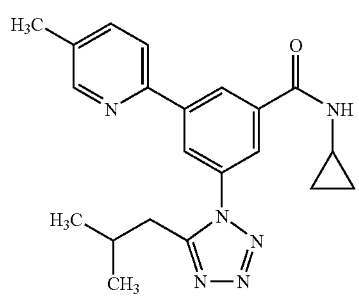 | N-Cyclopropyl-3-(5-isobutyl-tetrazol-1-yl)-5-(5-methyl-pyridin-2-yl)-benzamide | 377 |
| 430 | 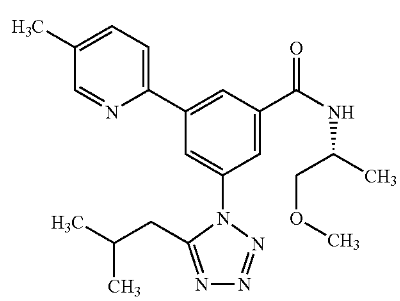 | 3-(5-Isobutyl-tetrazol-1-yl)-N-((R)-2-methoxy-1-methyl-ethyl)-5-(5-methyl-pyridin-2-yl)-benzamide | 409 |

TABLE 1-continued

| # | Structure | Name (Autonom ™) | Mp or M + H |
|---|---|---|---|
| 431 | 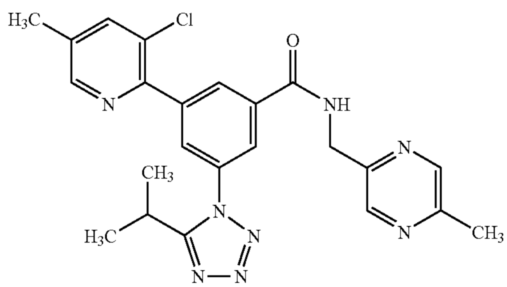 | 3-(3-Chloro-5-methyl-pyridin-2-yl)-5-(5-isopropyl-tetrazol-1-yl)-N-(5-methyl-pyrazin-2-ylmethyl)-benzamide | 125.4-128.3° C. (HCl salt) |
| 432 | 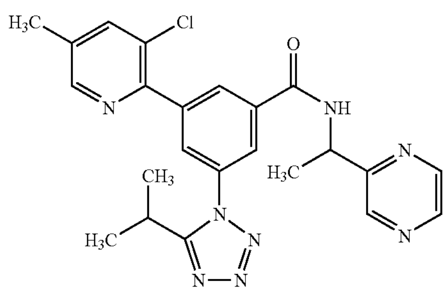 | 3-(3-Chloro-5-methyl-pyridin-2-yl)-5-(5-isopropyl-tetrazol-1-yl)-N-(1-pyrazin-2-yl-ethyl)-benzamide | 185.4-186.3 (HCl salt) |
| 433 | 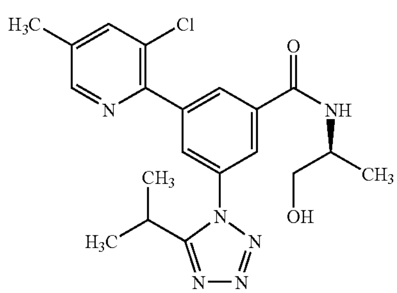 | 3-(3-Chloro-5-methyl-pyridin-2-yl)-N-((S)-2-hydroxy-1-methyl-ethyl)-5-(5-isopropyl-tetrazol-1-yl)-benzamide | 110.0-112.0° C. |
| 434 | 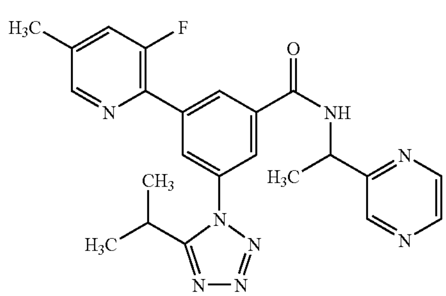 | 3-(3-Fluoro-5-methyl-pyridin-2-yl)-5-(5-isopropyl-tetrazol-1-yl)-N-(1-pyrazin-2-yl-ethyl)-benzamide | 447 |
| 435 | 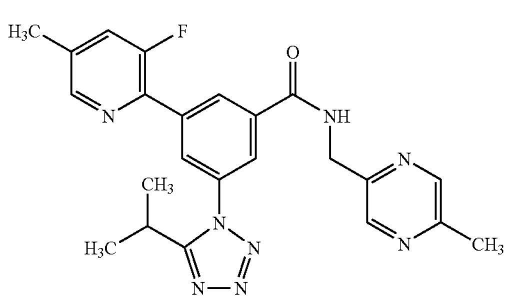 | 3-(3-Fluoro-5-methyl-pyridin-2-yl)-5-(5-isopropyl-tetrazol-1-yl)-N-(5-methyl-pyrazin-2-ylmethyl)-benzamide | 447 |

TABLE 1-continued

| # | Structure | Name (Autonom ™) | Mp or M + H |
|---|---|---|---|
| 436 | 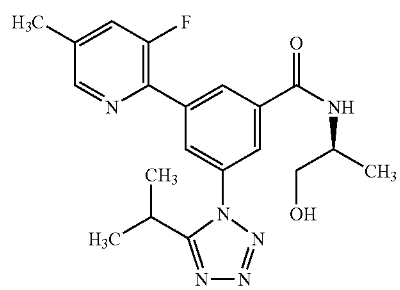 | 3-(3-Fluoro-5-methyl-pyridin-2-yl)-N-((S)-2-hydroxy-1-methyl-ethyl)-5-(5-isopropyl-tetrazol-1-yl)-benzamide | 399 |
| 437 | 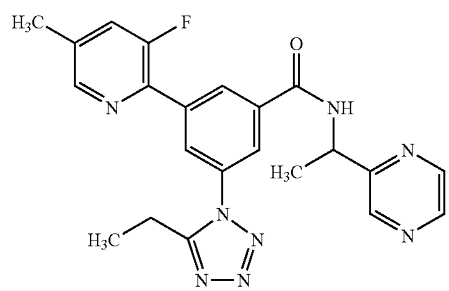 | 3-(5-Ethyl-tetrazol-1-yl)-5-(3-fluoro-5-methyl-pyridin-2-yl)-N-(1-pyrazin-2-yl-ethyl)-benzamide | 433 |
| 438 | 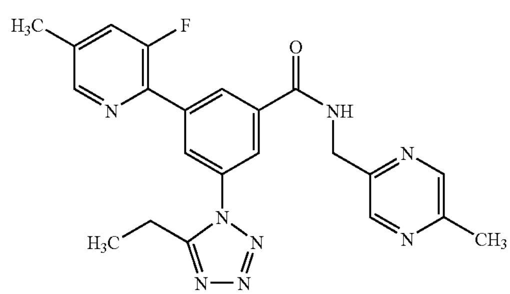 | 3-(5-Ethyl-tetrazol-1-yl)-5-(3-fluoro-5-methyl-pyridin-2-yl)-N-(5-methyl-pyrazin-2-ylmethyl)-benzamide | 433 |
| 439 | 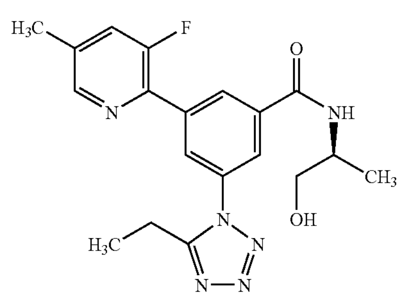 | 3-(5-Ethyl-tetrazol-1-yl)-5-(3-fluoro-5-methyl-pyridin-2-yl)-N-((S)-2-hydroxy-1-methyl-ethyl)-benzamide | 385 |
| 440 | 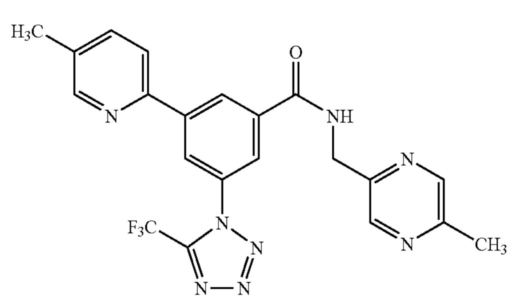 | N-(5-Methyl-pyrazin-2-ylmethyl)-3-(5-methyl-pyridin-2-yl)-5-(5-trifluoromethyl-tetrazol-1-yl)-benzamide | 167.0-170.0° C. |

TABLE 1-continued

| # | Structure | Name (Autonom ™) | Mp or M + H |
|---|---|---|---|
| 441 | 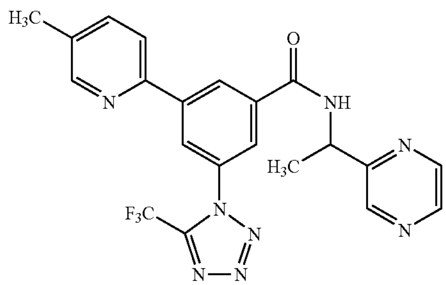 | 3-(5-Methyl-pyridin-2-yl)-N-(1-pyrazin-2-yl-ethyl)-5-(5-trifluoromethyl-tetrazol-1-yl)-benzamide | 144.0-146.0° C. |
| 442 | 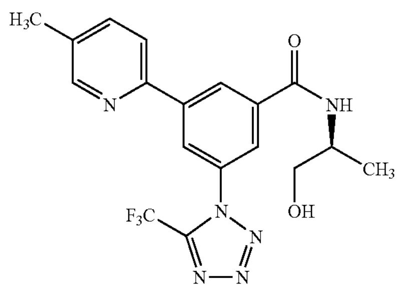 | N-((S)-2-Hydroxy-1-methyl-ethyl)-3-(5-methyl-pyridin-2-yl)-5-(5-trifluoromethyl-tetrazol-1-yl)-benzamide | 184.3-185.1° C. (HCl salt) |
| 443 | 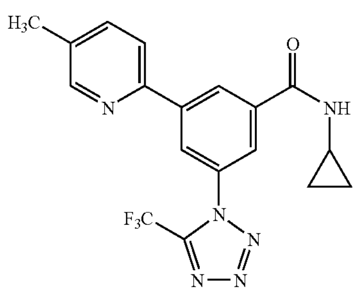 | N-Cyclopropyl-3-(5-methyl-pyridin-2-yl)-5-(5-trifluoromethyl-tetrazol-1-yl)-benzamide | 204.2-205.1° C. (HCl salt) |
| 444 | 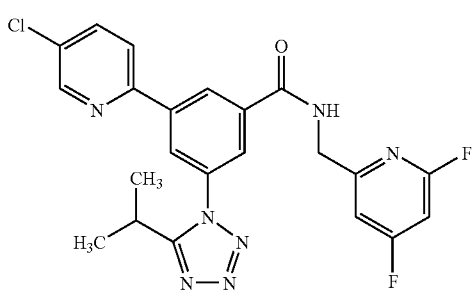 | 3-(5-Chloro-pyridin-2-yl)-N-(3,5-difluoro-pyridin-2-ylmethyl)-5-(5-isopropyl-tetrazol-1-yl)-benzamide | 80.0-82.0° C. |
| 445 | 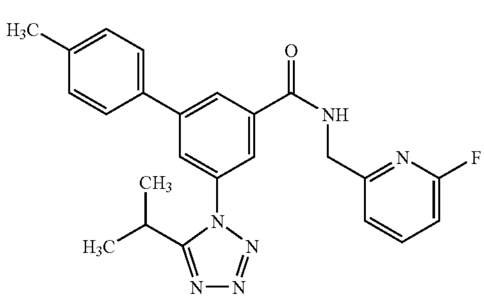 | 5-(5-Isopropyl-tetrazol-1-yl)-4'-methyl-biphenyl-3-carboxylic acid (6-fluoro-pyridin-2-ylmethyl)-amide | 80.0-81.0° C. |

TABLE 1-continued

| # | Structure | Name (Autonom ™) | Mp or M + H |
|---|-----------|------------------|-------------|
| 446 | 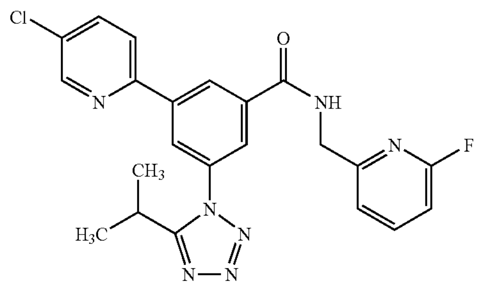 | 3-(5-Chloro-pyridin-2-yl)-N-(6-fluoro-pyridin-ylmethyl)-5-(5-isopropyl-tetrazol-1-yl)-benzamide | 80.0-81.0° C. |
| 447 | 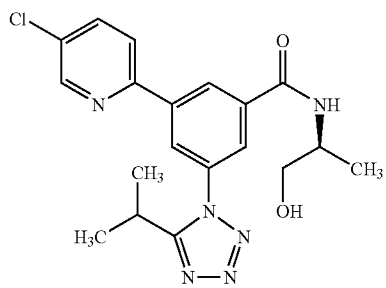 | 3-(5-Chloro-pyridin-2-yl)-N-((S)-2-hydroxy-1-methyl-ethyl)-5-(5-isopropyl-tetrazol-1-yl)-benzamide | 124.0-125.0° C. |
| 448 | 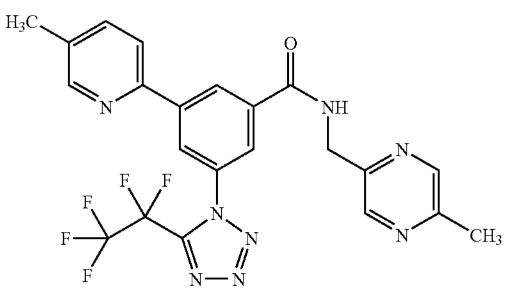 | N-(5-Methyl-pyrazin-2-ylmethyl)-3-(5-methyl-pyridin-2-yl)-5-(5-pentafluoroethyl-tetrazol-1-yl)-benzamide | 132.0-133.0° C. (HCl salt) |
| 449 | 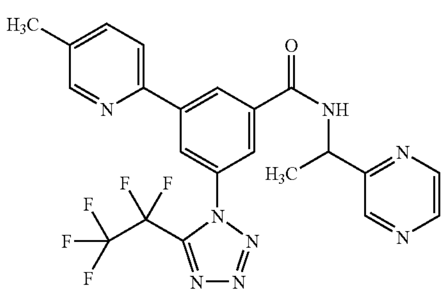 | 3-(5-Methyl-pyridin-2-yl)-5-(5-pentafluoroethyl-tetrazol-1-yl)-N-(1-pyrazin-2-yl-ethyl)-benzamide | 134.0-135.0° C. (HCl salt) |
| 450 | 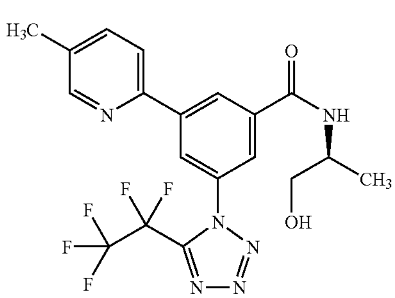 | N-((S)-2-Hydroxy-1-methyl-ethyl)-3-(5-methyl-pyridin-2-yl)-5-(5-pentafluoroethyl-tetrazol-1-yl)-benzamide | 193.0-193.5° C. (HCl salt) |

TABLE 1-continued

| # | Structure | Name (Autonom ™) | Mp or M + H |
|---|---|---|---|
| 451 | 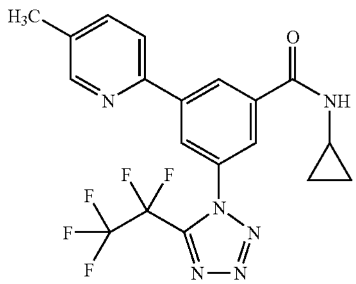 | N-Cylcopropyl-3-(5-methyl-pyridin-2-yl)-5-(5-pentafluoroethyl-tetrazol-1-yl)-benzamide | 182.0-183.0° C. |
| 452 | 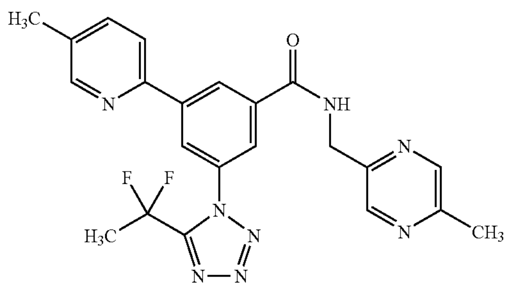 | 3-[5-(1,1-Difluoro-ethyl)-tetrazol-1-yl]-N-(5-methyl-pyrazin-2-ylmethyl)-5-(5-methyl-pyridin-2-yl)-benzamide | 188.0-190.0° C. (HCl salt) |
| 453 | 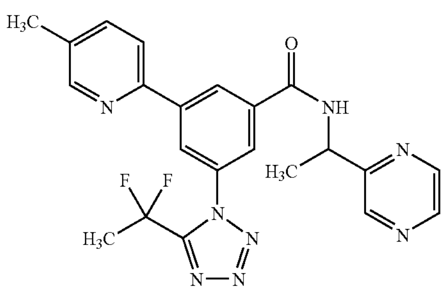 | 3-[5-(1,1-Difluoro-ethyl)-tetrazol-1-yl]-5-(5-methyl-pyridin-2-yl)-N-(1-pyrazin-2-yl-ethyl)-benzamide | 187.5-188.0° C. (HCl salt) |
| 454 | 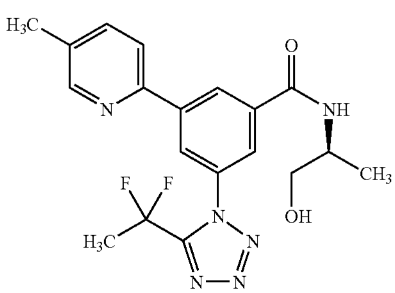 | 3-[5-(1,1-Difluoro-ethyl)-tetrazol-1-yl]-N-((S)-2-hydroxy-1-methyl-ethyl)-5-(5-methyl-pyridin-2-yl)-benzamide | 207.5-208.5° C. (HCl salt) |
| 455 | 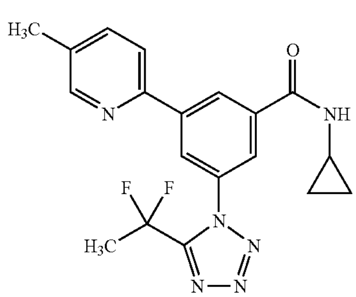 | N-Cyclopropyl-3-[5-(1,1-difluoro-ethyl)-tetrazol-1-yl]-5-(5-methyl-pyridin-2-yl)-benzamide | 190.4-192.0° C. (HCl salt) |

TABLE 1-continued

| # | Structure | Name (Autonom ™) | Mp or M + H |
|---|---|---|---|
| 456 | 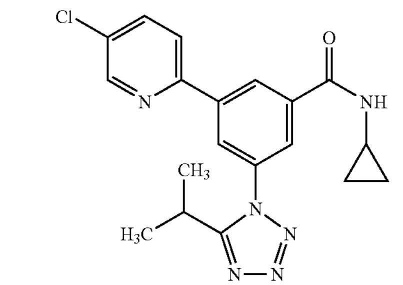 | 3-(5-Chloro-pyridin-2-yl)-N-cyclopropyl-5-(5-isopropyl-tetrazol-1-yl)-benzamide | 107.0-108.0° C. (HCl salt) |
| 457 | 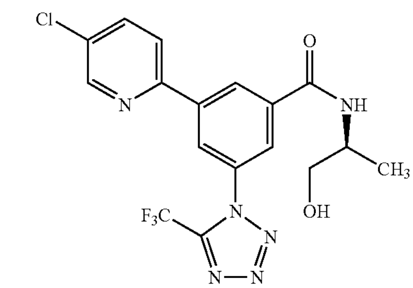 | 3-(5-Chloro-pyridin-2-yl)-N-((S)-2-hydroxy-1-methyl-ethyl)-5-(5-trifluoromethyl-tetrazol-1-yl)-benzamide | 172.0-173.0° C. (HCl salt) |
| 458 | 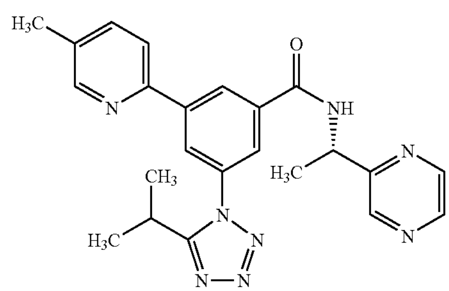 | 3-(5-Isopropyl-tetrazol-1-yl)-5-(5-methyl-pyridin-2-yl)-N-((S)-1-pyrazin-2-yl-ethyl)-benzamide | 165.0-165.6° C. (HCl salt) |
| 459 | 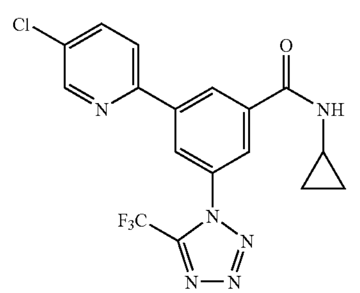 | 3-(5-Chloro-pyridin-2-yl)-N-cylcopropyl-5-(5-trifluoromethyl-tetrazol-1-yl)-benzamide | 221.3-223.0 (HCl salt) |
| 460 | 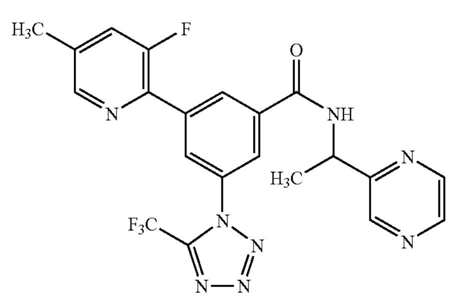 | 3-(3-Fluoro-5-methyl-pyridin-2-yl)-N-(1-pyrazin-2-yl-ethyl)-5-(5-trifluoromethyl-tetrazol-1-yl)-benzamide | 473 |

TABLE 1-continued

| # | Structure | Name (Autonom ™) | Mp or M + H |
|---|---|---|---|
| 461 | 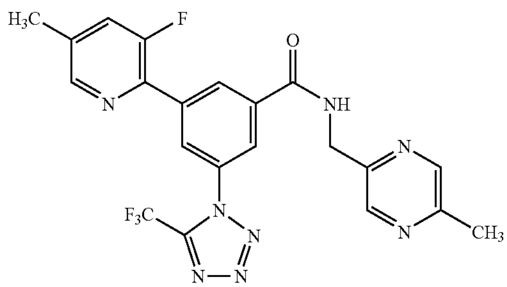 | 3-(3-Fluoro-5-methyl-pyridin-2-yl)-N-(5-methyl-pyrazin-2-ylmethyl)-5-(5-trifluoromethyl-tetrazol-1-yl)-benzamide | 473 |
| 462 | 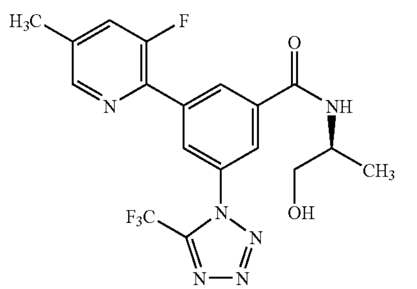 | 3-(3-Fluoro-5-methyl-pyridin-2-yl)-N-((S)-2-hydroxy-1-methyl-ethyl)-5-(5-trifluoromethyl-tetrazol-1-yl)-benzamide | 425 |
| 463 | 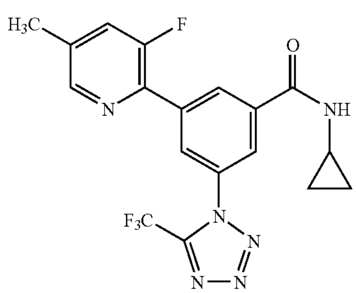 | N-Cylcopropyl-3-(3-fluoro-5-methyl-pyridin-5-2-yl)-5-(5-trifluoromethyl-tetrazol-1-yl)-benzamide | 407 |
| 464 | 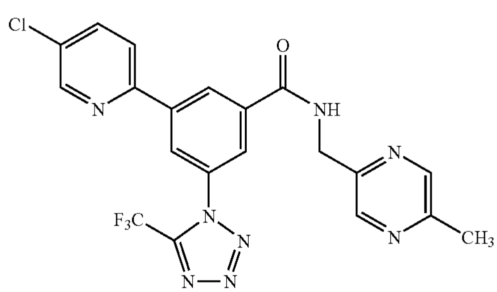 | 3-(5-Chloro-pyridin-2-yl)-N-(5-methyl-pyrazin-2-ylmethyl)-5-(5-trifluoromethyl-tetrazol-1-yl)-benzamide | 166.0-168.0° C. (HCl salt) |
| 465 | 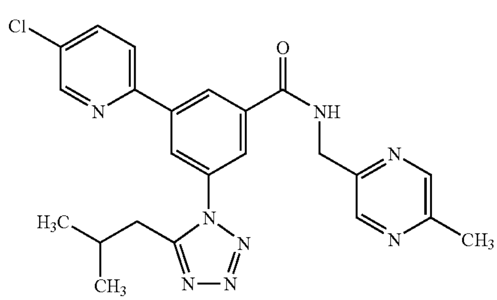 | 3-(5-Chloro-pyridin-2-yl)-5-(5-isobutyl-tetrazol-1-yl)-N-(5-methyl-pyrazin-2-ylmethyl)-benzamide | 109.0-110.0° C. (HCl salt) |

TABLE 1-continued

| # | Structure | Name (Autonom ™) | Mp or M + H |
|---|---|---|---|
| 466 | 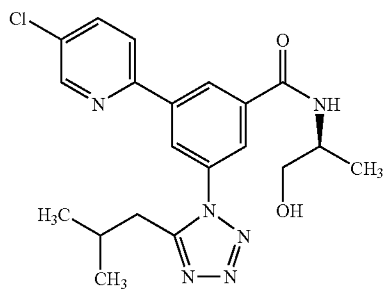 | 3-(5-Chloro-pyridin-2-yl)-N-((S)-2-hydroxy-1-methyl-ethyl)-5-(5-isobutyl-tetrazol-1-yl)-benzamide | 94.5-96.0° C. (HCl salt) |
| 467 | 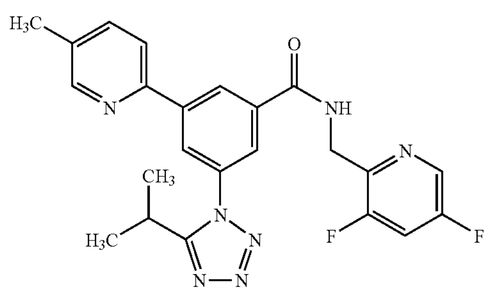 | N-(3,5-Difluoro-pyridin-2-ylmethyl)-3-(5-isopropyl-tetrazol-1-yl)-5-(5-methyl-pyridin-2-yl)-benzamide | 450 |
| 468 | 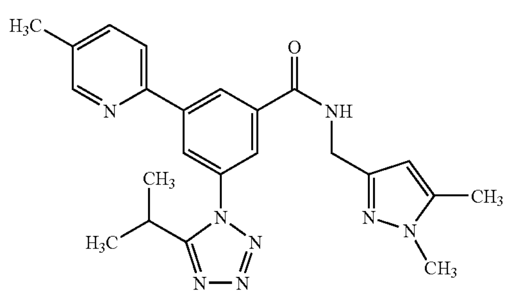 | N-(1,5-Dimethyl-1H-pyrazol-3-ylmethyl)-3-(5-isopropyl-tetrazol-1-yl)-5-(5-methyl-pyridin-2-yl)-benzamide | 152.0-153.0° C. (HCl salt) |
| 469 | 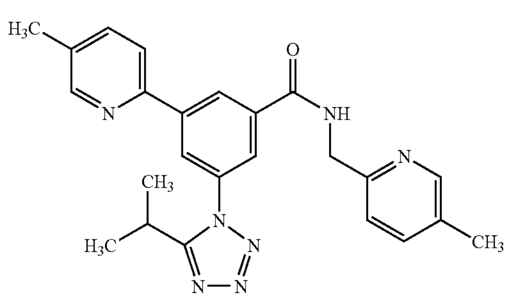 | 3-(5-Isopropyl-tetrazol-1-yl)-5-(5-methyl-pyridin-2-yl)-N-[1-(5-methyl-pyridin-2-yl)-ethyl]-benzamide | 153.0-155.0° C. (HCl salt) |
| 470 | 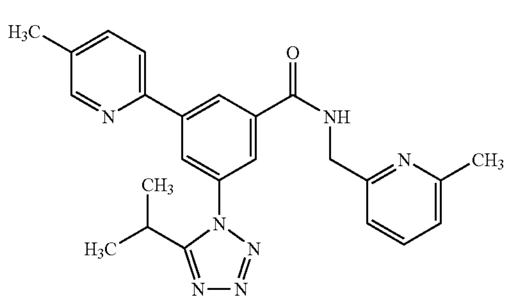 | 3-(5-Isopropyl-tetrazol-1-yl)-5-(5-methyl-pyridin-2-yl)-N-[1-(6-methyl-pyridin-2-yl)-ethyl]-benzamide | 161.5-162.0° C. (HCl salt) |

TABLE 1-continued

| # | Structure | Name (Autonom ™) | Mp or M + H |
|---|---|---|---|
| 471 | 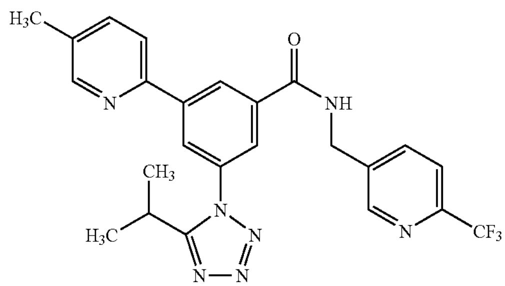 | 3-(5-Isopropyl-tetrazol-1-yl)-5-(5-methyl-pyridin-2-yl)-N-(6-trifluoromethyl-pyridin-3-ylmethyl)-benzamide | 149.0-151.0° C. (HCl salt) |
| 472 | 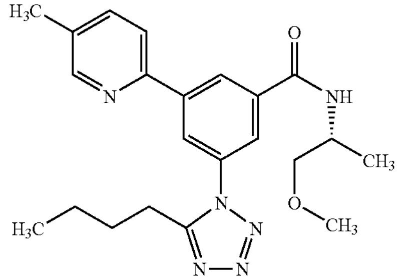 | 3-(5-Butyl-tetrazol-1-yl)-N-((R)-2-methoxyl-1-methyl-ethyl)-5-(5-methyl-pyridin-2-yl)-benzamide | 409 |
| 473 | 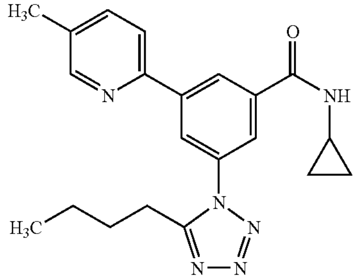 | 3-(5-Butyl-tetrazol-1-yl)-N-cyclopropyl-5-(5-methyl-pyridin-2-yl)-benzamide | 377 |
| 474 | 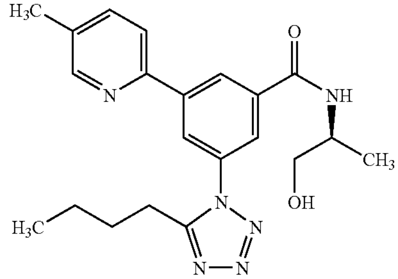 | 3-(5-Butyl-tetrazol-1-yl)-N-((S)-2-hydroxy-1-methyl-ethyl)-5-(5-methyl-pyridin-2-yl)-benzamide | 395 |
| 475 | 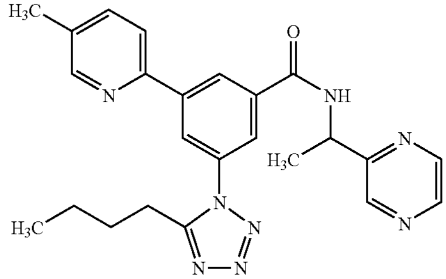 | 3-(5-Butyl-tetrazol-1-yl)-5-(5-methyl-pyridin-2-yl)-N-(1-pyrazin-2-yl-ethyl)-benzamide | 443 |

TABLE 1-continued

| # | Structure | Name (Autonom ™) | Mp or M + H |
|---|---|---|---|
| 476 | 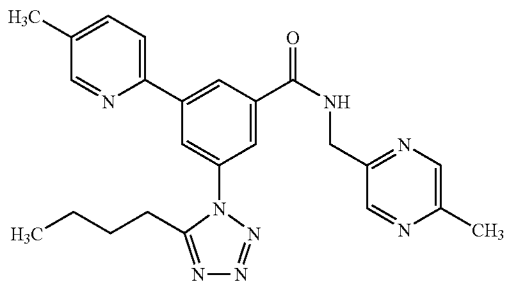 | 3-(5-Butyl-tetrazol-1-yl)-N-(5-methyl-pyrazin-2-ylmethyl)-5-(5-methyl-pyridin-2-yl)-benzamide | 443 |
| 477 | 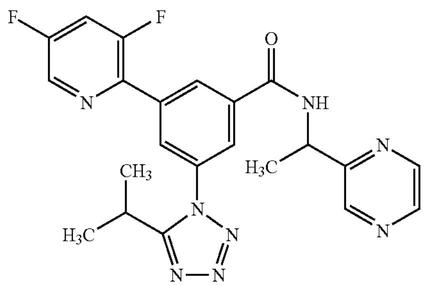 | 3-(3,5-Difluoro-pyridin-2-yl)-5-(5-isopropyl-tetrazol-1-yl)-N-(1-pyrazin-2-yl-ethyl)-benzamide | 451 |
| 478 | 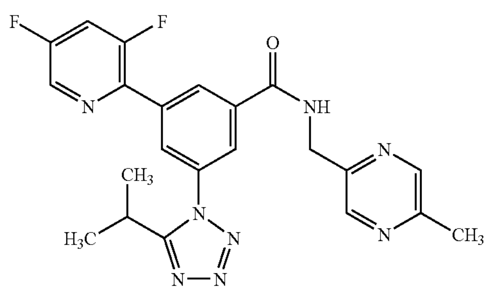 | 3-(3,5-Difluoro-pyridin-2-yl)-5-(5-isopropyl-tetrazol-1-yl)-N-(5-methyl-pyrazin-2-ylmethyl)-benzamide | 451 |
| 479 | 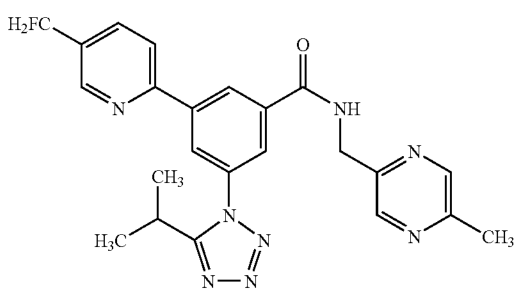 | 3-(5-Fluoromethyl-pyridin-2-yl)-5-(5-isopropyl-tetrazol-1-yl)-N-(5-methyl-pyrazin-2-ylmethyl)-benzamide | 135.6-137.5° C. (HCl salt) |
| 480 | 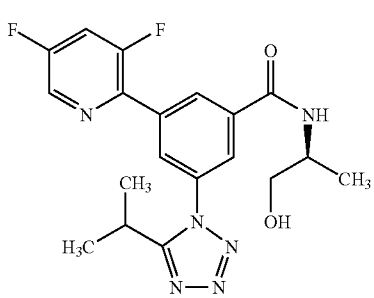 | 3-(3,5-Difluoro-pyridin-2-yl)-N-((S)-2-hydroxy-1-methyl-ethyl)-5-(5-isopropyl-tetrazol-1-yl)-benzamide | 403 |

TABLE 1-continued

| # | Structure | Name (Autonom ™) | Mp or M + H |
|---|---|---|---|
| 481 | 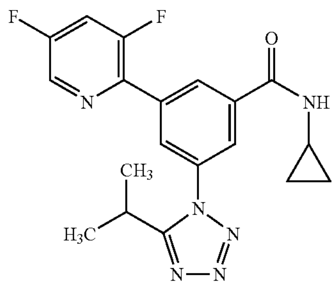 | N-Cyclopropyl-3-(3,5-: luoro-pyridin-2-yl)-5- mx,1 dif (5-isopropyl-tetrazol-1-yl)-benzamide | 385 |
| 482 | 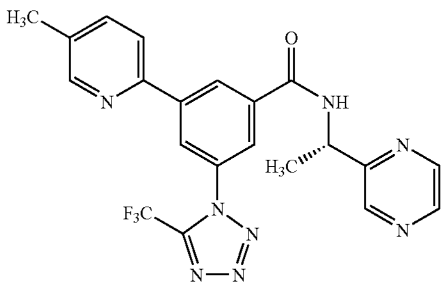 | N-[(S)-1-(5-Methyl-pyrazin-2-yl)-ethyl]-3-(5-methyl-pyridin-2-yl)-5-(5-trifluoromethyl-tetrazol-1-yl)-benzamide | 455 |
| 483 | 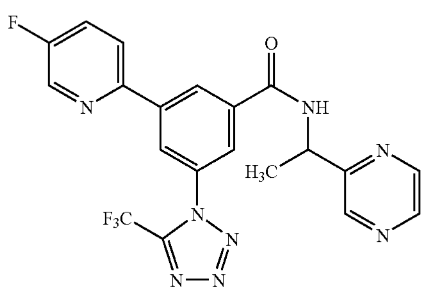 | 3-(5-Fluoro-pyridin-2-yl)-5-(5-isopropyl-tetrazol-1-yl)-N-(1-pyrazin-2-yl-ethyl)-benzamide | 88.0-89.0° C. (HCl salt) |
| 484 | 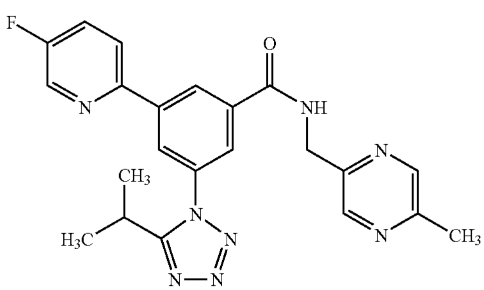 | 3-(5-Fluoro-pyridin-2-yl)-5-(5-isopropyl-tetrazol-1-yl)-N-(5-methyl-pyrazin-2-ylmethyl)-benzamide | 149.0-150.0° C. (HCl salt) |
| 485 | 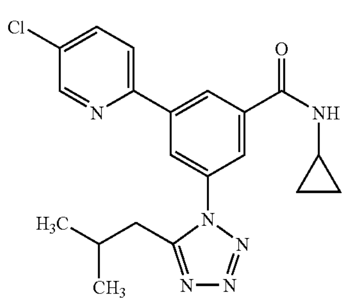 | 3-(5-Chloro-pyridin-2-yl)-N-cyclopropyl-5-(5-isobutyl-tetrazol-1-yl)-benzamide | 104.0-105.0 (HCl salt) |

TABLE 1-continued

| # | Structure | Name (Autonom ™) | Mp or M + H |
|---|---|---|---|
| 486 | 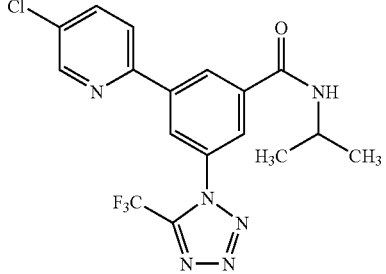 | 3-(5-Chloro-pyridin-2-yl)-N-isopropyl-5-(5-trifluoromethyl-tetrazol-1-yl)-benzamide | 216.5-217.7° C. (HCl salt) |
| 487 | 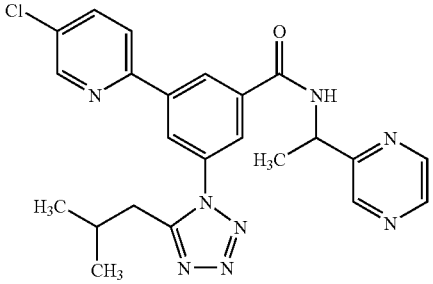 | 3-(5-Chloro-pyridin-2-yl)-5-(5-isobutyl-tetrazol-1-yl)-N-(1-pyrazin-2-yl-ethyl)-benzamide | 114.0-115.0° C. (HCl salt) |
| 488 | 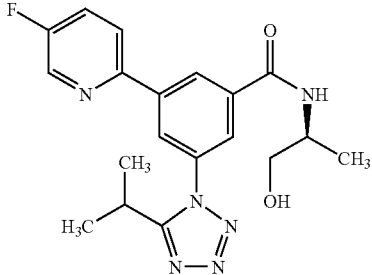 | 3-(5-Fluoro-pyridin-2-yl)-N-((S)-2-hydroxy-1-methyl-ethyl)-5-(5-isopropyl-tetrazol-1-yl)-benzamide | 104.5-105.0° C. (HCl salt) |
| 489 | 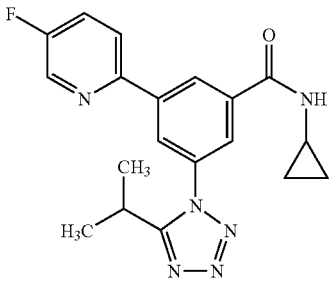 | N-Cyclopropyl-3-(5-fluoro-pyridin-2-yl)-5-(5-isopropyl-tetrazol-1-yl)-benzamide | 94.0-95.0° C. (HCl salt) |
| 490 | 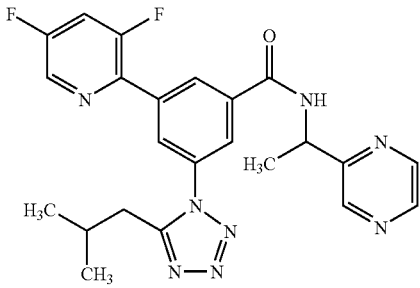 | 3-(3,5-Difluoro-pyridin-2-yl)-5-(5-isobutyl-tetrazol-1-yl)-N-(1-pyrazin-2-yl-ethyl)-benzamide | 465 |

| # | Structure | Name (Autonom ™) | Mp or M + H |
|---|---|---|---|
| 491 | 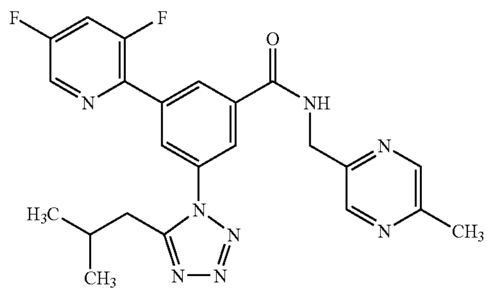 | 3-(3,5-Difluoro-pyridin-2-yl)-5-(5-isobutyl-tetrazol-1-yl)-N-(5-methyl-pyrazin-2-ylmethyl)-benzamide | 465 |
| 492 | 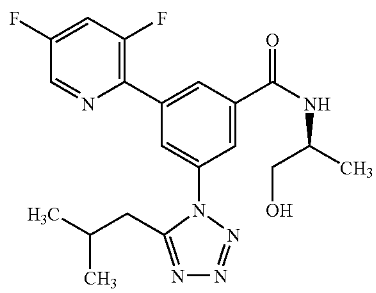 | 3-(3,5-Difluoro-pyridin-2-yl)-N-((S)-2-hydroxy-1-methyl-ethyl)-5-(5-isobutyl-tetrazol-1-yl)-benzamide | 417 |
| 493 | 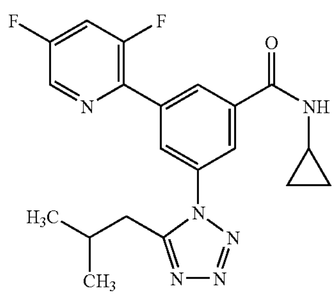 | N-Cyclopropyl-3-(3,5-difluoro-pyridin-2-yl)-5-(5-isobutyl-tetrazol-1-yl)-benzamide | 399 |
| 494 | 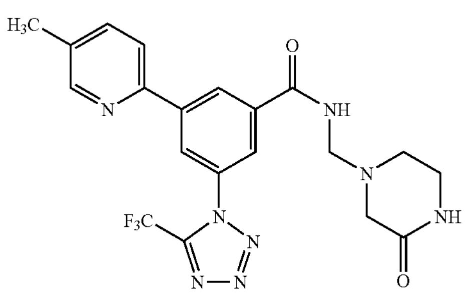 | 3-(5-Methyl-pyridin-2-yl)-N-[2-(3-oxo-piperazin-1-yl)-ethyl]-5-(5-trifluromethyl-tetrazol-1-yl)-benzamide | 178.0-179.0° C. (HCl salt) |
| 495 | 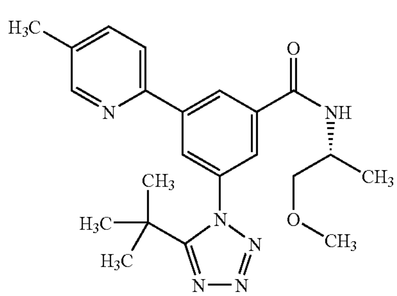 | 3-(5-tert-Butyl-tetrazol-1-yl)-N-((R)-2-methoxy-1-methyl-ethyl)-5-(5-methyl-pyridin-2-yl)-benzamide | 409 |

TABLE 1-continued

| # | Structure | Name (Autonom ™) | Mp or M + H |
|---|---|---|---|
| 496 | 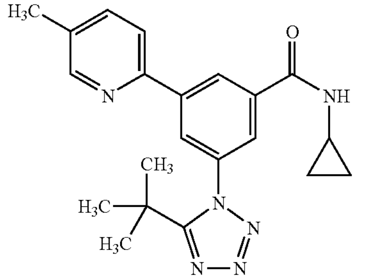 | 3-(5-tert-Butyl-tetrazol-1-yl)-N-cyclopropyl-5-(5-methyl-pyridin-2-yl)-benzamide | 377 |
| 497 | 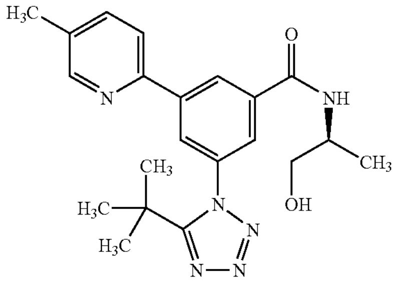 | 3-(5-tert-Butyl-tetrazol-1-yl)-N-((S)-2-hydroxy-1-methyl-ethyl)-5-(5-methyl-pyridin-2-yl)-benzamide | 395 |
| 498 | 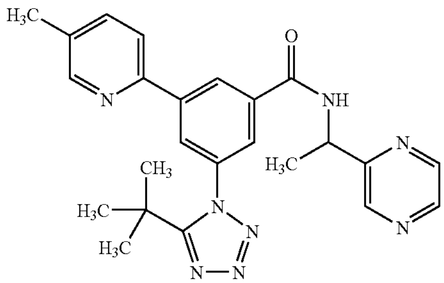 | 3-(5-tert-Butyl-tetrazol-1-yl)-5-(5-methyl-pyridin-2-yl)-N-(1-pyrazin-2-yl-ethyl)-benzamide | 443 |
| 499 | 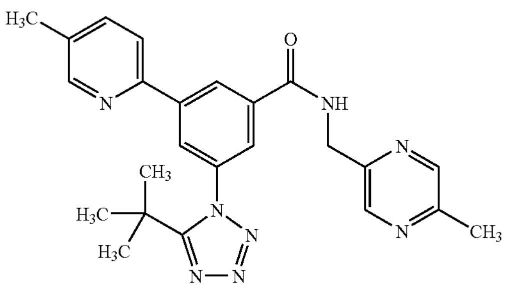 | 3-(5-tert-Butyl-tetrazol-1-yl)-N-(5-methyl-pyrazin-2-ylmethyl)-5-(5-methyl-pyridin-2-yl)-benzamide | 443 |
| 500 | 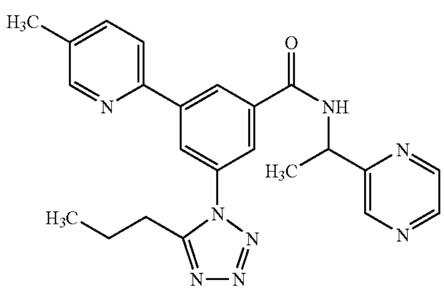 | 3-(5-Methyl-pyridin-2-yl)-5-(5-propyl-tetrazol-1-yl)-N-(1-pyrazin-2-yl-ethyl)-benzamide | 114.0-115.0° C. (HCl salt) |

TABLE 1-continued

| # | Structure | Name (Autonom ™) | Mp or M + H |
|---|---|---|---|
| 501 | 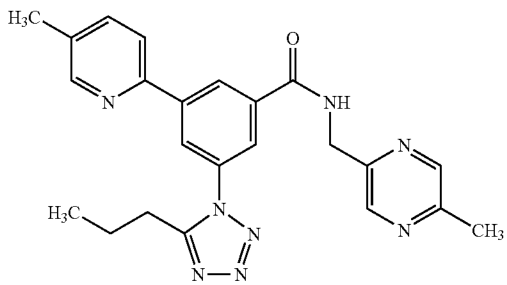 | N-(5-Methyl-pyrazin-2-ylmethyl)-3-(5-methyl-pyridin-2-yl)-5-(5-propyl-tetrazol-1-yl)-benzamide | 148.0-149.0° C. (HCl salt) |
| 502 | 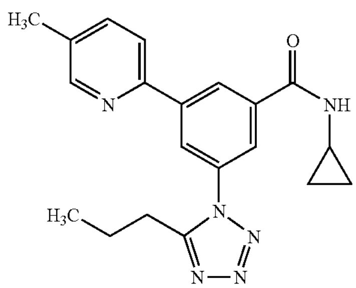 | N-Cylcopropyl-3-(5-methyl-pyridin-2-yl)-5-(5-propyl-tetrazol-1-yl)-benzamide | 120.0-121.0° C. (HCl salt) |
| 503 | 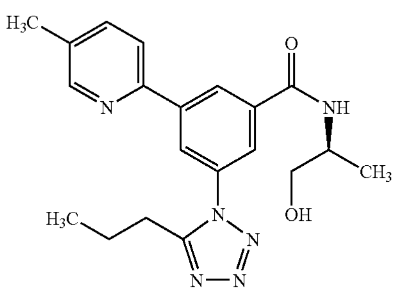 | N-((S)-2-Hydroxy-1-methyl-ethyl)-3-(5-methyl-pyridin-2-yl)-5-(5-propyl-tetrazol-1-yl)-benzamide | 121.0-122.0° C. (HCl salt) |
| 504 | 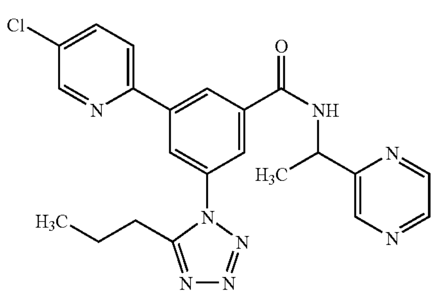 | 3-(5-Chloro-pyridin-2-yl)-5-(5-propyl-tetrazol-1-yl)-N-(1-pyrazin-2-yl-ethyl)-benzamide | 85.0-86.0° C. (HCl salt) |
| 505 | 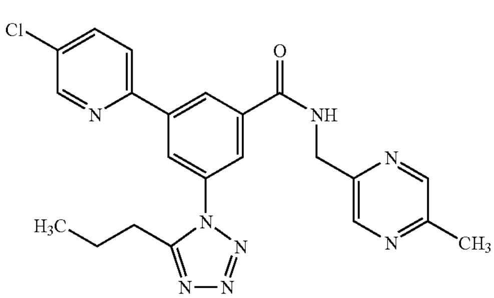 | 3-(5-Chloro-pyridin-2-yl)-N-(5-methyl-pyrazin-2-ylmethyl)-5-(5-propyl-tetrazol-1-yl)-benzamide | 90.0-91.0° C. (HCl salt) |

TABLE 1-continued

| # | Structure | Name (Autonom ™) | Mp or M + H |
|---|---|---|---|
| 506 | 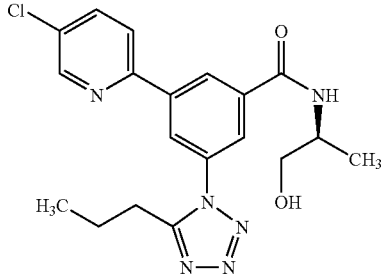 | 3-(5-Chloro-pyridin-2-yl)-((S)-2-hydroxy-1-methyl-ethyl)-5-(5-propyl-tetrazol-1-yl)-benzamide | |
| 507 | 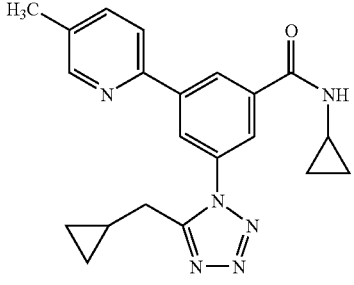 | N-Cyclopropyl-3-(5-cylcopropylmethyl-tetrazol-1-yl)-5-(5-methyl-pyridin-2-yl)-benzamide | 375 |
| 508 | 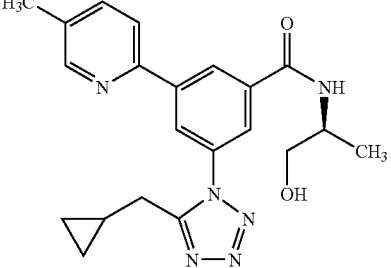 | 3-(5-Cyclopropylmethyl-tetrazol-1-yl)-N-((S)-2-hydroxy-1-methyl-ethyl)-5-(5-methyl-pyridin-2-yl)-benzamide | 393 |
| 509 | 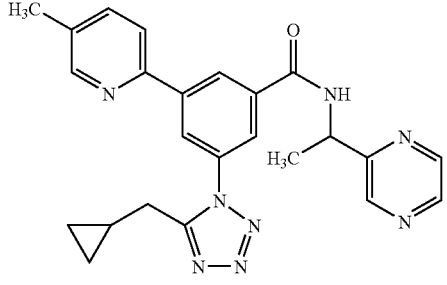 | 3-(5-Cyclopropylmethyl-tetrazol-1-yl)-5-(5-methyl-pyridin-2-yl)-N-(1-pyrazin-2-yl-ethyl)-benzamide | 441 |
| 510 | 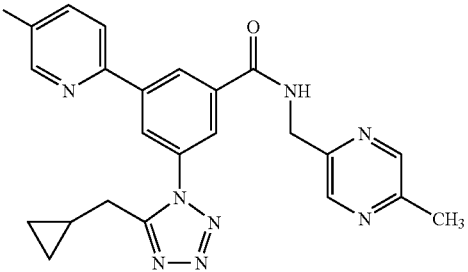 | 3-(5-Cyclopropylmethyl-tetrazol-1-yl)-N-(5-methyl-pyrazin-2-ylmethyl)-5-(5-methyl-pyridin-2-yl)-benzamide | 441 |

TABLE 1-continued

| # | Structure | Name (Autonom ™) | Mp or M + H |
|---|---|---|---|
| 511 | 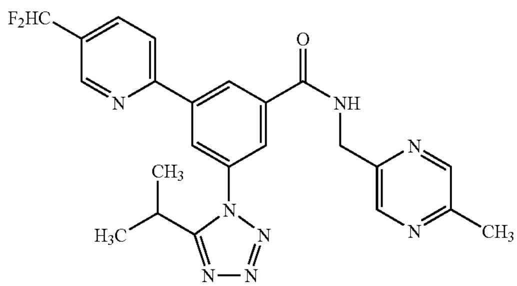 | 3-(5-Difluoromethyl-pyridin-2-yl)-5-(5-isopropyl-tetrazol-1-yl)-N-(5-methyl-pyrazin-2-ylmethyl)-benzamide | 465 |
| 512 | 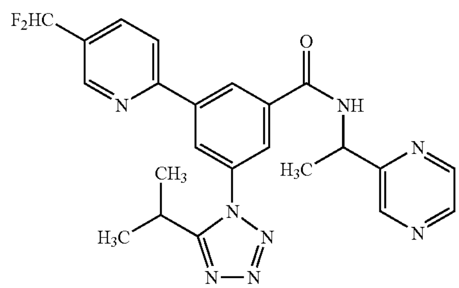 | 3-(5-Difluoromethyl-pyridin-2-yl)-5-(5-isopropyl-tetrazol-1-yl)-N-(1-pyrazin-2-yl-ethyl)-benzamide | 465 |
| 513 | 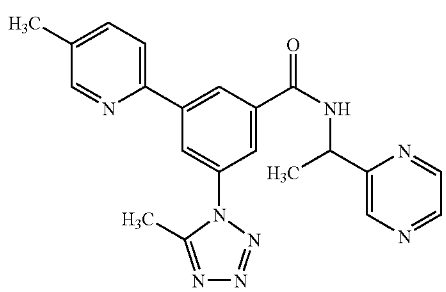 | 3-(5-Methyl-pyridin-2-yl)-5-(5-methyl-tetrazol-1-yl)-N-(1-pyrazin-2-yl-ethyl)-benzamide | 144.5-146.0° C. (HCl salt) |
| 514 | 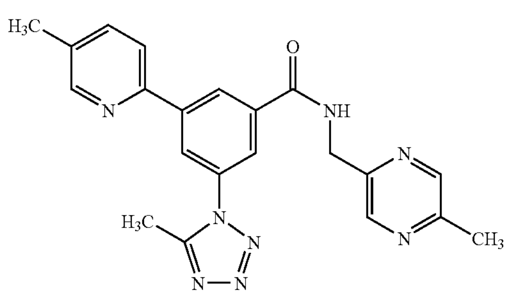 | N-(5-Methyl-pyrazin-2-ylmethyl)-3-(5-methyl-pyridin-2-yl)-5-(5-methyl-tetrazol-1-yl)-benzamide | 158.0-160.0° C. (HCl salt) |
| 515 | 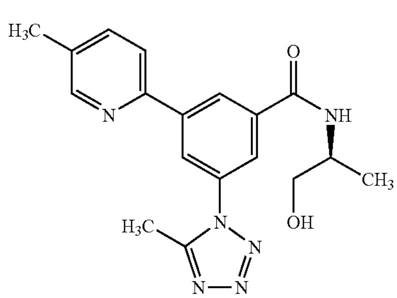 | N-((S)-2-Hydroxy-1-methyl-ethyl)-3-(5-methyl-pyridin-2-yl)-5-(5-methyl-tetrazol-1-yl)-benzamide | 192.3-193.4° C. (HCl salt) |

TABLE 1-continued

| # | Structure | Name (Autonom ™) | Mp or M + H |
|---|---|---|---|
| 516 | 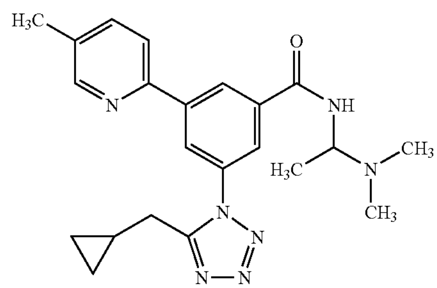 | 3-(5-Cyclopropylmethyl-tetrazol-1-yl)-N-(2-dimethylamino-1-methyl-ethyl)-5-(5-methyl-pyridin-2-yl)-benzamide | 406 |
| 517 | 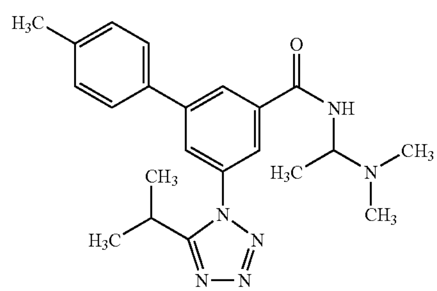 | 5-(5-Isopropyl-tetrazol-1-yl)-4'-methyl-biphenyl-3-carboxylic acid (2-dimethylamino-1-methyl-ethyl)-amide | 393 |
| 518 | 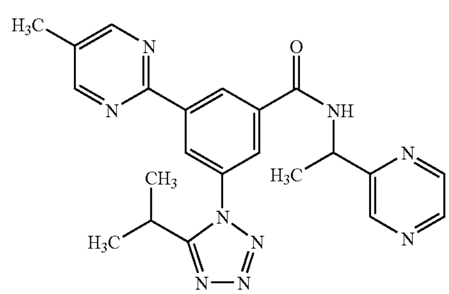 | 3-(5-Isopropyl-tetrazol-1-yl)-5-(5-methyl-pyrimidin-2-yl)-N-(1-pyrazin-2-yl-ethyl)-benzamide | 430 |
| 519 | 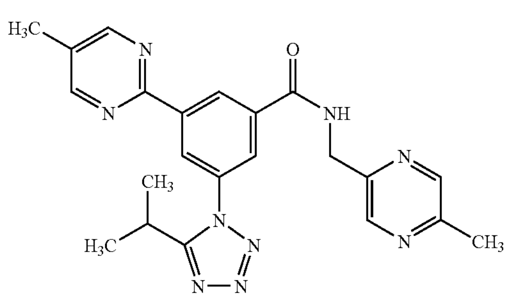 | 3-(5-Isopropyl-tetrazol-1-yl)-N-(5-methyl-pyrazin-2-ylmethyl)-5-(5-methyl-pyrimidin-2-yl)-benzamide | 430 |
| 520 | 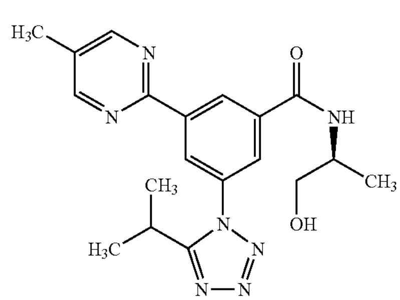 | N-((S)-2-Hydroxy-1-methyl-ethyl)-3-(5-isopropyl-tetrazol-1-yl)-5-(5-methyl-pyrimidin-2-yl)-benzamide | 382 |

TABLE 1-continued

| # | Structure | Name (Autonom ™) | Mp or M + H |
|---|---|---|---|
| 521 | 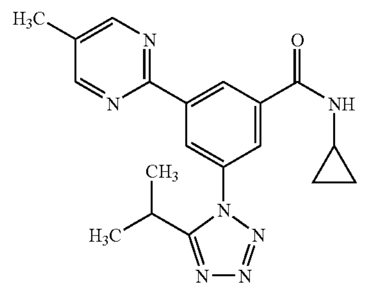 | N-Cyclopropyl-3-(5-isopropyl-tetrazol-1-yl)-5-(5-methyl-pyrimidin-2-yl)-benzamide | 364 |
| 522 | 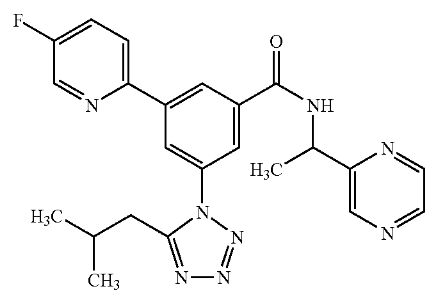 | 3-(5-Fluoro-pyridin-2-yl)-5-(5-isobutyl-tetrazol-1-yl)-N-(1-pyrazin-2-yl-ethyl)-benzamide | 84.0-86.0° C. (HCl salt) |
| 523 | 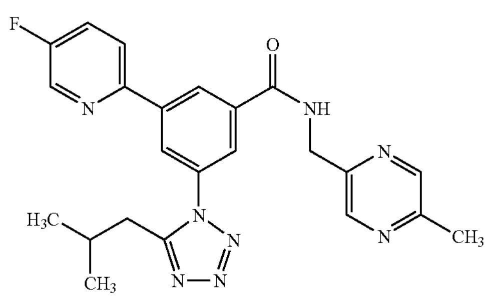 | 3-(5-Fluoro-pyridin-2-yl)-5-(5-isobutyl-tetrazol-1-yl)-N-(5-methyl-pyrazin-2-ylmethyl)-benzamide | 80.0-83.0° C. (HCl salt) |
| 524 | 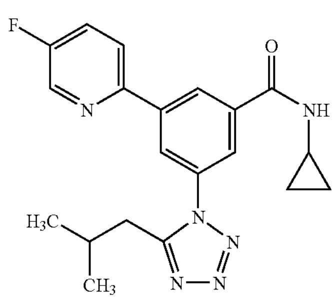 | N-Cyclopropyl-3-(5-fluoro-pyridin-2-yl)-5-(5-isobutyl-tetrazol-1-yl)-benzamide | 78.0-80.0° C. (HCl salt) |
| 525 | 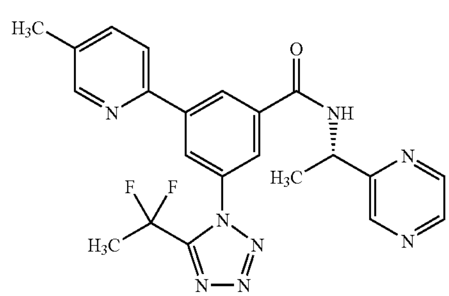 | 3-[5-(1,1-Difluoro-ethyl)-tetrazol-1-yl]-5-(5-methyl-pyridin-2-yl)-N-((S)-1-pyrazin-2-yl-ethyl)-benzamide | 85.0-86.0° C. |

| # | Structure | Name (Autonom ™) | Mp or M + H |
|---|---|---|---|
| 526 | 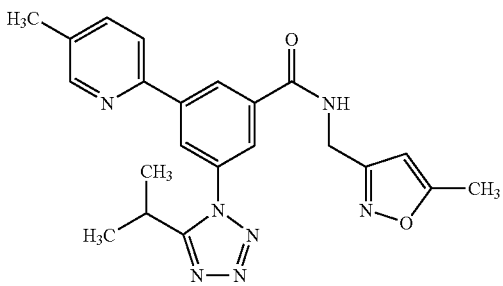 | 3-(5-Isopropyl-tetrazol-1-yl)-N-(5-methyl-isoxazol-3-ylmethyl)-5-(5-methyl-pyridin-2-yl)-benzamide | 418 |
| 527 | 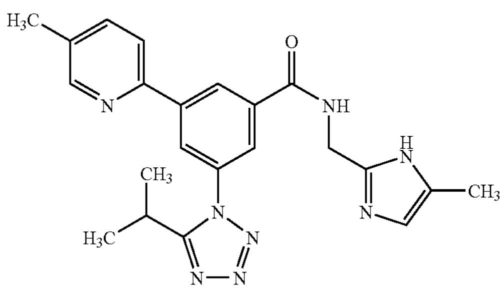 | 3-(5-Isopropyl-tetrazol-1-yl)-N-(5-methyl-1 H-imidazol-2-ylmethyl)-5-(5-methyl-pyridin-2-yl)-benzamide | 417 |
| 528 | 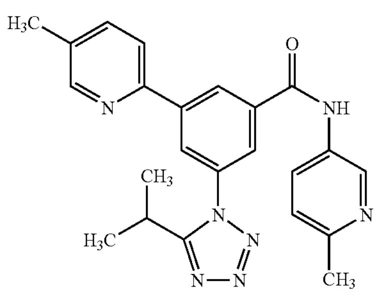 | 3-(5-Isopropyl-tetrazol-1-yl)-N-(6-methyl-pyridin-3-yl)-5-(5-methyl-pyridin-2-yl)-benzamide | 414 |
| 529 | 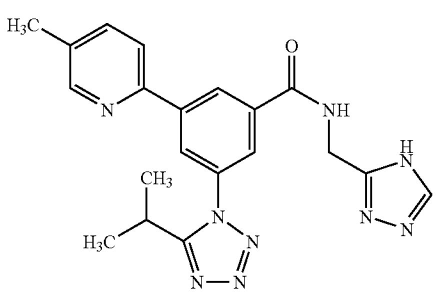 | 3-(5-Isopropyl-tetrazol-1-yl)-5-(5-methyl-pyridin-2-yl)-N-(4 H-[1,2,4]triazol-3-ylmethyl)-benzamide | 404 |
| 530 | 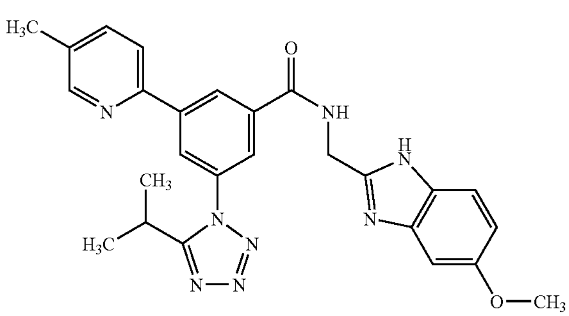 | 3-(5-Isopropyl-tetrazol-1-yl)-N-(5-methoxy-1 H-benzoimidazol-2-ylmethyl)-5-(5-methyl-pyridin-2-yl)-benzamide | 483 |

TABLE 1-continued

| # | Structure | Name (Autonom ™) | Mp or M + H |
|---|---|---|---|
| 531 | 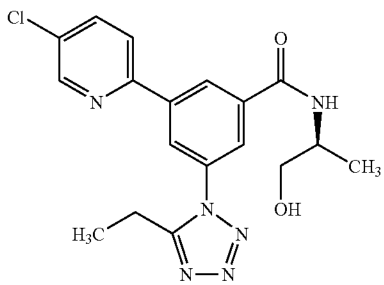 | 3-(5-Chloro-pyridin-2-yl)-5-(5-ethyl-tetrazol-1-yl)-N-(2-hydroxy-1-methyl-ethyl)-benzamide | 89.0-90.0° C. (HCl salt) |
| 532 | 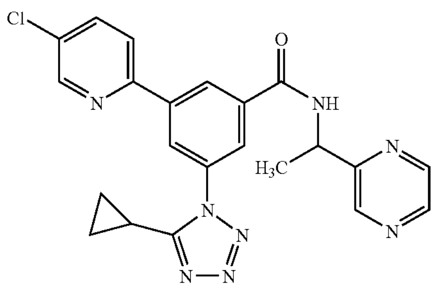 | 3-(5-Chloro-pyridin-2-yl)-5-(5-cyclopropyl-tetrazol-1-yl)-N-(1-methyl-pyrazin-2-ylmethyl)-benzamide | 447 |
| 533 | 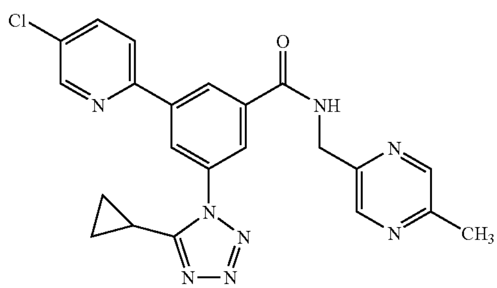 | 3-(5-Chloro-pyridin-2-yl)-5-(5-cyclopropyl-tetrazol-1-yl)-N-(5-methyl-pyrazin-2-ylmethyl)-benzamide | 447 |
| 534 | 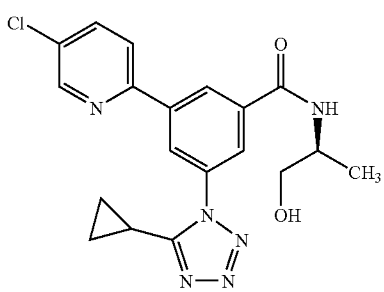 | 3-(5-Chloro-pyridin-2-yl)-5-(5-cyclopropyl-tetrazol-1-yl)-N-(2-hydroxy-1-methyl-ethyl)-benzamide | 399 |
| 535 | 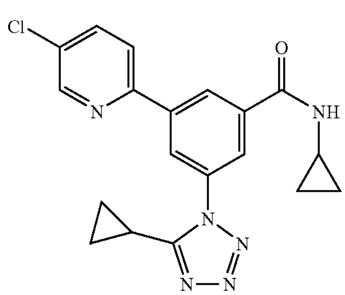 | 3-(5-Chloro-pyridin-2-yl)-N-cyclopropyl-5-(5-cyclopropy-tetrazol-1-yl)-benzamide | 381 |

TABLE 1-continued

| # | Structure | Name (Autonom ™) | Mp or M + H |
|---|---|---|---|
| 536 | 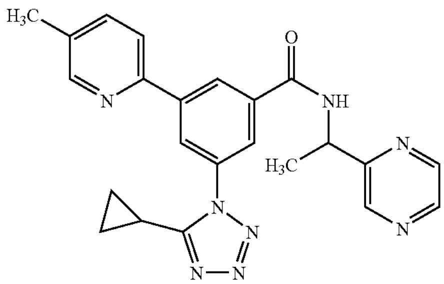 | 3-(5-Cyclopropyl-tetrazol-1-yl)-5-(5-methyl-pyridin-2-yl)-N-(1-pyrazin-2-yl-ethyl)-benzamide | 427 |
| 537 | 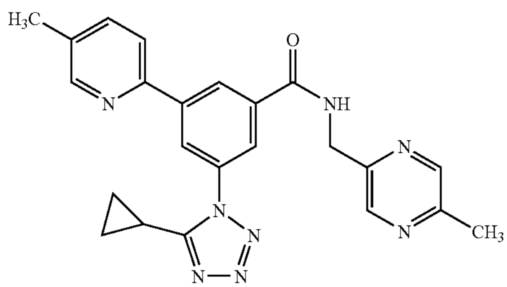 | 3-(5-Cyclopropyl-tetrazol-1-yl)-N-(5-methyl-pyrazin-2-ylmethyl)-5-(5-pyridin-2-yl)-benzamide | 427 |
| 538 | 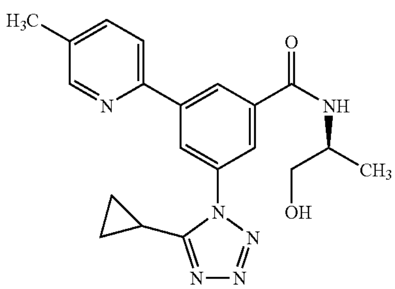 | 3-(5-Cyclopropyl-tetrazol-1-yl)-N-(2-hydroxy-1-methyl-pyridin-2-yl)-benzamide | 379 |
| 539 | 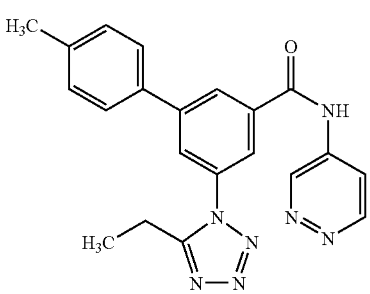 | 5-(5-Ethyl-tetrazol-1-yl)-4'-methyl-biphenyl-3-carboxylic acid pyridazin-4-ylamide | 386 |
| 540 | 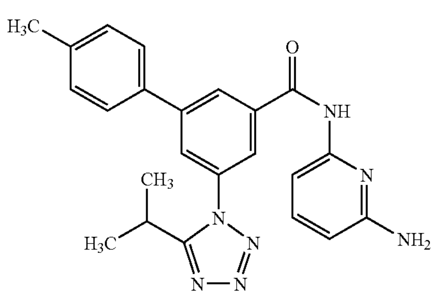 | 5-(5-Isopropyl-tetrazol-1-yl)-4'-methyl-biphenyl-3-carboxylic acid (6-amino-pyridin-2-yl)-amide | 115.7-118.5° C. |

TABLE 1-continued

| # | Structure | Name (Autonom ™) | Mp or M + H |
|---|---|---|---|
| 541 | 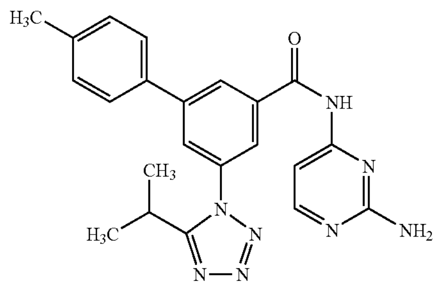 | 5-(5-Isopropyl-tetrazol-1-yl)-4'-methyl-biphenyl-3-carboxylic acid (2-amino-pyrimidin-4-yl)-amide | 415 |
| 542 | 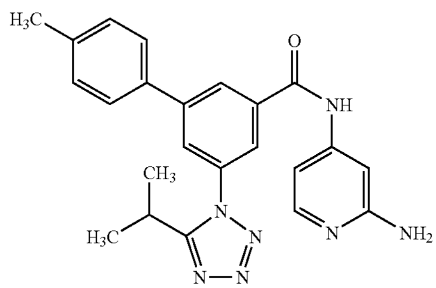 | 5-(5-Isopropyl-tetrazol-1-yl)-4'-methyl-biphenyl-3-carboxylic acid (2-amino-pyridin-4-yl)-amide | 249.7-251.0° C. |
| 543 | 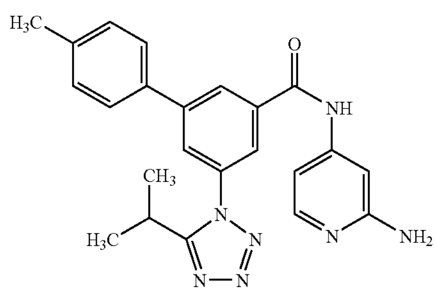 | 5-(5-Isopropyl-tetrazol-1-yl)-4'-methyl-biphenyl-3-carboxylic acid (2-amino-pyridin-4-yl)-amide | 414 |
| 544 | 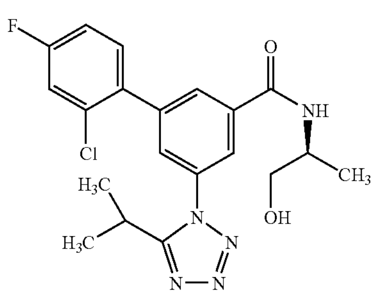 | 2'-Chloro-4'-fluoro-5-(5-isopropyl-tetrazol-1-yl)-biphenyl-3-carboxylic acid ((S)-2-hydroxy-1-methyl-ethyl)-amide | 418 |
| 545 | 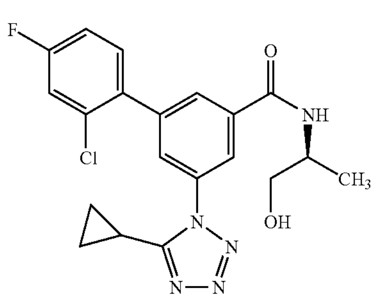 | 2'-Chloro-5-(5-cyclopropyl-tetrazol-1-yl)-4'-fluoro-biphenyl-3-carboxylic acid ((S)-2-hydroxy-1-methyl-ethyl)-amide | 416 |

TABLE 1-continued

| # | Structure | Name (Autonom ™) | Mp or M + H |
|---|---|---|---|
| 546 | 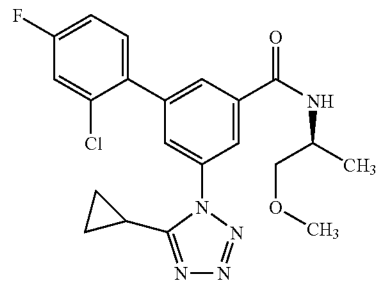 | 2'-Chloro-5-(5-cyclopropyl-tetrazol-1-yl)-4'-fluoro-biphenyl-3-carboxylic acid ((S)-2-methoxy-1-methyl-ethyl)-amide | 430 |
| 547 | 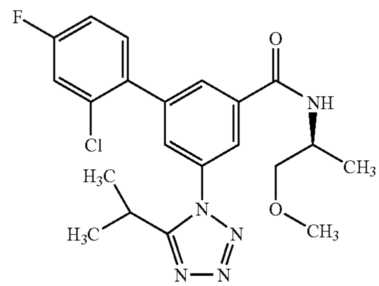 | 2'-Chloro-4'-fluoro-5-(5-isopropyl-tetrazol-1-yl)-biphenyl-3-carboxylic acid ((S)-2-methoxy-1-methyl-ethyl)-amide | 431 |
| 548 | 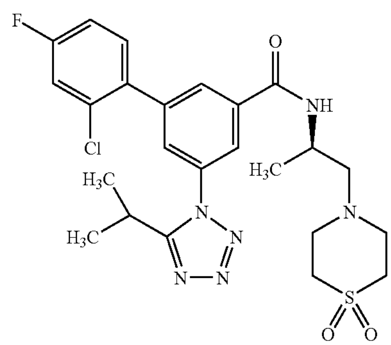 | 2'-Chloro-4'-fluoro-5-(5-isopropyl-tetrazol-1-yl)-biphenyl-3-carboxylic acid [(R)-2-(1,1-dioxo-1$\gamma^6$-thiomorpholin-4-yl)-1-methyl-ethyl]-amide | 535 |
| 549 | 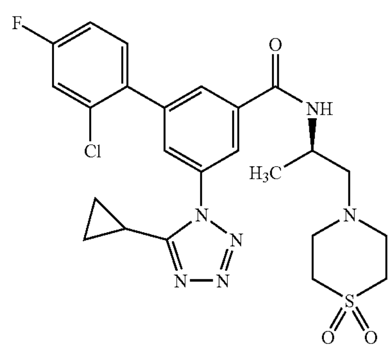 | 2'-Chloro-5-(5-cyclopropyl-tetrazol-1-yl)-4'-fluoro-biphenyl-3-carboxylic acid [(R)-2-(1,1-dioxo1$\gamma^6$-thiomorpholin-4-yl)-1-methyl-ethyl]-amide | 533 |
| 550 | 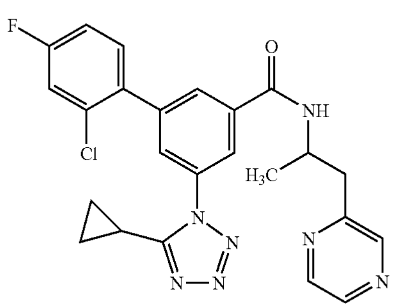 | 2'-Chloro-5-(5-cyclopropyl-tetrazol-1-yl)-4'-fluoro-biphenyl-3-carboxylic acid (1-pyrazin-2-yl-ethyl)-amide | 478 |

TABLE 1-continued

| # | Structure | Name (Autonom ™) | Mp or M + H |
|---|---|---|---|
| 551 | 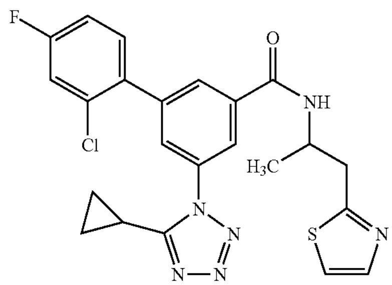 | 2'-Chloro-5-(5-cyclopropyl-tetrazol-1-yl)-4'-fluoro-biphenyl-3-carboxylic acid (1-thiazol-2-yl-ethyl)-amide | 483 |
| 552 | 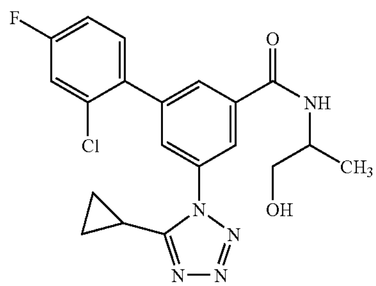 | 2'-Chloro-5-(5-cyclopropyl-tetrazol-1-yl)-4'-fluoro-biphenyl-3-carboxylic acid (2-hydroxy-1-methyl-ethyl)-amide | 416 |
| 553 | 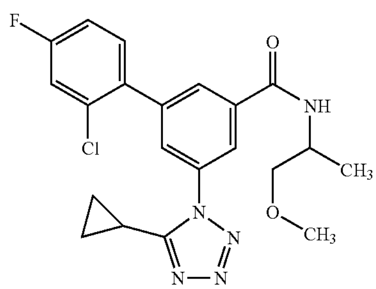 | 2'-Chloro-5-(5-cyclopropyl-tetrazol-1-yl)-4'-fluoro-biphenyl-3-carboxylic acid (2-methoxy-1-methyl-ethyl)-amide | 430 |
| 554 | 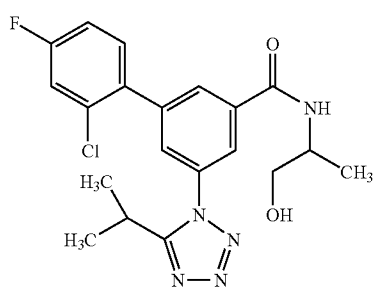 | 2'-Chloro-4'-fluoro-5-(5-isopropyl-tetrazol-1-yl)-biphenyl-3-carboxylic acid (2-hydroxy-1-methyl-ethyl)-amide | 418 |
| 555 | 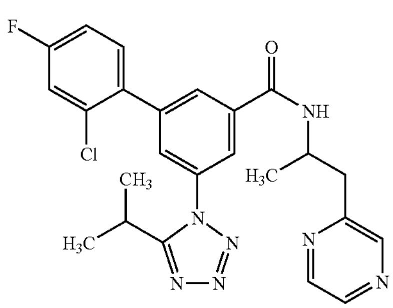 | 2'-Chloro-4'-fluoro-5-(5-isopropyl-tetrazol-1-yl)-biphenyl-3-carboxylic acid (1-pyrazin-2-yl-ethyl)-amide | 480 |

TABLE 1-continued

| # | Structure | Name (Autonom ™) | Mp or M + H |
|---|---|---|---|
| 556 | 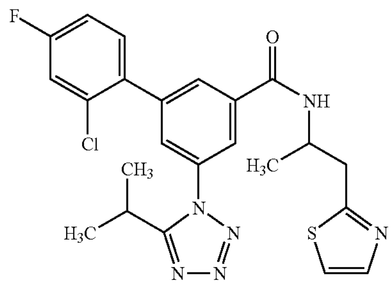 | 2'-Chloro-4'-fluoro-5-(5-isopropyl-tetrazol-1-yl)-biphenyl-3-carboxylic acid (1-thiazol-2-yl-ethyl)-amide | 485 |
| 557 | 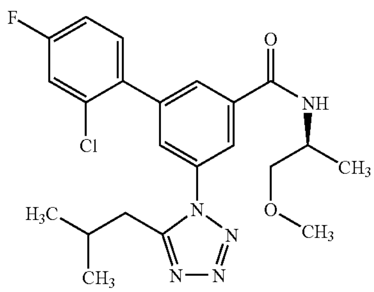 | 2'-Chloro-4'-fluoro-5-(5-isobutyl-tetrazol-1-yl)-biphenyl-3-carboxylic acid ((S)-2-methoxy-1-methyl-ethyl)-amide | 446 |
| 558 | 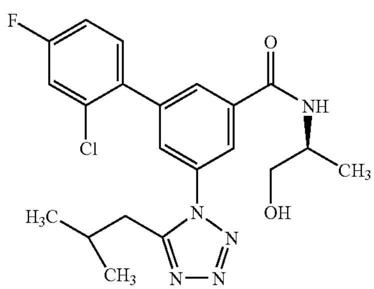 | 2'-Chloro-4'-fluoro-5-(5-isobutyl-tetrazol-1-yl)-biphenyl-3-carboxylic acid ((S)-2-hydroxy-1-methyl-ethyl)-amide | 432 |
| 559 | 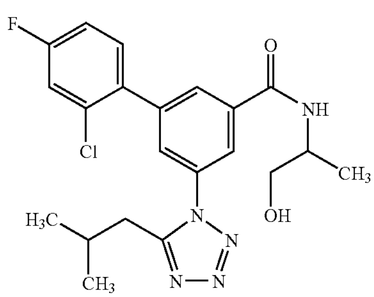 | 2'-Chloro-4'-fluoro-5-(5-isobutyl-tetrazol-1-yl)-biphenyl-3-carboxylic acid (2-hydroxy-1-methyl-ethyl)-amide | 432 |
| 560 | 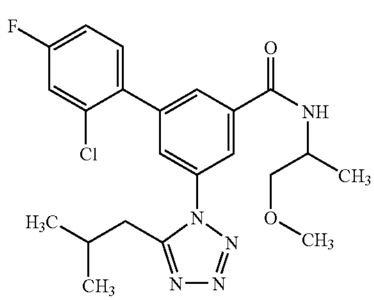 | 2'-Chloro-4'-fluoro-5-(5-isobutyl-tetrazol-1-yl)-biphenyl-3-carboxylic acid (2-methoxy-1-methyl-ethyl)-amide | 446 |

TABLE 1-continued

| # | Structure | Name (Autonom ™) | Mp or M + H |
|---|---|---|---|
| 561 | 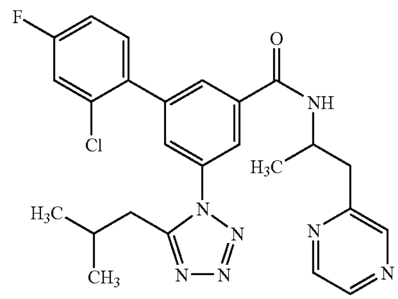 | 2'-Chloro-4'-fluoro-5-(5-isobutyl-tetrazol-1-yl)-biphenyl-3-carboxylic acid (1-pyrazin-2-yl-ethyl)-amide | 494 |
| 562 | 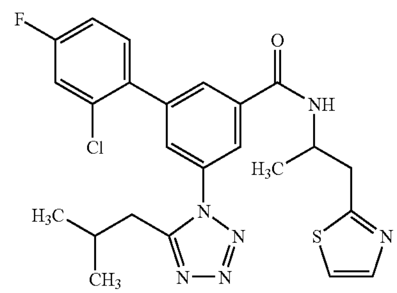 | 2'-Chloro-4'-fluoro-5-(5-isobutyl-tetrazol-1-yl)-biphenyl-3-carboxylic acid (1-thiazol-2-yl-ethyl)-amide | 499 |
| 563 | 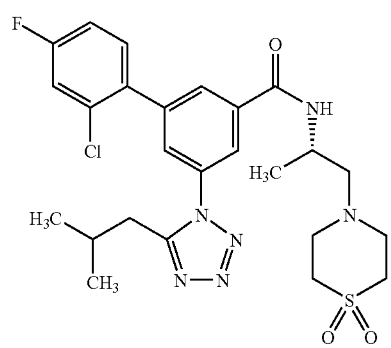 | 2'-Chloro-4'-fluoro-5-(5-isobutyl-tetrazol-1-yl)-biphenyl-3-carboxylic acid [(R)-2-(1,1-dioxo-1$\gamma^6$-thiomorpholin-4-yl)-1-methyl-ethyl]-amide | 549 |
| 564 | 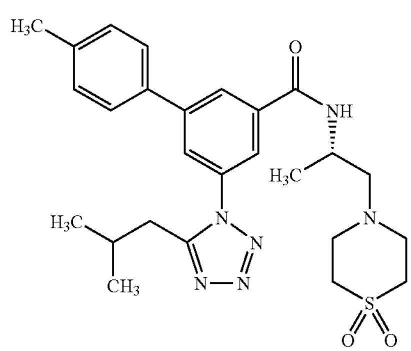 | 5-(5-Isobutyl-tetrazol-1-yl)-4'-methyl-biphenyl-3-carboxylic acid [(R)-2-(1,1-dioxo-1$\gamma^6$-thiomorpholin-4-yl)-1-methyl-ethyl]-amide | 511 |

TABLE 1-continued

| # | Structure | Name (Autonom ™) | Mp or M + H |
|---|---|---|---|
| 565 | 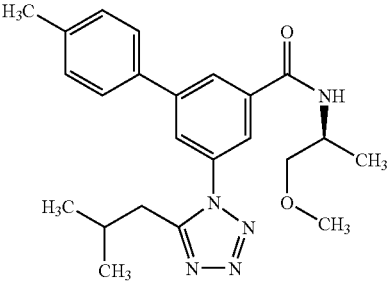 | 5-(5-Isobutyl-tetrazol-1-yl)-4'-methyl-biphenyl-3-carboxylic acid ((S)-2-methoxy-1-methyl-ethyl)-amide | 408 |
| 566 | 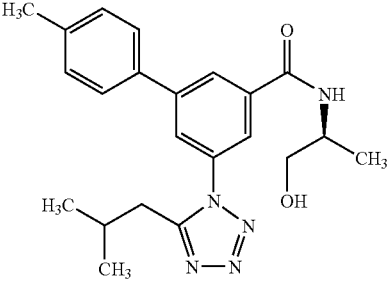 | 5-(5-Isobutyl-tetrazol-1-yl)-4'-methyl-biphenyl-3-carboxylic acid ((S)-2-hydroxy-1-methyl-ethyl)-amide | 394 |
| 567 | 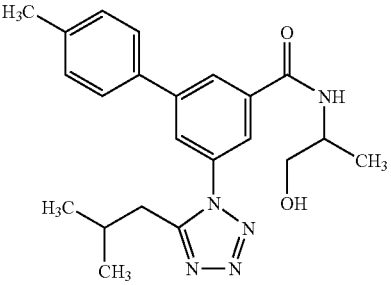 | 5-(5-Isobutyl-tetrazol-1-yl)-4'-methyl-biphenyl-3-carboxylic acid ((S)-2-hydroxy-1-methyl-ethyl)-amide | 394 |
| 568 | 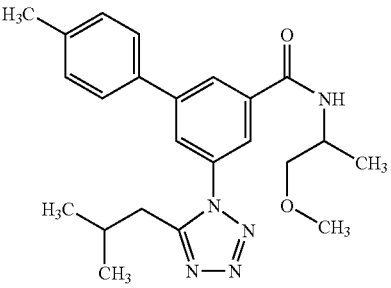 | 5-(5-Isobutyl-tetrazol-1-yl)-4'-methyl-biphenyl-3-carboxylic acid (2-hydroxy-1-methyl-ethyl)-amide | 394 |
| 569 | 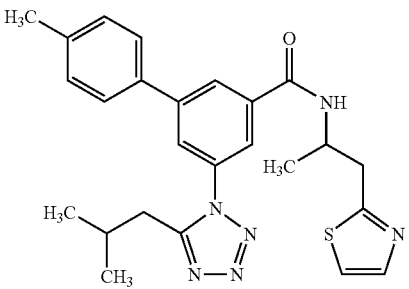 | 5-(5-Isobutyl-tetrazol-1-yl)-4'-methyl-biphenyl-3-carboxylic acid (1-thiazol-2-yl-ethyl)-amide | 461 |

TABLE 1-continued

| # | Structure | Name (Autonom ™) | Mp or M + H |
|---|---|---|---|
| 570 | 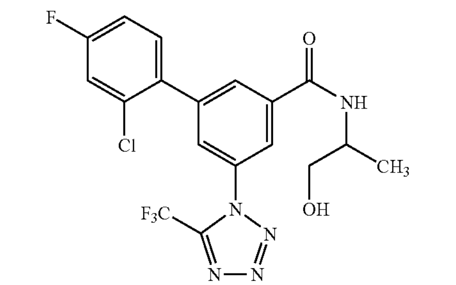 | 2'-Chloro-4'-fluoro-5-(5-trifluoromethyl-tetrazol-1-yl)-biphenyl-3-carboxylic acid (2-hydroxy-1-methyl-ethyl)-amide | 444 |
| 571 | 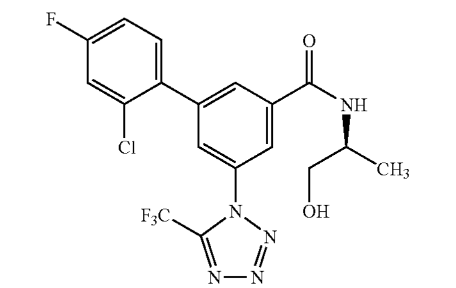 | 2'-Chloro-4'-fluoro-5-(5-trifluoromethyl-tetrazol-1-yl)-biphenyl-3-carboxylic acid ((S)-2-hydroxy-1-methyl-ethyl)-amide | 444 |
| 572 | 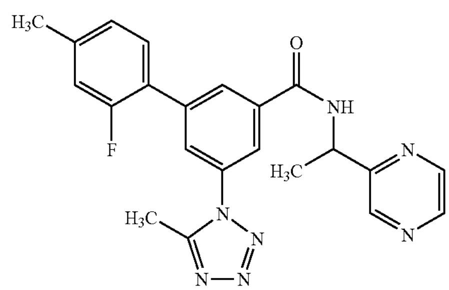 | 2'-Fluoro-4'-methyl-5-(5-methyl-tetrazol-1-yl)-biphenyl-3-carboxylic acid (1-pyrazin-2-yl-ethyl)-amide | 418 |
| 573 | 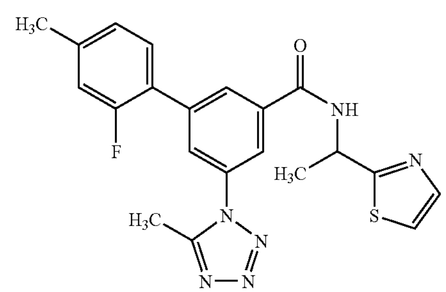 | 2'-Fluoro-4'-methyl-5-(5-methyl-tetrazol-1-yl)-biphenyl-3-carboxylic acid (1-thiazol-2-yl-ethyl)-amide | 423 |
| 574 | 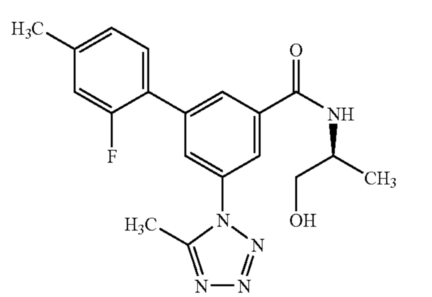 | 2'-Fluoro-4'-methyl-5-(5-methyl-tetrazol-1-yl)-biphenyl-3-carboxylic acid ((S)-2-hydroxy-1-methyl-ethyl)-amdie | 370 |

TABLE 1-continued

| # | Structure | Name (Autonom ™) | Mp or M + H |
|---|---|---|---|
| 575 | 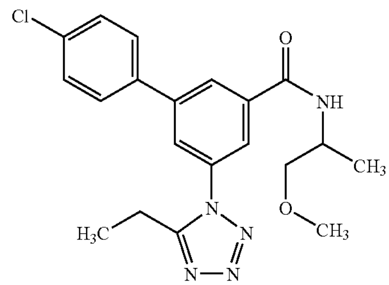 | 4'-Chloro-5-(5-ethyl-tetrazol-1-yl)-biphenyl-3-carboxylic acid (2-methoxy-1-methyl-ethyl)-amide | 400 |
| 576 | 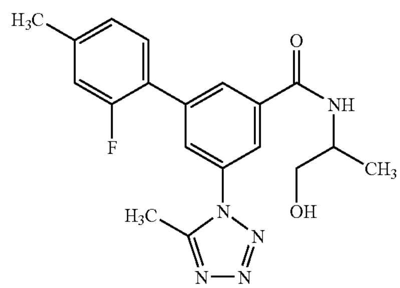 | 2'-Fluoro-4'-methyl-5-(5-methyl-tetrazol-1-yl)-biphenyl-3-carboxylic acid (2-hydroxy-1-methyl-ethyl)-amide | 370 |
| 577 | 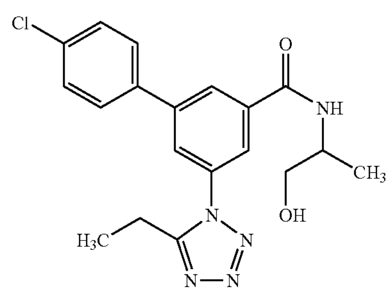 | 4'-Chloro-5-(5-ethyl-tetrazol-1-yl)-biphenyl-3-carboxylic acid (2-hydroxy-1-methyl-ethyl)-amide | 386 |
| 578 | 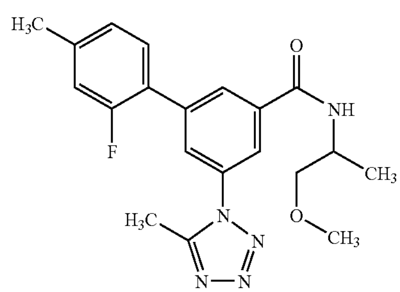 | 2'-Fluoro-4'-methyl-5-(5-methyl-tetrazol-1-yl)-biphenyl-3-carboxylic acid (2-methoxy-1-methyl-ethyl)-amide | 384 |
| 579 | 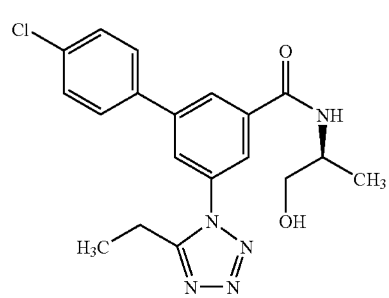 | 4'-Chloro-5-(5-ethyl-tetrazol-1-yl)-biphenyl-3-carboxylic acid ((S)-2-hydroxy-1-methyl-ethyl)-amide | 396 |

TABLE 1-continued

| # | Structure | Name (Autonom ™) | Mp or M + H |
|---|---|---|---|
| 580 | 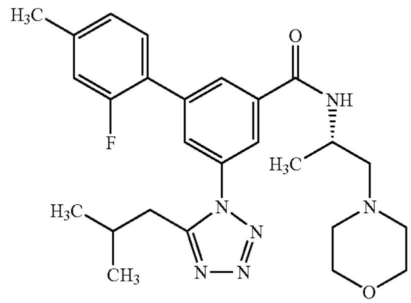 | 2'-Fluoro-4'-methyl-5-(5-methyl-tetrazol-1-yl)-biphenyl-3-carboxylic acid((R)-1-methyl-2-morpholin-4-yl-ethyl)-amide | 481 |
| 581 | 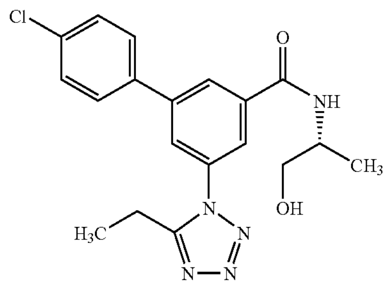 | 4'-Chloro-5-(5-ethyl-tetrazol-1-yl)-biphenyl-3-carboxylic acid ((R)-2-hydroxy-1-methyl-ethyl)-amide | 386 |
| 582 | 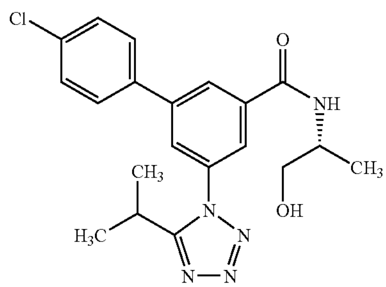 | 4'-Chloro-5-(5-isopropyl-tetrazol-1-yl)-biphenyl-3-carboxylic acid ((R)-2-hydroxy-1-methyl-ethyl)-amide | 400 |
| 583 | 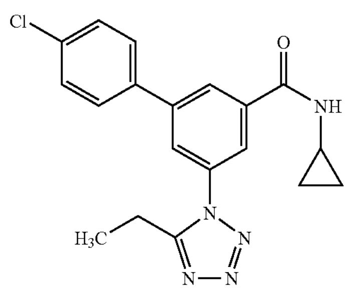 | 4'-Chloro-5-(5-ethyl-tetrazol-1-yl)-biphenyl-3-carboxylic acid cyclopropylamide | 368 |
| 584 | 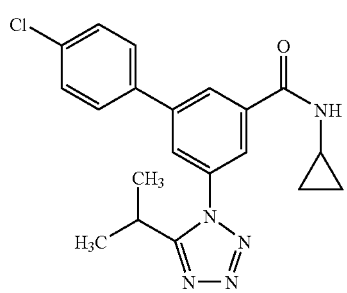 | 4'-Chloro-5-(5-isopropyl-tetrazol-1-yl)-biphenyl-3-carboxylic acid cyclopropylamide | 382 |

TABLE 1-continued

| # | Structure | Name (Autonom ™) | Mp or M + H |
|---|---|---|---|
| 585 | 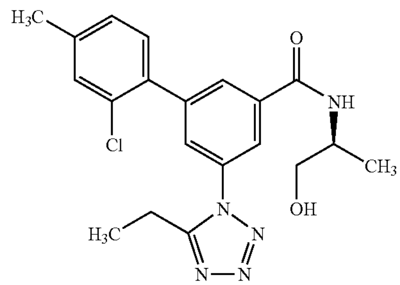 | 2'-Chloro-5-(5-ethyl-tetrazol-1-yl)-4'-methyl-biphenyl-3-carboxylic acid ((S)-3-hydroxy-1-methyl-ethyl)-amide | 400 |
| 586 | 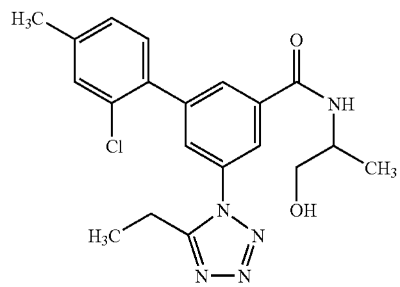 | 2'-Chloro-5-(5-ethyl-tetrazol-1-yl)-4'-methyl-biphenyl-3-carboxylic acid (2-hydroxy-1-methyl-ethyl)-amide | 400 |
| 587 | 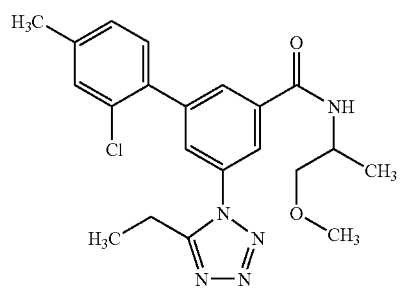 | 2'-Chloro-5-(5-ethyl-tetrazol-1-yl)-4'-methyl-biphenyl-3-carboxylic acid (2-methoxy-1-methyl-ethyl)-amdie | 414 |
| 588 | 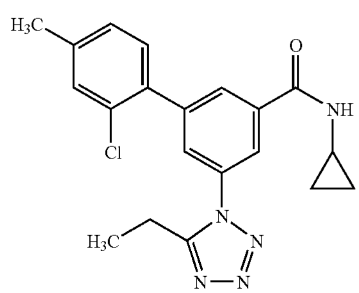 | 2'-Chloro-5-(5-ethyl-tetrazol-1-yl)-4'-methyl-biphenyl-3-carboxylic acid cyclopropylamide | 382 |
| 589 | 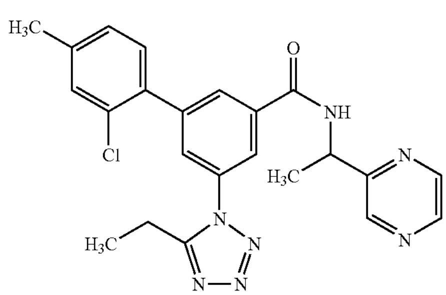 | 2'-Chloro-5-(5-ethyl-tetrazol-1-yl)-4'-methyl-biphenyl-3-carboxylic acid (1-pyrazin-2-yl-ethyl)-amide | 464 |

TABLE 1-continued

| # | Structure | Name (Autonom ™) | Mp or M + H |
|---|---|---|---|
| 590 | 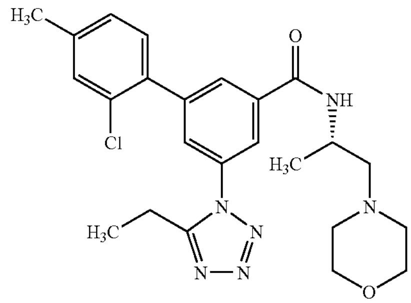 | 2'-Chloro-5-(5-ethyl-tetrazol-1-yl)-4'-methyl-biphenyl-3-carboxylic acid ((R)-1-methyl-2-morpholin-4-yl-ethyl)-amide | 469 |
| 591 | 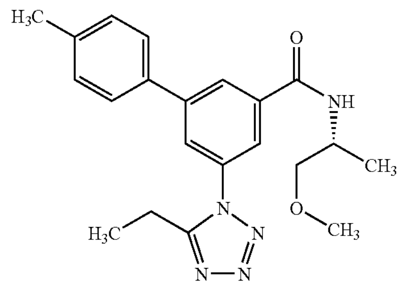 | 5-(5-Ethyl-tetrazol-1-yl)-4'-methyl-biphenyl-3-carboxylic acid ((R)-2-methoxy-1-methyl-ethyl)-amide | 380 |
| 592 | 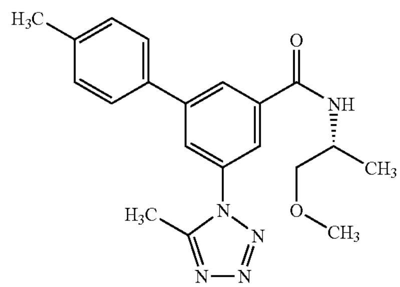 | 4'-Methyl-5-(5-methyl-tetrazol-1-yl)-biphenyl-3-carboxylic acid ((R)-2-methoxy-1-methyl-ethyl)-amide | 366 |
| 593 | 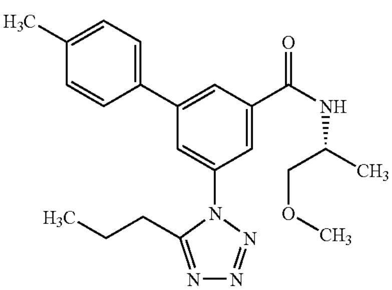 | 4'-Methyl-5-(5-propyl-tetrazol-1-yl)-biphenyl-3-carboxylic acid ((R)-2-methoxy-1-methyl-ethyl)-amide | 394 |
| 594 | 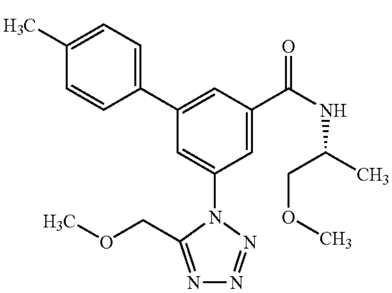 | 5-(5-Methoxymethyl-tetrazol-1-yl)-4'-methyl-biphenyl-3-carboxylic acid ((R)-2-methoxy-1-methyl-ethyl)-amide | 396 |

TABLE 1-continued

| # | Structure | Name (Autonom ™) | Mp or M + H |
|---|---|---|---|
| 595 | 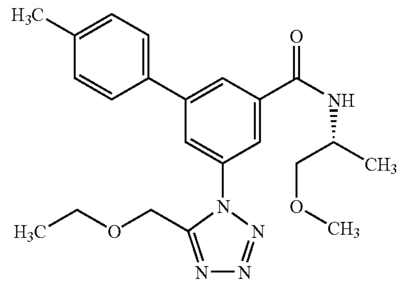 | 5-(5-Ethoxymethyl-tetrazol-1-yl)-4'-methyl-biphenyl-3-carboxylic acid ((R)-2-methoxy-1-methyl-ethyl)-amide | 410 |
| 596 | 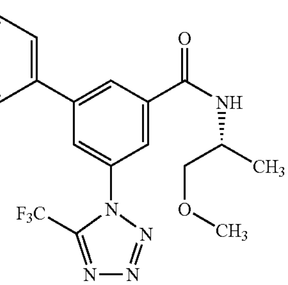 | 4'-Methyl-5-(5-trifluoromethyl-tetrazol-1-yl)-biphenyl-3-carboxylic acid ((R)-2-methoxy-1-methyl-ethyl)-amide | 420 |
| 597 | 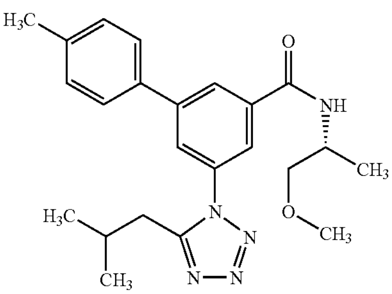 | 5-(5-Isobutyl-tetrazol-1-yl)-4'-methyl-biphenyl-3-carboxylic acid ((R)-2-methoxy-1-methyl-ethyl)-amide | 408 |
| 598 | 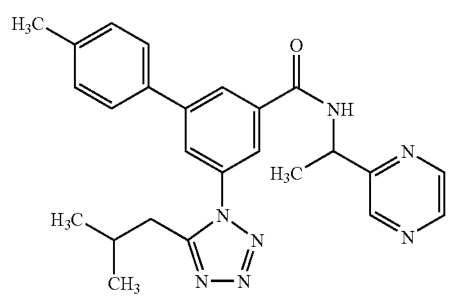 | 5-(5-Isobutyl-tetrazol-1-yl)-4'-methyl-biphenyl-3-carboxylic acid (1-pyrazin-2-yl-ethyl-amide | 442 |
| 599 | 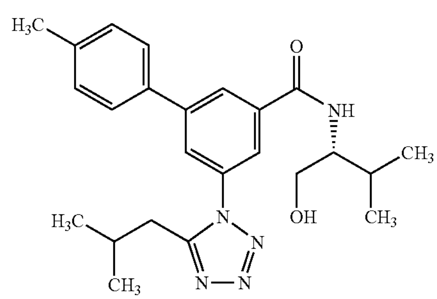 | 5-(5-Ethyl-tetrazol-1-yl)-4'-methyl-biphenyl-3-carboxylic acid (1-hydroxymethyl-2-methyl-propyl)-amide | 422 |

TABLE 1-continued

| # | Structure | Name (Autonom ™) | Mp or M + H |
|---|---|---|---|
| 600 | 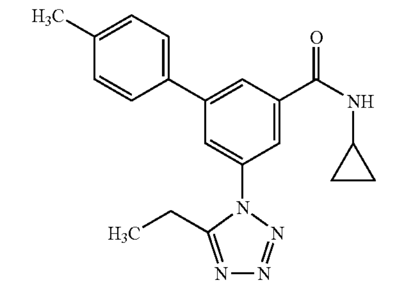 | 5-(5-Ethyl-tetrazol-1-yl)-4'-methyl-biphenyl-3-carboxylic acid cyclopropylamide | 348 |
| 601 | 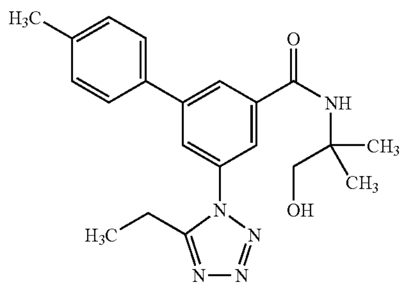 | 5-(5-Ethyl-tetrazol-1-yl)-4'-methyl-biphenyl-3-carboxylic acid (2-hydroxy-1,1-dimethyl-ethyl)-amide | 380 |
| 602 | 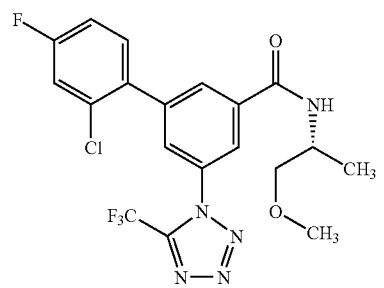 | 2'-Chloro-4'-fluoro-5-(5-trifluoromethyl-tetrazol-1-yl)-biphenyl-3-carboxylic acid ((S)-2-methoxy-1-methyl-ethyl)-amide | 458 |
| 603 | 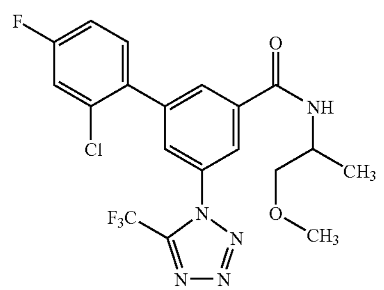 | 2'-Chloro-4'-fluoro-5-(5-trifluoromethyl-tetrazol-1-yl)-biphenyl-3-carboxylic acid (2-methoxy-1-methyl-ethyl)-amide | 458 |
| 604 | 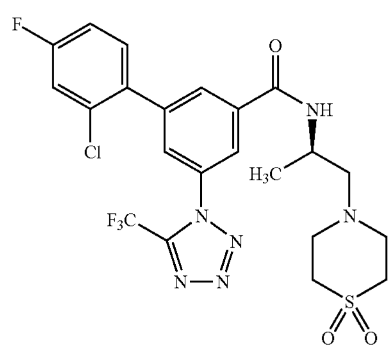 | 2'-Chloro-4'-fluoro-5-(5-trifluoromethyl-tetrazol-1-yl)-biphenyl-3-carboxylic acid [(R)-2-(1,1-dioxo-1=65 6-thiomorpholin-4-yl)-1-methyl-ethyl]-amide | 561 |

TABLE 1-continued

| # | Structure | Name (Autonom ™) | Mp or M + H |
|---|---|---|---|
| 605 | 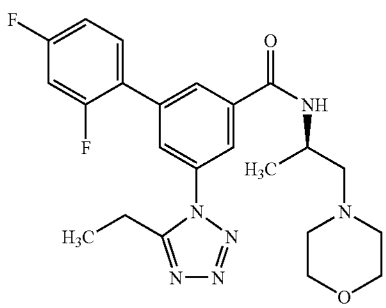 | 5-(5-Ethyl-tetrazol-1-yl)-2',4'-difluoro-biphenyl-3-carboxylic acid ((R)-1-methyl-2-morpholin-4-yl-ethyl)-amide | 457 |
| 606 | 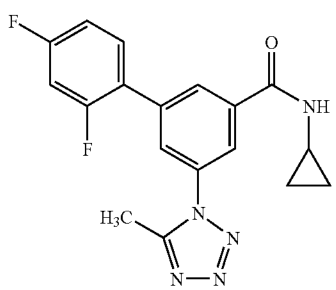 | 2',4'-Difluoro-5-(5-methyl-tetrazol-1-yl)-biphenyl-3-carboxylic acid cyclopropylamide | 356 |
| 607 | 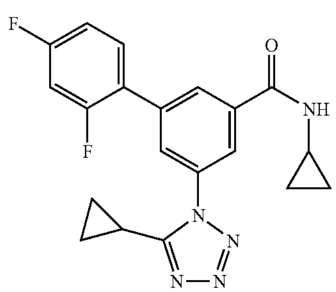 | 5-(5-Cyclopropyl-tetrazol-1-yl)-2',4'-difluoro-biphenyl-3-carboxylic acid cyclopropylamide | 382 |
| 608 | 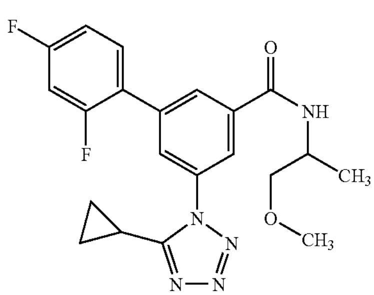 | 5-(5-Cyclopropyl-tetrazol-1-yl)-2',4'-difluoro-biphenyl-3-carboxylic acid (2-methoxy-1-methyl-ethyl)-amide | 414 |
| 609 | 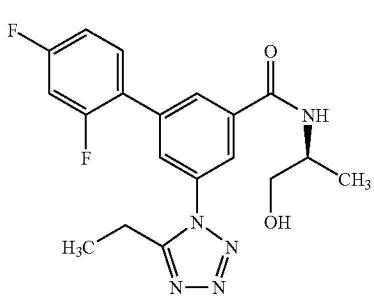 | 5-(5-Ethyl-tetrazol-1-yl)-2',4'-difluoro-biphenyl-3-carboxylic acid ((S)-2-hydroxy-1-methyl-ethyl)-amide | 388 |

TABLE 1-continued

| # | Structure | Name (Autonom ™) | Mp or M + H |
|---|---|---|---|
| 610 | 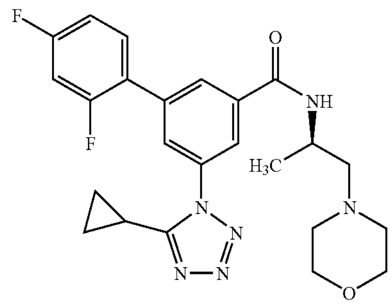 | 5-(5-Cyclopropyl-tetrazol-1-yl)-2',4'-difluoro-biphenyl-3-carboxylic acid ((R)-1-methyl-2-morpholin-4-yl-ethyl)-amide | 469 |
| 611 | 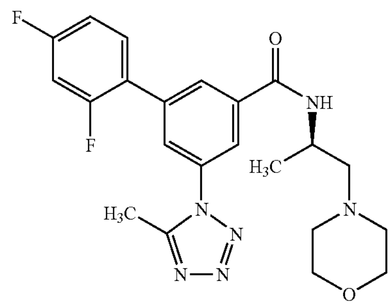 | 2',4'-Difluoro-5-(5-methyl-tetrazol-1-yl)-biphenyl-3-carboxylic acid ((R)-1-methyl-2-morpholin-4-yl-ethyl)-amide | 443 |
| 612 | 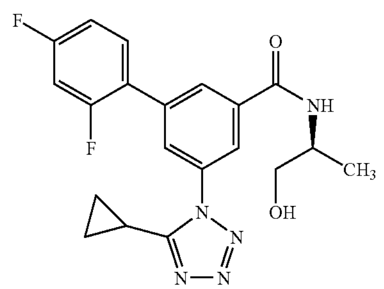 | 5-(5-Cyclopropyl-tetrazol-1-yl)-2',4'-difluoro-biphenyl-3-carboxylic acid ((S)-2-hydroxy-1-methyl-ethyl)-amide | 400 |
| 613 | 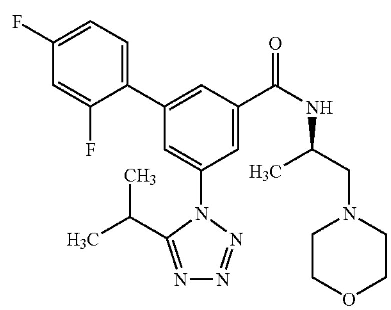 | 2',4'-Difluoro-5-(5-isopropyl-tetrazol-1-yl)-biphenyl-3-carboxylic acid ((R)-1-methyl-2-morpholin-4-yl-ethyl)-amide | 471 |
| 614 | 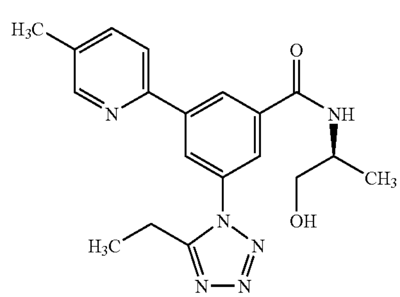 | 3-(5-Ethyl-tetrazol-1-yl)-N-((S)-2-hydroxy-1-methyl-ethyl)-5-(5-methyl-pyridin-2-yl)-benzamide | 367 |

TABLE 1-continued

| # | Structure | Name (Autonom ™) | Mp or M + H |
|---|---|---|---|
| 615 | 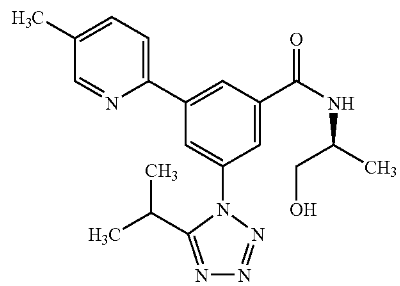 | N-((S)-2-Hydroxy-1-methyl-ethyl)-3-(5-isopropyl-tetrazol-1-yl)-5-(5-methyl-pyridin-2-yl)-benzamide | 381 |
| 616 | 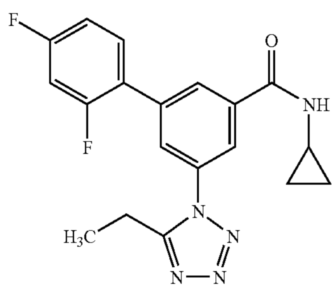 | 5-(5-Ethyl-tetrazol-1-yl)-2',4'-difluoro-biphenyl-3-carboxylic acid cyclopropylamide | 370 |
| 617 | 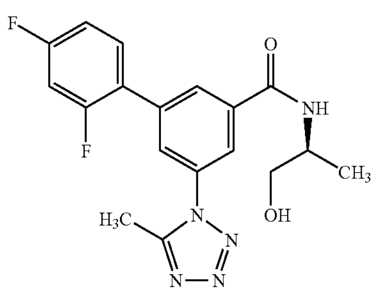 | 2',4'-Difluoro-5-(5-methyl-tetrazol-1-yl)-biphenyl-3-carboxylic acid ((S)-2-hydroxy-1-methyl-ethyl)-amide | 374 |
| 618 | 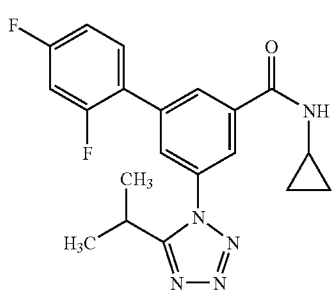 | 2',4'-Difluoro-5-(5-methyl-tetrazol-1-yl)-biphenyl-3-carboxylic acid cyclopropylamide | 384 |
| 619 | 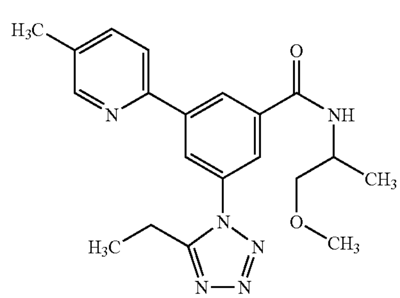 | 3-(5-Ethyl-tetrazol-1-yl)-N-(2-methoxy-1-methyl-ethyl)-5-(5-methyl-pyridin-2-yl)-benzamide | 381 |

TABLE 1-continued

| # | Structure | Name (Autonom ™) | Mp or M + H |
|---|---|---|---|
| 620 | 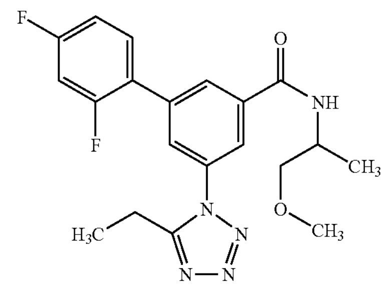 | 5-(5-Ethyl-tetrazol-1-yl)-2',4'-difluoro-biphenyl-3-carboxylic acid (2-methoxy-1-methyl-ethyl)-amide | 402 |
| 621 | 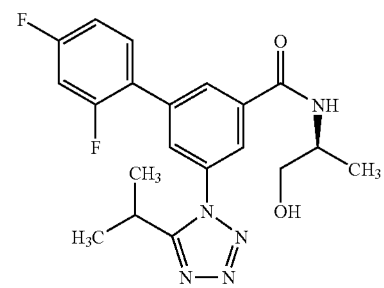 | 2',4'-Difluoro-5-(5-isopropyl-tetrazol-1-yl)-biphenyl-3-carboxylic acid ((S)-2-hydroxy-1-methyl-ethyl)-amide | 402 |
| 622 | 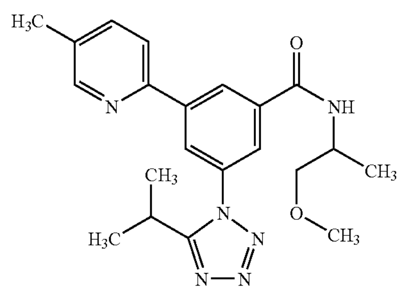 | 3-(5-Isopropyl-tetrazol-1-yl)-N-(2-methoxy-1-methyl-ethyl)-5-(5-methyl-pyridin-2-yl)-benzamide | 395 |
| 623 | 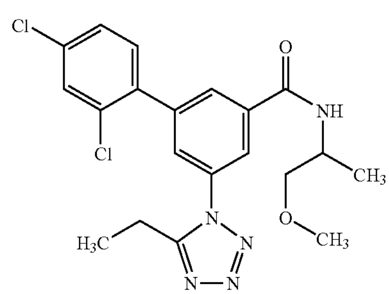 | 2',4'-Dichloro-5-(5-ethyl-tetrazol-1-yl)-biphenyl-3-carboxylic acid (2-methoxy-1-methyl-ethyl)-amide | 434 |
| 624 | 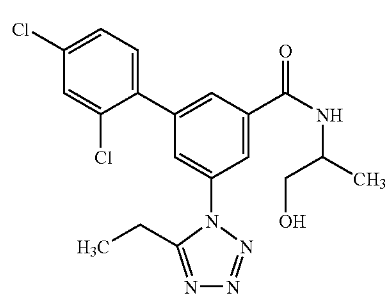 | 2',4'-Dichloro-5-(5-ethyl-tetrazol-1-yl)-biphenyl-3-carboxylic acid (2-hydroxy-1-methyl-ethyl)-amide | 420 |

TABLE 1-continued

| # | Structure | Name (Autonom ™) | Mp or M + H |
|---|---|---|---|
| 625 | 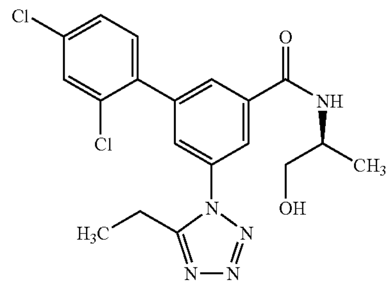 | 2',4'-Dichloro-5-(5-ethyl-tetrazol-1-yl)-biphenyl-3-carboxylic acid ((S)-2-hydroxy-1-methyl-ethyl)-amide | 420 |
| 626 | 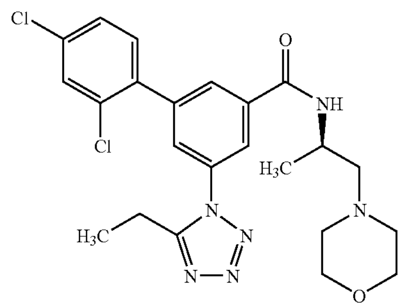 | 2',4'-Dichloro-5-(5-ethyl-tetrazol-1-yl)-biphenyl-3-carboxylic acid ((R)-1-methyl-2-morpholin-4-yl-ethyl)-amide | 489 |
| 627 | 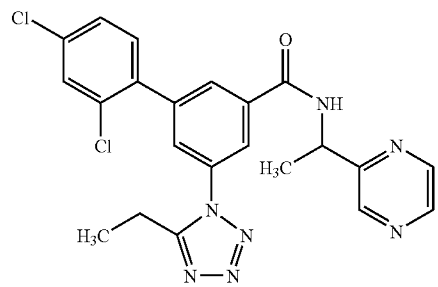 | 2',4'-Dichloro-5-(5-ethyl-tetrazol-1-yl)-biphenyl-3-carboxylic acid (1-pyrazin-2-yl-ethyl)-amide | 484 |
| 628 | 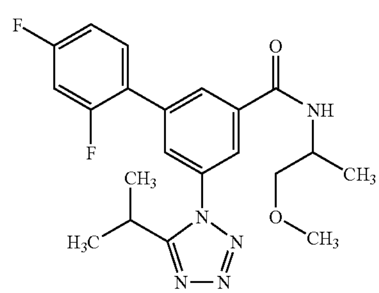 | 2',4'-Dichloro-5-(5-isopropyl-tetrazol-1-yl)-biphenyl-3-carboxylic acid (2-methoxy-1-methyl-ethyl)-amide | 416 |
| 629 | 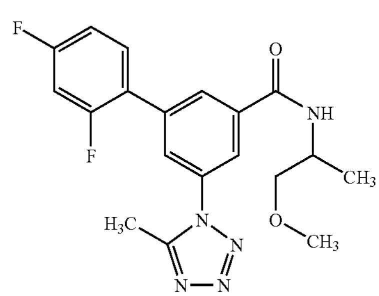 | 2',4'-Difluoro-5-(5-methyl-tetrazol-1-yl)-biphenyl-3-carboxylic acid (2-methoxy-1-methyl-ethyl)-amide | 388 |

TABLE 1-continued

| # | Structure | Name (Autonom ™) | Mp or M + H |
|---|---|---|---|
| 630 | 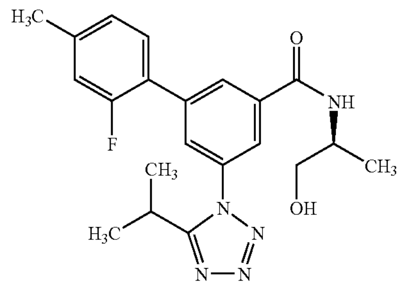 | 2'-Fluoro-5-(5-isopropyl-tetrazol-1-yl)-4'-methyl-biphenyl-3-carboxylic acid ((S)-2-hydroxy-1-methyl-ethyl)-amide | 120.0-121.0° C. |
| 631 | 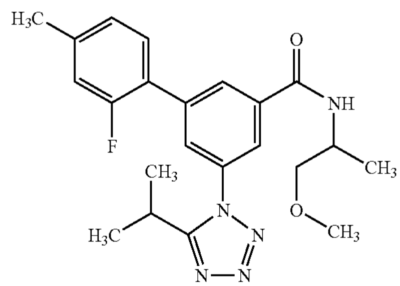 | 2'-Fluoro-5-(5-isopropyl-tetrazol-1-yl)-4'-methyl-biphenyl-3-carboxylic acid (2-methoxy-1-methyl-ehtyl)-amide | 412 |
| 632 | 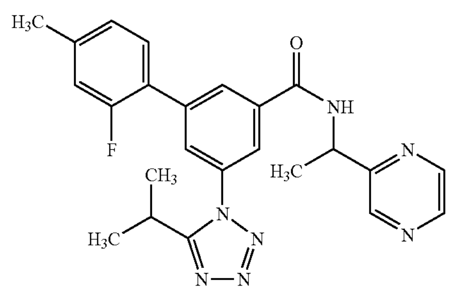 | 2'-Fluoro-5-(5-isopropyl-tetrazol-1-yl)-4'-methyl-biphenyl-3-carboxylic acid (1-pyrazin-2-yl-ethyl)-amide | 446 |
| 633 | 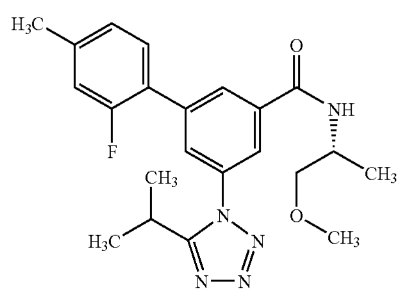 | 2'-Fluoro-5-(5-isopropyl-tetrazol-1-yl)-4'-methyl-biphenyl-3-carboxylic acid ((R)-2-methoxy-1-methyl-ethyl)-amide | 412 |
| 634 | 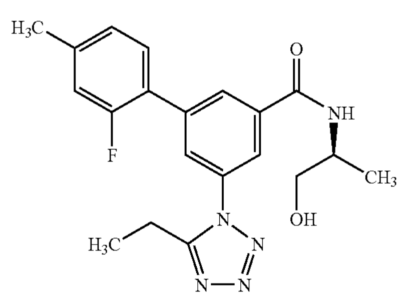 | 5-(5-Ethyl-tetrazol-1-yl)-2'-fluoro-4'-methyl-biphenyl-3-carboxylic acid ((S)-2-hydroxy-1-methyl-ethyl)-amide | 384 |

TABLE 1-continued

| # | Structure | Name (Autonom ™) | Mp or M + H |
|---|---|---|---|
| 635 | 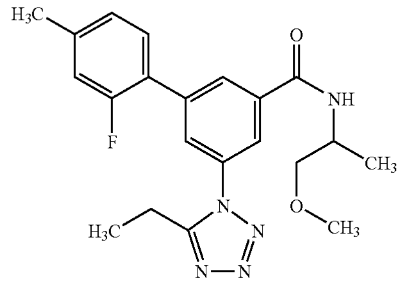 | 5-(5-Ethyl-tetrazol-1-yl)-2'-fluoro-4'-methyl-biphenyl-3-carboxylic acid (2-methoxy-1-methyl-ethyl)-amide | 398 |
| 636 | 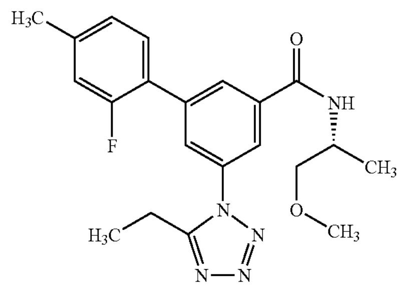 | 5-(5-Ethyl-tetrazol-1-yl)-2'-fluoro-4'-methyl-biphenyl-3-carboxylic acid ((R)-2-methoxy-1-methyl-ethyl)-amide | 398 |
| 637 | 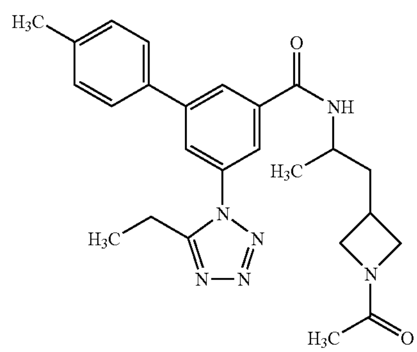 | 5-(5-Ethyl-tetrazol-1-yl)-4'-methyl-biphenyl-3-carboxylic acid [2-(1-acetyl-azetidin-3-yl)-1-methyl-ethyl]-amide | 447 |
| 638 | 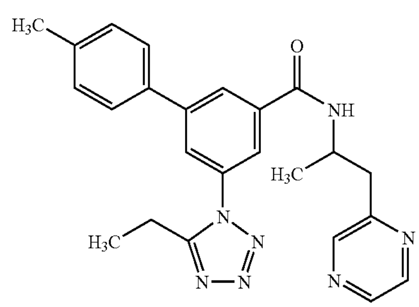 | 5-(5-Ethyl-tetrazol-1-yl)-4'-methyl-biphenyl-3-carboxylic acid (1-methyl-2-pyrazin-2-yl-ethyl)-amide | 428 |
| 639 | 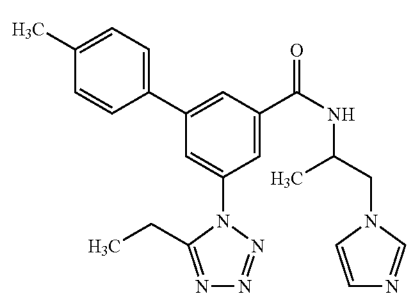 | 5-(5-Ethyl-tetrazol-1-yl)-4'-methyl-biphenyl-3-carboxylic acid (2-imidazol-1-yl-1-methyl-ethyl)-amide | 416 |

TABLE 1-continued

| # | Structure | Name (Autonom™) | Mp or M + H |
|---|---|---|---|
| 640 | 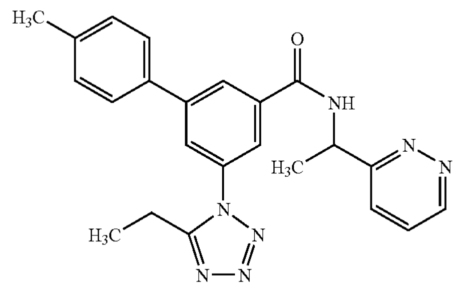 | 5-(5-Ethyl-tetrazol-1-yl)-4'-methyl-biphenyl-3-carboxylic acid (1-pyridazin-2-yl-ethyl)-amide | 93.3-96.6° C. |
| 641 | 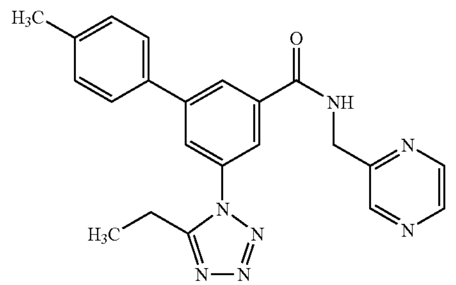 | 5-(5-Ethyl-tetrazol-1-yl)-4'-methyl-biphenyl-3-carboxylic acid (pyrazin-2-ylmethyl)-amide | 400 |
| 642 | 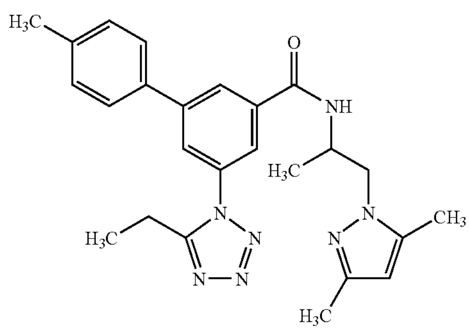 | 5-(5-Ethyl-tetrazol-1-yl)-4'-methyl-biphenyl-3-carboxylic acid [2-(3,5-dimethyl-pyrazol-1-yl)-1-methyl-ethyl]-amide | 444 |
| 643 | 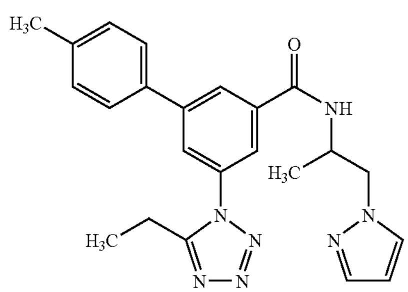 | 5-(5-Ethyl-tetrazol-1-yl)-4'-methyl-biphenyl-3-carboxylic acid (1-methyl-2-pyrazol-1-yl-ethyl)-amide | 416 |
| 644 | 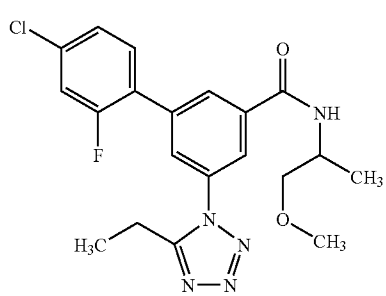 | 4'-Chloro-5-(5-ethyl-tetrazol-1-yl)-2'-fluoro-biphenyl-3-carboxylic acid (2-methoxy-1-methyl-ethyl)-amide | 418 |

TABLE 1-continued

| # | Structure | Name (Autonom ™) | Mp or M + H |
|---|---|---|---|
| 645 | 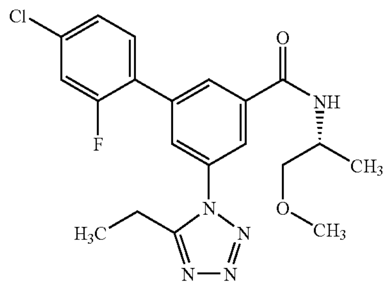 | 4'-Chloro-5-(5-ethyl-tetrazol-1-yl)-2'-fluoro-biphenyl-3-carboxylic acid ((R)-2-methoxy-1-methyl-ethyl)-amide | 418 |
| 646 | 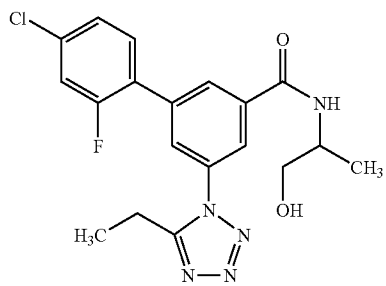 | 4'-Chloro-5-(5-ethyl-tetrazol-1-yl)-2'-fluoro-biphenyl-3-carboxylic acid (2-hydroxy-1-methyl-ethyl)-amide | 404 |
| 647 | 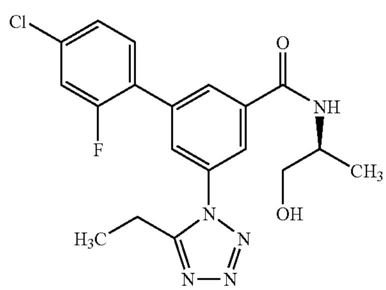 | 4'-Chloro-5-(5-ethyl-tetrazol-1-yl)-2'-fluoro-biphenyl-3-carboxylic acid ((S)-2-hydroxy-1-methyl-ethyl)-amide | 404 |
| 648 | 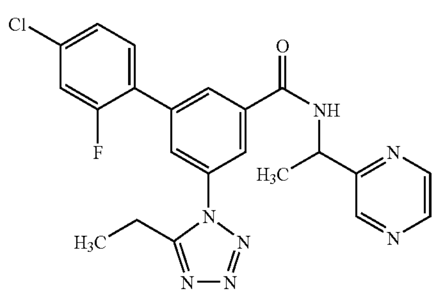 | 4'-Chloro-5-(5-ethyl-tetrazol-1-yl)-2'-fluoro-biphenyl-3-carboxylic acid (1-pyrazin-2-yl-ethyl)-amide | 452 |
| 649 | 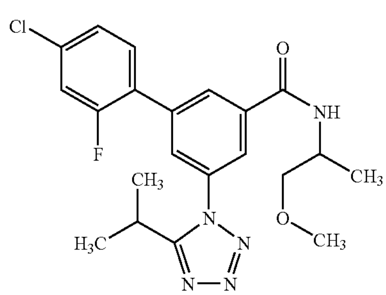 | 4'-Chloro-2'-fluoro-5-(5-isopropyl-tetrazol-1-yl)-biphenyl-3-carboxylic acid (2-methoxy-1-methyl-ethyl)-amide | 432 |

TABLE 1-continued

| # | Structure | Name (Autonom ™) | Mp or M + H |
|---|---|---|---|
| 650 | 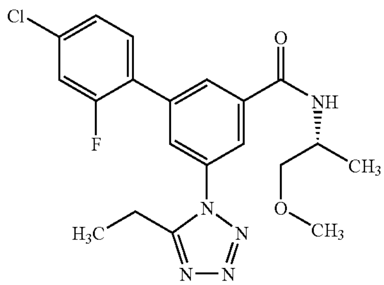 | 4'-Chloro-2'-fluoro-5-(5-isopropyl-tetrazol-1-yl)-biphenyl-3-carboxylic acid ((R)-2-methoxy-1-methyl-ethyl)-amide | 432 |
| 651 | 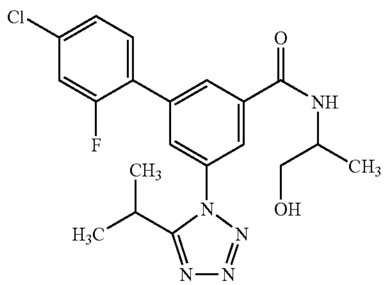 | 4'-Chloro-2'-fluoro-5-(5-isopropyl-tetrazol-1-yl)-biphenyl-3-carboxylic acid (2-hydroxy-1-methyl-ethyl)-amide | 418 |
| 652 | 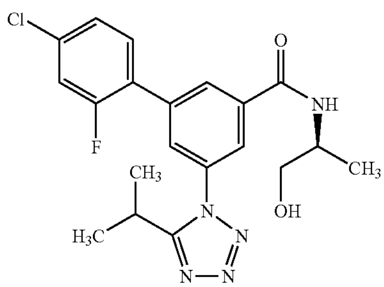 | 4'-Chloro-2'-fluoro-5-(5-isopropyl-tetrazol-1-yl)-biphenyl-3-carboxylic acid ((S)-2-hydroxy-1-methyl-ethyl)-amide | 418 |
| 653 | 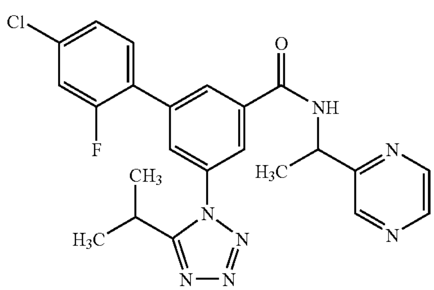 | 4'-Chloro-2'-fluoro-5-(5-isopropyl-tetrazol-1-yl)-biphenyl-3-carboxylic acid (1-pyrazin-2-yl-ethyl)-amide | 466 |
| 654 | 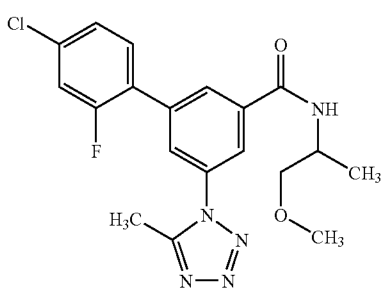 | 4'-Chloro-2'-fluoro-5-(5-methyl-tetrazol-1-yl)-biphenyl-3-carboxylic acid (2-methoxy-1-methyl-ethyl)-amide | 404 |

TABLE 1-continued

| # | Structure | Name (Autonom ™) | Mp or M + H |
|---|---|---|---|
| 655 | 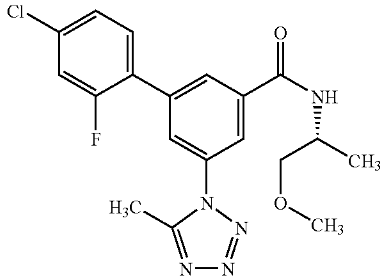 | 4'-Chloro-2'-fluoro-5-(5-methyl-tetrazol-1-yl)-biphenyl-3-carboxylic acid ((R)-2-methyl-ethyl)-amide | 404 |
| 656 | 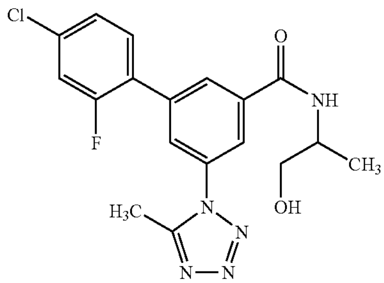 | 4'-Chloro-2'-fluoro-5-(5-methyl-tetrazol-1-yl)-biphenyl-3-carboxylic acid (2-hydroxy-1-methyl-ethyl)-amide | 390 |
| 657 | 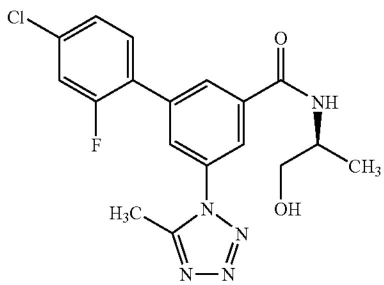 | 4'-Chloro-2'-fluoro-5-(5-methyl-tetrazol-1-yl)-biphenyl-3-carboxylic acid ((S)-2-hydroxy-1-methyl-ethyl)-amide | 390 |
| 658 | 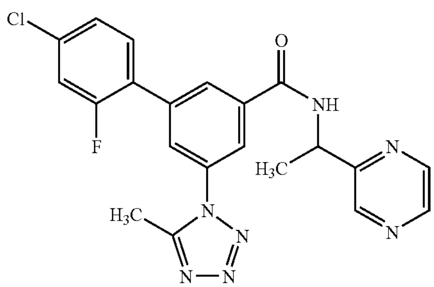 | 4'-Chloro-2'-fluoro-5-(5-methyl-tetrazol-1-yl)-biphenyl-3-carboxylic acid (1-pyrazin-2-yl-ethyl)-amide | 438 |
| 659 | 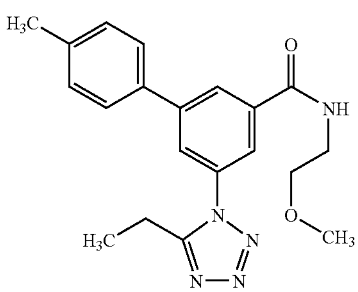 | 5-(5-Ethyl-tetrazol-1-yl)-4'-methyl-biphenyl-3-carboxylic acid (2-methoxy-ethyl)-amide | 366 |

TABLE 1-continued

| # | Structure | Name (Autonom ™) | Mp or M + H |
|---|---|---|---|
| 660 | 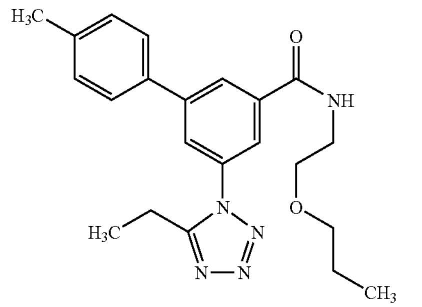 | 5-(5-Ethyl-tetrazol-1-yl)-4'-methyl-biphenyl-3-carboxylic acid [2-(2-hydroxy-ethoxy)-ethyl]-amide | 394 |
| 661 | 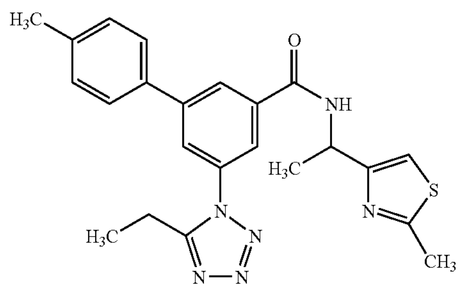 | 5-(5-Ethyl-tetrazol-1-yl)-4'-methyl-biphenyl-3-carboxylic acid [1-(2-methyl-thiazol-4-yl)-ethyl]-amide | 433 |
| 662 | 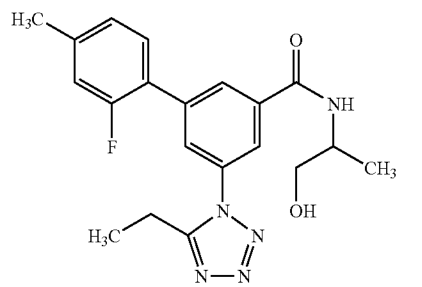 | 5-(5-Ethyl-tetrazol-1-yl)-2'-fluoro-4'-methyl-biphenyl-3-carboxylic acid (2-hydroxy-1-methyl-ethyl)-amide | 384 |
| 663 | 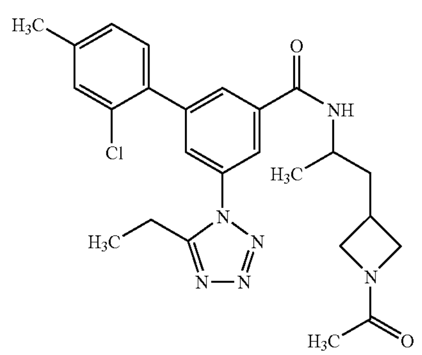 | 2'-Chloro-5-(5-ethyl-tetrazol-1-yl)-4'-methyl-biphenyl-3-carboxylic acid [2-(1-acetyl-azetidin-3-yl)-1-methyl-ethyl]-amide | 481 |
| 664 | 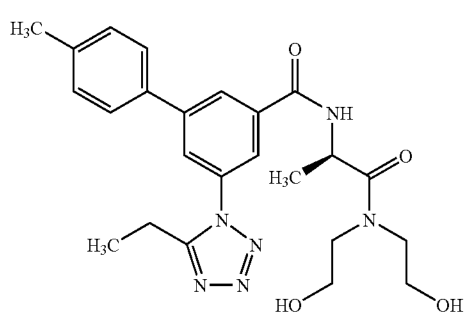 | 5-(5-Ethyl-tetrazol-1-yl)-4'-methyl-biphenyl-3-carboxylic acid {(R)-1-[bis-(2-hydroxy-ethyl)-carbamoyl]-ethyl}-amide | 467 |

TABLE 1-continued

| # | Structure | Name (Autonom ™) | Mp or M + H |
|---|---|---|---|
| 665 | 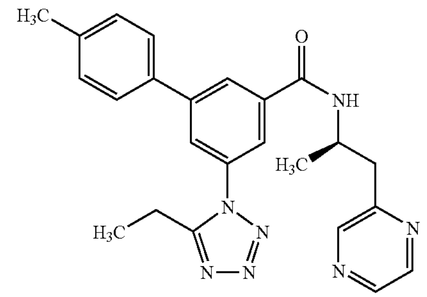 | 5-(5-Ethyl-tetrazol-1-yl)-4'-methyl-biphenyl-3-carboxylic acid ((R)-1-methyl-2-pyrazin-2-yl-ethyl)-amide | 428 |
| 666 | 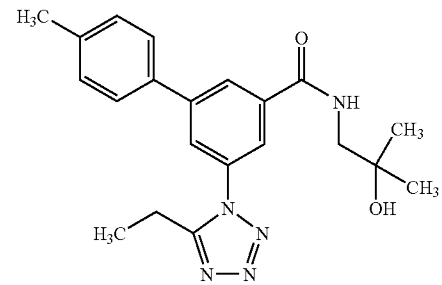 | 5-(5-Ethyl-tetrazol-1-yl)-4'-methyl-biphenyl-3-carboxylic acid (2-hydroxy-2-methyl-propyl)-amide | 380 |
| 667 | 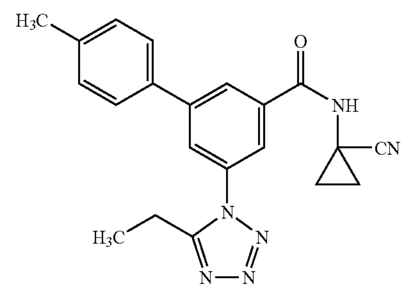 | 5-(5-Ethyl-tetrazol-1-yl)-4'-methyl-biphenyl-3-carboxylic acid (1-cyano-cyclopropyl)-amide | 373 |
| 668 | 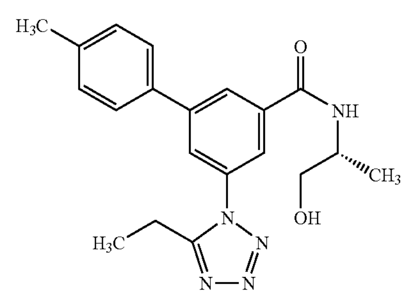 | 5-(5-Ethyl-tetrazol-1-yl)-4'-methyl-biphenyl-3-carboxylic acid ((R)-2-hydroxy-1-methyl-ethyl)-amide | 366 |
| 669 | 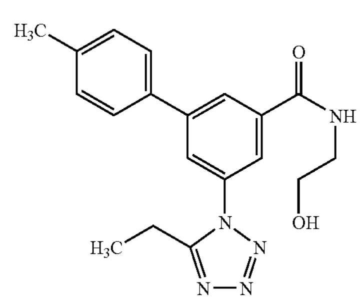 | 5-(5-Ethyl-tetrazol-1-yl)-4'-methyl-biphenyl-3-carboxylic acid (2-hydroxy-ethyl)-amide | 352 |

TABLE 1-continued

| # | Structure | Name (Autonom ™) | Mp or M + H |
|---|---|---|---|
| 670 | 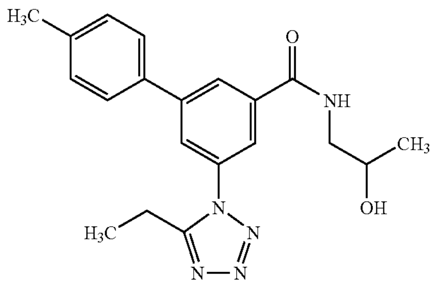 | 5-(5-Ethyl-tetrazol-1-yl)-4'-methyl-biphenyl-3-carboxylic acid (2-hydroxy-propyl)-amide | 366 |
| 671 | 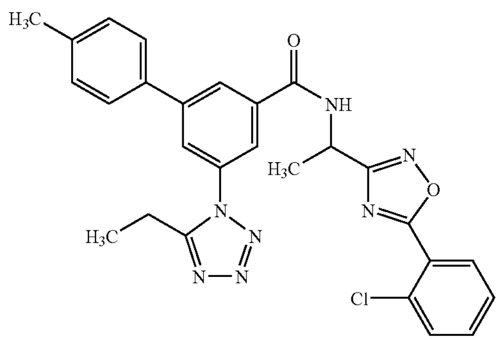 | 5-(5-Ethyl-tetrazol-1-yl)-4'-methyl-biphenyl-3-carboxylic acid {1-[3-(2-chloro-phenyl)-[1,2,4]oxadiazol-5-yl]-ethyl}-amide | 514 |
| 672 | 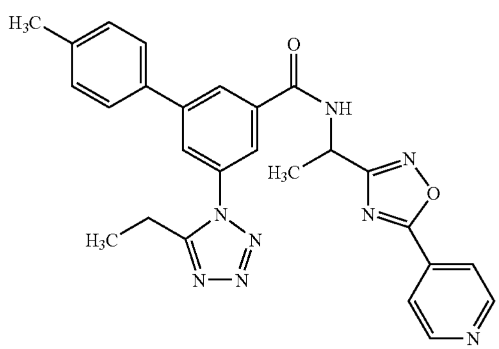 | 5-(5-Ethyl-tetrazol-1-yl)-4'-methyl-biphenyl-3-carboxylic acid [1-(3-pyridin-4-yl-[1,2,4]oxadiazol-5-yl)-ethyl]-amide | 481 |
| 673 | 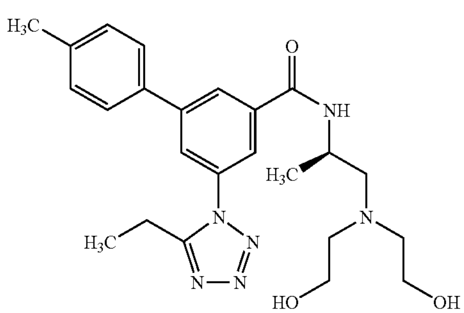 | 5-(5-Ethyl-tetrazol-1-yl)-4'-methyl-biphenyl-3-carboxylic acid {(R)-2-[bis-(2-hydroxy-ethyl)-amino]-1-methyl-ethyl}-amide | 453 |
| 674 | 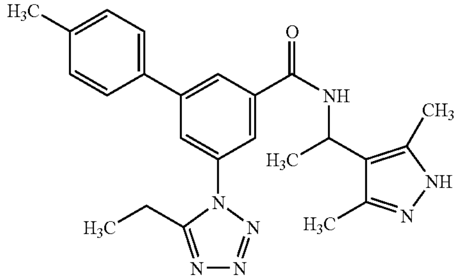 | 5-(5-Ethyl-tetrazol-1-yl)-4'-methyl-biphenyl-3-carboxylic acid [1-(3,5-dimethyl-1 H-pyrazol-4-yl)-ethyl]-amide | 430 |

TABLE 1-continued

| # | Structure | Name (Autonom ™) | Mp or M + H |
|---|---|---|---|
| 675 | 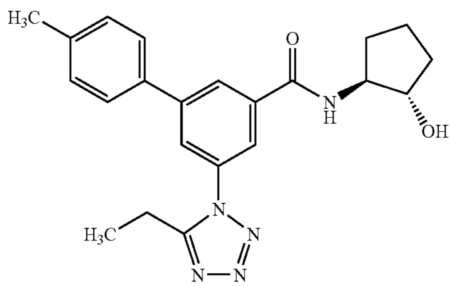 | 5-(5-Ethyl-tetrazol-1-yl)-4'-methyl-biphenyl-3-carboxylic acid ((1S,2S)-2-hydroxy-cyclopentyl)-amide | 392 |
| 676 | 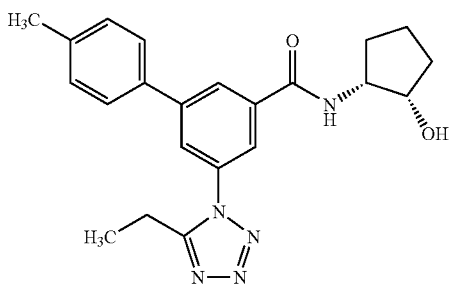 | 5-(5-Ethyl-tetrazol-1-yl)-4'-methyl-biphenyl-3-carboxylic acid ((1R,2S)-2-hydroxy-cyclopentyl)-amide | 392 |
| 677 | 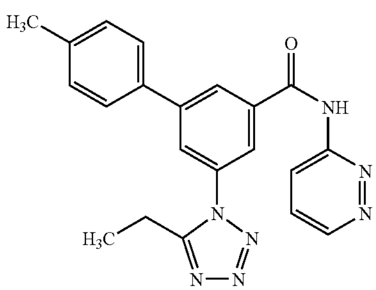 | 5-(5-Ethyl-tetrazol-1-yl)-4'-methyl-biphenyl-3-carboxylic acid pyridizan-4-ylamide | 386 |
| 678 | 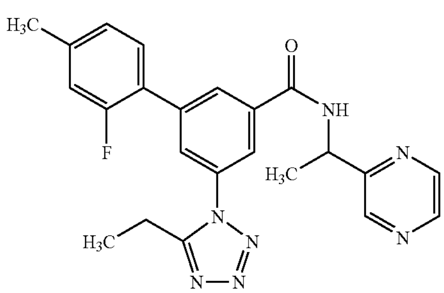 | 5-(5-Ethyl-tetrazol-1-yl)-2'-fluoro-4'-methyl-biphenyl-3-carboxylic acid (1-pyrazin-2-yl-ethyl)-amide | 407 |
| 679 | 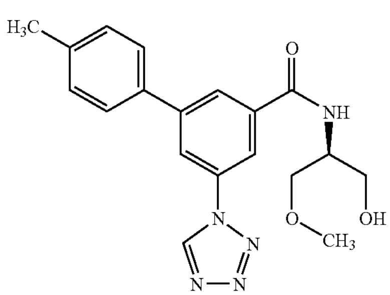 | 4'-Methyl-5-tetrazol-1-yl-biphenyl-3-carboxylic acid ((R)-2-hydroxyl-1-methoxymethyl-ethyl)-amide | 114.3-115.0° C. |

TABLE 1-continued

| # | Structure | Name (Autonom ™) | Mp or M + H |
|---|---|---|---|
| 680 | 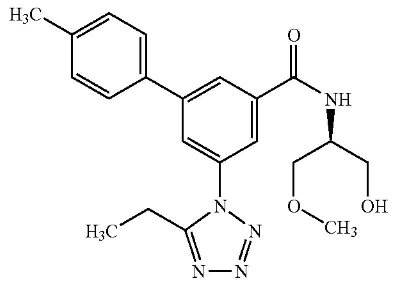 | 5-(5-Ethyl-tetrazol-1-yl)-4'-methyl-biphenyl-3-carboxylic acid ((R)-2-hydroxy-1-methoxymethyl-ethyl)-amide | 396 |
| 681 | 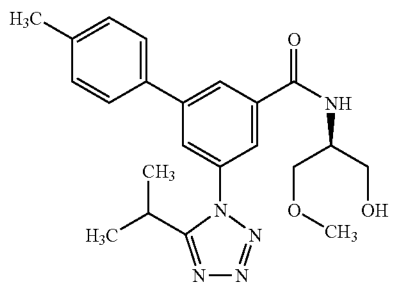 | 5-(5-Isopropyl-tetrazol-1-yl)-4'-methyl-biphenyl-3-carboxylic acid ((R)-2-hydroxy-1-methoxymethyl-ethyl)-amide | 410 |
| 682 | 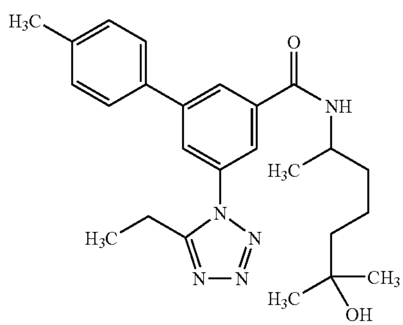 | 5-(5-Ethyl-tetrazol-1-yl)-4'-methyl-biphenyl-3-carboxylic acid (5-hydroxy-1,5-dimethyl-hexyl)-amide | 436 |
| 683 | 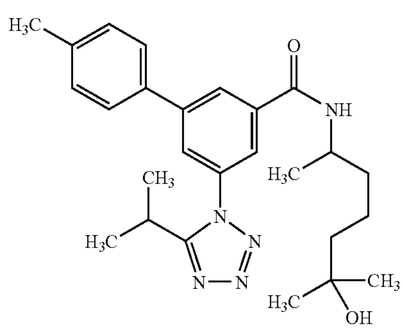 | 5-(5-Isopropyl-tetrazol-1-yl)-4'-methyl-biphenyl-3-carboxylic acid (5-hydroxy-1,5-dimethyl-hexyl)-amide | 450 |
| 684 | 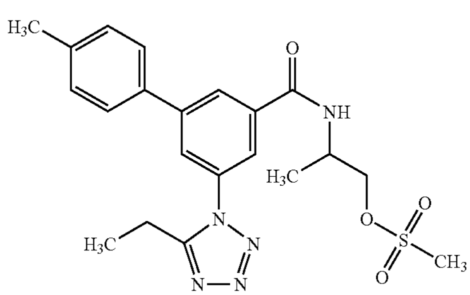 | Methanesulfonic acid (R)-2-{[5-(5-ethyl-tetrazol-1-yl)-4'-methyl-biphenyl-3-carbonyl]-amino}-propyl ester | |

TABLE 1-continued

| # | Structure | Name (Autonom ™) | Mp or M + H |
|---|---|---|---|
| 685 | 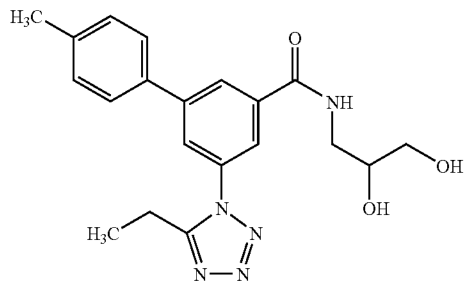 | 5-(5-Ethyl-tetrazol-1-yl)-4'-methyl-biphenyl-3-carboxylic acid (2,3 dihydroxy-propyl)-amide | 382 |
| 686 | 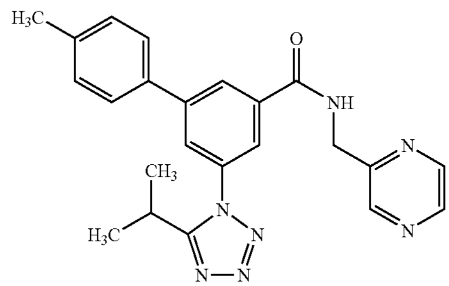 | 5-(5-Isopropyl-tetrazol-1-yl)-4'-methyl-biphenyl-3-carboxylic acid (pyrazin-2-ylmethyl)-amide | 414 |
| 687 | 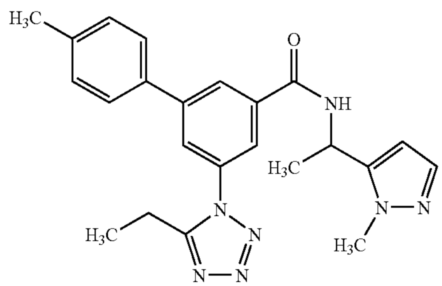 | 5-(5-Ethyl-tetrazol-1-yl)-4'-methyl-biphenyl-3-carboxylic acid [1-(2-methyl-2 H-pyrazol-3-yl)-ethyl]-amide | 172.8-174.2° C. |
| 688 | 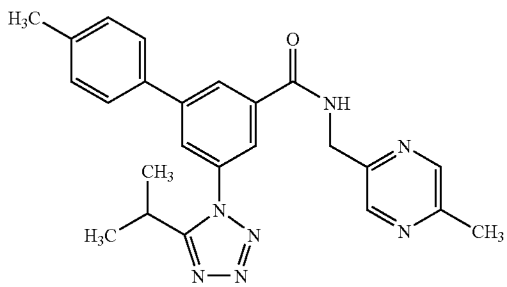 | 5-(5-Ethyl-tetrazol-1-yl)-4'-methyl-biphenyl-3-carboxylic acid (5-methyl-pyrazin-2-ylmethyl)-amide | 96.9-99.3° C. |
| 689 | 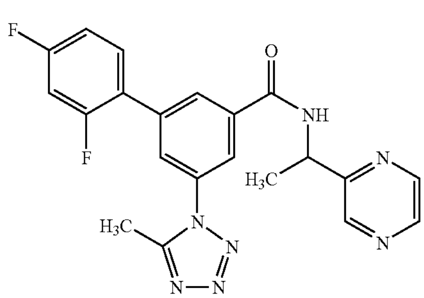 | 2',4'-Difluoro-5-(5-methyl-tetrazol-1-yl)-biphenyl-3-carboxylic acid (1-pyrazin-2-yl-ethyl)-amide | 422 |

TABLE 1-continued

| # | Structure | Name (Autonom ™) | Mp or M + H |
|---|---|---|---|
| 690 | 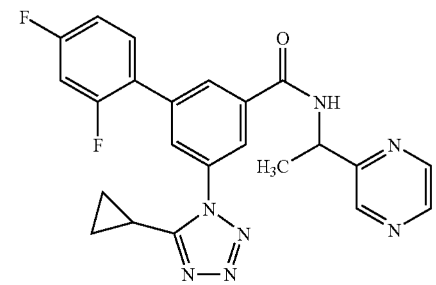 | 5-(5-Cyclopropyl-tetrazol-1-yl)-2',4'-difluoro-biphenyl-3-carboxylic acid (1-pyrazin-2-yl-ethyl)-amide | 448 |
| 691 | 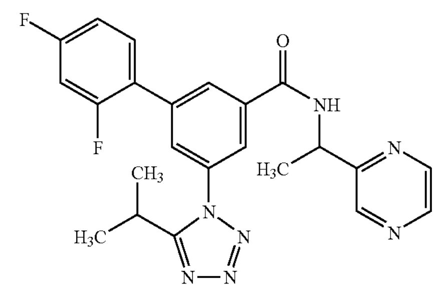 | 2',4'-Difluoro-5-(5-isopropyl-tetrazol-1-yl)-biphenyl-3-carboxylic acid (1-pyrazin-2-yl-ethyl)-amide | 450 |
| 692 | 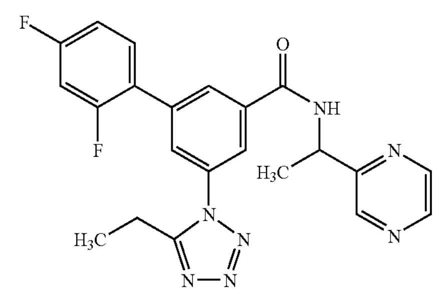 | 5-(5-Ethyl-tetrazol-1-yl)-2',4'-difluoro-biphenyl-3-carboxylic acid (1-pyrazin-2-yl-ethyl)-amide | 436 |
| 693 | 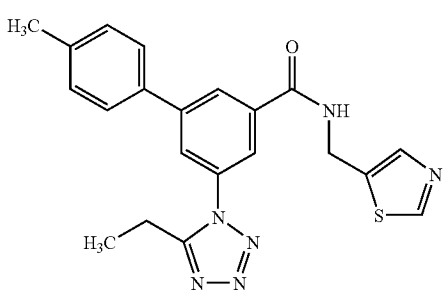 | 5-(5-Ethyl-tetrazol-1-yl)-4'-methyl-biphenyl-3-carboxylic acid (thiazol-5-ylmethyl)-amide | 76.0-79.0° C. |
| 694 | 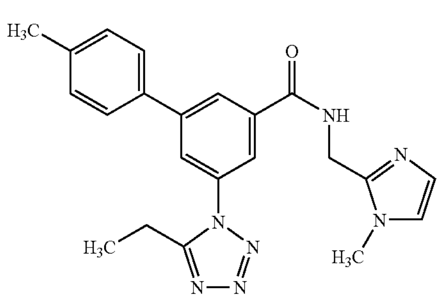 | 5-(5-Ethyl-tetrazol-1-yl)-4'-methyl-biphenyl-3-carboxylic acid (1-methyl-1H-imidazol-2-ylmethyl)-amide | 205.0-207.0° C. |

TABLE 1-continued

| # | Structure | Name (Autonom ™) | Mp or M + H |
|---|---|---|---|
| 695 | 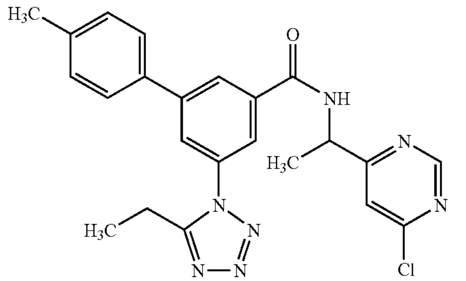 | 5-(5-Ethyl-tetrazol-1-yl)-4'-methyl-biphenyl-3-carboxylic acid [1-(6-chloro-pyrimidin-4-yl)-ethyl]-amide | 75.0-78.5° C. |
| 696 | 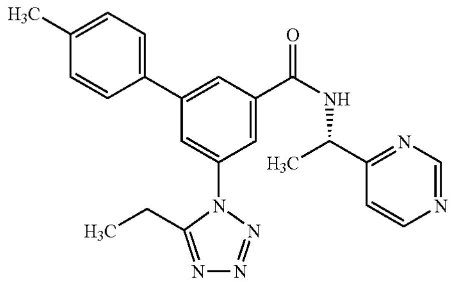 | 5-(5-Ethyl-tetrazol-1-yl)-4'-methyl-biphenyl-3-carboxylic acid ((S)-1-pyrazin-2-yl-ethyl)-amide | 113.8-117.7° C. |
| 697 | 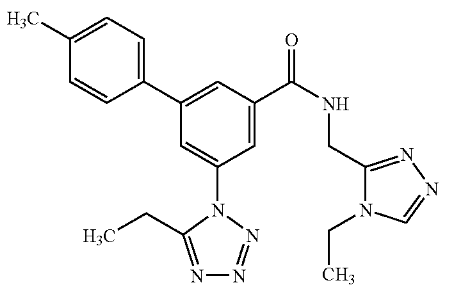 | 5-(5-Ethyl-tetrazol-1-yl)-4'-methyl-biphenyl-3-carboxylic acid [1-(4-ethyl-4 H-[1,2,4]triazol-3-yl)-ethyl]-amide | 417 |
| 698 | 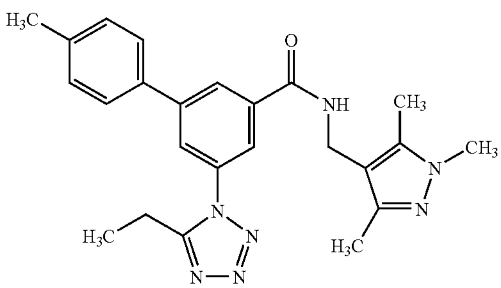 | 5-(5-Ethyl-tetrazol-1-yl)-4'-methyl-biphenyl-3-carboxylic acid [1-(1,3,5-trimethyl-1 H-pyrazol-4-yl)-ethyl]-amide | 430 |
| 699 | 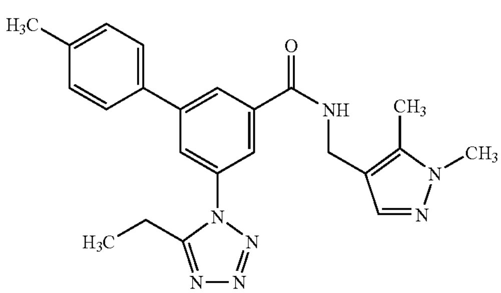 | 5-(5-Ethyl-tetrazol-1-yl)-4'-methyl-biphenyl-3-carboxylic acid [1-(1,5-dimethyl-1 H-pyrazol-4-yl)-ethyl]-amide | 416 |

TABLE 1-continued

| # | Structure | Name (Autonom ™) | Mp or M + H |
|---|---|---|---|
| 700 | 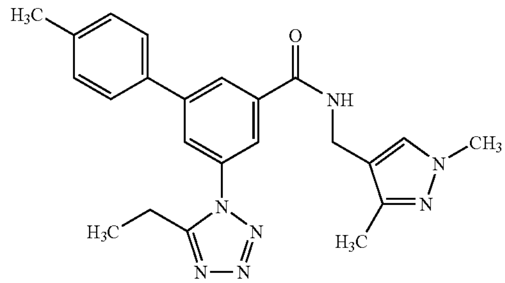 | 5-(5-Ethyl-tetrazol-1-yl)-4'-methyl-biphenyl-3-carboxylic acid [1-(1,3-dimethyl-1 H-pyrazol-4-yl)-ethyl]-amide | 416 |
| 701 | 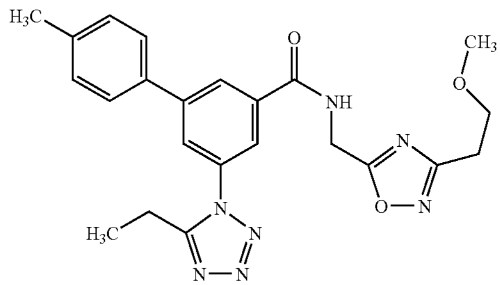 | 5-(5-Ethyl-tetrazol-1-yl)-4'-methyl-biphenyl-3-carboxylic acid {3-[3-(2-methoxy-ethyl)-[1,2,4]oxadiazol-5-yl]-ethyl}-amide | 448 |
| 702 | 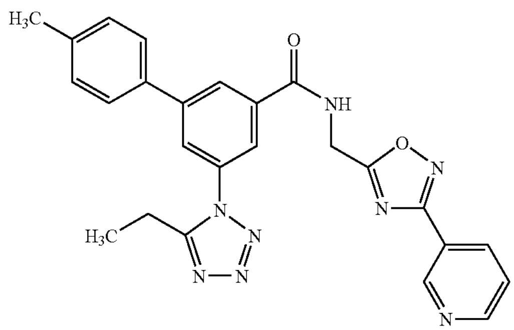 | 5-(5-Ethyl-tetrazol-1-yl)-4'-methyl-biphenyl-3-carboxylic acid [1-(3-pyridin-3-yl-[1,2,4]oxadiazol-5-yl)-ethyl]-amide | 483 |
| 703 | 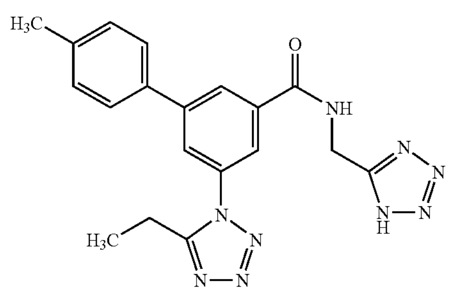 | 5-(5-Ethyl-tetrazol-1-yl)-4'-methyl-biphenyl-3-carboxylic acid [1-(1 H-tetrazol-5-yl)-ethyl]-amide | 390 |
| 704 | 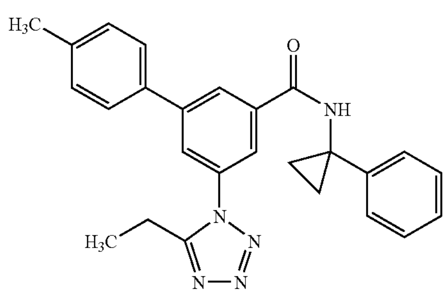 | 5-(5-Ethyl-tetrazol-1-yl)-4'-methyl-biphenyl-3-carboxylic acid (1-phenyl-cyclopropyl)-amide | 424 |

TABLE 1-continued

| # | Structure | Name (Autonom ™) | Mp or M + H |
|---|---|---|---|
| 705 | 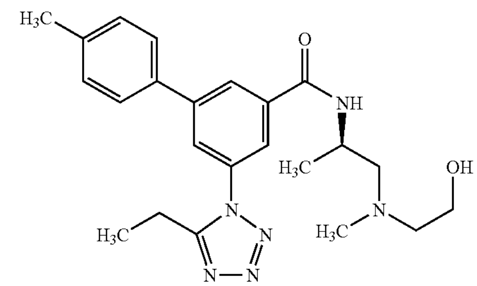 | 5-(5-Ethyl-tetrazol-1-yl)-4'-methyl-biphenyl-3-carboxylic acid {(R)-2-[2-hydroxy-ethyl)-methyl-amino]-1-methyl-ethyl}-amide | 439 |
| 706 | 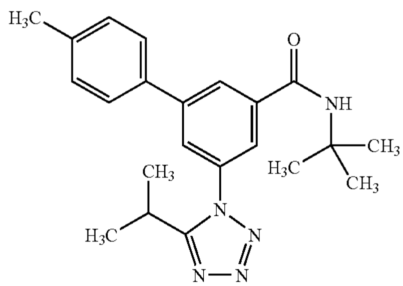 | 5-(5-Isopropyl-tetrazol-1-yl)-4'-methyl-biphenyl-3-carboxylic acid tert-butylamide | 378 |
| 707 | 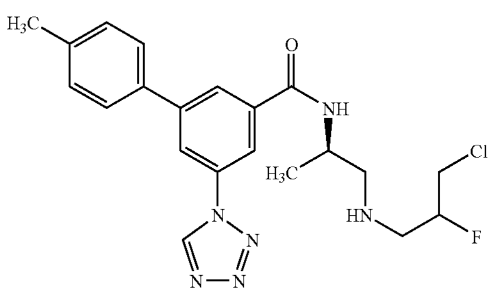 | 4'-Methyl-5-tetrazol-1-yl-biphenyl-3-carboxylic acid [(R)-2-(3-chloro-2-fluoro-propylamino)-1-methyl-ethyl]-amide | 447 |
| 708 | 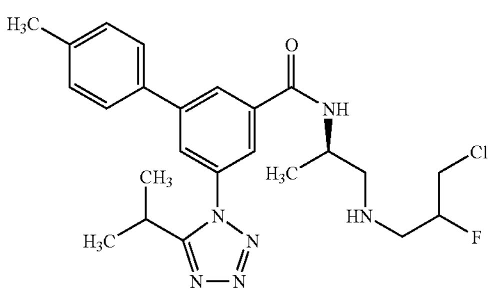 | 5-(5-Isopropyl-tetrazol-1-yl)-4'-methyl-biphenyl-3-carboxylic acid [(R)-2-(3-chloro-2-fluoro-propylamino)-1-methyl-ethyl]-amide | |
| 709 | 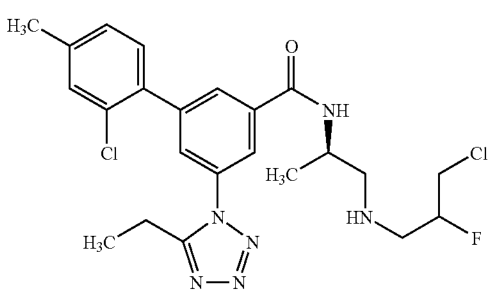 | 2'-Chloro-5-(5-ethyl-tetrazol-1-yl)-4'-methyl-biphenyl-3-carboxylic acid [(R)-2-(3-chloro-2-fluoro-propylamino)-1-methyl-ethyl]-amide | 493 |

TABLE 1-continued

| # | Structure | Name (Autonom ™) | Mp or M + H |
|---|---|---|---|
| 710 | 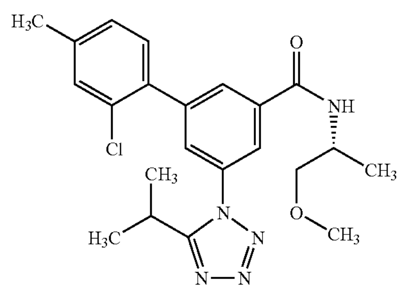 | 2'-Chloro-5-(5-isopropyl-tetrazol-1-yl)-4'-methyl-biphenyl-3-carboxylic acid ((R)-2-methoxy-1-methyl-ethyl)-amide | 428 |
| 711 | 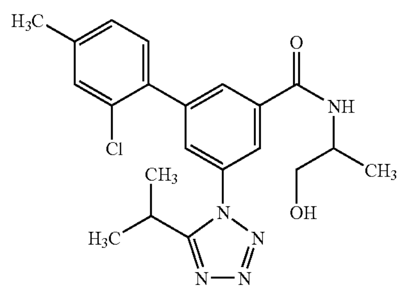 | 2'-Chloro-5-(5-isopropyl-tetrazol-1-yl)-4'-methyl-biphenyl-3-carboxylic acid (2-hydroxy-1-methyl-ethyl)-amide | 414 |
| 712 | 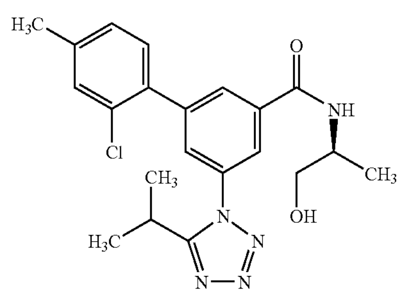 | 2'-Chloro-5-(5-isopropyl-tetrazol-1-yl)-4'-methyl-biphenyl-3-carboxylic acid ((S)-2-hydroxy-1-methyl-ethyl)-amide | 414 |
| 713 | 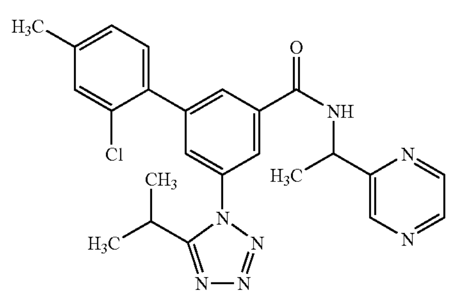 | 2'-Chloro-5-(5-isopropyl-tetrazol-1-yl)-4'-methyl-biphenyl-3-carboxylic acid (1-pyrazin-2-yl-ethyl)-amide | 462 |
| 714 | 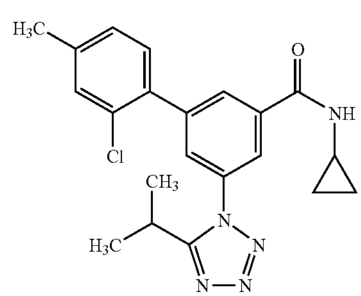 | 5-(5-Isopropyl-tetrazol-1-yl)-4'-methyl-biphenyl-3-carboxylic acid cyclopropylamide | 396 |

TABLE 1-continued

| # | Structure | Name (Autonom ™) | Mp or M + H |
|---|---|---|---|
| 715 | 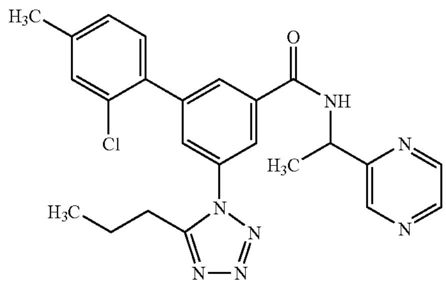 | 2'-Chloro-4'-methyl-5-(5-propyl-tetrazol-1-yl)-biphenyl-3-carboxylic acid (1-pyrazin-2-yl-ethyl)-amide | 462 |
| 716 | 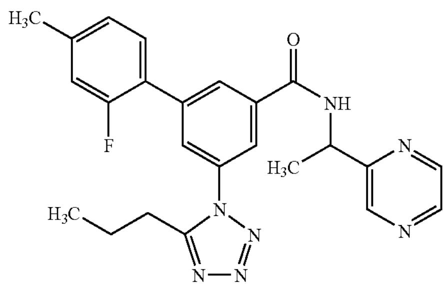 | 2'-Fluoro-4'-methyl-5-(5-propyl-tetrazol-1-yl)-biphenyl-3-carboxylic acid (1-pyrazin-2-yl-ethyl)-amide | 446 |
| 717 | 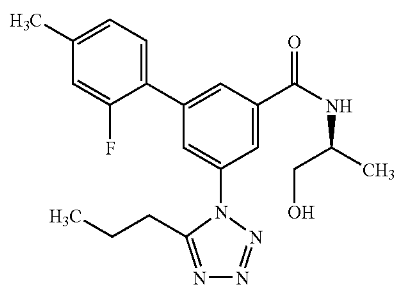 | 2'-Fluoro-4'-methyl-5-(5-propyl-tetrazol-1-yl)-biphenyl-3-carboxylic acid ((S)-2-hydroxy-1-methyl-ethyl)-amide | 398 |
| 718 | 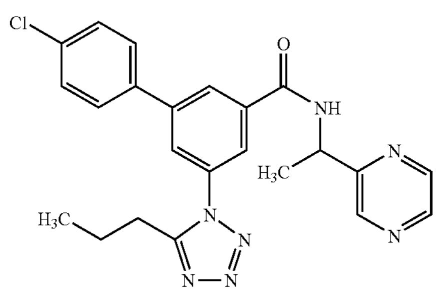 | 4'-Chloro-5-(5-propyl-tetrazol-1-yl)-biphenyl-3-carboxylic acid (1-pyrazin-2-yl-ethyl)-amide | 448 |
| 719 | 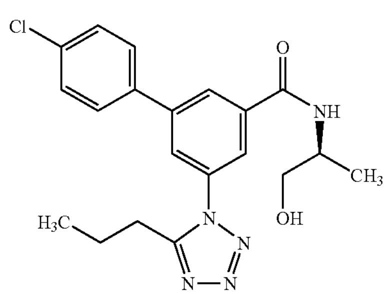 | 4'-Chloro-5-(5-propyl-tetrazol-1-yl)-biphenyl-3-carboxylic acid ((S)-2-hydroxy-1-methyl-ethyl)-amide | |

TABLE 1-continued

| # | Structure | Name (Autonom ™) | Mp or M + H |
|---|---|---|---|
| 720 | 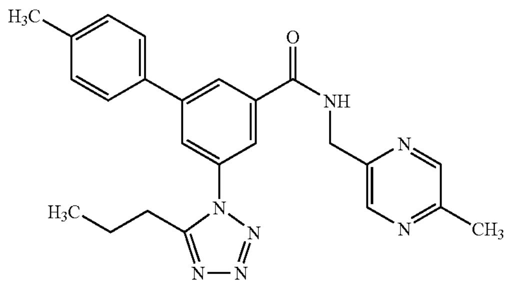 | 4'-Methyl-5-(5-propyl-tetrazol-1-yl)-biphenyl-3-carboxylic acid (5-methyl-pyrazin-2-ylmethyl)-amide | 75.3-81.0° C. |
| 721 | 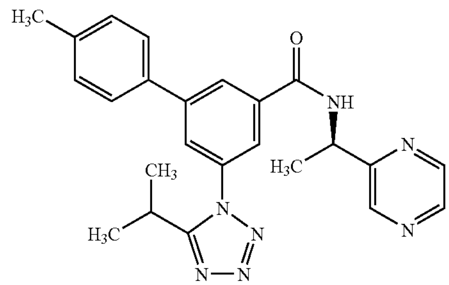 | 5-(5-Isopropyl-tetrazol-1-yl)-4'-methyl-biphenyl-3-carboxylic acid ((R)-1-pyrazin-2-yl-ethyl)-amide | 83.0-86.9° C. |
| 722 | 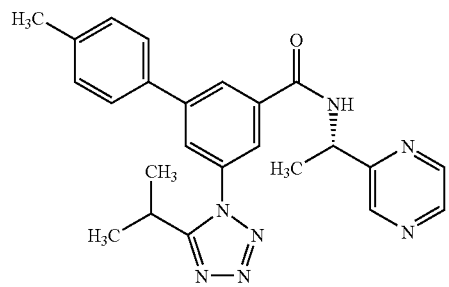 | 5-(5-Isopropyl-tetrazol-1-yl)-4'-methyl-biphenyl-3-carboxylic acid ((S)-1-pyrazin-2-yl-ethyl)-amide | 95.5-99.0° C. |
| 723 | 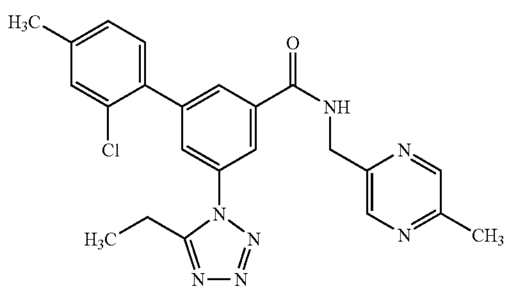 | 2'-Chloro-5-(5-tetrazol-1-yl)-4'-methyl-biphenyl-3-carboxylic acid (5-methyl-pyrazin-2-ylmethyl)-amide | 448 |
| 724 | 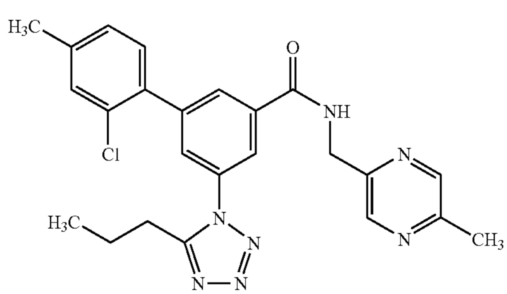 | 2'-Chloro-4'-methyl-5-(5-propyl-tetrazol-1-yl)-biphenyl-3-carboxylic acid (5-methyl-pyrazin-2-ylmethyl)-amide | 462 |

TABLE 1-continued

| # | Structure | Name (Autonom ™) | Mp or M + H |
|---|---|---|---|
| 725 | 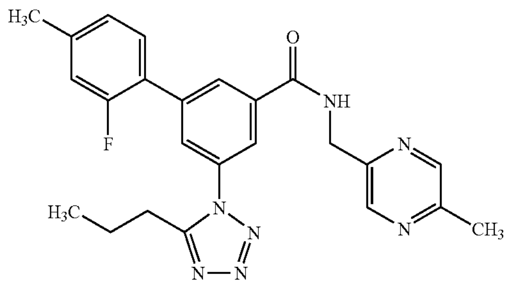 | 2'-Fluoro-4'-methyl-5-(5-propyl-tetrazol-1-yl)-biphenyl-3-carboxylic acid (5-methyl-pyrazin-2-ylmethyl)-amide | 446 |
| 736 | 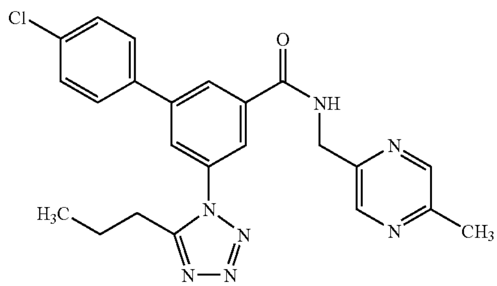 | 4'-Chloro-5-(5-propyl-tetrazol-1-yl)-biphenyl-3-carboxylic acid (5-methyl-pyrazin-2-ylmethyl)-amide | 448 |
| 727 | 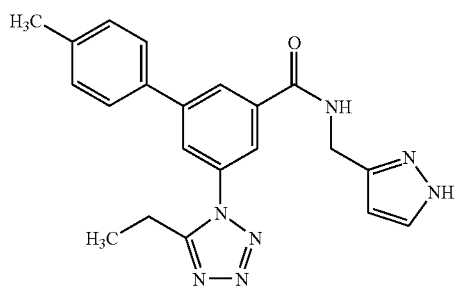 | 5-(5-Ethyl-tetrazol-1-yl)-4'-methyl-biphenyl-3-carboxylic acid (1H-pyrazol-3-ylmethyl)-amide | 190.1-191.3° C. |
| 728 | 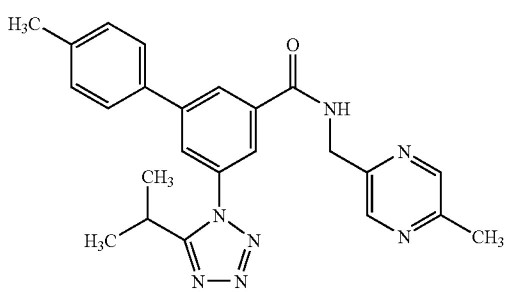 | 5-(5-Isopropyl-tetrazol-1-yl)-4'-methyl-biphenyl-3-carboxylic acid (5-methyl-pyrazin-2-ylmethyl)-amide | 152.0-154.5° C. |
| 729 | 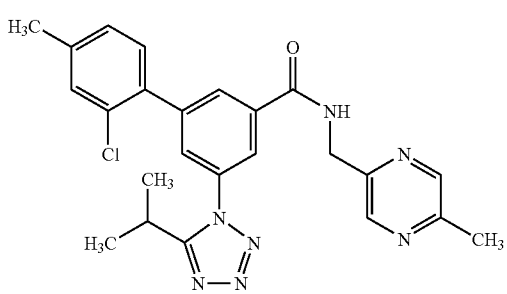 | 2'-Chloro-5-(5-isopropyl-tetrazol-1-yl)-4'-methyl-biphenyl-3-carboxylic acid (5-methyl-pyrazin-2-ylmethyl)-amide | 71.0-76.0° C. |

| # | Structure | Name (Autonom ™) | Mp or M + H |
|---|---|---|---|
| 730 | 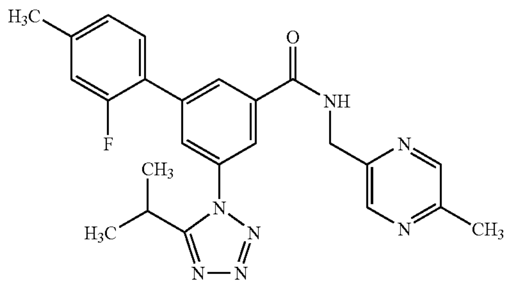 | 2'-Fluoro-5-(5-isopropyl-tetrazol-1-yl)-4'-methyl-biphenyl-3-carboxylic acid (5-methyl-pyrazin-2-ylmethyl)-amide | 85.0-90.0° C. |
| 731 | 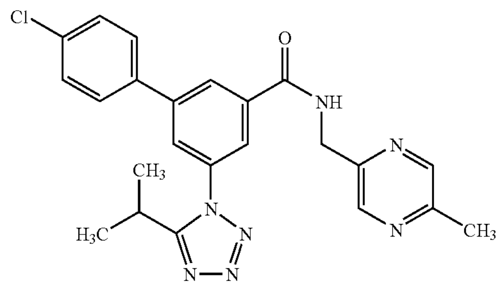 | 4'-Chloro-5-(5-isopropyl-tetrazol-1-yl)-biphenyl-3-carboxylic acid (5-methyl-pyrazin-2-ylmethyl)-amide | 448 |
| 732 | 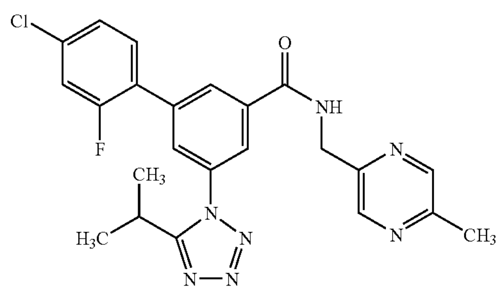 | 4'-Chloro-2'-fluoro-5-(5-isopropyl-tetrazol-1-yl)-biphenyl-3-carboxylic acid (5-methyl-pyrazin-2-ylmethyl)-amide | 80.1-86.0° C. |
| 733 | 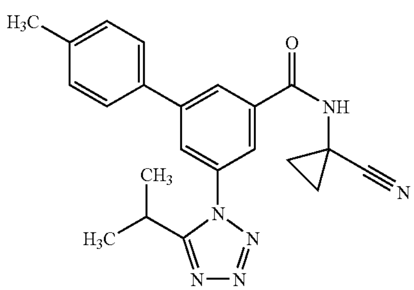 | 5-(5-Isopropyl-tetrazol-1-yl)-4'-methyl-biphenyl-3-carboxylic acid (1-cyano-cyclopropyl)-amide | 85.0-89.6° C. |
| 734 | 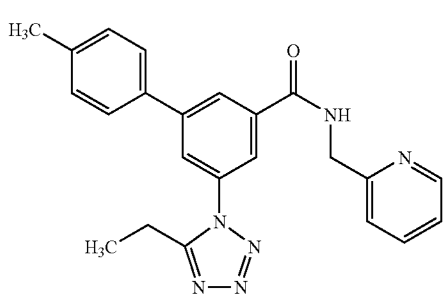 | 5-(5-Ethyl-tetrazol-1-yl)-4'-methyl-biphenyl-3-carboxylic acid (pyridin-2-ylmethyl)-amide | 399 |

TABLE 1-continued

| # | Structure | Name (Autonom ™) | Mp or M + H |
|---|---|---|---|
| 735 | 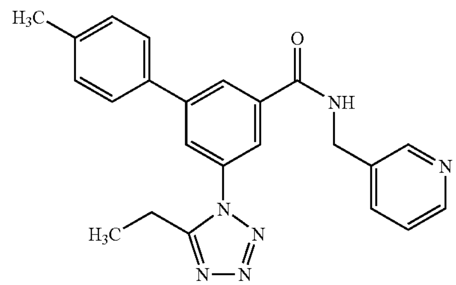 | 5-(5-Ethyl-tetrazol-1-yl)-4'-methyl-biphenyl-3-carboxylic acid (pyridin-3-ylmethyl)-amide | 399 |
| 736 | 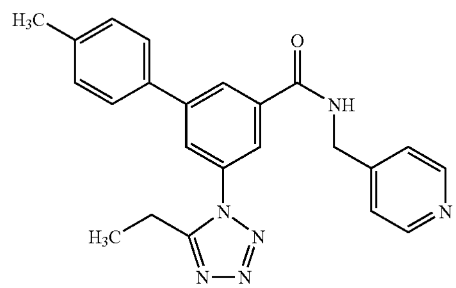 | 5-(5-Ethyl-tetrazol-1-yl)-4'-methyl-biphenyl-3-carboxylic acid (pyridin-4-ylmethyl)-amide | 399 |
| 737 | 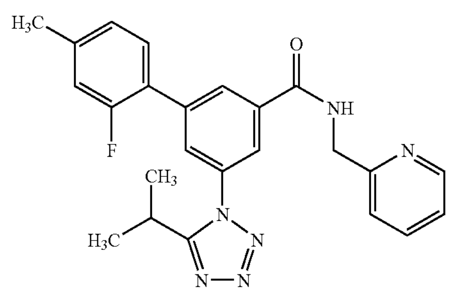 | 2'-Fluoro-5-(5-isopropyl tetrazol-1-yl)-4'-methyl-biphenyl-3-carboxylic acid (pyridin-2-ylmethyl)-amide | 431 |
| 738 | 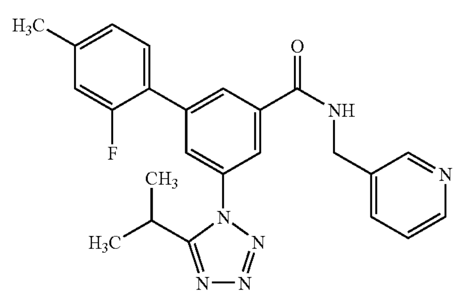 | 2'-Fluoro-5-(5-isopropyl tetrazol-1-yl)-4'-methyl-biphenyl-3-carboxylic acid (pyridin-3-ylmethyl)-amide | 431 |
| 739 | 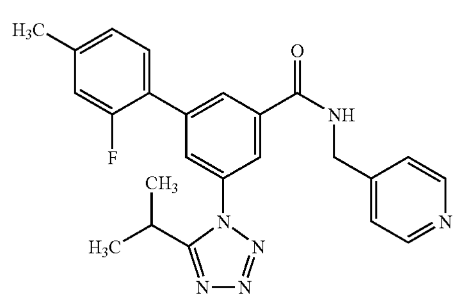 | 2'-Fluoro-5-(5-isopropyl tetrazol-1-yl)-4'-methyl-biphenyl-3-carboxylic acid (pyridin-4-ylmethyl)-amide | 431 |

TABLE 1-continued

| # | Structure | Name (Autonom ™) | Mp or M + H |
|---|---|---|---|
| 740 | 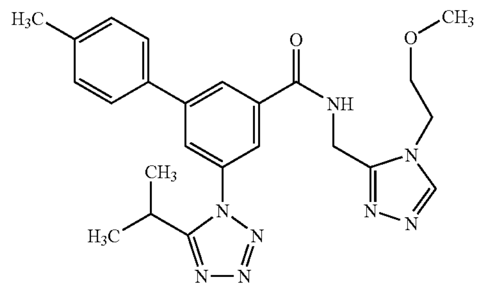 | 5-(5-Ethyl-tetrazol-1-yl)-4'-methyl-biphenyl-3-carboxylic acid {1-[4-(2-methoxy-ethyl)-4 H-[1,2,4]triazol-3-yl]-ethyl}-amide | 88.0-94.0° C. |
| 741 | 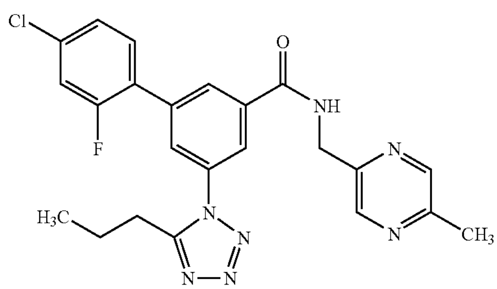 | 4'-Chloro-2'-fluoro-5-(5-propyl-tetrazol-1-yl)-biphenyl-3-carboxylic acid (5-methyl-pyrazin-2-ylmethyl)-amide | 52.0-55.0° C. |
| 742 | 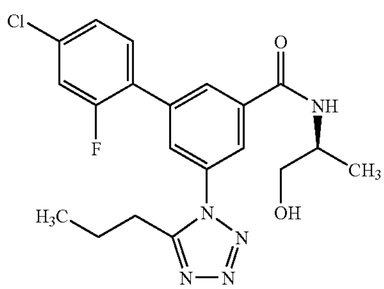 | 4'-Chloro-2'-fluoro-5-(5-propyl-tetrazol-1-yl)-biphenyl-3-carboxylic acid ((S)-2-hydroxy-1-methyl-ethyl)-amide | 58.0-60.3° C. |
| 743 | 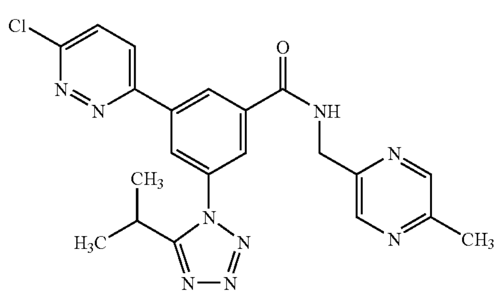 | 3-(6-Chloro-pyridazin-3-yl)-5-(5-isopropyl-tetrazol-1-yl)-N-(5-methyl-pyrazin-2-ylmethyl)-benzamide | 450 |
| 744 | 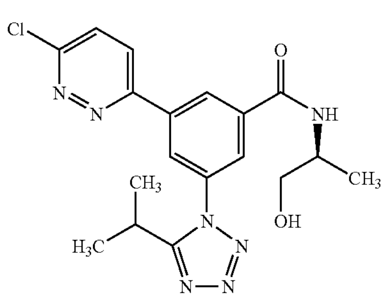 | 3-(6-Chloro-pyridazin-3-yl)-N-((S)-2-hydroxy-1-methyl-ethyl)-5-(5-isopropyl-tetrazol-1-yl)-benzamide | 402 |

TABLE 1-continued

| # | Structure | Name (Autonom ™) | Mp or M + H |
|---|---|---|---|
| 745 | 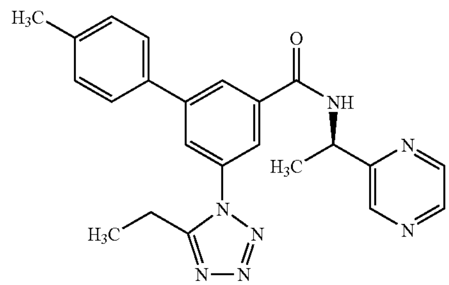 | 5-(5-Ethyl-tetrazol-1-yl)-4'-methyl-biphenyl-3-carboxylic acid ((R)-1-pyrazin-2-yl-ethyl)-amide | 77.0-83.0° C. |
| 746 | 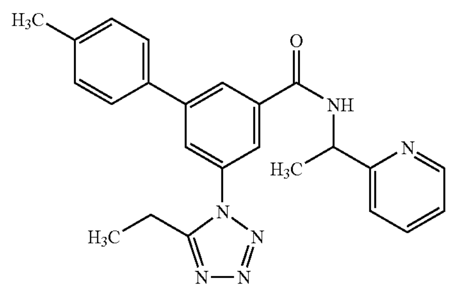 | 5-(5-Ethyl-tetrazol-1-yl)-4'-methyl-biphenyl-3-carboxylic acid (1-pyridin-2-yl-ethyl)-amide | 413 |
| 747 | 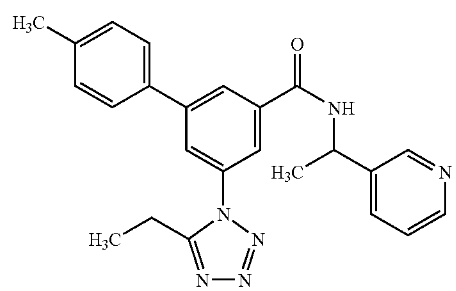 | 5-(5-Ethyl-tetrazol-1-yl)-4'-methyl-biphenyl-3-carboxylic acid (1-pyridin-3-yl-ethyl)-amide | 413 |
| 748 | 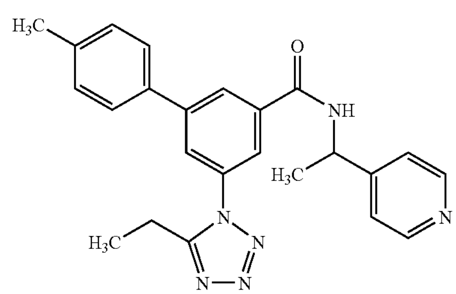 | 5-(5-Ethyl-tetrazol-1-yl)-4'-methyl-biphenyl-3-carboxylic acid (1-pyridin-4-yl-ethyl)-amide | 413 |
| 749 | 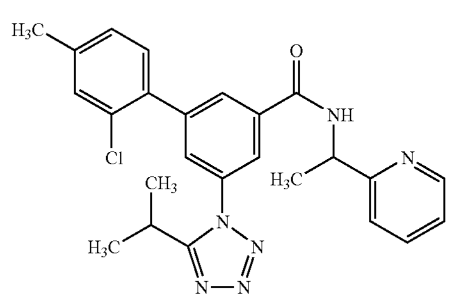 | 2'-Chloro-5-(5-isopropyl-tetrazol-1-yl)-4'-methyl-biphenyl-3-carboxylic acid (1-pyridin-2-yl-ethyl)-amide | 461 |

TABLE 1-continued

| # | Structure | Name (Autonom ™) | Mp or M + H |
|---|---|---|---|
| 750 | 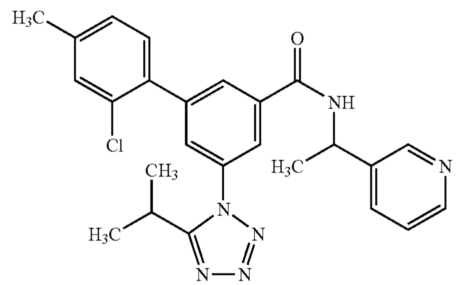 | 2'-Chloro-5-(5-isopropyl-tetrazol-1-yl)-4'-methyl-biphenyl-3-carboxylic acid (1-pyridin-3-yl-ethyl)-amide | 461 |
| 751 | 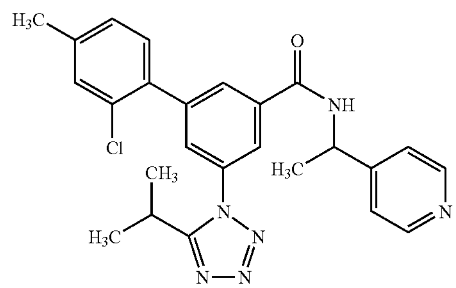 | 2'-Chloro-5-(5-isopropyl-tetrazol-1-yl)-4'-methyl-biphenyl-3-carboxylic acid (1-pyridin-4-yl-ethyl)-amide | 461 |
| 752 | 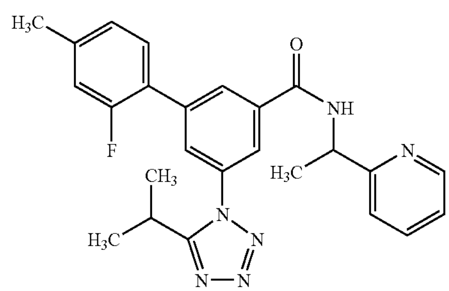 | 2'-Fluoro-5-(5-isopropyl-tetrazol-1-yl)-4'-methyl-biphenyl-3-carboxylic acid (1-pyridin-2-yl-ethyl)-amide | 445 |
| 753 | 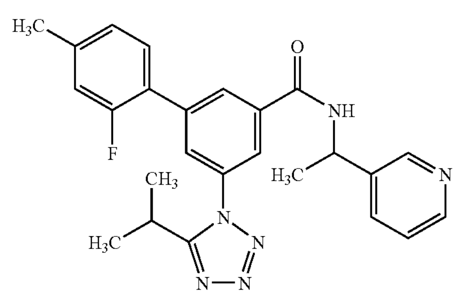 | 2'-Fluoro-5-(5-isopropyl-tetrazol-1-yl)-4'-methyl-biphenyl-3-carboxylic acid (1-pyridin-3-yl-ethyl)-amide | 445 |
| 754 | 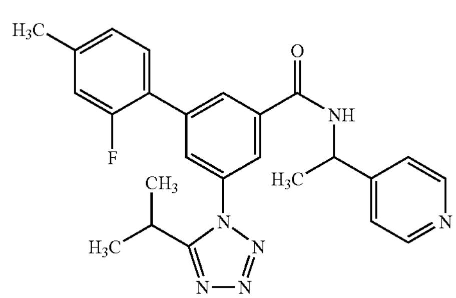 | 2'-Fluoro-5-(5-isopropyl-tetrazol-1-yl)-4'-methyl-biphenyl-3-carboxylic acid (1-pyridin-4-yl-ethyl)-amide | 445 |

TABLE 1-continued

| # | Structure | Name (Autonom ™) | Mp or M + H |
|---|---|---|---|
| 755 | 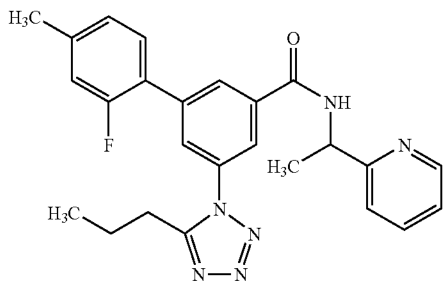 | 2'-Fluoro-4'-methyl-5-(5-propyl-tetrazol-1-yl)-biphenyl-3-carboxylic acid (1-pyridin-2-yl-ethyl)-amide | 445 |
| 756 | 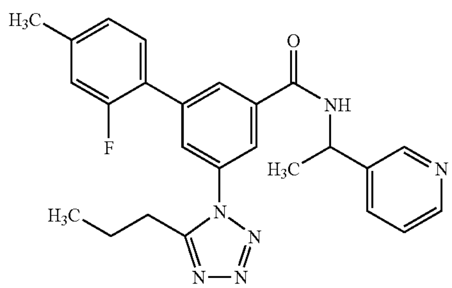 | 2'-Fluoro-4'-methyl-5-(5-propyl-tetrazol-1-yl)-biphenyl-3-carboxylic acid (1-pyridin-3-yl-ethyl)-amide | 445 |
| 757 | 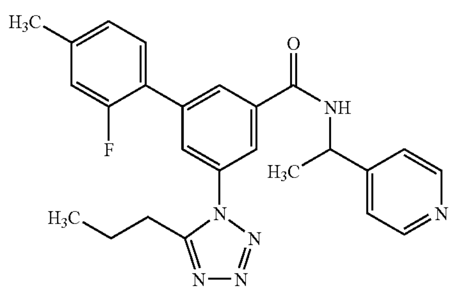 | 2'-Fluoro-4'-methyl-5-(5-propyl-tetrazol-1-yl)-biphenyl-3-carboxylic acid (1-pyridin-4-yl-ethyl)-amide | 445 |
| 758 | 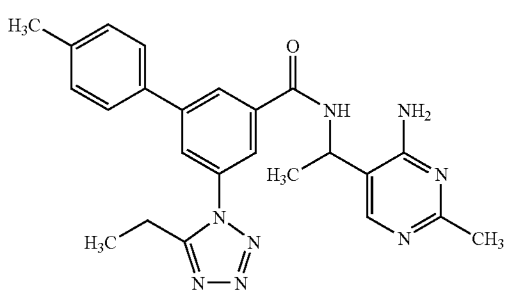 | 5-(5-Ethyl-tetrazol-1-yl)-4'-methyl-biphenyl-3-carboxylic acid (4-amino-2-methyl-pyrimidin-5-ylmethyl)-amide | 443 |
| 759 | 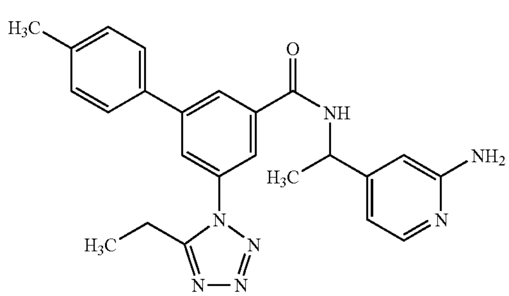 | 5-(5-Ethyl-tetrazol-1-yl)-4'-methyl-biphenyl-3-carboxylic acid (2-amino-pyridin-4-ylmethyl)-amide | 428 |

TABLE 1-continued

| # | Structure | Name (Autonom ™) | Mp or M + H |
|---|---|---|---|
| 760 | 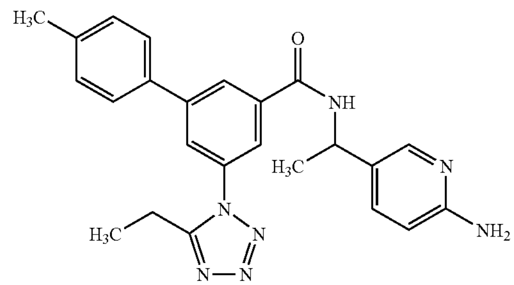 | 5-(5-Ethyl-tetrazol-1-yl)-4'-methyl-biphenyl-3-carboxylic acid (6-amino-pyridin-3-ylmethyl)-amide | 428 |
| 761 | 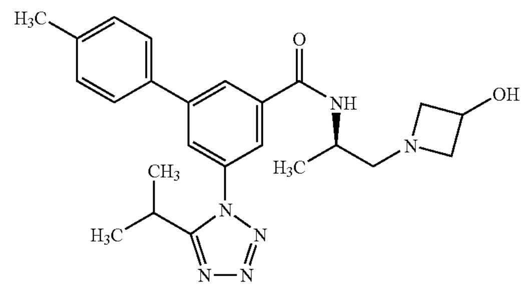 | 5-(5-Isopropyl-tetrazol-1-yl)-4'-methyl-biphenyl-3-carboxylic acid [(R)-2-(3-hydroxy-azetidin-1-yl)-1-methyl-ethyl]-amide | 435 |
| 762 | 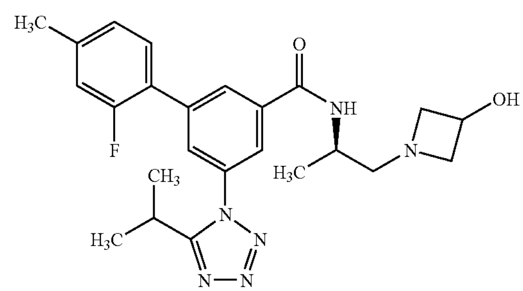 | 2'-Fluoro-5-(5-isopropyl tetrazol-1-yl)-4'-methyl-biphenyl-3-carboxylic acid [(R)-2-(3-hydroxy-azetidin-1-yl)-1-methyl-ethyl]-amide | 453 |
| 763 | 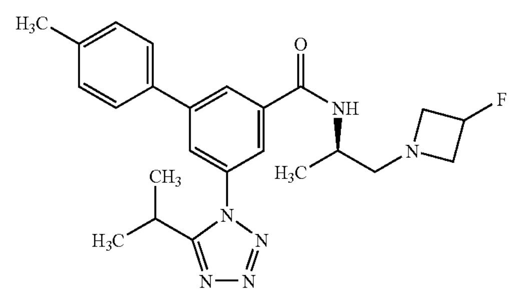 | 5-(5-Isopropyl-tetrazol-1-yl)-4'-methyl-biphenyl-3-carboxylic acid [(R)-2-(3-fluoro-azetidin-1-yl)-1-methyl-ethyl]-amide | 437 |
| 764 | 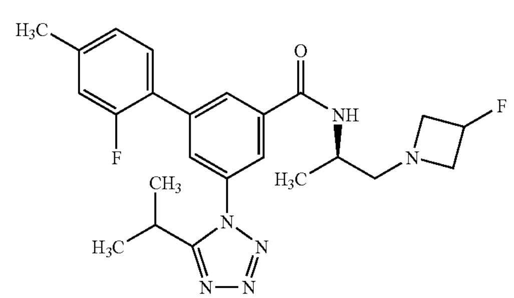 | 2'-Fluoro-5-(5-isopropyl-tetrazol-1-yl)-4'-methyl-biphenyl-3-carboxylic acid [(R)-2-(3-fluoro-azetidin-1-yl)-1-methyl-ethyl]-amide | 455 |

TABLE 1-continued

| # | Structure | Name (Autonom ™) | Mp or M + H |
|---|---|---|---|
| 765 | 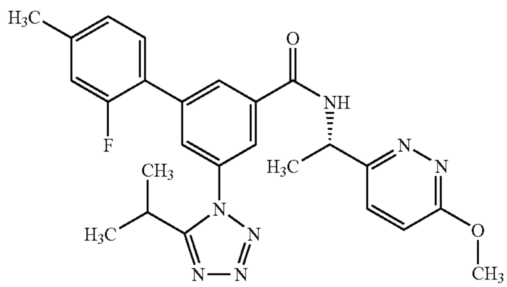 | 5-(5-Isopropyl-tetrazol-1-yl)-4'-methyl-biphenyl-3-carboxylic acid [(S)-1-(6-methoxy-pyridazin-3-yl)-ethyl]-amide | 104.9-109.0° C. |
| 766 | 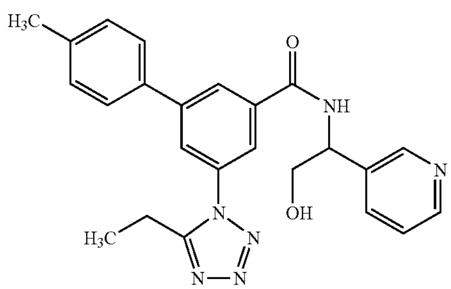 | 5-(5-Ethyl-tetrazol-1-yl)-4'-methyl-biphenyl-3-carboxylic acid (2-hydroxy-1-pyridin-3-yl-ethyl)-amide | 429 |
| 767 | 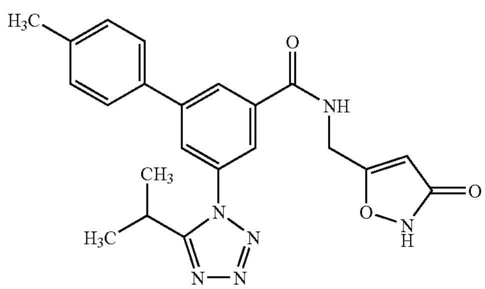 | 5-(5-Isopropyl-tetrazol-1-yl)-4'-methyl-biphenyl-3-carboxylic acid (3-oxo-2,3-dihydro-isoxazol-5-ylmethyl)-amide | 419 |
| 768 | 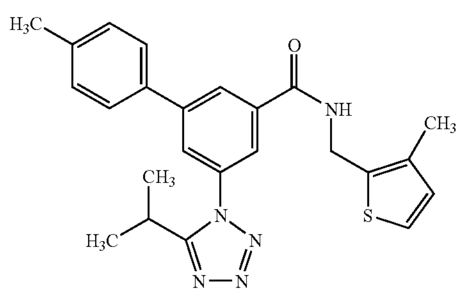 | 5-(5-Isopropyl-tetrazol-1-yl)-4'-methyl-biphenyl-3-carboxylic acid (3-methyl-thiophen-2-ylmethyl)-amide | 432 |
| 769 | 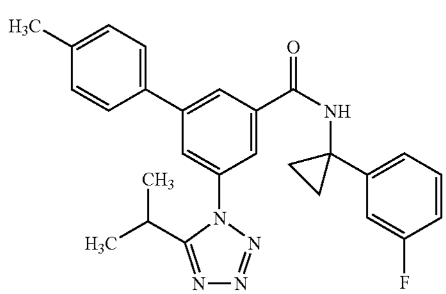 | 5-(5-Isopropyl-tetrazol-1-yl)-4'-methyl-biphenyl-3-carboxylic acid [1-(3-fluoro-phenyl)-cyclopropyl]-amide | 456 |

TABLE 1-continued

| # | Structure | Name (Autonom ™) | Mp or M + H |
|---|---|---|---|
| 770 | 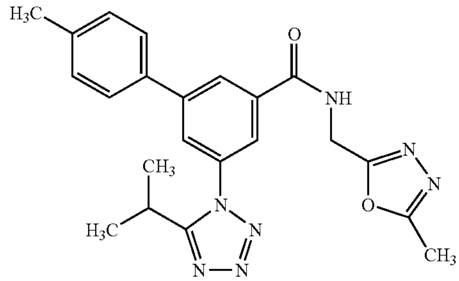 | 5-(5-Isopropyl-tetrazol-1-yl)-4'-methyl-biphenyl-3-carboxylic acid (5-methyl-[1,3,5]oxadiazol-2-ylmethyl)-amide | 418 |
| 771 | 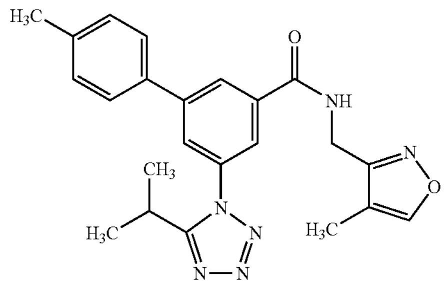 | 5-(5-Isopropyl-tetrazol-1-yl)-4'-methyl-biphenyl-3-carboxylic acid (4-methyl-isoxazol-3-ylmethyl)-amide | 417 |
| 772 | 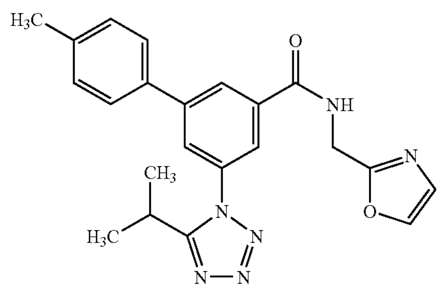 | 5-(5-Isopropyl-tetrazol-1-yl)-4'-methyl-biphenyl-3-carboxylic acid (oxazol-2-ylmethyl)-amide | 403 |
| 773 | 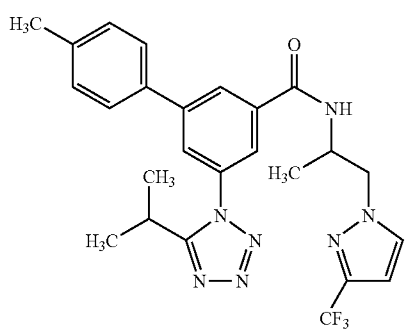 | 5-(5-Isopropyl-tetrazol-1-yl)-4'-methyl-biphenyl-3-carboxylic acid [1-(1-methyl-1H-pyrazol-3-yl)-ethyl]-amide | 444 |
| 774 | 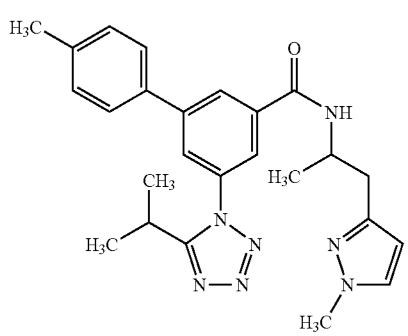 | 5-(5-Isopropyl-tetrazol-1-yl)-4'-methyl-biphenyl-3-carboxylic acid [1-(1-methyl-1H-pyrazol-3-yl)-ethyl]-amide | 444 |

TABLE 1-continued

| # | Structure | Name (Autonom ™) | Mp or M + H |
|---|---|---|---|
| 775 | 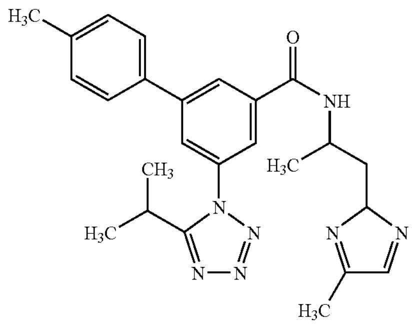 | 5-(5-Isopropyl-tetrazol-1-yl)-4'-methyl-biphenyl-3-carboxylic acid [1-methyl-2-(3-methyl-pyrazol-1-yl)-ethyl]-amide | 444 |
| 776 | 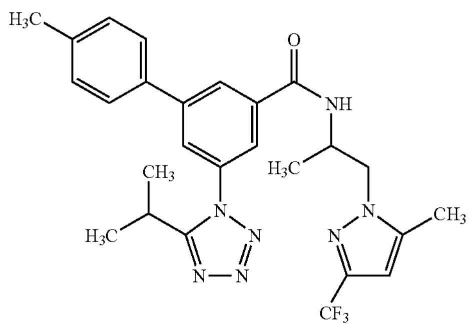 | 5-(5-Isopropyl-tetrazol-1-yl)-4'-methyl-biphenyl-3-carboxylic acid [1-methyl-2-(5-methyl-3-trifluoromethyl-pyrazol-1-yl)-ethyl]-amide | 512 |
| 777 | 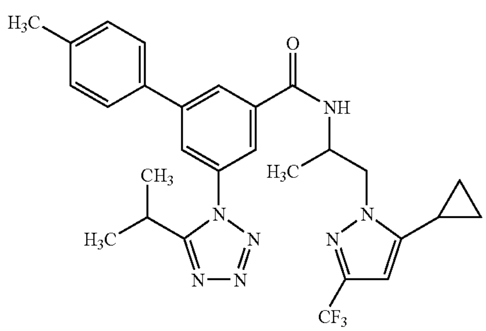 | 5-(5-Isopropyl-tetrazol-1-yl)-4'-methyl-biphenyl-3-carboxylic acid [2-(5-cyclopropyl-3-trifluoromethyl-pyrazol-1-yl)-1-methyl-ethyl]-amide | 538 |
| 778 | 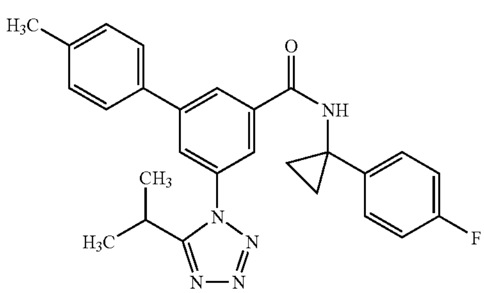 | 5-(5-Isopropyl-tetrazol-1-yl)-4'-methyl-biphenyl-3-carboxylic acid [1-(4-fluoro-phenyl)-cylcopropyl]-amide | 456 |
| 779 | 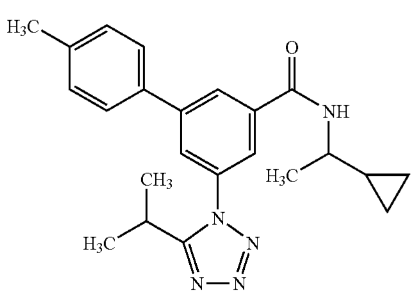 | 5-(5-Isopropyl-tetrazol-1-yl)-4'-methyl-biphenyl-3-carboxylic acid (1-cyclopropyl-ethyl)-amide | 390 |

TABLE 1-continued

| # | Structure | Name (Autonom ™) | Mp or M + H |
|---|---|---|---|
| 780 | 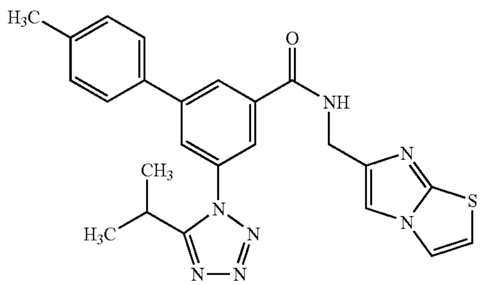 | 5-(5-Isopropyl-tetrazol-1-yl)-4'-methyl-biphenyl-3-carboxylic acid (imidazo[2,1-β]-thiazol1-6-ylmethyl)-amide | 458 |
| 781 | 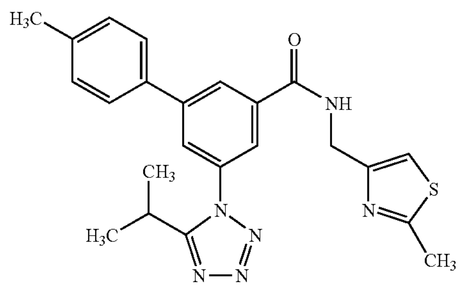 | 5-(5-Isopropyl-tetrazol-1-yl)-4'-methyl-biphenyl-3-carboxylic acid [1-(2-methyl-thiazol-4-yl)-ethyl]-amide | 433 |
| 782 | 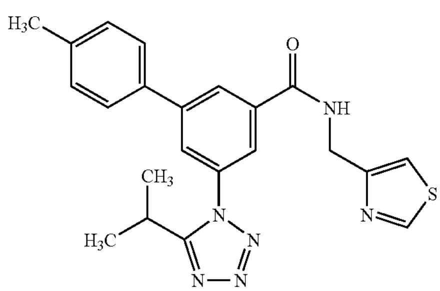 | 5-(5-Isopropyl-tetrazol-1-yl)-4'-methyl-biphenyl-3-carboxylic acid (1-thiazol-4-yl-ethyl)-amide | 419 |
| 783 | 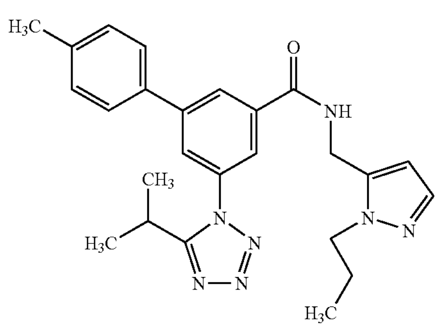 | 5-(5-Isopropyl-tetrazol-1-yl)-4'-methyl-biphenyl-3-carboxylic acid (2-propyl-2H-pyrazol-3-ylmethyl)-amide | 444 |
| 784 | 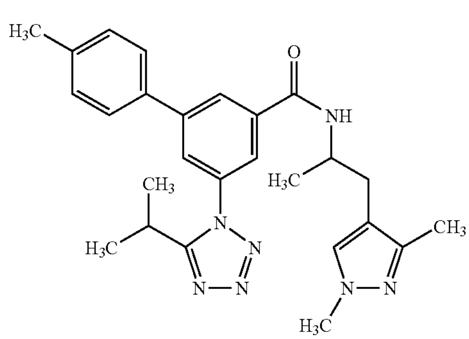 | 5-(5-Isopropyl-tetrazol-1-yl)-4'-methyl-biphenyl-3-carboxylic acid [2-(1,3-dimethyl-1H-pyrazol-4-yl)-1-methyl-ethyl]-amide | 458 |

TABLE 1-continued

| # | Structure | Name (Autonom ™) | Mp or M + H |
|---|---|---|---|
| 785 | 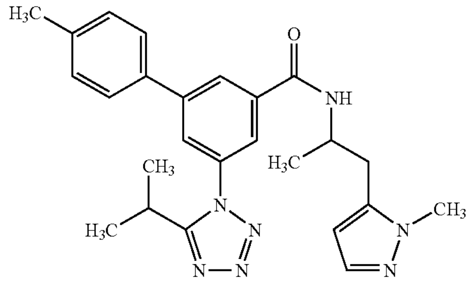 | 5-(5-Isopropyl-tetrazol-1-yl)-4'-methyl-biphenyl-3-carboxylic acid (2-methyl-2 H-pyrazol-3-ylmethyl)-amide | 444 |
| 786 | 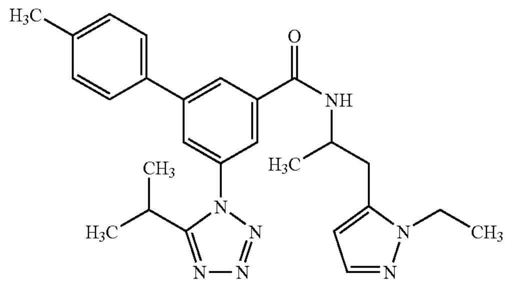 | 5-(5-Isopropyl-tetrazol-1-yl)-4'-methyl-biphenyl-3-carboxylic acid (2-ethyl-2 H-pyrazol-3-ylmethyl)-amide | 458 |
| 787 | 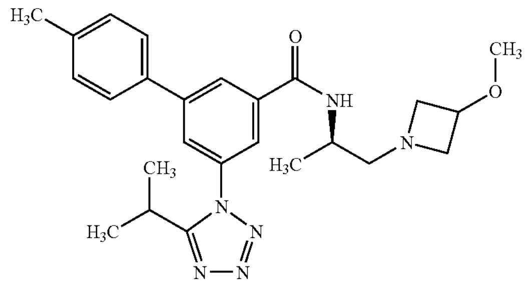 | 5-(5-Isopropyl-tetrazol-1-yl)-4'-methyl-biphenyl-3-carboxylic acid [(R)-2-(3-methoxy-azetidin-1-yl)-1-methyl-ethyl]-amide | 449 |
| 788 | 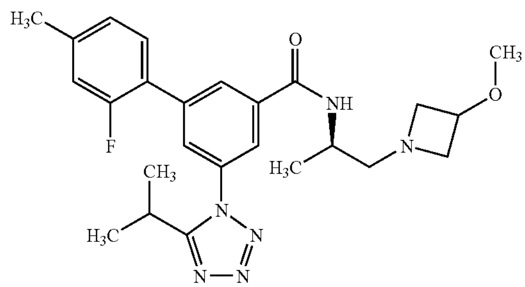 | 2'-Fluoro-5-(5-isopropyl-tetrazol-1-yl)-4'-methyl-biphenyl-3-carboxylic acid [(R)-2-(3-methoxy-azetidin-1-yl)-1-methyl-ethyl]-amide | 467 |
| 789 | 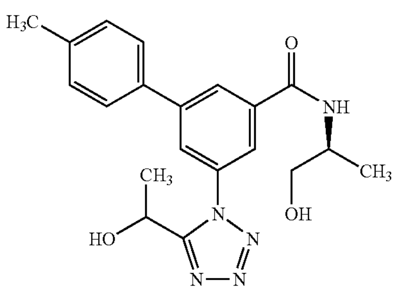 | 5-[5-(1-Hydroxy-ethyl)-tetrazol-1-yl]-4'-methyl-biphenyl-3-carboxylic acid ((S)-2-hydroxy-1-methyl-ethyl)-amide | 382 |

TABLE 1-continued

| # | Structure | Name (Autonom ™) | Mp or M + H |
|---|---|---|---|
| 790 | 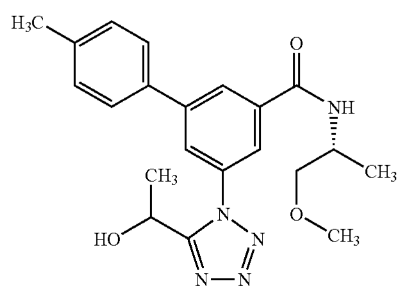 | 5-[5-(1-Hydroxy-ethyl)-tetrazol-1-yl]-4'-methyl-biphenyl-3-carboxylic acid ((R)-2-hydroxy-1-methyl-ethyl)-amide | 382 |
| 791 | 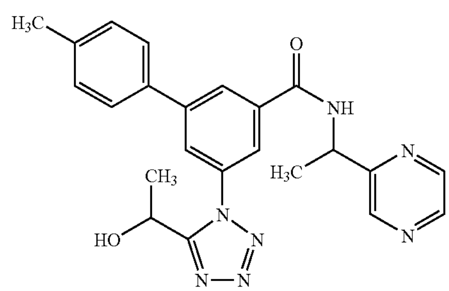 | 5-[5-(1-Hydroxy-ethyl)-tetrazol-1-yl]-4'-methyl-biphenyl-3-carboxylic acid (1-pyrazin-2-yl-ethyl)-amide | 430 |
| 792 | 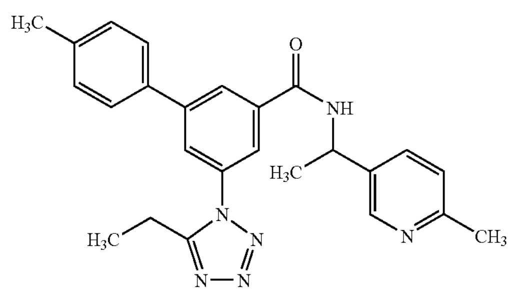 | 5-(5-Ethyl-tetrazol-1-yl)-4'-methyl-biphenyl-3-carboxylic acid (6-methyl-pyridin-3-ylmethyl)-amide | 427 |
| 793 | 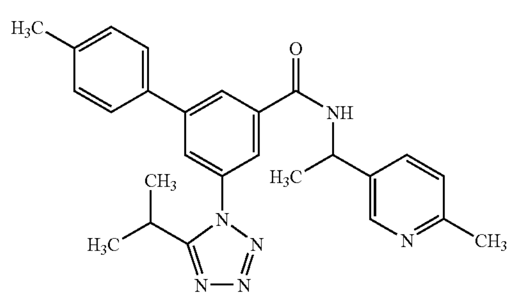 | 5-(5-Isopropyl-tetrazol-1-yl)-4'-methyl-biphenyl-3-carboxylic acid (6-methyl-pyridin-3-ylmethyl)-amide | 441 |
| 794 | 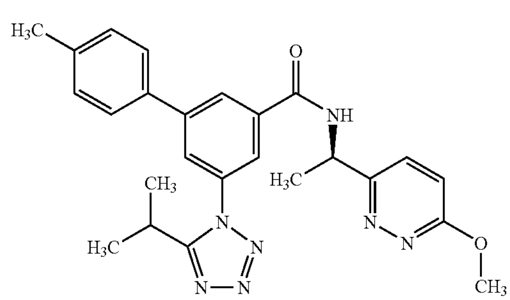 | 5-(5-Isopropyl-tetrazol-1-yl)-4'-methyl-biphenyl-3-carboxylic acid [(R)-1-(6-methoxy-pyridazin-3-yl)-ethyl]-amide | 458 |

TABLE 1-continued

| # | Structure | Name (Autonom ™) | Mp or M + H |
|---|-----------|------------------|-------------|
| 795 | 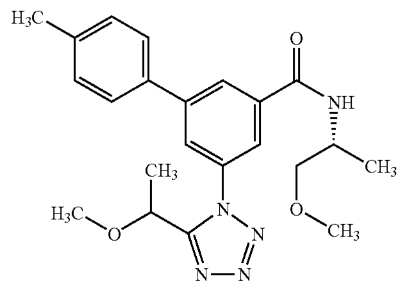 | 5-[5-(1-Methoxy-ethyl)-tetrazol-1-yl]-4'-methyl-biphenyl-3-carboxylic acid ((R)-2-methoxy-1-methyl-ethyl)-amide | 410 |
| 796 | 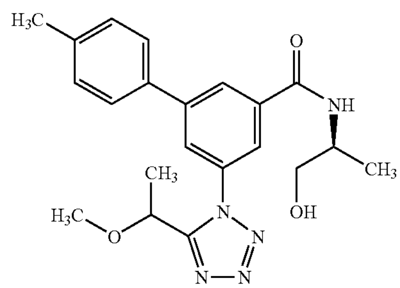 | 5-[5-(1-Methoxy-ethyl)-tetrazol-1-yl]-4'-methyl-biphenyl-3-carboxylic acid ((S)-2-hydroxy-1-methyl-ethyl)-amide | 396 |
| 797 | 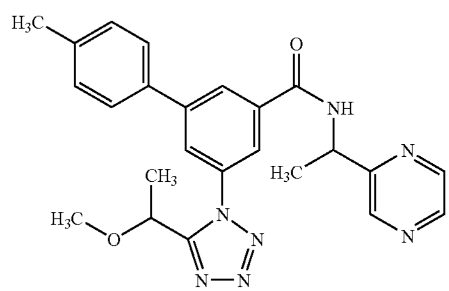 | 5-[5-(1-Methoxy-ethyl)-tetrazol-1-yl]-4'-methyl-biphenyl-3-carboxylic acid (1-pyrazin-2-yl-ethyl)-amide | 444 |
| 798 | 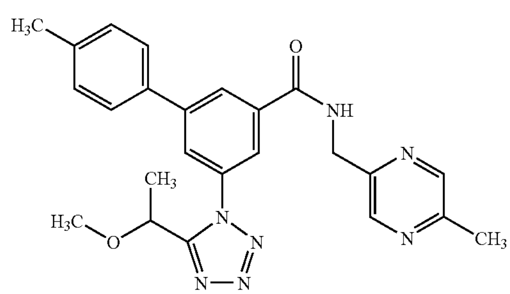 | 5-[5-(1-Methoxy-ethyl)-tetrazol-1-yl]-4'-methyl-biphenyl-3-carboxylic acid (5-methyl-pyrazin-2-ylmethyl)-amide | 444 |
| 799 | 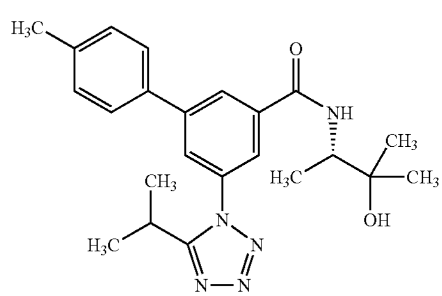 | 5-(5-Isopropyl-tetrazol-1-yl)-4'-methyl-biphenyl-3-carboxylic acid ((S)-2-hydroxy-1,2-dimethyl-propyl)-amide | 86.0-89.0° C. |

TABLE 1-continued

| # | Structure | Name (Autonom ™) | Mp or M + H |
|---|---|---|---|
| 800 | 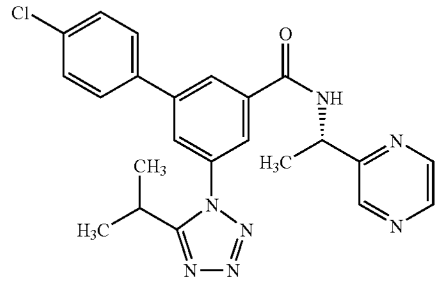 | 4'-Chloro-5-(5-isopropyl-tetrazol-1-yl)-biphenyl-3-carboxylic acid ((S)-1-pyrazin-2-yl-ethyl)-amide | 448 |
| 801 | 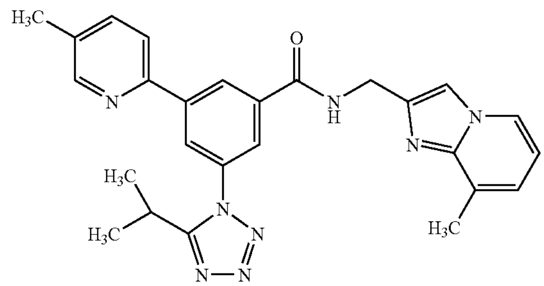 | 3-(5-Isopropyl-tetrazol-1-yl)-N-(8-methyl-imidazo[1,2-a]pyridin-2-ylmethyl)-5-(5-methyl-pyridin-2-yl)-benzamide | 467 |
| 802 | 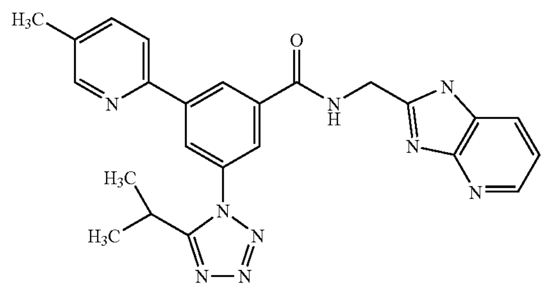 | N-(1 H-Imidazo[4,5-b]pyridin-2-ylmethyl)-3-(5-isopropyl-tetrazol-1-yl)-5-(5-methyl-pyridin-2-yl)-benzamide | 454 |
| 803 | 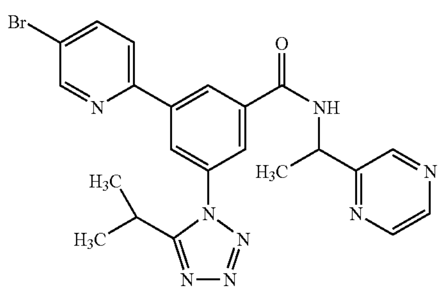 | 3-(5-Bromo-pyridin-2-yl)-5-(5-isopropyl-tetrazol-1-yl)-N-(1-pyrazin-2-yl-ethyl)-benzamide | 494 |
| 804 | 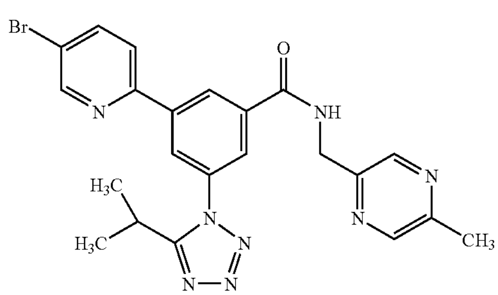 | 3-(5-Bromo-pyridin-2-yl)-5-(5-isopropyl-tetrazol-1-yl)-N-(5-methyl-pyrazin-2-ylmethyl)-benzamide | 494 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula (I), wherein $R^6$, $R^{11}$, $R^{12}$ and $R^{13}$ are as defined herein.

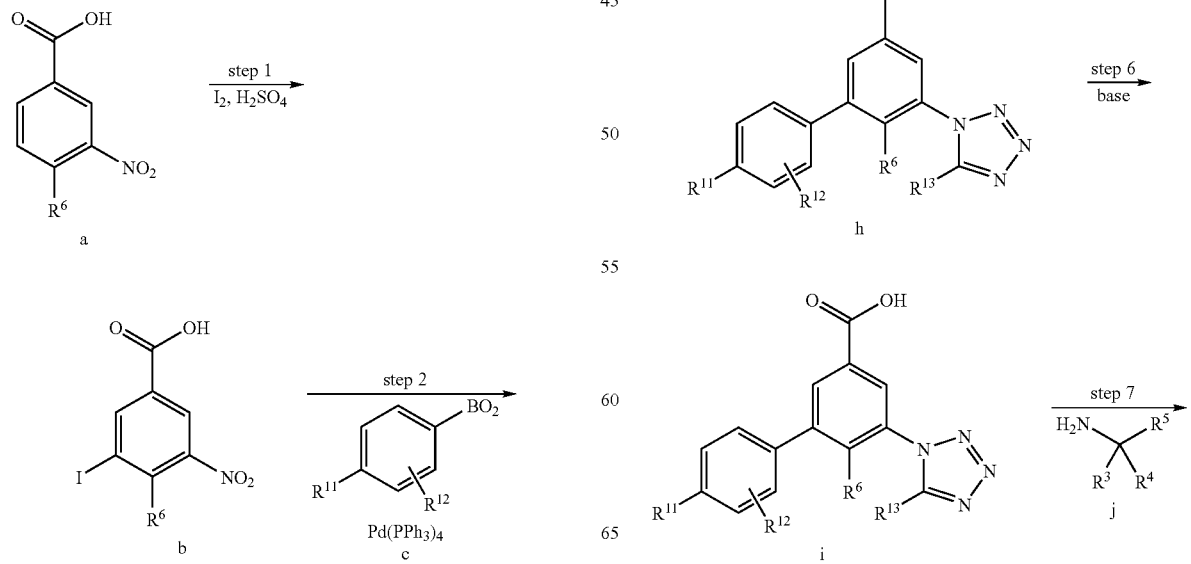

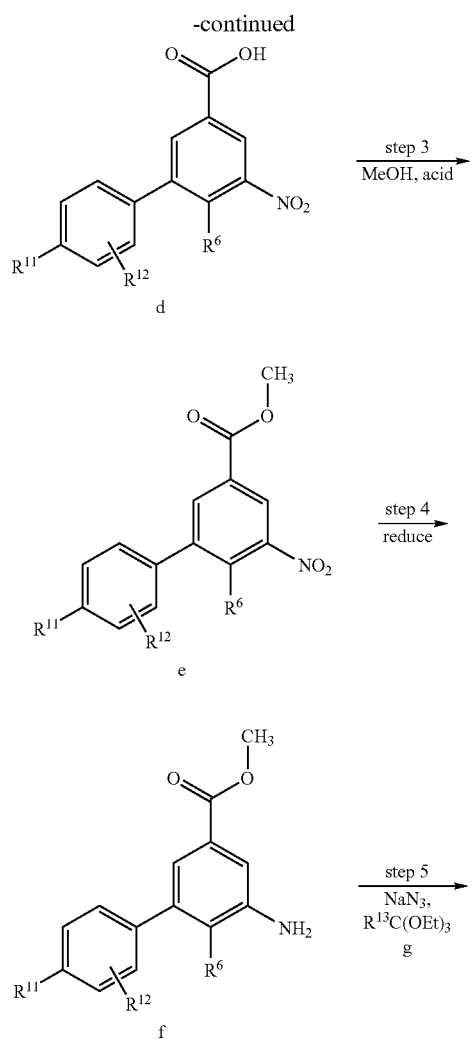

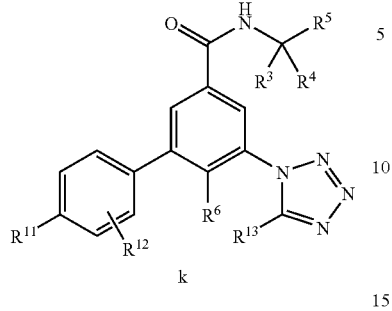

In step 1 of Scheme A, nitrobenzoic acid a is subject to iodination under sulfuric acid conditions to afford iodo-nitrobenzoic acid b. Benzoic acid compound b is reacted with arylboronic acid compound c in the presence of tetrakis-(triphenylphosphine)palladium catalyst to afford biphenyl acid compound d. The acid group of biphenyl acid d is protected by esterification in step 3 to form biphenyl acid methyl ester e. Biphenyl ester e is then subject to reduction to form biphenylamine f in step 4. A cyclization reaction is carried out in step 5 by treating biphenylamine f with sodium azide and acetal compound g to provide biphenyl tetrazole compound h. In step 6 the ester group of compound h is hydrolyzed to give acid compound i. In step 7 an amide formation is achieved by reaction of biphenyl tetrazole compound i with amine i in the presence of carbodiimide, to afford compound k, which is a compound of formula I in accordance with the invention.

Many variations of Scheme A are possible and will suggest themselves to those skilled in the art. The aryl boronic acid is shown in step 2 as being a phenyl boronic acid, but may be replaced by pyridinyl boronic acids in other embodiments of the invention. In many embodiments amine compound h is a secondary amine with specific stereochemistry. In certain embodiments the amide formation of step 7 may be carried out prior to tetrazole formation in step 5. Methanol in step 3 may be relaced with other lower alcohols.

Scheme B below illustrates another synthetic procedure usable to prepare specific compounds of formula (I), wherein $R^6$, $R^{11}$, $R^{12}$ and $R^{13}$ are as defined herein.

SCHEME B

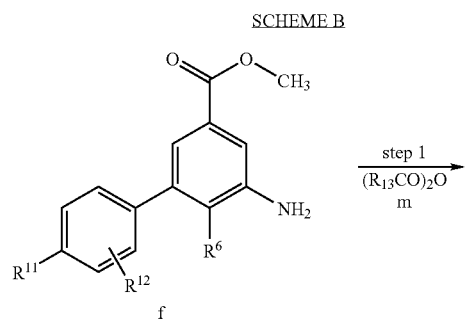

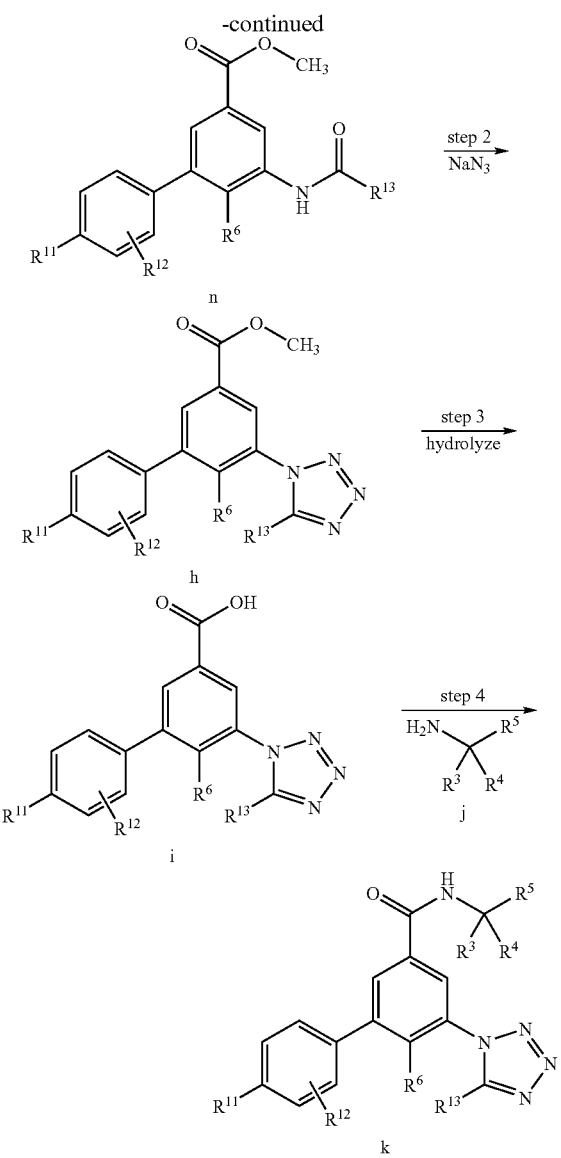

In step 1 of Scheme B, biphenyl amine compound f undergoes an N-acylation by reaction with anhydride m to provide amide compound n. Anhydride m may be replaced with the corresponding acid chloride in many embodiments. Amide n undergoes cyclization in step 2 by reaction with sodium azide to yield biphenyl tetrazole compound h. Following the procedure of Scheme A above, compound h may then be hydrolized in step 3 to form acid compound i, which is reacted amine i to afford compound k, which is a compound of formula I as noted above.

As in Scheme A, many variations of Scheme B are possible and will suggest themselves to those skilled in the art.

Specific details for producing compounds of the invention are described in the Examples section below.

Utility

The compounds of the invention are usable for the treatment of a wide range of genitorurinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitits, pelvic pain syndrome, prostatodynia, cystitis, and idiophatic bladder hypersensitivity, and other symptoms related to overactive bladder.

The compounds of the invention are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

Additionally, compounds of the invention are useful for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

| ABBREVIATIONS | |
|---|---|
| DBU | 1,8-diazabicyclo[5.4.0]undec-7-ene |
| DCM | dichloromethane/methylene chloride |
| DMF | N,N-dimethylformamide |
| DMAP | 4-dimethylaminopyridine |
| EDCI | 1-ethyl-3-(3'-dimethylaminopropyl)carbodiimide |
| EtOAc | ethyl acetate |
| EtOH | ethanol |
| gc | gas chromatography |
| HMPA | hexamethylphosphoramide |
| HOBt | N-Hydroxybenzotriazole |

-continued

| ABBREVIATIONS | |
|---|---|
| hplc | high performance liquid chromatography |
| mCPBA | m-chloroperbenzoic acid |
| MeCN | acetonitrile |
| NMM | N-methyl-morpholine |
| NMP | N-methyl pyrrolidinone |
| TEA | triethylamine |
| THF | tetrahydrofuran |
| LDA | lithium diisopropylamine |
| TLC | thin layer chromatography |

Preparation 1

4'-Methyl-5-tetrazol-1-yl-biphenyl-3-carboxylic acid

The synthetic procedure used in this preparation is outlined below in Scheme C.

SCHEME C

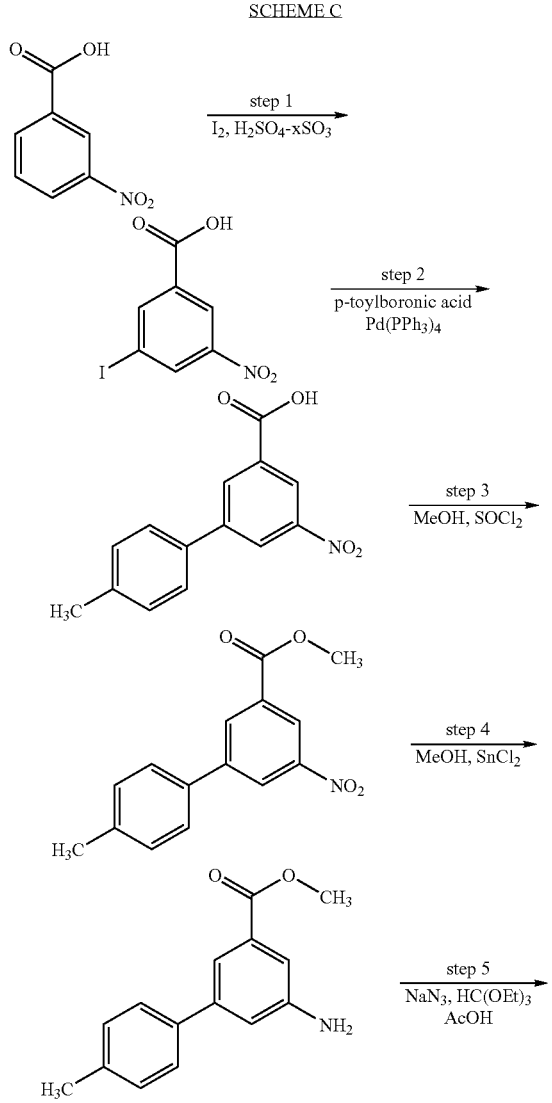

-continued

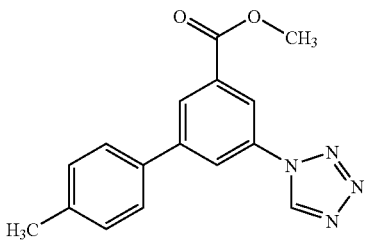

step 6
LiOH
THF/H2O

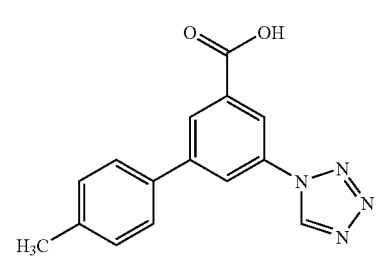

Step 1 3-Iodo-5-nitro-benzoic acid

To a stirred solution of iodine (137.95 g, 0.5436 mmol) in fuming sulfuric acid (250 ml) was added m-nitrobenzoic acid (64.6 g, 0.3866 mmol) at room temperature. The reaction mixture was slowly heated to 85° C. over 2 hours and stirred at the same temperature for another 12 hours. The reaction mixture was cooled to room temperature and poured into ice, and the aqueous solution was extracted with dichloromethane. The organic phase was separated and washed with water, 2.0 M solution of $Na_2S_2O_3$ and brine, and then dried over $Na_2SO_4$. Solvent was removed under reduced pressure to yield 3-iodo-5-nitrobenzoic acid as slight yellow solid 111 g, yield 98%. MS (M+H)=294.

Step 2 4'-Methyl-5-nitro-biphenyl-3-carboxylic acid

To a stirred solution of 3-iodo-5-nitrobenzoic acid (15.48 g, 52.83 mmol) and $Pd(Ph_3P)_4$ (1.84 g, 1.69 mmol) in 300 ml of toluene and 50 ml of ethanol was added p-tolylboronic acid (7.87 g, 58.11 mmol) and a solution of $Cs_2CO_3$ (18.89 g, 58.11 mmol) in 20 ml water at room temperature. The reaction was brought to reflux for 18 hours and then cooled to room temperature. To the solution was added 2N NaOH, and the reaction mixture was stirred for 30 minutes. The organic phase was separated, and the aqueous phase was adjusted to PH<4 using 12N HCl. The resulting solid precipitate was filtered and washed with toluene to afford 13.2 g of 4'-Methyl-5-nitro-biphenyl-3-carboxylic acid as light yellow solid (97.2%). MS (M+H)=258.

Step 3 4'-Methyl-5-nitro-biphenyl-3-carboxylic acid methyl ester

To a solution of 4'-Methyl-5-nitro-biphenyl-3-carboxylic acid (10.00 g, 0.039 mol) in methanol was added $SOCl_2$ (5.09 g, 0.043 mol) at 0° C. The reaction mixture was allowed to warm to room temperature and was then heated to reflux for 2 hours. The solvent was removed in vacuo to afford 4'-Methyl-5-nitro-biphenyl-3-carboxylic acid methyl ester (9.72 g, 92%) as light yellow solid. MS (M+H)=273.

Step 4 5-Amino-4'-methyl-biphenyl-3-carboxylic acid methyl ester

To a solution of 4'-Methyl-5-nitro-biphenyl-3-carboxylic acid methyl ester (10.00 g, 36.9 mmol) in methanol was added $SnCl_2$ (27.98 g, 147.6 mmol) at room temperature. The reaction mixture was refluxed for 3 hours, then cooled. Solvent was removed in vacuo and the residue was dissolved in $H_2O$, then basified by addition of $Na_2CO_3$ to pH=9. The mixture was extracted by $CH_2Cl_2$, and the organic phase was washed with water followed by brine, and dried over $Na_2SO_4$. The solvent was removed under vacuum to give 5-Amino-4'-methyl-biphenyl-3-carboxylic acid methyl ester (8.48 g, 95%) as yellow oil. MS (M+H)=242.

Step 5 4'-Methyl-5-tetrazol-1-yl-biphenyl-3-carboxylic acid methyl ester

To a solution of 5-Amino-4'-methyl-biphenyl-3-carboxylic acid methyl ester (10 g, 41.5 mmol) and $NaN_3$ (4.99 g, 76.76 mmol) in AcOH (80 mL) was added $HC(OEt)_3$ (29.5 g, 199.2 mmol) at room temperature, then heated to reflux for 4 h. The solvent was removed in vacuo and the residue was purified by silica-gel chromatography to give 4'-Methyl-5-tetrazol-1-yl-biphenyl-3-carboxylic acid methyl ester as light yellow solid (11.22 g, 92%). MS (M+H)=295.

Step 6 4'-Methyl-5-tetrazol-1-yl-biphenyl-3-carboxylic acid

A solution of $LiOH \cdot H_2O$ (1.86 g, 44.2 mmol) in $H_2O$ (40 mL) was added dropwise to a suspension of 4'-Methyl-5-tetrazol-1-yl-biphenyl-3-carboxylic acid methyl ester (10 g, 34 mmol) in THF (25 mL) at 0° C. The reaction mixture was allowed to warm to room temperature and was stirred until the reaction solution turned clear. Solvent was removed under vacuum and the aqueous solution was acidified by addition of 10% HCl to pH=3. The resulting precipitate was collected and dried to afford 4'-Methyl-5-tetrazol-1-yl-biphenyl-3-carboxylic acid as white solid (8.85 g, 93%). MS (M+H)=281.

Similarly prepared, using the appropriately substituted phenyl boronic acids in step 2, were:

2'-Fluoro-4'-methyl-5-tetrazol-1-yl-biphenyl-3-carboxylic acid, MS (M+H)=299;
2'-Chloro-4'-methyl-5-tetrazol-1-yl-biphenyl-3-carboxylic acid, MS (M+H)=315;
2',4'-Difluoro-5-tetrazol-1-yl-biphenyl-3-carboxylic acid, MS (M+H)=303;
2'-Chloro-4'-fluoro-5-tetrazol-1-yl-biphenyl-3-carboxylic acid, MS (M+H)=319;
2',4'-Dichloro-5-tetrazol-1-yl-biphenyl-3-carboxylic acid, MS (M+H)=335; and
4'-Chloro-2'-fluoro-5-tetrazol-1-yl-biphenyl-3-carboxylic acid, MS (M+H)=319.

Preparation 2

3-(5-Methyl-pyridin-2-yl)-5-tetrazol-1-yl-benzoic acid

The synthetic procedure used in this preparation is outlined below in Scheme D.

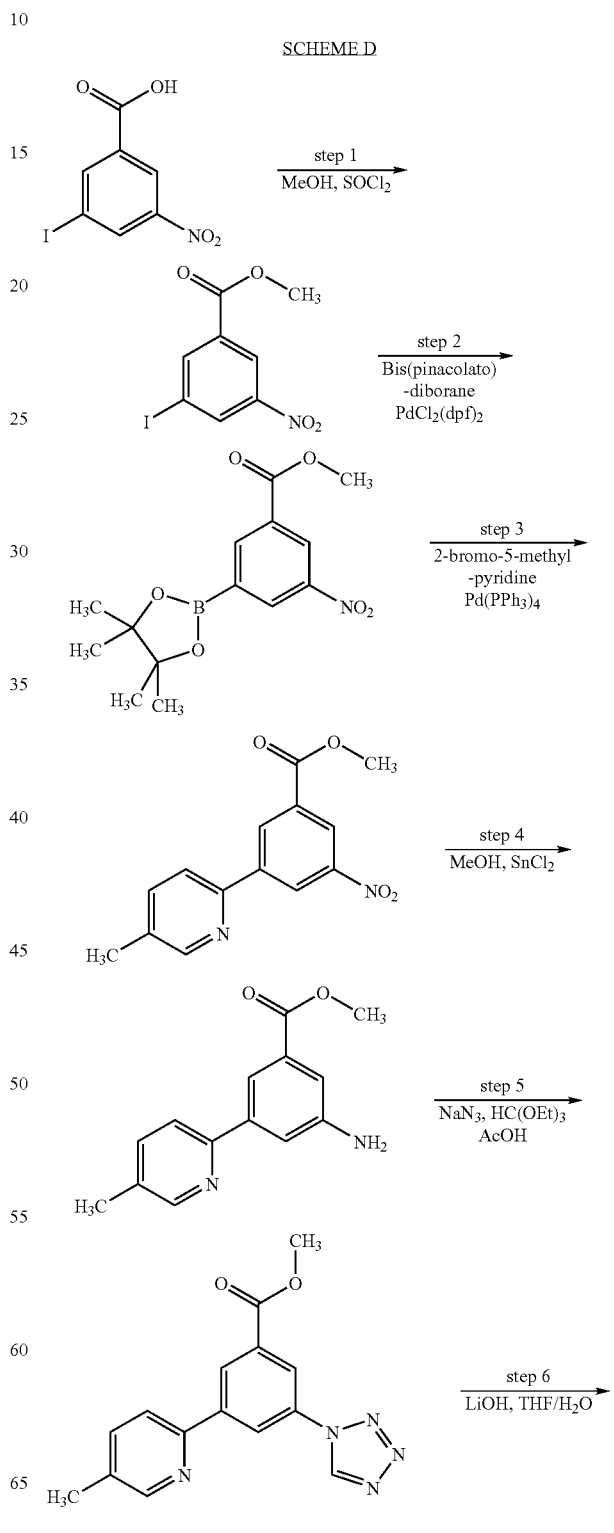

-continued

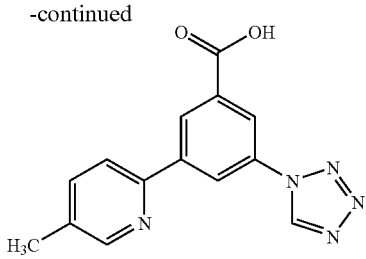

Step 1 3-Iodo-5-nitro-benzoic acid methyl ester

To a solution of 3-iodo-5-nitrobenzoic acid (20.00 g, 0.068 mol) in methanol (50 mL) was added $SOCl_2$ (5.45 mL, 0.075 mol) at 0° C. The reaction mixture was allowed to warm to room temperature and was then heated to reflux for 2 hours. The reaction was cooled and solvent was removed in vacuo to afford 3-Iodo-5-nitro-benzoic acid methyl ester as light yellow solid (20.67 g, 99%). MS (M+H)=309.

Step 2 3-Nitro-5-(4,4,5,5-tetramethyl-[1,3,2]dioxaborolan-2-yl)-benzoic acid methyl ester To a stirred solution of 3-Iodo-5-nitro-benzoic acid methyl ester (5.0 g, 0.016 mol), bis(pinacolato)diborane (4.55 g, 0.018 mol) and KOAc (4.80 g, 0.049 mol) in DMSO (50 mL) was added $PdCl_2(dpf)_2$ (0.40 g, 0.50 mmol). The mixture was flushed with $N_2$ and heated to 80 C. for 2 h. After the reaction mixture was cooled down to room temperature, $H_2O$ (20 mL) was added and the mixture was extracted with $Et_2O$ (3×30 mL). The organic layer was separated and washed with $H_2O$, brine and dried over $Na_2SO_4$. Solvent was removed and the residue was purified by column chromatography (EtOAc/hexane=1:3) to afford 3-Nitro-5-(4,4,5,5-tetramethyl-[1,3,2]dioxaborolan-2-yl)-benzoic acid methyl ester as a white solid (3.30 g, 67%) MS (M+H)=308.

Step 3 3-(5-Methyl-pyridin-2-yl)-5-nitro-benzoic acid methyl ester

To a solution of 3-Nitro-5-(4,4,5,5-tetramethyl-[1,3,2]dioxaborolan-2-yl)-benzoic acid methyl ester (100 mg, 0.326 mmol), 2-bromo-5 methyl-pyridine (56 mg, 0.326 mmol), $K_3PO_4$ (138 mg, 0.652 mmol) in dimethoxy ethylene (3 mL) and water (1 mL) was added $Pd(Pph_3)_4$ (11.3 mg, 0.001 mmol). The mixture was flushed with $N_2$ and heated under microwave at 130° C. for 30 minutes. The reaction mixture was cooled, solvent was removed under reduced pressure, and the residue was purified by column chromatography (EtOAc/hexane=1:3) to afford 3-(5-Methyl-pyridin-2-yl)-5-nitro-benzoic acid methyl ester as a white solid (50 mg, 56%). MS (M+H)=273.

Step 4 3-Amino-5-(5-methyl-pyridin-2-yl)-benzoic acid methyl ester

To a solution of 3-(5-Methyl-pyridin-2-yl)-5-nitro-benzoic acid methyl ester (410 mg, 36.9 mmol) in methanol was added $SnCl_2$ (1.36 g, 6.03 mmol) at room temperature. The reaction mixture was refluxed for 3 hours and then cooled. Solvent was removed in vacuo and the residue was dissolved in $H_2O$ and basified by $Na_2CO_3$ to pH=9. The mixture was extracted with $CH_2Cl_2$, and the organic phase was washed with water, brine, and dried over $Na_2SO_4$. The solvent was removed under vacuum to give 3-amino-5-(5-methyl-pyridin-2-yl)-benzoic acid methyl ester (362 m g, 100%) as yellow oil. MS (M+H)=244.

Step 5 3-(5-Methyl-pyridin-2-yl)-5-tetrazol-1-yl-benzoic acid methyl ester

To a solution of 3-amino-5-(5-methyl-pyridin-2-yl)-benzoic acid methyl ester (362 mg, 1.51 mmol) and $NaN_3$ (182 g, 2.8 mmol) in AcOH was added $HC(OEt)_3$ (1074 mg, 7.25 mmol) at room temperature. The reaction mixture was heated to reflux for 4 hours and then cooled to room temperature. The solvent was removed in vacuo and the residue was purified by silica-gel chromatography to give 3-(5-methyl-pyridin-2-yl)-5-tetrazol-1-yl-benzoic acid methyl ester as a light yellow solid (440 mg, 100%). MS (M+H)=296.

Step 6 3-(5-Methyl-pyridin-2-yl)-5-tetrazol-1-yl-benzoic acid

A solution of LiOH hydrate (82 mg, 1.94 mmol) in $H_2O$ (7 mL) was added dropwise to a suspension of 3-(5-methyl-pyridin-2-yl)-5-tetrazol-1-yl-benzoic acid methyl ester (440 mg, 1.49 mmol) in THF (4 mL) at 0° C. The reaction mixture was allowed to warm to room temperature and was stirred until the reaction solution turned into clear. Solvent was removed under vacuum and the resulting aqueous solution was acidified by 10% HCl to pH=6~7. The resulting precipitate was collected and dried to afford 3-(5-Methyl-pyridin-2-yl)-5-tetrazol-1-yl-benzoic acid as a yellow solid (390 mg, 93%). MS (M+H)=282.

Similarly prepared was 3-(5-Fluoro-pyridin-2-yl)-N-(1-methyl-2-morpholin-4-yl-ethyl)-5-tetrazol-1-yl-benzamide, MS (M+H)=412.

Similarly prepared, but omitting step 6, was 3-amino-5-(5-methyl-pyridin-2-yl)-benzoic acid, MS (M+H)=229.

Similarly prepared, but replacing 2-bromo-5-methyl-pyridine with 2,5-dichloro-pyridine in step 3 and omitting step 6, was 3-amino-5-(chloro-pyridin-2-yl)-benzoic acid, MS (M+H)=249.

Preparation 3

3-(4-Methyl-2-oxo-2H-pyridin-1-yl)-5-tetrazol-1-yl-benzoic acid

The synthetic procedure used in this preparation is outlined below in Scheme E.

SCHEME E

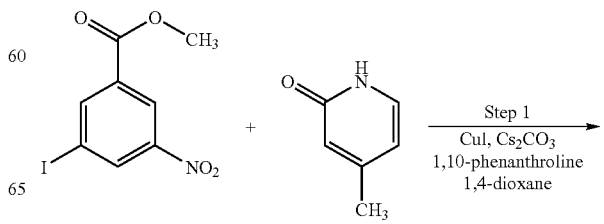

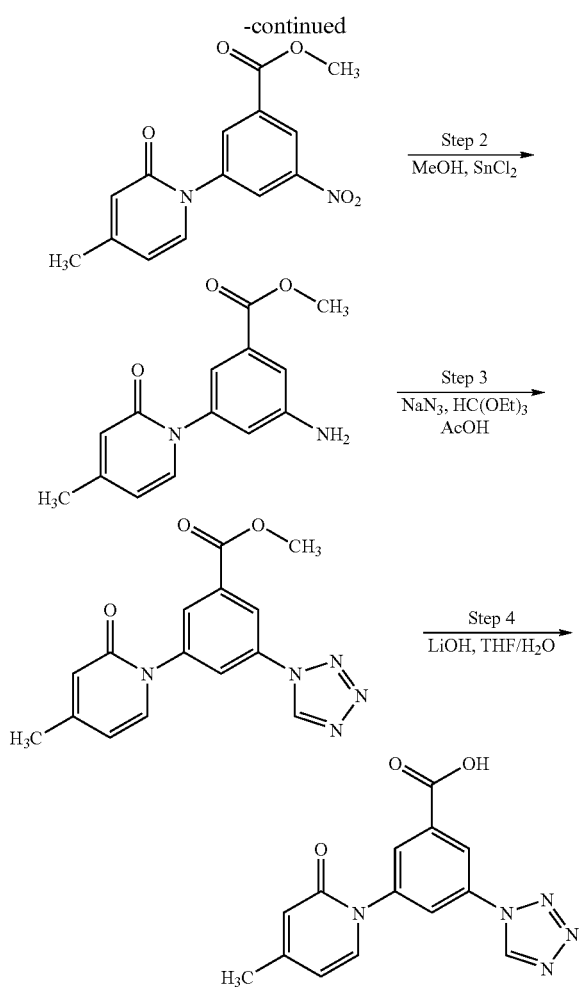

Step 1 3-(4-Methyl-2-oxo-2H-pyridin-1-yl)-5-nitro-benzoic acid methyl ester

To a 25 ml round-bottomed flask was added 2-Hydroxy-4-methylpyridine (17.9 mg, 0.164 mmol), 3-Iodo-5-nitro-benzoic acid methyl ester (40 mg, 0.137 mmol), CuI (5.2 mg, 0.027 mmol) and 1,4-dioxane (10 ml). The reaction mixture was stirred for 5 minutes to the dissolve 2-Hydroxy-4-methylpyridine and 3-iodo-5-nitro-benzoic acid methyl ester, after which 1,10-phenanthroline (9.84 mg, 0.055 mmol) was added, followed by $K_3PO_4$ (174 mg, 0.082 mmol). The reaction mixture was flushed with $N_2$, and heated to 110° C. for 24 hours. After cooling to room temperature, the mixture was diluted with $H_2O$, and extracted with ethyl acetate. The combined organic layer was washed with brine, dried over $Na_2SO_4$ and concentrated under reduced pressure. The residue was purified by flash chromatography to give 3-(4-Methyl-2-oxo-2H-pyridin-1-yl)-5-nitro-benzoic acid methyl ester (39.45 mg, 61%) as light yellow solid. MS (M+H)=289.

Step 2 3-Amino-5-(4-Methyl-2-oxo-2H-pyridin-1-yl) benzoic acid methyl ester

To a solution of 3-(4-Methyl-2-oxo-2H-pyridin-1-yl)-5-nitro-benzoic acid methyl ester (1000 mg, 3.47 mmol) in methanol was added $SnCl_2$ (2.63 g, 13.9 mmol) at room temperature. The reaction mixture was refluxed for 3 hours, then cooled to room temperature. Solvent was removed in vacuo, and the residue was dissolved in $H_2O$ and basified by addition of $Na_2CO_3$ to pH=9. The mixture was extracted with $CH_2Cl_2$, and the combined organic phase was washed with water, brine, and dried over $Na_2SO_4$. Solvent was removed under vacuum to give 3-Amino-5-(4-Methyl-2-oxo-2H-pyridin-1-yl)benzoic acid methyl ester (895 mg, 100%) as yellow solid. MS (M+H)=260.

Step 3 3-(4-Methyl-2-oxo-2H-pyridin-1-yl)5-tetrazol-1-yl-benzoic acid methyl ester To a solution of 3-Amino-5-(4-Methyl-2-oxo-2H-pyridin-1-yl)benzoic acid methyl ester (500 mg, 1.93 mmol) and $NaN_3$ (233 g, 3.58 mmol) in AcOH was added $HC(OEt)_3$ (1378.6 mg, 9.3 mmol) at room temperature. The reaction mixture was heated to reflux for 4 hours and then cooled to room temperature. The solvent was removed in vacuo and the residue was purified by silica-gel chromatography to give 3-(4-Methyl-2-oxo-2H-pyridin-1-yl)5-tetrazol-1-yl-benzoic acid methyl ester as a light yellow solid (602 mg, 100%). MS (M+H)=312.

Step 4 3-(4-methyl-2-oxo-2H-pyridin-1-yl)-5-tetrazol-1-yl-benzoic acid

A solution of LiOH $H_2O$ (95 mg, 2.25 mmol) in $H_2O$ (7 mL) was added dropwise to a suspension of 3-(4-methyl-2-oxo-2H-pyridin-1-yl)5-tetrazol-1-yl-benzoic acid methyl ester (500 mg, 1.61 mmol) in THF (4 mL) at 0° C. The reaction mixture was allowed to warm to room temperature and was stirred until the reaction solution turned into clear. Solvent was removed under vacuum and the aqueous solution was acidified by addition of 10% HCl to pH=2. The resulting precipitate was collected and dried to afford 3-(4-methyl-2-oxo-2H-pyridin-1-yl)-5-tetrazol-1-yl-benzoic acid as yellow solid (453 mg, 95%). MS (M+H)=298.

Preparation 4

3-Iodo-N-(2-methoxy-1-methyl-ethyl)-5-tetrazol-1-yl-benzamide

The synthetic procedure used in this preparation is outlined below in Scheme F.

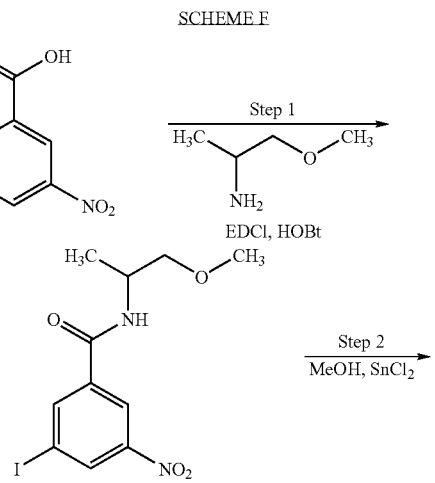

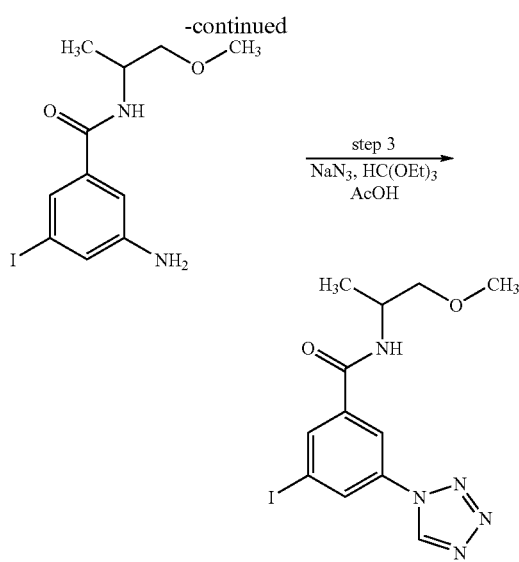

Step 1 3-Iodo-N-(2-methoxy-1-methyl-ethyl)-5-nitro-benzamide

EDCI (7.07 g, 36.9 mmol) was added in one portion to a stirred solution of 3-Iodo-5-nitro-benzoic acid (2.31 g, 24.6 mmol), HOBt (4.985 g, 36.9 mmol), 2-Amino-1-methoxypropane (2.73 ml, 24.6 mmol) and NMP (4.06 ml 36.9 mmol) in $CH_2Cl_2$ (120 ml) and DMF (10 ml) at 0° C. The reaction was allowed to warm to room temperature and was stirred over night. The reaction mixture was then washed with 2N NaOH, water, brine, and dried over $Na_2SO_4$. Solvent was removed in vacuo to give 2.50 g of 3-Iodo-N-(2-methoxy-1-methyl-ethyl)-5-nitro-benzamide as a yellow solid, MS (M+H)=365. This material was used without further purification.

Step 2 3-Iodo-5-(2-methoxy-1-methyl-ethylcarbamoyl)-phenyl-ammonium

To a solution of 3-Iodo-N-(2-methoxy-1-methyl-ethyl)-5-nitro-benzamide (8.05 g, 20.5 mmol) in methanol was added $SnCl_2$ (17.34 g, 76.87 mmol) at room temperature. The reaction mixture was refluxed for 3 hours. Solvent was removed in vacuo and the residue was dissolved in $H_2O$, then basified by addition of $Na_2CO_3$ to pH=9. The mixture was extracted with $CH_2Cl_2$, and the organic phase was washed with water, brine, and dried over $Na_2SO_4$. The solvent was removed under vacuum to give 3-Iodo-5-(2-methoxy-1-methyl-ethylcarbamoyl)-phenyl-ammonium (7.40 g, 92.5%) as yellow oil. MS (M+H)=336.

Step 3 3-Iodo-N-(2-methoxy-1-methyl-ethyl)-5-tetrazol-1-yl-benzamide

To a solution of 3-Iodo-5-(2-methoxy-1-methyl-ethylcarbamoyl)-phenyl-ammonium (7.47 g, 22.4 mmol) and $NaN_3$ (2.68 g, 41.2 mmol) in AcOH (100 mL) was added $HC(OEt)_3$ (18.3 mL, 110 mmol) at room temperature. The reaction mixture was brought to reflux for 4 hours, then cooled to room temperature. The solvent was removed in vacuo and the residue was purified by silica-gel chromatography to give 3-Iodo-N-(2-methoxy-1-methyl-ethyl)-5-tetrazol-1-yl-benzamide as a white solid (6.30 g, 72%). MS (M+H)=388.

Similarly prepared using the appropriate amines in step 1 were:

N-(1-Furan-2-yl-ethyl)-3-iodo-5-tetrazol-1-yl-benzamide, MS (M+H)=410; and

3-Iodo-N-(1-methyl-2-morpholin-4-yl-ethyl)-5-tetrazol-1-yl-benzamide, MS (M+H)=443.

Preparation 5

(S)-2-Methoxy-1-methyl-ethylamine

The synthetic procedure used in this preparation is outlined below in Scheme G.

CHEME G

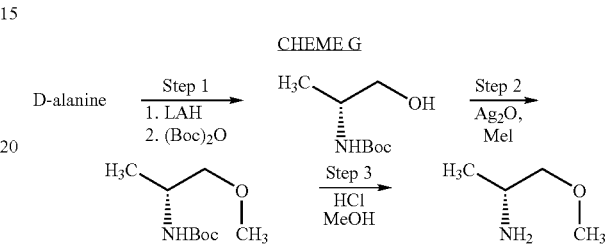

Step 1 (S)-Boc-2-amino-propanol

D-Alanine (3.5 g, 39.3 mmol) was added in small portions to a suspension of $LiAlH_4$ (2.89 g, 76.26 mmol) in refluxing THF. Refluxing continued for 12 hours, then the reaction mixture was cooled to 0° C., and excess reagent was quenched by careful addition of an aqueous 15% NaOH solution (3 ml) and water (9 ml). After stirring at room temperature for 10 minutes, a solution of $(Boc)_2O$ (8.31 g, 38.13 mmol) in $CH_2Cl_2$ (40 ml) was added. The reaction mixture was stirred at 60° C. for 6 hours, cooled to room temperature, filtered through a pad of anhydrous $Na_2SO_4$, and the filtrate concentrated under vacuum. Purification of the residue by silica-gel column chromatography afforded (S)-Boc-2-amino-propanol as a white solid, yield: 63%. MS (M+H)=176.

Step 2 (S)-Boc-2-methoxy-1-methyl-ethylamine

To a solution of (S)-Boc-2-amino-propanol (2.00 g, 11.4 mmol) was successively added $Ag_2O$ (5.89 g, 25.4 mmol) and Methyl iodide (16.00 g, 112.7 mmol) at room temperature. The reaction mixture was stirred at room temperature for 2 days. Solid was filtered off and the filtrate was concentrated under vacuum to afford (S)-Boc-2-methoxy-1-methyl-ethylamine as a colorless oil that was used without further purification.

Step 3 (S)-2-methoxy-1-methyl-ethylamine (S)-Boc-2-methoxy-1-methyl-ethylamine was dissolved in MeOH (40 mL) and 3 M HCl (10 mL) was added. The reaction mixture was stirred overnight at room temperature, then solvent was removed under reduced pressure and the residue was co-evaporated with additional EtOH (20 mL) to afford (S)-2-methoxy-1-methyl-ethylamine as light-brown oil in hydrochloride form (1.42 g, 100%). MS (M+H)=90.

Similarly prepared was (S)-2-ethoxy-1-methyl-ethylamine.

Similarly prepared from L-alanine were (R)-2-methoxy-1-methyl-ethylamine and (R)-2-ethoxy-1-methyl-ethylamine.

Preparation 6

(S)-1-Methyl-2-morpholin-4-yl-ethylamine

The synthetic procedure used in this preparation is outlined below in Scheme H.

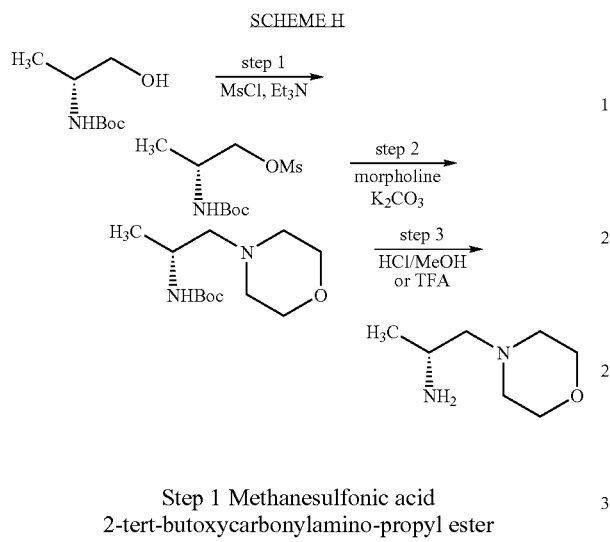

Step 1 Methanesulfonic acid 2-tert-butoxycarbonylamino-propyl ester

To a solution of (S)-Boc-2-amino-propanol (4.91 g, 0.028 mol), Et$_3$N (1.5 equiv.) in CH$_2$Cl$_2$ at 0° C. was added methanesulfonyl chloride (1.1-1.2 equiv). The reaction was stirred at 0° C. for 30 minutes. Water (5 ml) was added and the organic layer was separated, washed with saturated aqueous NaHCO$_3$, brine, and dried with MgSO$_4$. Solvent was removed under vacuum to afford methanesulfonic acid 2-tert-butoxycarbonylamino-propyl ester as a white solid, yield: 98%. MS (M+H)=254.

Step 2 (1-Methyl-2-morpholin-4-yl-ethyl)-carbamic acid tert-butyl ester

To a solution of methanesulfonic acid 2-tert-butoxycarbonylamino-propyl ester (23 mmol) in CH$_3$CN (20 mL) was added morpholine (28 mmol) and K$_2$CO$_3$ (23 mmol) at room temperature. The reaction mixture was brought to 50° C. and kept at the same temperature overnight. The reaction mixture was cooled and solvent was removed under reduced pressure, and the residue was treated with CH$_2$Cl$_2$ (50 mL) and H$_2$O (50 mL). The organic layer was separated and the aqueous layer was extracted with CH$_2$Cl$_2$. The combined organic layer was dried over Na$_2$SO$_4$. Solvent was removed under reduced pressure and the residue was purified by column chromatography (ethyl acetate) to afford (1-methyl-2-morpholin-4-yl-ethyl)-carbamic acid tert-butyl ester as viscous liquid, yield: 62%. MS (M+H)=245.

Step 3 (S)-1-Methyl-2-morpholin-4-yl-ethylamine

To a solution of (1-methyl-2-morpholin-4-yl-ethyl)-carbamic acid tert-butyl ester (0.30 g, 1.22 mmol) in methanol (10 mL) was added 2N HCl (5 mL) at 0° C. The reaction mixture was allowed to warm to room temperature and was stirred overnight. The solvent was removed under vacuum to give (S)-1-Methyl-2-morpholin-4-yl-ethylamine as a light yellow solid (250 mg, 96%). MS (M+H)=145.

Similarly prepared were (S)-1-Methyl-2-thiomorpholin-4-yl-ethylamine, (S)-1-[4-(2-Amino-propyl)-piperazin-1-yl]-ethanone, (S)-1-(2-Amino-propyl)-piperidin-4-ol, (S)-1-(2-Amino-propyl)-piperidin-3-ol, (S)-1-Methyl-2-(4-methyl-piperazin-1-yl)-ethylamine, (S)-1-Methyl-2-(4-methanesulfonyl-piperazin-1-yl)-ethylamine, (S)-4-(2-Amino-propyl)-piperazin-2-one, 1-Methyl-2-piperidin-1-yl-ethylamine, 1-(2-Amino-propyl)-pyrrolidin-3-ol, (S)-2-(4-Methoxy-piperidin-1-yl)-1-methyl-ethylamine, (S)-2-(3-Methoxy-piperidin-1-yl)-1-methyl-ethylamine, (S)-2-(4-Methanesulfonyl-piperidin-1-yl)-1-methyl-ethylamine, and other 2-amino-1-heterocyclyl propanes.

Preparation 7

(S)-2-(1,1-Dioxo-1lambda*6*-thiomorpholin-4-yl)-1-methyl-ethylamine

The synthetic procedure used in this preparation is outlined below in Scheme I.

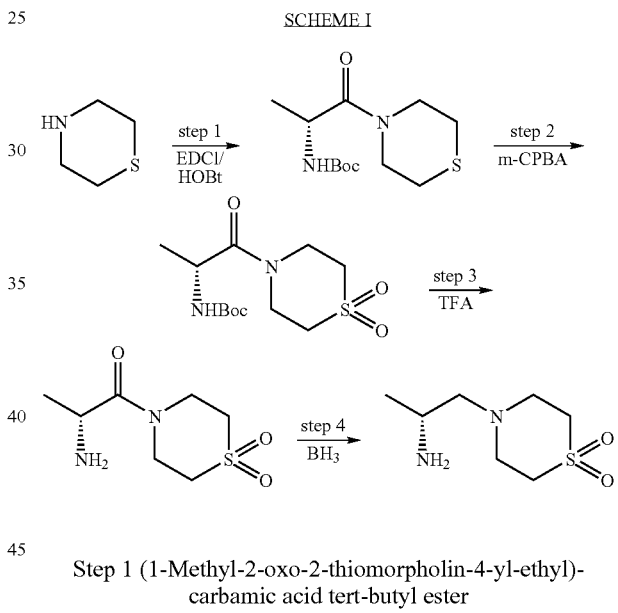

Step 1 (1-Methyl-2-oxo-2-thiomorpholin-4-yl-ethyl)-carbamic acid tert-butyl ester To a solution of 2-tert-Butoxycarbonylamino-propionic acid (3.5 g, 18.5 mmol), HOBt (22.2 mmol), NMP (22.2 mmol) and EDCI (22.2 mmol) in CH$_2$Cl$_2$ was added thiomorpholine (2.29 g, 22.2 mmol) at 0° C. The reaction mixture was stirred at 0° C. overnight, then washed with 2% aqueous NaOH, water, brine, and dried over Na$_2$SO$_4$. The solvent was removed under vacuum to give (1-Methyl-2-oxo-2-thiomorpholin-4-yl-ethyl)-carbamic acid tert-butyl ester (5.0 g) yield 98%. MS (M+H)=275.

Step 2 [2-(1,1-Dioxo-1lambda*6*-thiomorpholin-4-yl)-1-methyl-2-oxo-ethyl]-carbamic acid tert-butyl ester To a solution of (1-methyl-2-oxo-2-thiomorphin-4-yl-ethyl)-carbamic acid ter-butyl ester (5.0 g, 18.2 mmol) in CH$_2$Cl$_2$ was added m-CPBA (11.4 g, 46.25 mmol) at 0° C. The reaction mixture was stirred at room temperature overnight. Solids were removed by filtration and the filtrate was washed by Na$_2$S$_2$O$_3$ and dried over Na$_2$SO$_4$. Solvent was removed under vacuum to give [2-(1,1-Dioxo-1lambda*6*-thiomorpholin-4-yl)-1-methyl-2-oxo-ethyl]-carbamic acid tert-butyl ester (5.6 g), yield 100%. MS (M+H)=307.

Step 3 2-Amino-1-(1,1-dioxo-1 lambda*6*-thiomorpholin-4-yl)-propan-1-one

To a solution of [2-(1,1-Dioxo-1lambda*6*-thiomorpholin-4-yl)-1-methyl-2-oxo-ethyl]-carbamic acid tert-butyl ester (5.6 g, 18.2 mmol) in CH$_2$Cl$_2$ (70 mL) was added trifluoroacetic acid (5 mL) at 0° C. The reaction mixture was allowed to warm to room temperature and was stirred for 3 hours. After removal of CH$_2$Cl$_2$ and excess trifluoroacetic acid under reduced pressure, 2-Amino-1-(1,1-dioxo-1lambda*6*-thiomorpholin-4-yl)-propan-1-one (6.0 g, yield 100%) was obtained as a white solid. MS (M+H)=207.

Step 4 (S)-2-(1,1-Dioxo-1lambda*6*-thiomorpholin-4-yl)-1-methyl-ethylamine

A mixture of 2-Amino-1-(1,1-dioxo-1lambda*6*-thiomorpholin-4-yl)-propan-1-one (6.0 g, 18.2 mmol) and BH$_3$ (1 M in THF, 110 mL) was heated to reflux for 48 h, then cooled to room temperature and quenched by MeOH. The volatile was removed under vacuum. 2 N HCl (100 mL) was added to the residue and heated to reflux for 18 h. Solvent was removed under vacuum to give (S)-2-(1,1-Dioxo-1lambda*6*-thiomorpholin-4-yl)-1-methyl-ethylamine (4.5 g) as white solid, yield 90%. MS (M+H)=193.

Preparation 8

1-Thiophen-3-yl-ethylamine

The synthetic procedure used in this preparation is outlined below in Scheme J.

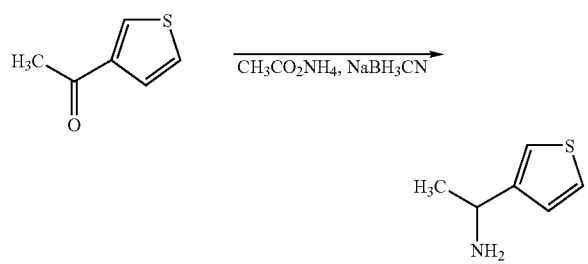

SCHEME J

To a solution of 3-Acetylthiophene (2.0 g, 15.85 mmol) and ammonium acetate (12.2 g, 158.5 mmol) in methanol (50 mL) was added sodium cyanoborohydride (0.7 g, 11.1 mmol) in one portion. The reaction mixture was stirred overnight at room temperature. After removal of methanol, water (20 mL) was added to the residue and the resulting solution was basified by addition of sodium hydroxide to pH=13. The aqueous solution was extracted with dicholromethane and the combined organic phase was dried over sodium sulfate. Removal of the solvent under reduced pressure afforded 1.5 g 1-thiophen-3-yl-ethylamine, yield: 75%. MS (M+H)=128.

Similarly prepared from the appropriate heteroaryl methyl ketones or phenyl methyl ketones were: 1-Pyridin-2-yl-ethylamine, 1-Pyridin-3-yl-ethylamine, 1-Pyridin-4-yl-ethylamine, 1-(2-Fluoro-phenyl)-ethylamine, 1-(3-Fluoro-phenyl)-ethylamine, 1-(4-methanesulfonyl-phenyl)-ethylamine, 1-furan-2-yl-ethylamine, 1-(5-methyl-furan)-2-yl-ethylamine, 1-thiazol-2-yl-ethylamine, 1-thien-2-yl-ethylamine, 1-Pyrazin-2-yl-ethylamine, 1-Pyrimidin-2-yl-ethylamine, 1-Pyridazin-4-yl-ethylamine, and other 1-heteoraryl ethylamines and 1-aryl ethylamines.

Example 1

4'-Methyl-5-tetrazol-1-yl-biphenyl-3-carboxylic acid (1-methyl-2-morpholin-4-yl-ethyl)-amide The synthetic procedure used in this example is outlined below in Scheme K.

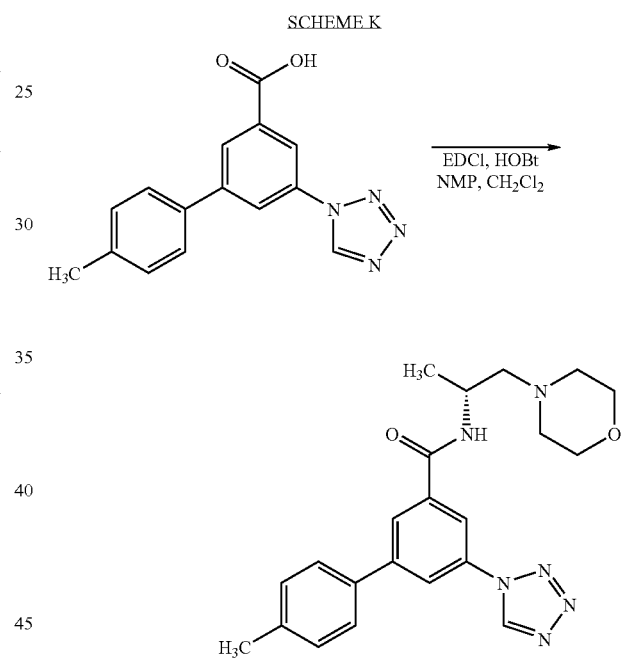

SCHEME K

EDCI (54.0 mg, 0.282 mmol) was added in one portion at 0° C. to a solution of 4'-Methyl-5-tetrazol-1-yl-biphenyl-3-carboxylic acid (60.0 mg, 0.214 mmol), HOBt (40.0 mg, 0.296 mmol) and NMP (101.5 mg, 1.000 mmol) in CH$_2$Cl$_2$ (3 mL). After the reaction stirred at 0° C. for 1 hour, (S)-1-Methyl-2-morpholin-4-yl-ethylamine (50.0 mg, 0.230 mmol) was added. The reaction mixture was allowed to warm to room temperature and was stirred overnight. Solvent was removed under reduced pressure and the residue was purified by column chromatography (EtOAc) to afford 4'-Methyl-5-tetrazol-1-yl-biphenyl-3-carboxylic acid (1-methyl-2-morpholin-4-yl-ethyl)-amide as a white solid (70 mg, 81%). MS (M+H)=407.

Additional compounds prepared by the procedure of Example 1, using the appropriate amine and tetrazole-biphenyl carboxylic acids are shown in Table 1.

Example 2

2'-Fluoro-4'-methyl-5-tetrazol-1-yl-biphenyl-3-carboxylic acid (1-furan-2-yl-ethyl)-amide

The synthetic procedure used in this example is outlined below in Scheme L.

SCHEME L

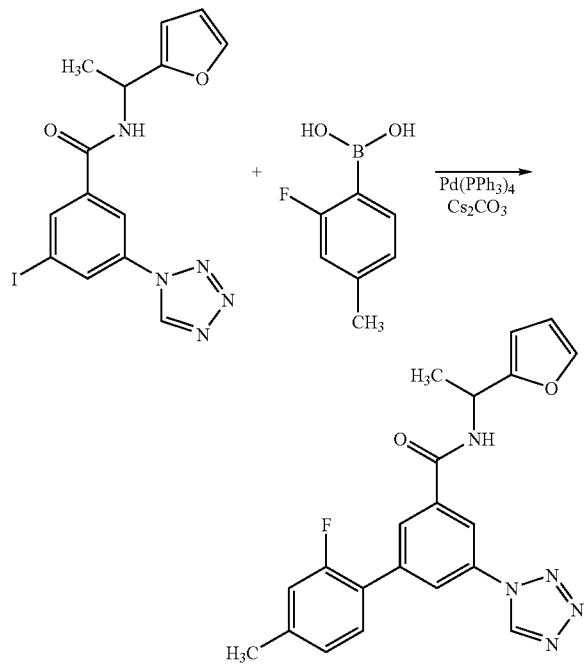

A mixture of N-(1-Furan-2-yl-ethyl)-3-iodo-5-tetrazol-1-yl-benzamide (60 mg, 0.146 mmol), 2-fluoro-4-methyl-phenylboronic acid (27.1 mg, 0.176 mmol), Cs$_2$CO$_3$ (0.35 mL, 0.5 N, 0.176 mmol) and Pd(Ph$_3$P)$_4$ (8.5 mg, 0.00735 mmol) in toluene (1.5 mL) and THF (1.5 mL) was stirred under microwave heating for 30 minutes at 130° C. After reaction mixture was cooled down, the solvent was removed under vacuum and the residue was purified by column chromatography (hexane/EtOAc=1:2) to afford 2'-Fluoro-4'-methyl-5-tetrazol-1-yl-biphenyl-3-carboxylic acid (1-furan-2-yl-ethyl)-amide as a white solid (57 mg, 98%). MS (M+H)=392.

Additional compounds prepared by the procedure of Example 2 are shown in Table 1.

Example 3

5-(1-Ethyl-1H-tetrazol-5-yl)-4'-methyl-biphenyl-3-carboxylic acid (2-methoxy-1-methyl-ethyl)-amide

The synthetic procedure used in this example is outlined below in Scheme M.

SCHEME M

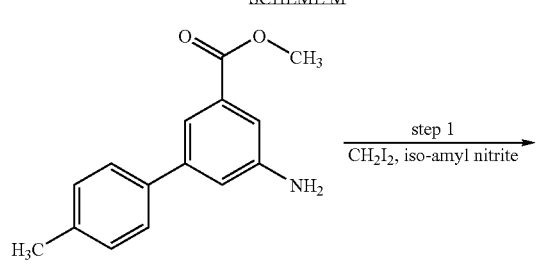

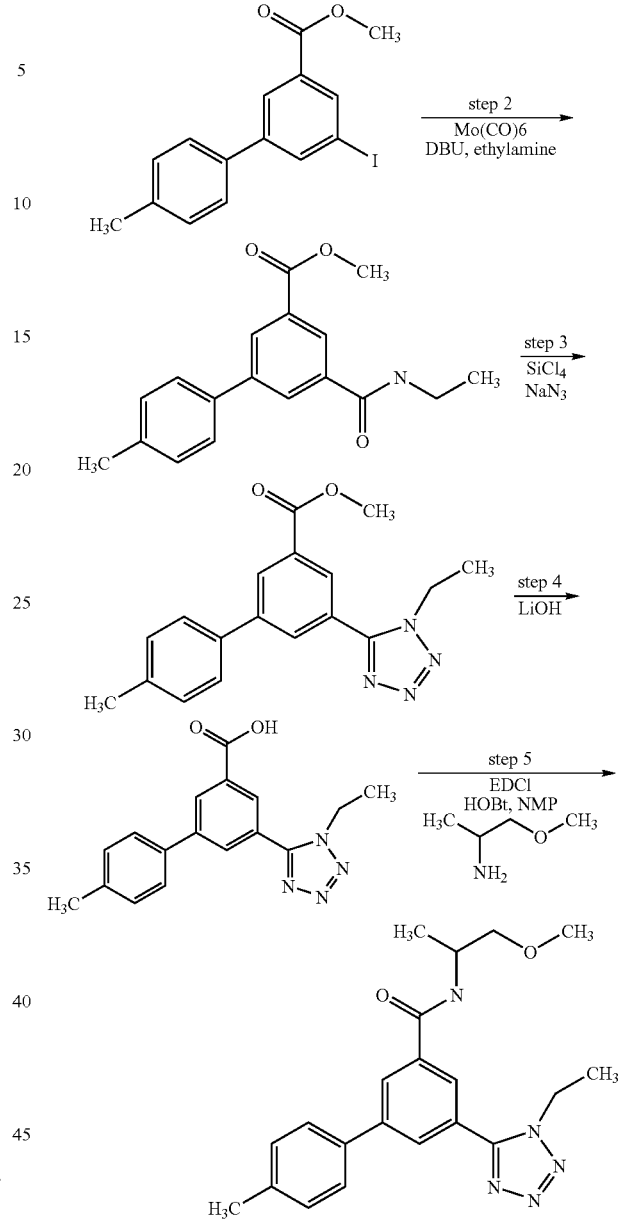

Step 1 5-Iodo-4'-methyl-biphenyl-3-carboxylic acid methyl ester

A mixture of 5-amino-4'-methyl-biphenyl-3-carboxylic acid methyl ester (10.9 g, 45.2 mmol), iso-amyl nitrite (36.5 ml, 271.4 mmol) and diiodomethane (23 ml, 271.4 mmol) was stirred at room temperature for 1 hour. The mixture was then heated to 65° C. and kept at this temperature for 8 hours. The reaction mixture to room temperature and then added to a stirred solution of piperidine/CH$_3$CN (V:V=90 ml:90 ml). A vigorous exothermic reaction ensued. The excess volatile reagents were removed by rotary evaporation. The residue was diluted with ethyl acetate, washed with 10% hydrochloric acid, water, brine, dried over anhydrous Na$_2$SO$_4$, filtered and concentrated in vacuo. The residue was purified by flash column chromatography, eluting with n-hexane, followed by n-hexane/ethyl acetate (20:1), giving 5-Iodo-4'-methyl-biphenyl-3-carboxylic acid methyl ester as white yellow solid (10.5 g, 66%).

Step 2 5-Ethylcarbamoyl-4'-methyl-biphenyl-3-carboxylic acid methyl ester

A 20 mL of vial was charged with 5-iodo-4'-methyl-biphenyl-3-carboxylic acid methyl ester (500 mg, 1.42 mmol), Pd(OAc)$_2$(9.6 mg, 0.043 mmol), Mo(CO)$_6$(413.5 mg, 1.566 mmol), ethylamine (2.0 M in MeOH, 1.068 mL, 2.136 mmol), DBU (426 uL, 2.848 mmol) and dry THF (10 mL). The vial was immediately capped with a Teflon septum under air and irradiated with microwaves to 100° C. for 15 minutes. After cooling, the reaction mixture was filtered through a short celite pad and the solvent, and excess DBU was removed under reduced pressure. The residue was purified by preparative HPLC to afford 210 mg of 5-ethylcarbamoyl-4'-methyl-biphenyl-3-carboxylic acid methyl ester (yield 50%). MS (M+H)=298.

Step 3 5-(1-Ethyl-1H-tetrazol-5-yl)-4'-methyl-biphenyl-3-carboxylic acid methyl ester Sodium azide (145.8 mg, 16.2 mmol) was added into a solution of 5-ethylcarbamoyl-4'-methyl-biphenyl-3-carboxylic acid methyl ester (210 mg, 0.7 mmol) and SiCl4 (0.62 mL, 5.4 mmol) in dry acetonitrile (14 mL). After the reaction was stirred at room temperature for 24 hours, the reaction mixture was poured into cold saturated aqueous Na$_2$CO$_3$ solution. This mixture was extracted with ethyl acetate and dried with anhydrous Na$_2$SO$_4$. Solvent was removed under reduced pressure to afford 200 mgs of 5-(1-ethyl-1H-tetrazol-5-yl)-4'-methyl-biphenyl-3-carboxylic acid methyl ester (yield 89%). MS (M+H)=323.

Step 4 5-(1-Ethyl-1H-tetrazol-5-yl)-4'-methyl-biphenyl-3-carboxylic acid

A solution of LiOH.H$_2$O (39.1 mg, 0.931 mmol) in H$_2$O (8 mL) was added dropwise to a suspension of 5-(1-ethyl-1H-tetrazol-5-yl)-4'-methyl-biphenyl-3-carboxylic acid methyl ester (200 mg, 0.621 mmol) in THF (5 mL) at 0° C. The reaction mixture was allowed to warm to room temperature and was stirred until the mixture turned clear. THF was removed under vacuum and the aqueous solution was acidified by 10% HCl to pH=3. The precipitate was collected and dried to afford 5-(1-ethyl-1H-tetrazol-5-yl)-4'-methyl-biphenyl-3-carboxylic acid as white solid (162 mg, 84%). MS (M+H)=309.

Step 5 5-(1-Ethyl-1H-tetrazol-5-yl)-4'-methyl-biphenyl-3-carboxylic acid (2-methoxy-1-methyl-ethyl)-amide EDCI (54.0 mg, 0.282 mmol) was added in one portion to a solution of 5-(1-ethyl-1H-tetrazol-5-yl)-4'-methyl-biphenyl-3-carboxylic acid (70.0 mg, 0.229 mmol), HOBt (40.0 mg, 0.296 mmol) and NMP (101.5 mg, 1.000 mmol) in CH$_2$Cl$_2$ (5 mL) at 0° C. After the reaction stirred at the same temperature for 1 hour, 2-methoxy-1-methyl-ethylamine (64.3 mg, 0.72 mmol) was added. The mixture was allowed to warm to room temperature and was stirred overnight. Solvent was removed under reduced pressure and the residue was purified by column chromatography to afford 5-(1-ethyl-1H-tetrazol-5-yl)-4'-methyl-biphenyl-3-carboxylic acid (2-methoxy-1-methyl-ethyl)-amide as white solid (40 mg, 46%). MS (M+H)=380.

Additional compounds made by the above procedure are shown in Table 1.

Example 4

4'-Methyl-5-(5-trifluoromethyl-tetrazol-1-yl)-biphenyl-3-carboxylic acid (2-methoxy-1-methyl-ethyl)-amide The synthetic procedure used in this example is outlined below in Scheme N.

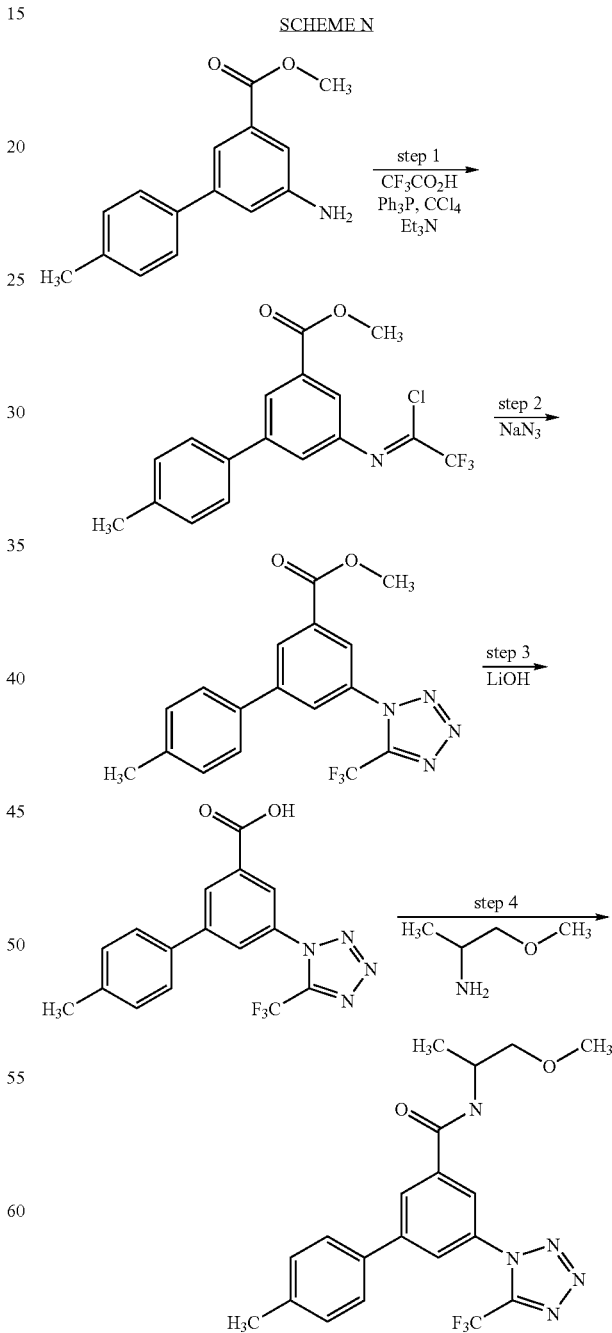

Step 1 5-[1-Chloro-2,2,2-trifluoro-eth-(Z)-ylidene-amino]-4'-methyl-biphenyl-3-carboxylic acid methyl ester A mixture of CF₃COOH (5.19 mmol, 398 mL), PPh₃ (15.56 mmol, 4.08 g) and NEt₃ (6.22 mmol, 868 μL) in 10 mL of CCl₄ was stirred at 0° C. for 10 minutes. 5-Amino-4'-methyl-biphenyl-3-carboxylic acid methyl ester (1.5 g, 6.22 mmol) was then added to the reaction mixture and the mixture was heated to reflux for 2 hours. Solvent was removed under reduced pressure and the residue was purified by flash column chromatography, eluting with n-hexane:ethyl acetate (10:1), giving the 5-[1-chloro-2,2,2-trifluoro-eth-(Z)-ylidene-amino]-4'-methyl-biphenyl-3-carboxylic acid methyl ester as light yellow oil (1.3 g, 60% yield).

Step 2 4'-Methyl-5-(5-trifluoromethyl-tetrazol-1-yl)-biphenyl-3-carboxylic acid methyl ester A mixture of NaN₃ (481 mg, 7.4 mmol) and 5-[1-chloro-2,2,2-trifluoro-eth-(Z)-ylideneamino]-4'-methyl-biphenyl-3-carboxylic acid methyl ester (1.3 g, 3.7 mmol) in 10 ml of dry ACN was stirred at room temperature for 16 hours. The reaction mixture were poured into ice-cold aqueous Na₂CO₃ solution, extracted with ethyl acetate. The organic layer washed with brine, dried over anhydrous Na₂SO₄, filtered, and concentrated in vacuo. The resulting crude 4'-methyl-5-(5-trifluoromethyl-tetrazol-1-yl)-biphenyl-3-carboxylic acid methyl ester (1.34 g, 99% yield) was used directly in the next step.

Step 3 4'-Methyl-5-(5-trifluoromethyl-tetrazol-1-yl)-biphenyl-3-carboxylic acid To a stirred solution of 4'-methyl-5-(5-trifluoromethyl-tetrazol-1-yl)-biphenyl-3-carboxylic acid methyl ester (3.7 mmol, 1.34 g) in 50 ml of THF was added a solution of LiOH.H₂O (18.5 mmol, 776.3 mg) in 12 mL of water. The reaction mixture was heated to reflux for 3.5 hours, then cooled to room temperature. Solvent was removed under reduced pressure, and the pH of the liquid residue was adjusted to 2.0 by addition of 2N aqueous HCl solution. The mixture was extracted with ethyl acetate and the combined ethyl acetate layers were dried over anhydrous Na₂SO₄ and concentrated in vacuo to give 4'-methyl-5-(5-trifluoromethyl-tetrazol-1-yl)-biphenyl-3-carboxylic acid as light yellow solid (1.25 g, 97% yield).

Step 4 4'-Methyl-5-(5-trifluoromethyl-tetrazol-1-yl)-biphenyl-3-carboxylic acid (2-methoxy-1-methyl-ethyl)-amide 4'-Methyl-5-(5-trifluoromethyl-tetrazol-1-yl)-biphenyl-3-carboxylic acid (2-methoxy-1-methyl-ethyl)-amide was reacted with 2-methoxy-1-methyl-ethylamine using the procedure of step 4 of Example 3 to give 4'-methyl-5-(5-trifluoromethyl-tetrazol-1-yl)-biphenyl-3-carboxylic acid. MS (M+H)=420.

Similarly prepared, but replacing 5-amino-4'-methyl-biphenyl-3-carboxylic acid methyl ester with 3-amino-5-(5-methyl-pyridin-2-yl)-benzoic acid methyl ester in step 1, and replacing 2-methoxy-1-methyl-ethylamine with C-(5-methyl-pyrazin-2-yl)-methylamine in step 4, N-(5-Methyl-pyrazin-2-ylmethyl)-3-(5-methyl-pyridin-2-yl)-5-(5-trifluoromethyl-tetrazol-1-yl)-benzamide was prepared, MS (M+H)=455.

Additional compounds prepared by the above procedure are shown in Table 1.

Example 5

4'-Methyl-5-(5-methyl-tetrazol-1-yl)-biphenyl-3-carboxylic acid (2-methoxy-1-methyl-ethyl)-amide The synthetic procedure used in this example is outlined below in Scheme O.

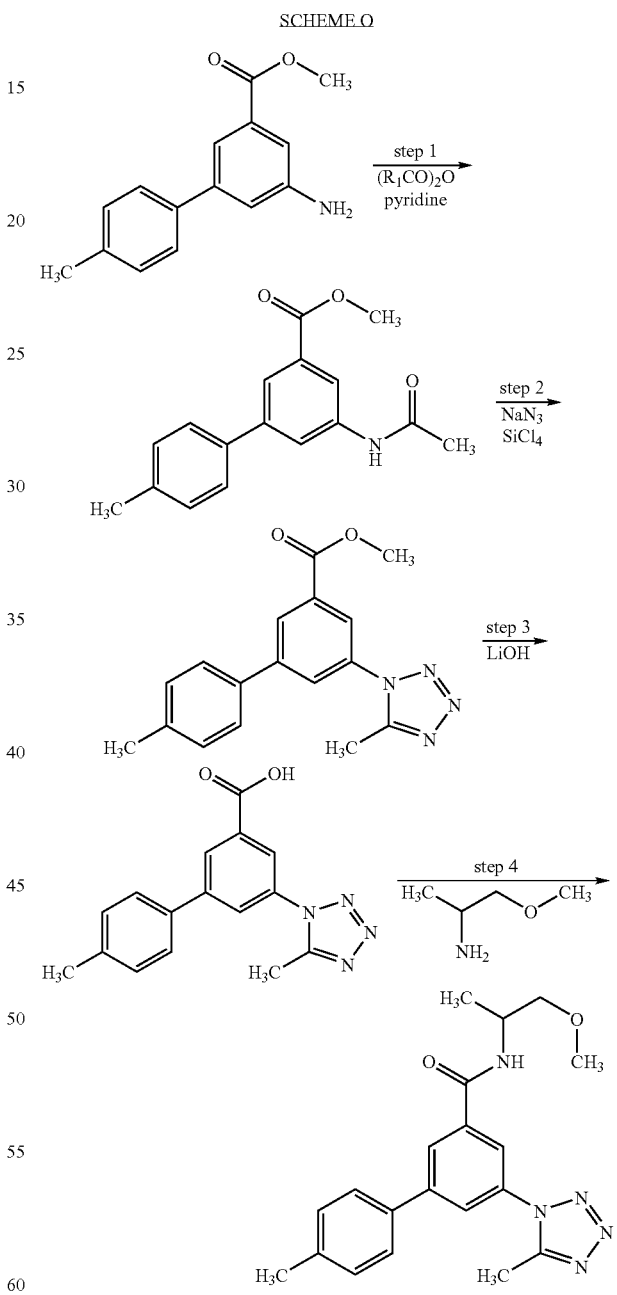

SCHEME O

Step 1 5-Acetylamino-4'-methyl-biphenyl-3-carboxylic acid methyl ester

To a stirred solution of 5-amino-4'-methyl-biphenyl-3-carboxylic acid methyl ester (3.672 mmol, 884.9 mg) and pyridine (36.7 mmol, 3 mL) in 8 mL of dry CH₂Cl₂ was added acetic anhydride (7.3 mmol) at room temperature. The mixture was stirred at room temperature for 1 hour, then diluted with ethyl acetate (150 mL). The organic layer was washed with saturated aqueous CuSO₄ solution, brine, dried over anhydrous Na₂SO₄, filtered, and concentrated in vacuo to give 5-acetylamino-4'-methyl-biphenyl-3-carboxylic acid methyl ester (quant. Yield), which was used directly in the next step.

Step 2 4'-Methyl-5-(5-methyl-tetrazol-1-yl)-biphenyl-3-carboxylic acid methyl ester A mixture of tetrachlorosilane (10.07 mmol, 2 mL), NaN₃ (30.21 mmol, 1.96 g) and 5-acetylamino-4'-methyl-biphenyl-3-carboxylic acid methyl ester (3.36 mmol, 950.9 mg) in 10 ml of dry acetonitrile was stirred at room temperature for 16 hours. The reaction mixture were poured into ice-cold aqueous Na₂CO₃ solution and extracted with ethyl acetate (100 mL). The organic layer was washed with brine, dried over anhydrous Na₂SO₄, filtered, and concentrated in vacuo. The resulting crude 4'-methyl-5-(5-methyl-tetrazol-1-yl)-biphenyl-3-carboxylic acid methyl ester was used for next step directly (880 mg, 85% yield).

Step 3 4'-Methyl-5-(5-methyl-tetrazol-1-yl)-biphenyl-3-carboxylic acid

To a stirred solution of 4'-methyl-5-(5-methyl-tetrazol-1-yl)-biphenyl-3-carboxylic acid methyl ester (1 mmol, 308 mg) in 10 ml of THF was added a solution of LiOH.H₂O (5 mmol, 210 mg) in 2 mL of water. The reaction mixture was heated to reflux for 3.5 hours and then cooled to room temperature. Solvent was removed under reduced pressure and the liquid residue was pH adjusted to 2.0 by addition of 2N aqueous HCl solution. The mixture was extracted with ethyl acetate and the combined ethyl acetate layers were dried over anhydrous Na₂SO₄ and concentrated in vacuo to give 4'-methyl-5-(5-methyl-tetrazol-1-yl)-biphenyl-3-carboxylic acid as white solid (279 mg, 95% yield).

Step 4 4'-Methyl-5-(5-methyl-tetrazol-1-yl)-biphenyl-3-carboxylic acid (2-methoxy-1-methyl-ethyl)-amide To a stirred solution of 4'-methyl-5-(5-methyl-tetrazol-1-yl)-biphenyl-3-carboxylic acid (0.3402 mmol, 100 mg), HOBt (0.6804 mmol, 91.9 mg), 2-methoxy-1-methyl-ethylamine (0.4083 mmol, 43 μL) and NMP (1.0206 mmol, 112 μL) in CH₂Cl₂(1 mL) and DMF (0.5 mL) was added EDCI (0.6804 mmol, 130.4 mg) at room temperature, and the mixture was stirred at room temperature for 18 hours. The mixture was extracted with ethyl acetate and the organic layer was washed with 2N aqueous NaOH, 1 N aqueous HCl, brine, dried over anhydrous Na₂SO₄, filtered, and concentrated in vacuo. The residue was purified by Flash column chromatography, eluting with n-hexane:ethyl acetate (4:1) to give 4'-methyl-5-(5-methyl-tetrazol-1-yl)-biphenyl-3-carboxylic acid (2-methoxy-1-methyl-ethyl)-amide (white powder, 90% yield). MS (M+H)=366.

Additional compounds prepared by the above procedure are shown in Table 1.

Example 6

3-[5-(1,1-Difluoro-ethyl)-tetrazol-1-yl]-N—((S)-2-hydroxy-1-methyl-ethyl)-5-(5-methyl-pyridin-2-yl)-benzamide The synthetic procedure used in this example is outlined below in Scheme P.

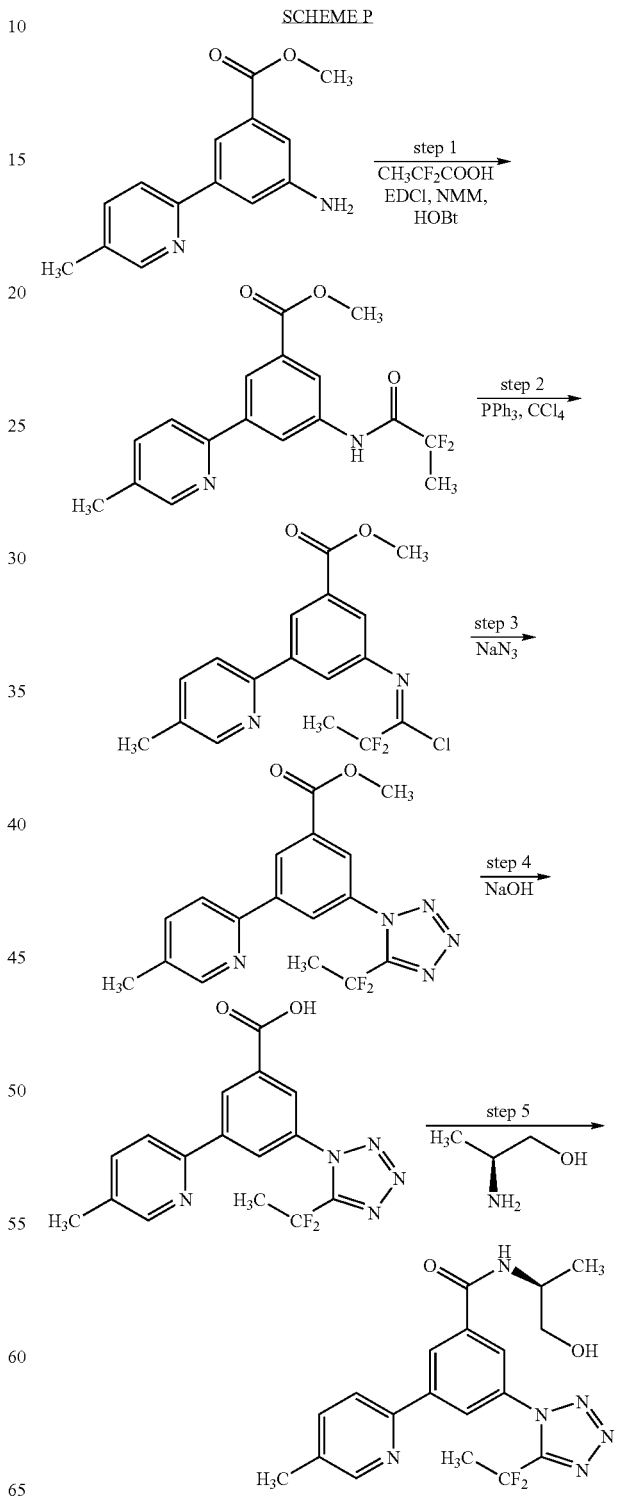

Step 1 3-(2,2-Difluoro-propionylamino)-5-(5-methyl-pyridin-2-yl)-benzoic acid methyl ester 3-Amino-5-(5-methyl-pyridin-2-yl)-benzoic acid methyl ester (0.7 g, 2.89 mmol, from Preparation 2), 2,2-difluoro-propionic acid (0.370 g, 2.89 mmol), EDCI (4.34 mmol), and HOBt (4.34 mmol) and NMM (14.45 mmol) were added to 25 mL of acetonitrile. The reaction mixture was stirred at room temperature for 21 hours, after which the acetonitrile was removed under reduced pressure. The residue was partitioned between water and EtOAc, and the combined organic layers were washed with water, dried (MgSO$_4$), filtered and concentrated under reduced pressure. The residue was purified by flash chromatography (EtOAc/hexanes 35:1) to give 0.630 g of 3-(2,2-difluoro-propionylamino)-5-(5-methyl-pyridin-2-yl)-benzoic acid methyl ester as a white solid, MS (M+H)=335.

Step 2 3-(1-Chloro-2,2-difluoro-propylideneamino)-5-(5-methyl-pyridin-2-yl)-benzoic acid methyl ester 3-(2,2-Difluoro-propionylamino)-5-(5-methyl-pyridin-2-yl)-benzoic acid methyl ester (0.630 g, 1.88 mmol) and triphenyl phosphine (0.989 g, 3.77 mmol) were added to 15 mL of CCl$_4$. The reaction mixture was heated to 95° C. and stirred under nitrogen for 48 hours. The reaction mixture was filtered, and the filtrate was concentrated under reduced pressure to give 0.612 g of 3-(1-chloro-2,2-difluoro-propylideneamino)-5-(5-methyl-pyridin-2-yl)-benzoic acid methyl ester, which was used directly in the next step without further purification.

Step 3 3-[5-(1,1-Difluoro-ethyl)-tetrazol-1-yl]-5-(5-methyl-pyridin-2-yl)-benzoic acid methyl ester 3-(1-Chloro-2,2-difluoro-propylideneamino)-5-(5-methyl-pyridin-2-yl)-benzoic acid methyl ester (0.611 g, 1.732 mmol) and NaN$_3$ (0.225 g, 3.464 mmol) were added to 10 mL acetonitrile, and the mixture was stirred at room temperature for 90 minutes. Solvent was removed under reduced pressure and the residue was partitioned between water and EtOAc. The combined organic layers were washed with water, dried (MgSO$_4$), filtered and concentrated under reduced pressure to give 0.605 g of 3-[5-(1,1-Difluoro-ethyl)-tetrazol-1-yl]-5-(5-methyl-pyridin-2-yl)-benzoic acid methyl ester as a white powder, MS (M+H)=360.

Step 4 3-[5-(1,1-Difluoro-ethyl)-tetrazol-1-yl]-5-(5-methyl-pyridin-2-yl)-benzoic acid 3-[5-(1,1-Difluoro-ethyl)-tetrazol-1-yl]-5-(5-methyl-pyridin-2-yl)-benzoic acid methyl ester (0.605 g, 0.68 mmol) was added to a mixture of methanol (10 mL), methylene chloride (2 mL) and 3N aqueous NaOH (0.5 mL). The reaction mixture was stirred at room temperature for 18 hours, then solvent was removed under reduced pressure. The liquid residue was diluted with water and acidified to pH 5 by addition of 1N aqueous HCl. The resulting mixture was extracted with EtOAc, and the combined organic layers were washed with water, dried (MgSO$_4$), filtered and concentrated under reduced pressure to give 0.552 g of 3-[5-(1,1-Difluoro-ethyl)-tetrazol-1-yl]-5-(5-methyl-pyridin-2-yl)-benzoic acid.

Step 5 3-[5-(1,1-Difluoro-ethyl)-tetrazol-1-yl]-N—((S)-2-hydroxy-1-methyl-ethyl)-5-(5-methyl-pyridin-2-yl)-benzamide 3-[5-(1,1-Difluoro-ethyl)-tetrazol-1-yl]-5-(5-methyl-pyridin-2-yl)-benzoic acid was reacted with (R)-2-amino-propan-1-ol using the procedure of step 4 of Example 5, to afford 3-[5-(1,1-Difluoro-ethyl)-tetrazol-1-yl]-N—((S)-2-hydroxy-1-methyl-ethyl)-5-(5-methyl-pyridin-2-yl)-benzamide, MS (M+H)=403.

Similarly prepared, but replacing (R)-2-amino-propan-1-ol in step 4 with C-(5-methyl-pyrazin-2-yl)-methylamine, was 3-[5-(1,1-Difluoro-ethyl)-tetrazol-1-yl]-N-(5-methyl-pyrazin-2-ylmethyl)-5-(5-methyl-pyridin-2-yl)-benzamide, MS (M+H)=451.

Similarly prepared, but replacing (R)-2-amino-propan-1-ol in step 4 with 1-pyrazin-2-yl-ethylamine, was 3-[5-(1,1-Difluoro-ethyl)-tetrazol-1-yl]-5-(5-methyl-pyridin-2-yl)-N-(1-pyrazin-2-yl-ethyl)-benzamide, MS (M+H)=451.

Similarly prepared, but replacing (R)-2-amino-propan-1-ol in step 4 with cyclopropylamine, was N-Cyclopropyl-3-[5-(1,1-difluoro-ethyl)-tetrazol-1-yl]-5-(5-methyl-pyridin-2-yl)-benzamide, MS (M+H)=385.

Additional compounds prepared by the above procedure are shown in Table 1.

Example 7

3-(5-Chloro-pyridin-2-yl)-5-(5-isopropyl-tetrazol-1-yl)-N-(5-methyl-pyrazin-2-ylmethyl)-benzamide The synthetic procedure used in this example is outlined below in Scheme Q.

SCHEME Q

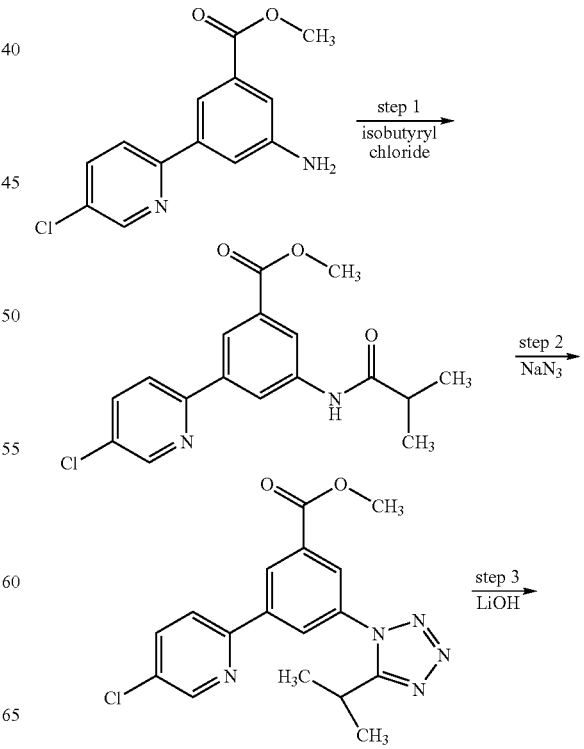

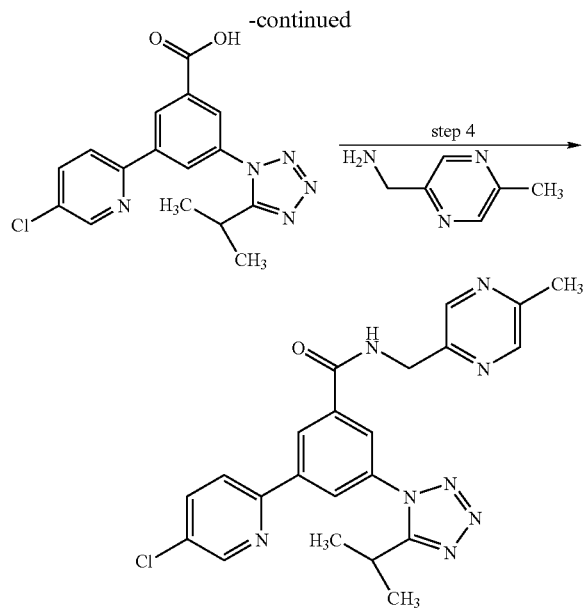

Step 1 3-(5-Chloro-pyridin-2-yl)-5-isobutyrylamino-benzoic acid methyl ester 3-Amino-5-(5-chloro-pyridin-2-yl)-benzoic acid methyl ester (1.5 g, 5.71 mmol, from Preparation 2) and Et$_3$N (2.39 mL, 17.13 mmol) were dissolved in 30 mL methylene chloride, and isobutyryl chloride (72 mL, 6.85 mmol) was added. The reaction mixture was stirred at room temperature for two hours, and then was partitioned between water and methylene chloride. The combined organic layers were dried (MgSO$_4$), filtered and concentrated under reduced pressure to give 1.29 g of 3-(5-chloro-pyridin-2-yl)-5-isobutyrylamino-benzoic acid methyl ester, MS (M+H)=333.

Step 2 3-(5-Chloro-pyridin-2-yl)-5-(5-isopropyl-tetrazol-1-yl)-benzoic acid methyl ester 3-(5-Chloro-pyridin-2-yl)-5-isobutyrylamino-benzoic acid methyl ester (1.90 g, 5.71 mmol) was dissolved in acetonitrile, and NaN$_3$ (3.71 g, 5.71 mmol) and SiCl$_4$ (1.64 mL, 14.28 mmol) were added. The reaction mixture was stirred at 60° C. for 18 hours, then cooled and poured in to cold saturated aqueous NaHCO$_3$. The resulting mixture was extracted with EtOAc, and the combined organic layers were dried (MgSO$_4$), filtered and concentrated under reduced pressure to give 1.84 g of 3-(5-chloro-pyridin-2-yl)-5-(5-isopropyl-tetrazol-1-yl)-benzoic acid methyl ester, MS (M+H)=358.

Step 3 3-(5-Chloro-pyridin-2-yl)-5-(5-isopropyl-tetrazol-1-yl)-benzoic acid 3-(5-Chloro-pyridin-2-yl)-5-(5-isopropyl-tetrazol-1-yl)-benzoic acid methyl ester (1.84 g, 5.14 mmol) was dissolved in a mixture of MeOH (15 mL), water (2 mL) and THF (2 mL), and LiOH 308 mg, 12.86 mmol) was added. The reaction mixture was stirred at room temperature for 18 hours and then partitioned between water and 1N aqueous HCl. The combined organic layers were dried (MgSO$_4$), filtered and concentrated under reduced pressure to give 1.70 g of 3-(5-chloro-pyridin-2-yl)-5-(5-isopropyl-tetrazol-1-yl)-benzoic acid, Mp=179.5-181.2° C., MS (M+H)=344.

Step 4 3-(5-Chloro-pyridin-2-yl)-5-(5-isopropyl-tetrazol-1-yl)-N-(5-methyl-pyrazin-2-ylmethyl)-benzamide 3-(5-Chloro-pyridin-2-yl)-5-(5-isopropyl-tetrazol-1-yl)-benzoic acid (650 mg, 1.89 mmol), C-(5-methyl-pyrazin-2-yl)-methylamine (233 mg, 1.89 mmol), EDCI (362 mg, 1.89 mmol), HOBt (255 mg, 1.89 mmol) and Et$_3$N (1.32 mL, 9.45 mmol) were added to 10 mL methylene chloride. The reaction mixture was stirred at room temperature for 18 hours, then was partitioned between water and methylene chloride. The combined organic layers were dried (MgSO$_4$), filtered and concentrated under reduced pressure. The resulting residue was purified via flash chromatography (80-100% EtOAc/hexanes) to give 492 mg of 3-(5-chloro-pyridin-2-yl)-5-(5-isopropyl-tetrazol-1-yl)-N-(5-methyl-pyrazin-2-ylmethyl)-benzamide, MS (M+H)=449.

Similarly prepared, but replacing C-(5-methyl-pyrazin-2-yl)-methylamine with 1-pyrazin-2-yl-ethylamine in step 4, was 3-(5-chloro-pyridin-2-yl)-5-(5-isopropyl-tetrazol-1-yl)-N-(1-pyrazin-2-yl-ethyl)-benzamide, MS (M+H)=449.

Similarly prepared, but replacing C-(5-methyl-pyrazin-2-yl)-methylamine with 3,5-difluoro-pyridin-2-ylmethylamine in step 4, was 3-(5-chloro-pyridin-2-yl)-N-(3,5-difluoro-pyridin-2-ylmethyl)-5-(5-isopropyl-tetrazol-1-yl)-benzamide, Mp=80.0-82.0° C.

Similarly prepared, but replacing C-(5-methyl-pyrazin-2-yl)-methylamine with (S)-2-hydroxy-1-methyl-ethylamine in step 4, was 3-(5-chloro-pyridin-2-yl)-N—((S)-2-hydroxy-1-methyl-ethyl)-5-(5-isopropyl-tetrazol-1-yl)-benzamide, Mp=124.0-125.0° C.

Similarly prepared, but replacing C-(5-methyl-pyrazin-2-yl)-methylamine with cyclopropylamine in step 4, was 3-(5-chloro-pyridin-2-yl)-N-cyclopropyl-5-(5-isopropyl-tetrazol-1-yl)-benzamide, Mp=107.0-108.0° C.

Similarly prepared, but replacing 3-amino-5-(5-chloro-pyridin-2-yl)-benzoic acid methyl ester with 3-amino-5-(5-methyl-pyridin-2-yl)-benzoic acid methyl ester, was 3-(5-isopropyl-tetrazol-1-yl)-N-(5-methyl-pyrazin-2-ylmethyl)-5-(5-methyl-pyridin-2-yl)-benzamide, MS (M+H)=429.

Similarly prepared, but replacing isobutyryl chloride in step 1 with 3-methyl-butyryl chloride, was 3-(5-chloro-pyridin-2-yl)-5-(5-isobutyl-tetrazol-1-yl)-N-(5-methyl-pyrazin-2-ylmethyl)-benzamide, MS (M+H)=463.

Similarly, but replacing 3-amino-5-(5-chloro-pyridin-2-yl)-benzoic acid methyl ester with 5-amino-4'-methyl-biphenyl-3-carboxylic acid methyl ester in step 1, was 5-(5-isopropyl-tetrazol-1-yl)-4'-methyl-biphenyl-3-carboxylic acid (5-methyl-pyrazin-2-ylmethyl)-amide, Mp=152-154.5° C.

Additional compounds prepared by the above procedure are shown in Table 1.

Example 8

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | Grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 9

$P2X_3/P2X_{2/3}$ FLIPR (Fluorometric Imaging Plate Reader) Assay

CHO-K1 cells were transfected with cloned rat $P2X_3$ or human $P2X_{2/3}$ receptor subunits and passaged in flasks. 18-24 hours before the FLIPR experiment, cells were released from their flasks, centrifuged, and resuspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25

μl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 μl/well agonist or vehicle addition. The agonist was a 2× solution of α,β-meATP producing a final concentration of 1 μM ($P2X_3$) or 5 μM ($P2X_{2/3}$). Fluorescence was measured for an additional 2 minutes at 1 second intervals after agonist addition. A final addition of ionomycin (5 μM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above assay, the compounds of Table 1 were all determined to be active for the $P2X_3$ receptor. Most of the compounds have an IC50 between about 6.0 and about 8.8 for P2X3. Many of the compounds have an IC50 of between about 8.0 and about 8.8 for P2X3. For example, 5-(5-isobutyl-tetrazol-1-yl)-4'-methyl-biphenyl-3-carboxylic acid ((S)-2-hydroxy-1-methyl-ethyl)-amide exhibited an IC50 of about 8.8.

Using the above assay, most of the compounds of Table 1 were determined to be active for the P2X2/3 receptor. Most of the compounds have an IC50 between about 5.5 and about 8.1 for P2X2/3. Many of the compounds have an IC50 of between about 7.0 and about 8.1 for P2X2/3. For example, 5-(5-ethyl-tetrazol-1-yl)-4'-methyl-biphenyl-3-carboxylic acid (1-pyrazin-2-yl-ethyl)-amide exhibited and IC50 of about 8.1.

Example 10

In Vivo Assay for Asthma and Lung Function

BALb/cJ mice are immunized with a standard immunization protocol. Briefly, mice (N=8/group) are immunized i.p. with ovalbumin (OVA; 10 μg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 11

Volume Induced Bladder Contraction Assay

Female Sprague-Dawley rats (200-300 g) were anesthetized with urethane (1.5 g/kg, sc). The animals were tracheotomized, and a carotid artery and femoral vein were cannulated for blood pressure measurement and drug administration, respectively. A laparotomy was performed and the ureters were ligated and transected proximal to the ligation. The external urethral meatus was ligated with silk suture and the urinary bladder was cannulated via the dome for saline infusion and bladder pressure measurement.

Following a 15-30 minute stabilization period the bladder was infused with room temperature saline at 100 μl/min until continuous volume-induced bladder contractions (VIBCs) were observed. The infusion rate was then lowered to 3-5 μl/min for 30 minutes before the bladder was drained and allowed to rest for 30 minutes. All subsequent infusions were performed as indicated except the lower infusion rate was maintained for only 15 minutes instead of 30 minutes. Bladder filling and draining cycles were repeated until the threshold volumes (TV; the volume needed to trigger the first micturition bladder contraction) varied by less than 10% for two consecutive baselines and contraction frequency was within 2 contractions for a 10 minute period following the slower infusion rate. Once reproducible TVs and VIBCs were established the bladder was drained and the animal was dosed with drug or vehicle (0.5 ml/kg, i.v.) 3 minutes prior to the start of the next scheduled infusion.

Example 12

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 μl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 13

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 14

Cold Allodynia in Rats with a Chronic Constriction Injury of the Sciatic Nerve

The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

Example 15

Cancer Bone Pain in C3H/HeJ Mice

The effects of compounds of this invention on bone pain are determined between Day 7 to Day 18 following intramedullary injection of 2472 sarcoma cells into the distal femur of C3H/HeJ mice.

Specifically, NCTC 2472 tumor cells (American Type Culture Collection, ATCC), previously shown to form lytic lesions in bone after intramedullary injection, are grown and maintained according to ATCC recommendations. Approximately $10^5$ cells are injected directly into the medullary cavity of the distal femur in anesthetized C3H/HeJ mice. Beginning on about Day 7, the mice are assessed for spontaneous nocifensive behaviors (flinching & guarding), palpation-evoked nocifensive behaviors (flinching & guarding), forced ambultory guarding and limb use. The effects of compounds of this invention are determined following a single acute (s.c.) administration on Day 7-Day 15. In addition, the effects of repeated (BID) administration of compounds of this invention from Day 7-Day 15 are determined within 1 hour of the first dose on Days 7, 9, 11, 13 and 15.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

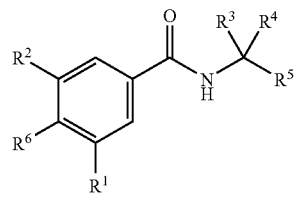

or a pharmaceutically acceptable salt thereof,
wherein:
$R^1$ is optionally substituted tetrazolyl;
$R^2$ is optionally substituted phenyl, optionally substituted pyridinyl, optionally substituted pyrimidinyl, optionally substituted pyridazinyl or optionally substituted thiophenyl;
$R^3$ is:
  hydrogen;
  $C_{1-6}$alkyl;
  hetero-$C_{1-6}$alkyl; or
  cyano;
$R^4$ is:
  hydrogen;
  $C_{1-6}$alkyl; or
  hetero-$C_{1-6}$alkyl;
or $R^3$ and $R^4$ together with the atom to which they are attached may form a $C_{3-6}$ carbocyclic ring;
$R^5$ is heteroaryl selected from pyridinyl, pyrimidinyl, pyrazinyl, pyridazinyl, pyrazolyl or thiazolyl, each of which may be optionally substituted once or twice with a group or groups independently selected from methyl, ethyl, n-propyl, fluoro, chloro, amino, methylamino and dimethylamino; and
$R^6$ is hydrogen.

2. The compound of claim 1, wherein $R^3$ is hydrogen.

3. The compound of claim 1, wherein $R^4$ is methyl.

4. The compound of claim 1, wherein $R^1$ is tetrazol-1-yl optionally substituted at the 5-position with $C_{1-6}$alkyl, halo-$C_{1-6}$alkyl, hetero-$C_{1-6}$alkyl, $C_{3-6}$-cycloalkyl, $C_{3-6}$cycloalkyl-$C_{1-6}$alkyl or cyano.

5. The compound of claim 4, wherein $R^2$ is phenyl optionally substituted once, twice or three times with a group or groups each independently selected from $C_{1-6}$alkyl, $C_{1-6}$alkyloxy, halo, $C_{1-6}$haloalkyl, hetero-$C_{1-6}$alkyl, $C_{1-6}$alkylsulfonyl or cyano.

6. The compound of claim 4, wherein $R^2$ is pyridin-2-yl optionally substituted once or twice with a group or groups each independently selected from $C_{1-6}$alkyl, $C_{1-6}$alkyloxy, halo, $C_{1-6}$haloalkyl, hetero-$C_{1-6}$alkyl, $C_{1-6}$alkylsulfonyl or cyano.

7. The compound of claim 4, wherein $R^4$ is tetrazol-1-yl optionally substituted at the 5-position with methyl, ethyl, n-propyl, n-butyl, isopropyl, isobutyl, tert-butyl, cyclopropyl, cyclopropylmethyl, trifluoromethyl, pentafluoro-ethyl, 1,1-difluoro-ethyl, 1-methoxy-ethyl, 1-ethoxy-ethyl, 2-methoxy-1-methyl-ethyl, 1-hydroxy-ethyl, or dimethylamino-methyl.

8. The compound of claim 1, wherein $R^3$ and $R^4$ are hydrogen.

9. The compound of claim 1, wherein $R^1$ is tetrazol-1-yl optionally substituted at the 5-position with $C_{1-6}$alkyl, halo-$C_{1-6}$alkyl, hetero-$C_{1-6}$alkyl, $C_{3-6}$-cycloalkyl, $C_{3-6}$cycloalkyl-$C_{1-6}$alkyl or cyano.

10. The compound of claim 9, wherein $R^2$ is 4-methyl-phenyl, 2-fluoro-4-methyl-phenyl, 2-chloro-4-fluoro-phenyl, 4-chloro-2-fluoro-phenyl, 2,4-dichloro-phenyl, 2,4-difluoro-phenyl, or 2-chloro-4-methyl-phenyl.

11. The compound of claim 9, wherein $R^2$ is 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-pyridin-2-yl.

12. The compound of claim 11, wherein $R^5$ is pyridinyl, pyrimidinyl, or pyrazinyl, each of which may be optionally substituted once or twice with a group or groups independently selected from methyl, fluoro, chloro, amino, methylamino or dimethylamino.

13. The compound of claim 12, wherein $R^1$ is tetrazol-1-yl substituted at the 5-position with halo-$C_{1-6}$alkyl.

14. The compound of claim 12, wherein $R^1$ is tetrazol-1-yl substituted at the 5-position with $C_{1-6}$alkyl.

15. The compound of claim 13, wherein $R^2$ is 5-methyl-pyridin-2-yl.

16. A compound of formula I:

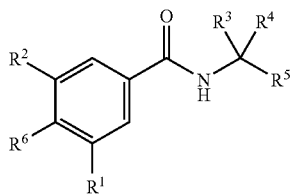

or a pharmaceutically acceptable salt thereof,
wherein:
$R^1$ is tetrazol-1-yl optionally substituted at the 5-position with $C_{1-6}$alkyl, halo-$C_{1-6}$alkyl, hetero-$C_{1-6}$alkyl, $C_{3-6}$-cycloalkyl, $C_{3-6}$cycloalkyl-$C_{1-6}$alkyl or cyano;
$R^2$ is optionally substituted phenyl, optionally substituted pyridinyl, optionally substituted pyrimidinyl, optionally substituted pyridazinyl or optionally substituted thiophenyl;
$R^3$ is hydrogen;
$R^4$ is methyl;
or $R^3$ and $R^4$ are both hydrogen;
$R^5$ is hydroxymethyl, methoxymethyl, pyrazin-2-yl or 5-methyl-pyrazin-2-yl; and
$R^6$ is hydrogen.

17. The compound of claim 16, wherein $R^2$ is 4-methyl-phenyl, 2-fluoro-4-methyl-phenyl, 2-chloro-4-fluoro-phenyl, 4-chloro-2-fluoro-phenyl, 2,4-dichloro-phenyl, 2,4-difluoro-phenyl, or 2-chloro-4-methyl-phenyl.

18. The compound of claim 16, wherein $R^2$ is 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-pyridin-2-yl.

19. The compound of claim 18, wherein $R^1$ is tetrazol-1-yl substituted at the 5-position with $C_{1-6}$alkyl.

20. The compound of claim 18, wherein $R^1$ is tetrazol-1-yl substituted at the 5-position with halo-$C_{1-6}$alkyl.

21. The compound of claim 18, wherein $R^2$ is 5-methyl-pyridin-2-yl.

22. A compound of formula I:

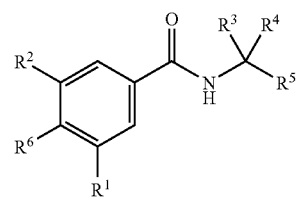

or a pharmaceutically acceptable salt thereof,
wherein:
$R^1$ is tetrazol-1-yl optionally substituted at the 5-position with $C_{1-6}$alkyl, halo-$C_{1-6}$alkyl, hetero-$C_{1-6}$alkyl, $C_{3-6}$-cycloalkyl, $C_{3-6}$cycloalkyl-$C_{1-6}$alkyl or cyano;
$R^2$ is 5-methyl-pyridin-2-yl, 5-chloro-pyridin-2-yl, 5-fluoro-pyridin-2-yl, 5-methyl-3-fluoro-pyridin-2-yl, 5-methyl-3-chloro-pyridin-2-yl, 3,5-difluoro-pyridin-2-yl or 3,5-dichloro-pyridin-2-yl;
$R^3$ is hydrogen;
$R^4$ is methyl;
or $R^3$ and $R^4$ are both hydrogen;
$R^5$ is pyridinyl, pyrimidinyl, or pyrazinyl, each of which may be optionally substituted once or twice with a group or groups independently selected from methyl, fluoro, chloro, amino, methylamino or dimethylamino; and
$R^6$ is hydrogen.

23. The compound of claim 22, wherein $R^3$ and $R^4$ are hydrogen.

24. The compound of claim 22, wherein $R^2$ is 5-methyl-pyridin-2-yl.

25. The compound of claim 24, wherein $R^1$ is tetrazol-1-yl substituted at the 5-position with $C_{1-6}$alkyl.

26. The compound of claim 24, wherein $R^1$ is tetrazol-1-yl substituted at the 5-position with halo-$C_{1-6}$alkyl.

27. A compound selected from the group consisting of:
N-(2-Methoxy-1-methyl-ethyl)-3-(5-methyl-pyridin-2-yl)-5-tetrazol-1-yl benzamide;
3-(5-Isopropyl-tetrazol-1-yl)-5-(5-methyl-pyridin-2-yl)-N-(1-pyrazin-2-yl-ethyl)-benzamide;
3-(5-Isopropyl-tetrazol-1-yl)-5-(5-methyl-pyridin-2-yl)-N-(1-pyrimidin-5-yl-ethyl)-benzamide;
3-(5-Isopropyl-tetrazol-1-yl)-N-(5-methyl-pyrazin-2-ylmethyl)-5-(5-methyl-pyridin-2-yl)-benzamide;
N-Cyclopropyl-3-(5-isopropyl-tetrazol-1-yl)-5-(5-methyl-pyridin-2-yl)-benzamide;

3-[5-(1-Methoxy-ethyl)-tetrazol-1-yl]-5-(5-methyl-pyridin-2-yl)-N-(1-pyrazin-2-yl-ethyl)-benzamide;
3-[5-(1-Methoxy-ethyl)-tetrazol-1-yl]-N-(5-methyl-pyrazin-2-ylmethyl)-5-(5-methyl-pyridin-2-yl)-benzamide
N—((S)-2-Hydroxy-1-methyl-ethyl)-3-[5-(1-methoxy-ethyl)-tetrazol-1-yl]-5-(5-methyl-pyridin-2-yl)-benzamide;
N-Cyclopropyl-3-[5-(1-methoxy-ethyl)-tetrazol-1-yl]-5-(5-methyl-pyridin-2-yl)-benzamide;
3-(5-Chloro-pyridin-2-yl)-5-(5-ethyl-tetrazol-1-yl)-N-(1-pyrazin-2-yl-ethyl)-benzamide;
3-(5-Chloro-pyridin-2-yl)-5-(5-ethyl-tetrazol-1-yl)-N-(5-methyl-pyrazin-2-ylmethyl)-benzamide;
3-(5-Chloro-pyridin-2-yl)-5-(5-isopropyl-tetrazol-1-yl)-N-(1-pyrazin-2-yl-ethyl)-benzamide;
3-(5-Ethyl-tetrazol-1-yl)-N-(5-methyl-pyrazin-2-ylmethyl)-5-(5-methyl-pyridin-2-yl)-benzamide;
3-(5-Chloro-pyridin-2-yl)-5-(5-isopropyl-tetrazol-1-yl)-N-(5-methyl-pyrazin-2-ylmethyl)-benzamide;
3-(5-Ethyl-tetrazol-1-yl)-5-(5-methyl-pyridin-2-yl)-N-(1-pyrazin-2-yl-ethyl)-benzamide;
3-(3,5-Dimethyl-pyridin-2-yl)-5-(5-ethyl-tetrazol-1-yl)-N-(1-pyrazin-2-yl-ethyl)-benzamide;
3-(3,5-Dimethyl-pyridin-2-yl)-5-(5-ethyl-tetrazol-1-yl)-N-(5-methyl-pyrazin-2-ylmethyl)-benzamide;
3-(3,5-Dimethyl-pyridin-2-yl)-5-(5-isopropyl-tetrazol-1-yl)-N-(1-pyrazin-2-yl-ethyl)-benzamide;
3-(3,5-Dimethyl-pyridin-2-yl)-5-(5-isopropyl-tetrazol-1-yl)-N-(5-methyl-pyrazin-2-ylmethyl)-benzamide;
3-(3,5-Dimethyl-pyridin-2-yl)-N—((S)-2-hydroxy-1-methyl-ethyl)-5-(5-isopropyl-tetrazol-1-yl)-benzamide;
N—((S)-2-Hydroxy-1-methyl-ethyl)-3-(5-isobutyl-tetrazol-1-yl)-5-(5-methyl-pyridin-2-yl)-benzamide;
3-(5-Isobutyl-tetrazol-1-yl)-5-(5-methyl-pyridin-2-yl)-N-(1-pyrazin-2-yl-ethyl)-benzamide;
3-(5-Isobutyl-tetrazol-1-yl)-N-(5-methyl-pyrazin-2-ylmethyl)-5-(5-methyl-pyridin-2-yl)-benzamide;
N-Cyclopropyl-3-(5-isobutyl-tetrazol-1-yl)-5-(5-methyl-pyridin-2-yl)-benzamide;
3-(5-Isobutyl-tetrazol-1-yl)-N—((R)-2-methoxy-1-methyl-ethyl)-5-(5-methyl-pyridin-2-yl)-benzamide;
3-(3-Chloro-5-methyl-pyridin-2-yl)-5-(5-isopropyl-tetrazol-1-yl)-N-(5-methyl-pyrazin-2-ylmethyl)-benzamide;
3-(3-Chloro-5-methyl-pyridin-2-yl)-5-(5-isopropyl-tetrazol-1-yl)-N-(1-pyrazin-2-yl-ethyl)-benzamide;
3-(3-Chloro-5-methyl-pyridin-2-yl)-N—((S)-2-hydroxy-1-methyl-ethyl)-5-(5-isopropyl-tetrazol-1-yl)-benzamide;
3-(3-Fluoro-5-methyl-pyridin-2-yl)-5-(5-isopropyl-tetrazol-1-yl)-N-(1-pyrazin-2-yl-ethyl)-benzamide;
3-(3-Fluoro-5-methyl-pyridin-2-yl)-5-(5-isopropyl-tetrazol-1-yl)-N-(5-methyl-pyrazin-2-ylmethyl)-benzamide;
3-(3-Fluoro-5-methyl-pyridin-2-yl)-N—((S)-2-hydroxy-1-methyl-ethyl)-5-(5-isopropyl-tetrazol-1-yl)-benzamide;
3-(5-Ethyl-tetrazol-1-yl)-5-(3-fluoro-5-methyl-pyridin-2-yl)-N-(1-pyrazin-2-yl-ethyl)-benzamide;
3-(5-Ethyl-tetrazol-1-yl)-5-(3-fluoro-5-methyl-pyridin-2-yl)-N-(5-methyl-pyrazin-2-ylmethyl)-benzamide;
3-(5-Ethyl-tetrazol-1-yl)-5-(3-fluoro-5-methyl-pyridin-2-yl)-N—((S)-2-hydroxy-1-methyl-ethyl)-benzamide;
N-(5-Methyl-pyrazin-2-ylmethyl)-3-(5-methyl-pyridin-2-yl)-5-(5-trifluoromethyl-tetrazol-1-yl)-benzamide;
3-(5-Methyl-pyridin-2-yl)-N-(1-pyrazin-2-yl-ethyl)-5-(5-trifluoromethyl-tetrazol-1-yl)-benzamide;
N—((S)-2-Hydroxy-1-methyl-ethyl)-3-(5-methyl-pyridin-2-yl)-5-(5-trifluoromethyl-tetrazol-1-yl)-benzamide;
N-Cyclopropyl-3-(5-methyl-pyridin-2-yl)-5-(5-trifluoromethyl-tetrazol-1-yl)-benzamide;
3-(5-Chloro-pyridin-2-yl)-N-(3,5-difluoro-pyridin-2-ylmethyl)-5-(5-isopropyl-tetrazol-1-yl)-benzamide;
5-(5-Isopropyl-tetrazol-1-yl)-4'-methyl-biphenyl-3-carboxylic acid (6-fluoro-pyridin-2-ylmethyl)-amide
3-(5-Chloro-pyridin-2-yl)-N-(6-fluoro-pyridin-2-ylmethyl)-5-(5-isopropyl-tetrazol-1-yl)-benzamide;
3-(5-Chloro-pyridin-2-yl)-N—((S)-2-hydroxy-1-methyl-ethyl)-5-(5-isopropyl-tetrazol-1-yl)-benzamide;
N-(5-Methyl-pyrazin-2-ylmethyl)-3-(5-methyl-pyridin-2-yl)-5-(5-pentafluoroethyl-tetrazol-1-yl)-benzamide;
3-(5-Methyl-pyridin-2-yl)-5-(5-pentafluoroethyl-tetrazol-1-yl)-N-(1-pyrazin-2-yl-ethyl)-benzamide;
N—((S)-2-Hydroxy-1-methyl-ethyl)-3-(5-methyl-pyridin-2-yl)-5-(5-pentafluoroethyl-tetrazol-1-yl)-benzamide;
N-Cyclopropyl-3-(5-methyl-pyridin-2-yl)-5-(5-pentafluoroethyl-tetrazol-1-yl)-benzamide;
3-[5-(1,1-Difluoro-ethyl)-tetrazol-1-yl]-N-(5-methyl-pyrazin-2-ylmethyl)-5-(5-methyl-pyridin-2-yl)-benzamide
3-[5-(1,1-Difluoro-ethyl)-tetrazol-1-yl]-5-(5-methyl-pyridin-2-yl)-N-(1-pyrazin-2-yl-ethyl)-benzamide;
3-[5-(1,1-Difluoro-ethyl)-tetrazol-1-yl]-N—((S)-2-hydroxy-1-methyl-ethyl)-5-(5-methyl-pyridin-2-yl)-benzamide;
N-Cyclopropyl-3-[5-(1,1-difluoro-ethyl)-tetrazol-1-yl]-5-(5-methyl-pyridin-2-yl)-benzamide;
3-(5-Chloro-pyridin-2-yl)-N-cyclopropyl-5-(5-isopropyl-tetrazol-1-yl)-benzamide;
3-(5-Chloro-pyridin-2-yl)-N—((S)-2-hydroxy-1-methyl-ethyl)-5-(5-trifluoromethyl-tetrazol-1-yl)-benzamide;
3-(5-Isopropyl-tetrazol-1-yl)-5-(5-methyl-pyridin-2-yl)-N—((S)-1-pyrazin-2-yl-ethyl)-benzamide;
3-(5-Chloro-pyridin-2-yl)-N-cyclopropyl-5-(5-trifluoromethyl-tetrazol-1-yl)-benzamide;
3-(3-Fluoro-5-methyl-pyridin-2-yl)-N-(1-pyrazin-2-yl-ethyl)-5-(5-trifluoromethyl-tetrazol-1-yl)-benzamide;
3-(3-Fluoro-5-methyl-pyridin-2-yl)-N-(5-methyl-pyrazin-2-ylmethyl)-5-(5-trifluoromethyl-tetrazol-1-yl)-benzamide;
3-(3-Fluoro-5-methyl-pyridin-2-yl)-N—((S)-2-hydroxy-1-methyl-ethyl)-5-(5-trifluoromethyl-tetrazol-1-yl)-benzamide;
N-Cyclopropyl-3-(3-fluoro-5-methyl-pyridin-2-yl)-5-(5-trifluoromethyl-tetrazol-1-yl)-benzamide;
3-(5-Chloro-pyridin-2-yl)-N-(5-methyl-pyrazin-2-ylmethyl)-5-(5-trifluoromethyl-tetrazol-1-yl)-benzamide;
3-(5-Chloro-pyridin-2-yl)-5-(5-isobutyl-tetrazol-1-yl)-N-(5-methyl-pyrazin-2-ylmethyl)-benzamide;
3-(5-Chloro-pyridin-2-yl)-N—((S)-2-hydroxy-1-methyl-ethyl)-5-(5-isobutyl-tetrazol-1-yl)-benzamide;
N-(3,5-Difluoro-pyridin-2-ylmethyl)-3-(5-isopropyl-tetrazol-1-yl)-5-(5-methyl-pyridin-2-yl)-benzamide;
3-(5-Isopropyl-tetrazol-1-yl)-5-(5-methyl-pyridin-2-yl)-N-[1-(5-methyl-pyridin-2-yl)-ethyl]-benzamide;
3-(5-Isopropyl-tetrazol-1-yl)-5-(5-methyl-pyridin-2-yl)-N-[1-(6-methyl-pyridin-2-yl)-ethyl]-benzamide;
3-(5-Isopropyl-tetrazol-1-yl)-5-(5-methyl-pyridin-2-yl)-N-(6-trifluoromethyl-pyridin-3-ylmethyl)-benzamide;
3-(5-Butyl-tetrazol-1-yl)-N—((R)-2-methoxy-1-methyl-ethyl)-5-(5-methyl-pyridin-
3-(5-Butyl-tetrazol-1-yl)-N-cyclopropyl-5-(5-methyl-pyridin-2-yl)-benzamide;
3-(5-Butyl-tetrazol-1-yl)-N—((S)-2-hydroxy-1-methyl-ethyl)-5-(5-methyl-pyridin-2-yl)-benzamide;
3-(5-Butyl-tetrazol-1-yl)-5-(5-methyl-pyridin-2-yl)-N-(1-pyrazin-2-yl-ethyl)-benzamide;
3-(5-Butyl-tetrazol-1-yl)-N-(5-methyl-pyrazin-2-ylmethyl)-5-(5-methyl-pyridin-2-yl)-benzamide;

3-(3,5-Difluoro-pyridin-2-yl)-5-(5-isopropyl-tetrazol-1-yl)-N-(1-pyrazin-2-yl-ethyl)-benzamide;
3-(3,5-Difluoro-pyridin-2-yl)-5-(5-isopropyl-tetrazol-1-yl)-N-(5-methyl-pyrazin-2-ylmethyl)-benzamide;
3-(5-Fluoromethyl-pyridin-2-yl)-5-(5-isopropyl-tetrazol-1-yl)-N-(5-methyl-pyrazin-2-ylmethyl)-benzamide;
3-(3,5-Difluoro-pyridin-2-yl)-N—((S)-2-hydroxy-1-methyl-ethyl)-5-(5-isopropyl-tetrazol-1-yl)-benzamide;
N-Cyclopropyl-3-(3,5-difluoro-pyridin-2-yl)-5-(5-isopropyl-tetrazol-1-yl)-benzamide;
N— [(S)-1-(5-Methyl-pyrazin-2-yl)-ethyl]-3-(5-methyl-pyridin-2-yl)-5-(5-trifluoromethyl-tetrazol-1-yl)-benzamide;
3-(5-Fluoro-pyridin-2-yl)-5-(5-isopropyl-tetrazol-1-yl)-N-(1-pyrazin-2-yl-ethyl)-benzamide;
3-(5-Fluoro-pyridin-2-yl)-5-(5-isopropyl-tetrazol-1-yl)-N-(5-methyl-pyrazin-2-ylmethyl)-benzamide;
3-(5-Chloro-pyridin-2-yl)-N-cyclopropyl-5-(5-isobutyl-tetrazol-1-yl)-benzamide;
3-(5-Chloro-pyridin-2-yl)-5-(5-isobutyl-tetrazol-1-yl)-N-(1-pyrazin-2-yl-ethyl)-benzamide;
3-(5-Fluoro-pyridin-2-yl)-N—((S)-2-hydroxy-1-methyl-ethyl)-5-(5-isopropyl-tetrazol-1-yl)-benzamide;
N-Cyclopropyl-3-(5-fluoro-pyridin-2-yl)-5-(5-isopropyl-tetrazol-1-yl)-benzamide;
3-(3,5-Difluoro-pyridin-2-yl)-5-(5-isobutyl-tetrazol-1-yl)-N-(1-pyrazin-2-yl-ethyl)-benzamide;
3-(3,5-Difluoro-pyridin-2-yl)-5-(5-isobutyl-tetrazol-1-yl)-N-(5-methyl-pyrazin-2-ylmethyl)-benzamide;
3-(3,5-Difluoro-pyridin-2-yl)-N—((S)-2-hydroxy-1-methyl-ethyl)-5-(5-isobutyl-tetrazol-1-yl)-benzamide;
N-Cyclopropyl-3-(3,5-difluoro-pyridin-2-yl)-5-(5-isobutyl-tetrazol-1-yl)-benzamide;
3-(5-tert-Butyl-tetrazol-1-yl)-N—((R)-2-methoxy-1-methyl-ethyl)-5-(5-methyl-pyridin-2-yl)-benzamide;
3-(5-tert-Butyl-tetrazol-1-yl)-N-cyclopropyl-5-(5-methyl-pyridin-2-yl)-benzamide;
3-(5-tert-Butyl-tetrazol-1-yl)-N—((S)-2-hydroxy-1-methyl-ethyl)-5-(5-methyl-pyridin-2-yl)-benzamide;
3-(5-tert-Butyl-tetrazol-1-yl)-5-(5-methyl-pyridin-2-yl)-N-(1-pyrazin-2-yl-ethyl)-benzamide;
3-(5-tert-Butyl-tetrazol-1-yl)-N-(5-methyl-pyrazin-2-ylmethyl)-5-(5-methyl-pyridin-2-yl)-benzamide;
3-(5-Methyl-pyridin-2-yl)-5-(5-propyl-tetrazol-1-yl)-N-(1-pyrazin-2-yl-ethyl)-benzamide;
N-(5-Methyl-pyrazin-2-ylmethyl)-3-(5-methyl-pyridin-2-yl)-5-(5-propyl-tetrazol-1-yl)-benzamide;
N-Cyclopropyl-3-(5-methyl-pyridin-2-yl)-5-(5-propyl-tetrazol-1-yl)-benzamide
N—((S)-2-Hydroxy-1-methyl-ethyl)-3-(5-methyl-pyridin-2-yl)-5-(5-propyl-tetrazol-1-yl)-benzamide;
3-(5-Chloro-pyridin-2-yl)-5-(5-propyl-tetrazol-1-yl)-N-(1-pyrazin-2-yl-ethyl)-benzamide;
3-(5-Chloro-pyridin-2-yl)-N-(5-methyl-pyrazin-2-ylmethyl)-5-(5-propyl-tetrazol-1-yl)-benzamide;
3-(5-Chloro-pyridin-2-yl)-N—((S)-2-hydroxy-1-methyl-ethyl)-5-(5-propyl-tetrazol-1-yl)-benzamide;
N-Cyclopropyl-3-(5-cyclopropylmethyl-tetrazol-1-yl)-5-(5-methyl-pyridin-2-yl)-benzamide;
3-(5-Cyclopropylmethyl-tetrazol-1-yl)-N—((S)-2-hydroxy-1-methyl-ethyl)-5-(5-methyl-pyridin-2-yl)-benzamide;
3-(5-Cyclopropylmethyl-tetrazol-1-yl)-5-(5-methyl-pyridin-2-yl)-N-(1-pyrazin-2-yl-ethyl)-benzamide;
3-(5-Cyclopropylmethyl-tetrazol-1-yl)-N-(5-methyl-pyrazin-2-ylmethyl)-5-(5-methyl-pyridin-2-yl)-benzamide;
3-(5-Difluoromethyl-pyridin-2-yl)-5-(5-isopropyl-tetrazol-1-yl)-N-(5-methyl-pyrazin-2-ylmethyl)-benzamide;
3-(5-Difluoromethyl-pyridin-2-yl)-5-(5-isopropyl-tetrazol-1-yl)-N-(1-pyrazin-2-yl-ethyl)-benzamide;
3-(5-Methyl-pyridin-2-yl)-5-(5-methyl-tetrazol-1-yl)-N-(1-pyrazin-2-yl-ethyl)-benzamide;
N-(5-Methyl-pyrazin-2-ylmethyl)-3-(5-methyl-pyridin-2-yl)-5-(5-methyl-tetrazol-1-yl)-benzamide;
N—((S)-2-Hydroxy-1-methyl-ethyl)-3-(5-methyl-pyridin-2-yl)-5-(5-methyl-tetrazol-1-yl)-benzamide;
3-(5-Fluoro-pyridin-2-yl)-5-(5-isobutyl-tetrazol-1-yl)-N-(1-pyrazin-2-yl-ethyl)-benzamide;
3-(5-Fluoro-pyridin-2-yl)-5-(5-isobutyl-tetrazol-1-yl)-N-(5-methyl-pyrazin-2-ylmethyl)-benzamide;
N-Cyclopropyl-3-(5-fluoro-pyridin-2-yl)-5-(5-isobutyl-tetrazol-1-yl)-benzamide;
3-[5-(1,1-Difluoro-ethyl)-tetrazol-1-yl]-5-(5-methyl-pyridin-2-yl)-N—((S)-1-pyrazin-2-yl-ethyl)-benzamide;
3-(5-Isopropyl-tetrazol-1-yl)-N-(6-methyl-pyridin-3-yl)-5-(5-methyl-pyridin-2-yl)-benzamide;
3-(5-Chloro-pyridin-2-yl)-5-(5-ethyl-tetrazol-1-yl)-N-(2-hydroxy-1-methyl-ethyl)-benzamide;
3-(5-Chloro-pyridin-2-yl)-5-(5-cyclopropyl-tetrazol-1-yl)-N-(1-pyrazin-2-yl-ethyl)-benzamide;
3-(5-Chloro-pyridin-2-yl)-5-(5-cyclopropyl-tetrazol-1-yl)-N-(5-methyl-pyrazin-2-ylmethyl)-benzamide;
3-(5-Chloro-pyridin-2-yl)-5-(5-cyclopropyl-tetrazol-1-yl)-N-(2-hydroxy-1-methyl-ethyl)-benzamide;
3-(5-Chloro-pyridin-2-yl)-N-cyclopropyl-5-(5-cyclopropyl-tetrazol-1-yl)-benzamide;
3-(5-Cyclopropyl-tetrazol-1-yl)-5-(5-methyl-pyridin-2-yl)-N-(1-pyrazin-2-yl-ethyl)-benzamide;
3-(5-Cyclopropyl-tetrazol-1-yl)-N-(5-methyl-pyrazin-2-ylmethyl)-5-(5-methyl pyridin-2-yl)-benzamide
3-(5-Cyclopropyl-tetrazol-1-yl)-N-(2-hydroxy-1-methyl-ethyl)-5-(5-methyl-pyridin-2-yl)-benzamide
3-(5-Ethyl-tetrazol-1-yl)-N—((S)-2-hydroxy-1-methyl-ethyl)-5-(5-methyl-pyridin-2-yl)-benzamide;
N—((S)-2-Hydroxy-1-methyl-ethyl)-3-(5-isopropyl-tetrazol-1-yl)-5-(5-methyl-pyridin-2-yl)-benzamide
3-(5-Ethyl-tetrazol-1-yl)-N-(2-methoxy-1-methyl-ethyl)-5-(5-methyl-pyridin-2-yl)-benzamide;
3-(5-Isopropyl-tetrazol-1-yl)-N-(2-methoxy-1-methyl-ethyl)-5-(5-methyl-pyridin-2-yl)-benzamide
3-(5-Bromo-pyridin-2-yl)-5-(5-isopropyl-tetrazol-1-yl)-N-(1-pyrazin-2-yl-ethyl)-benzamide; and
3-(5-Bromo-pyridin-2-yl)-5-(5-isopropyl-tetrazol-1-yl)-N-(5-methyl-pyrazin-2-ylmethyl)-benzamide.

28. The compound of claim 27, wherein said compound is selected from the group consisting of:
3-(5-Isopropyl-tetrazol-1-yl)-5-(5-methyl-pyridin-2-yl)-N-(1-pyrazin-2-yl-ethyl)-benzamide;
3-(5-Isopropyl-tetrazol-1-yl)-5-(5-methyl-pyridin-2-yl)-N-(1-pyrimidin-5-yl-ethyl)-benzamide;
3-(5-Isopropyl-tetrazol-1-yl)-N-(5-methyl-pyrazin-2-ylmethyl)-5-(5-methyl-pyridin-2-yl)-benzamide;
3-(5-Chloro-pyridin-2-yl)-5-(5-ethyl-tetrazol-1-yl)-N-(1-pyrazin-2-yl-ethyl)-benzamide;
3-(5-Chloro-pyridin-2-yl)-5-(5-ethyl-1-tetrazol-1-yl)-N-(5-methyl-pyrazin-2-ylmethyl)-benzamide;
3-(5-Chloro-pyridin-2-yl)-5-(5-isopropyl-tetrazol-1-yl)-N-(1-pyrazin-2-yl-ethyl)-benzamide;
3-(5-Ethyl-tetrazol-1-yl)-N-(5-methyl-pyrazin-2-ylmethyl)-5-(5-methyl-pyridin-2-yl)-benzamide;
3-(5-Chloro-pyridin-2-yl)-5-(5-isopropyl-tetrazol-1-yl)-N-(5-methyl-pyrazin-2-ylmethyl)-benzamide;
3-(5-Ethyl-tetrazol-1-yl)-5-(5-methyl-pyridin-2-yl)-N-(1-pyrazin-2-yl-ethyl)-benzamide;

3-(3,5-Dimethyl-pyridin-2-yl)-5-(5-ethyl-tetrazol-1-yl)-N-(1-pyrazin-2-yl-ethyl)-benzamide;
3-(3,5-Dimethyl-pyridin-2-yl)-5-(5-ethyl-tetrazol-1-yl)-N-(5-methyl-pyrazin-2-ylmethyl)-benzamide;
3-(3,5-Dimethyl-pyridin-2-yl)-5-(5-isopropyl-tetrazol-1-yl)-N-(1-pyrazin-2-yl-ethyl)-benzamide;
3-(3,5-Dimethyl-pyridin-2-yl)-5-(5-isopropyl-tetrazol-1-yl)-N-(5-methyl-pyrazin-2-ylmethyl)-benzamide;
3-(3,5-Dimethyl-pyridin-2-yl)-N—((S)-2-hydroxy-1-methyl-ethyl)-5-(5-isopropyl-tetrazol-1-yl)-benzamide;
N—((S)-2-Hydroxy-1-methyl-ethyl)-3-(5-isobutyl-tetrazol-1-yl)-5-(5-methyl-pyridin-2-yl)-benzamide;
3-(5-Isobutyl-tetrazol-1-yl)-5-(5-methyl-pyridin-2-yl)-N-(1-pyrazin-2-yl-ethyl)-benzamide;
3-(5-Isobutyl-tetrazol-1-yl)-N-(5-methyl-pyrazin-2-ylmethyl)-5-(5-methyl-pyridin-2-yl)-benzamide;
3-(5-Isobutyl-tetrazol-1-yl)-N—((R)-2-methoxy-1-methyl-ethyl)-5-(5-methyl-pyridin-2-yl)-benzamide;
3-(3-Chloro-5-methyl-pyridin-2-yl)-5-(5-isopropyl-tetrazol-1-yl)-N-(5-methyl-pyrazin-2-ylmethyl)-benzamide;
3-(3-Chloro-5-methyl-pyridin-2-yl)-5-(5-isopropyl-tetrazol-1-yl)-N-(1-pyrazin-2-yl-ethyl)-benzamide;
3-(3-Chloro-5-methyl-pyridin-2-yl)-N—((S)-2-hydroxy-1-methyl-ethyl)-5-(5-isopropyl-tetrazol-1-yl)-benzamide;
3-(3-Fluoro-5-methyl-pyridin-2-yl)-5-(5-isopropyl-tetrazol-1-yl)-N-(1-pyrazin-2-yl-ethyl)-benzamide;
3-(3-Fluoro-5-methyl-pyridin-2-yl)-5-(5-isopropyl-tetrazol-1-yl)-N-(5-methyl-pyrazin-2-ylmethyl)-benzamide;
3-(3-Fluoro-5-methyl-pyridin-2-yl)-N—((S)-2-hydroxy-1-methyl-ethyl)-5-(5-isopropyl-tetrazol-1-yl)-benzamide;
3-(5-Ethyl-tetrazol-1-yl)-5-(3-fluoro-5-methyl-pyridin-2-yl)-N-(1-pyrazin-2-yl-ethyl)-benzamide;
3-(5-Ethyl-tetrazol-1-yl)-5-(3-fluoro-5-methyl-pyridin-2-yl)-N-(5-methyl-pyrazin-2-ylmethyl)-benzamide;
3-(5-Ethyl-tetrazol-1-yl)-5-(3-fluoro-5-methyl-pyridin-2-yl)-N—((S)-2-hydroxy-1-methyl-ethyl)-benzamide;
N-(5-Methyl-pyrazin-2-ylmethyl)-3-(5-methyl-pyridin-2-yl)-5-(5-trifluoromethyl-tetrazol-1-yl)-benzamide;
3-(5-Methyl-pyridin-2-yl)-N-(1-pyrazin-2-yl-ethyl)-5-(5-trifluoromethyl-tetrazol-1-yl)-benzamide;
N—((S)-2-Hydroxy-1-methyl-ethyl)-3-(5-methyl-pyridin-2-yl)-5-(5-trifluoromethyl-tetrazol-1-yl)-benzamide;
3-(5-Chloro-pyridin-2-yl)-N—((S)-2-hydroxy-1-methyl-ethyl)-5-(5-isopropyl-tetrazol-1-yl)-benzamide;
N-(5-Methyl-pyrazin-2-ylmethyl)-3-(5-methyl-pyridin-2-yl)-5-(5-pentafluoroethyl-tetrazol-1-yl)-benzamide;
3-(5-Methyl-pyridin-2-yl)-5-(5-pentafluoroethyl-tetrazol-1-yl)-N-(1-pyrazin-2-yl-ethyl)-benzamide;
N—((S)-2-Hydroxy-1-methyl-ethyl)-3-(5-methyl-pyridin-2-yl)-5-(5-pentafluoroethyl-tetrazol-1-yl)-benzamide;
3-[5-(1,1-Difluoro-ethyl)-tetrazol-1-yl]-N-(5-methyl-pyrazin-2-ylmethyl)-5-(5-methyl-pyridin-2-yl)-benzamide
3-[5-(1,1-Difluoro-ethyl)-tetrazol-1-yl]-5-(5-methyl-pyridin-2-yl)-N-(1-pyrazin-2-yl-ethyl)-benzamide;
3-[5-(1,1-Difluoro-ethyl)-tetrazol-1-yl]-N—((S)-2-hydroxy-1-methyl-ethyl)-5-(5-methyl-pyridin-2-yl)-benzamide
3-(5-Chloro-pyridin-2-yl)-N—((S)-2-hydroxy-1-methyl-ethyl)-5-(5-trifluoromethyl-tetrazol-1-yl)-benzamide;
3-(5-Isopropyl-tetrazol-1-yl)-5-(5-methyl-pyridin-2-yl)-N—((S)-1-pyrazin-2-yl-ethyl)-benzamide;
3-(3-Fluoro-5-methyl-pyridin-2-yl)-N-(1-pyrazin-2-yl-ethyl)-5-(5-trifluoromethyl-tetrazol-1-yl)-benzamide;
3-(3-Fluoro-5-methyl-pyridin-2-yl)-N-(5-methyl-pyrazin-2-ylmethyl)-5-(5-trifluoromethyl-tetrazol-1-yl)-benzamide;
3-(3-Fluoro-5-methyl-pyridin-2-yl)-N—((S)-2-hydroxy-1-methyl-ethyl)-5-(5-trifluoromethyl-tetrazol-1-yl)-benzamide;
3-(5-Chloro-pyridin-2-yl)-N-(5-methyl-pyrazin-2-ylmethyl)-5-(5-trifluoromethyl-tetrazol-1-yl)-benzamide;
3-(5-Chloro-pyridin-2-yl)-5-(5-isobutyl-tetrazol-1-yl)-N-(5-methyl-pyrazin-2-ylmethyl)-benzamide;
3-(5-Chloro-pyridin-2-yl)-N—((S)-2-hydroxy-1-methyl-ethyl)-5-(5-isobutyl-tetrazol-1-yl)-benzamide;
N-(3,5-Difluoro-pyridin-2-ylmethyl)-3-(5-isopropyl-tetrazol-1-yl)-5-(5-methyl-pyridin-2-yl)-benzamide;
3-(5-Isopropyl-tetrazol-1-yl)-5-(5-methyl-pyridin-2-yl)-N-[1-(5-methyl-pyridin-2-yl)-ethyl]-benzamide;
3-(5-Isopropyl-tetrazol-1-yl)-5-(5-methyl-pyridin-2-yl)-N-[1-(6-methyl-pyridin-2-yl)-ethyl]-benzamide;
3-(5-Isopropyl-tetrazol-1-yl)-5-(5-methyl-pyridin-2-yl)-N-(6-trifluoromethyl-pyridin-3-ylmethyl)-benzamide;
3-(5-Butyl-tetrazol-1-yl)-N—((R)-2-methoxy-1-methyl-ethyl)-5-(5-methyl-pyridin-2-yl)-benzamide;
3-(5-Butyl-tetrazol-1-yl)-N—((S)-2-hydroxy-1-methyl-ethyl)-5-(5-methyl-pyridin-2-yl)-benzamide;
3-(5-Butyl-tetrazol-1-yl)-5-(5-methyl-pyridin-2-yl)-N-(1-pyrazin-2-yl-ethyl)-benzamide;
3-(5-Butyl-tetrazol-1-yl)-N-(5-methyl-pyrazin-2-ylmethyl)-5-(5-methyl-pyridin-2-yl)-benzamide;
3-(3,5-Difluoro-pyridin-2-yl)-5-(5-isopropyl-tetrazol-1-yl)-N-(1-pyrazin-2-yl-ethyl)-benzamide;
3-(3,5-Difluoro-pyridin-2-yl)-5-(5-isopropyl-tetrazol-1-yl)-N-(5-methyl-pyrazin-2-ylmethyl)-benzamide;
3-(Fluoromethyl-pyridin-2-yl)-5-(5-isopropyl-tetrazol-1-yl)-N-(5-methyl-pyrazin-2-ylmethyl)-benzamide;
3-(3,5-Difluoro-pyridin-2-yl)-N—((S)-2-hydroxy-1-methyl-ethyl)-5-(5-isopropyl-tetrazol-1-yl)-benzamide;
N—[(S)-1-(5-Methyl-pyrazin-2-yl)-ethyl]-3-(5-methyl-pyridin-2-yl)-5-(5-trifluoromethyl-tetrazol-1-yl)-benzamide;
3-(5-Fluoro-pyridin-2-yl)-5-(5-isopropyl-tetrazol-1-yl)-N-(1-pyrazin-2-yl-ethyl)-benzamide;
3-(5-Fluoro-pyridin-2-yl)-5-(5-isopropyl-tetrazol-1-yl)-N-(5-methyl-pyrazin-2-ylmethyl)-benzamide;
3-(5-Chloro-pyridin-2-yl)-5-(5-isobutyl-tetrazol-1-yl)-N-(1-pyrazin-2-yl-ethyl)-benzamide;
3-(5-Fluoro-pyridin-2-yl)-N—((S)-2-hydroxy-1-methyl-ethyl)-5-(5-isopropyl-tetrazol-1-yl)-benzamide;
3-(3,5-Difluoro-pyridin-2-yl)-5-(5-isobutyl-tetrazol-1-yl)-N-(1-pyrazin-2-yl-ethyl)-benzamide;
3-(3,5-Difluoro-pyridin-2-yl)-5-(5-isobutyl-tetrazol-1-yl)-N-(5-methyl-pyrazin-2-ylmethyl)-benzamide;
3-(3,5-Difluoro-pyridin-2-yl)-N—((S)-2-hydroxy-1-methyl-ethyl)-5-(5-isobutyl-tetrazol-1-yl)-benzamide;
3-(5-tert-Butyl-tetrazol-1-yl)-N—((R)-2-methoxy-1-methyl-ethyl)-5-(5-methyl-pyridin-2-yl)-benzamide;
3-(5-tert-Butyl-tetrazol-1-yl)-N—((S)-2-hydroxy-1-methyl-ethyl)-5-(5-methyl-pyridin-2-yl)-benzamide;
3-(5-tert-Butyl-tetrazol-1-yl)-5-(5-methyl-pyridin-2-yl)-N-(1-pyrazin-2-yl-ethyl)-benzamide;
3-(5-tert-Butyl-tetrazol-1-yl)-N-(5-methyl-pyrazin-2-ylmethyl)-5-(5-methyl-pyridin-2-yl)-benzamide;
3-(5-Methyl-pyridin-2-yl)-5-(5-propyl-tetrazol-1-yl)-N-(1-pyrazin-2-yl-ethyl)-benzamide;
N-(5-Methyl-pyrazin-2-ylmethyl)-3-(5-methyl-pyridin-2-yl)-5-(5-propyl-tetrazol-1-yl)-benzamide;
N—((S)-2-Hydroxy-1-methyl-ethyl)-3-(5-methyl-pyridin-2-yl)-5-(5-propyl-tetrazol-1-yl)-benzamide;
3-(5-Chloro-pyridin-2-yl)-5-(5-propyl-tetrazol-1-yl)-N-(1-pyrazin-2-yl-ethyl)-benzamide;
3-(5-Chloro-pyridin-2-yl)-N-(5-methyl-pyrazin-2-ylmethyl)-5-(5-propyl-tetrazol-1-yl)-benzamide;

3-(5-Chloro-pyridin-2-yl)-N—((S)-2-hydroxy-1-methyl-ethyl)-5-(5-propyl-tetrazol-1-yl)-benzamide;
3-(5-Cyclopropylmethyl-tetrazol-1-yl)-N—((S)-2-hydroxy-1-methyl-ethyl)-5-(5-methyl-pyridin-2-yl)-benzamide;
3-(5-Cyclopropylmethyl-tetrazol-1-yl)-5-(5-methyl-pyridin-2-yl)-N-(1-pyrazin-2-yl-ethyl)-benzamide;
3-(5-Cyclopropylmethyl-tetrazol-1-yl)-N-(5-methyl-pyrazin-2-ylmethyl)-5-(5-methyl-pyridin-2-yl)-benzamide;
3-(5-Difluoromethyl-pyridin-2-yl)-5-(5-isopropyl-tetrazol-1-yl)-N-(5-methyl-pyrazin-2-ylmethyl)-benzamide;
3-(5-Difluoromethyl-pyridin-2-yl)-5-(5-isopropyl-tetrazol-1-yl)-N-(1-pyrazin-2-yl-ethyl)-benzamide;
3-(5-Methyl-pyridin-2-yl)-5-(5-methyl-tetrazol-1-yl)-N-(1-pyrazin-2-yl-ethyl)-benzamide;
N-(5-Methyl-pyrazin-2-ylmethyl)-3-(5-methyl-pyridin-2-yl)-5-(5-methyl-tetrazol-1-yl)-benzamide;
N—((S)-2-Hydroxy-1-methyl-ethyl)-3-(5-methyl-pyridin-2-yl)-5-(5-methyl-tetrazol-1-yl)-benzamide;
3-(5-Fluoro-pyridin-2-yl)-5-(5-isobutyl-tetrazol-1-yl)-N-(1-pyrazin-2-yl-ethyl)-benzamide;
3-(5-Fluoro-pyridin-2-yl)-5-(5-isobutyl-tetrazol-1-yl)-N-(5-methyl-pyrazin-2-ylmethyl)-benzamide;
3-[5-(1,1-Difluoro-ethyl)-tetrazol-1-yl]-5-(5-methyl-pyridin-2-yl)-N—((S)-1-pyrazin-2-yl-ethyl)-benzamide;
3-(5-Chloro-pyridin-2-yl)-5-(5-ethyl-tetrazol-1-yl)-N-(2-hydroxy-1-methyl-ethyl)-benzamide;
3-(5-Chloro-pyridin-2-yl)-5-(5-cyclopropyl-tetrazol-1-yl)-N-(1-pyrazin-2-yl-ethyl)-benzamide;
3-(5-Chloro-pyridin-2-yl)-5-(5-cyclopropyl-tetrazol-1-yl)-N-(5-methyl-pyrazin-2-ylmethyl)-benzamide;
3-(5-Chloro-pyridin-2-yl)-5-(5-cyclopropyl-tetrazol-1-yl)-N-(2-hydroxy-1-methyl-ethyl)-benzamide;
3-(5-Cyclopropyl-tetrazol-1-yl)-5-(5-methyl-pyridin-2-yl)-N-(1-pyrazin-2-yl-ethyl)-benzamide;
3-(5-Cyclopropyl-tetrazol-1-yl)-N-(5-methyl-pyrazin-2-ylmethyl)-5-(5-methyl-pyridin-2-yl)-benzamide;
3-(5-Cyclopropyl-tetrazol-1-yl)-N-(2-hydroxy-1-methyl-ethyl)-5-(5-methyl-pyridin-2-yl)-benzamide;
3-(5-Ethyl-tetrazol-1-yl)-N—((S)-2-hydroxy-1-methyl-ethyl)-5-(5-methyl-pyridin-2-yl)-benzamide;
N—((S)-2-Hydroxy-1-methyl-ethyl)-3-(5-isopropyl-tetrazol-1-yl)-5-(5-methyl-pyridin-2-yl)-benzamide;
3-(5-Ethyl-tetrazol-1-yl)-N-(2-methoxy-1-methyl-ethyl)-5-(5-methyl-pyridin-2-yl)-benzamide;
3-(5-Isopropyl-tetrazol-1-yl)-N-(2-methoxy-1-methyl-ethyl)-5-(5-methyl-pyridin-2-yl)-benzamide
3-(5-Bromo-pyridin-2-yl)-5-(5-isopropyl-tetrazol-1-yl)-N-(1-pyrazin-2-yl-ethyl)-benzamide; and
3-(5-Bromo-pyridin-2-yl)-5-(5-isopropyl-tetrazol-1-yl)-N-(5-methyl-pyrazin-2-ylmethyl)-benzamide.

29. The compound of claim 28, wherein said compound is selected from the group consisting of:
3-(5-Isopropyl-tetrazol-1-yl)-N-(5-methyl-pyrazin-2-ylmethyl)-5-(5-methyl-pyridin-2-yl)-benzamide;
3-(5-Ethyl-tetrazol-1-yl)-N-(5-methyl-pyrazin-2-ylmethyl)-5-(5-methyl-pyridin-2-yl)-benzamide;
3-(5-Ethyl-tetrazol-1-yl)-5-(5-methyl-pyridin-2-yl)-N-(1-pyrazin-2-yl-ethyl)-benzamide;
N—((S)-2-Hydroxy-1-methyl-ethyl)-3-(5-isobutyl-tetrazol-1-yl)-5-(5-methyl-pyridin-2-yl)-benzamide;
3-(5-Isobutyl-tetrazol-1-yl)-5-(5-methyl-pyridin-2-yl)-N-(1-pyrazin-2-yl-ethyl)-benzamide;
3-(5-Isobutyl-tetrazol-1-yl)-N-(5-methyl-pyrazin-2-ylmethyl)-5-(5-methyl-pyridin-2-yl)-benzamide;
3-(5-Isobutyl-tetrazol-1-yl)-N—((R)-2-methoxy-1-methyl-ethyl)-5-(5-methyl-pyridin-2-yl)-benzamide;
N-(5-Methyl-pyrazin-2-ylmethyl)-3-(5-methyl-pyridin-2-yl)-5-(5-trifluoromethyl-tetrazol-1-yl)-benzamide;
3-(5-Methyl-pyridin-2-yl)-N-(1-pyrazin-2-yl-ethyl)-5-(5-trifluoromethyl-tetrazol-1-yl)-benzamide;
N—((S)-2-Hydroxy-1-methyl-ethyl)-3-(5-methyl-pyridin-2-yl)-5-(5-trifluoromethyl-tetrazol-1-yl)-benzamide;
N-(5-Methyl-pyrazin-2-ylmethyl)-3-(5-methyl-pyridin-2-yl)-5-(5-pentafluoroethyl-tetrazol-1-yl)-benzamide;
3-(5-Methyl-pyridin-2-yl)-5-(5-pentafluoroethyl-tetrazol-1-yl)-N-(1-pyrazin-2-yl-ethyl)-benzamide;
N—((S)-2-Hydroxy-1-methyl-ethyl)-3-(5-methyl-pyridin-2-yl)-5-(5-pentafluoroethyl-tetrazol-1-yl)-benzamide;
3-[5-(1,1-Difluoro-ethyl)-tetrazol-1-yl]-N-(5-methyl-pyrazin-2-ylmethyl)-5-(5-methyl-pyridin-2-yl)-benzamide;
3-[5-(1,1-Difluoro-ethyl)-tetrazol-1-yl]-5-(5-methyl-pyridin-2-yl)-N-(1-pyrazin-2-yl-ethyl)-benzamide;
3-[5-(1,1-Difluoro-ethyl)-tetrazol-1-yl]-N—((S)-2-hydroxy-1-methyl-ethyl)-5-(5-methyl-pyridin-2-yl)-benzamide;
3-(5-Isopropyl-tetrazol-1-yl)-5-(5-methyl-pyridin-2-yl)-N—((S)-1-pyrazin-2-yl-ethyl)-benzamide;
3-(3-Fluoro-5-methyl-pyridin-2-yl)-N-(1-pyrazin-2-yl-ethyl)-5-(5-trifluoromethyl-tetrazol-1-yl)-benzamide;
3-(3-Fluoro-5-methyl-pyridin-2-yl)-N-(5-methyl-pyrazin-2-ylmethyl)-5-(5-trifluoromethyl-tetrazol-1-yl)-benzamide;
3-(5-Butyl-tetrazol-1-yl)-N—((R)-2-methoxy-1-methyl-ethyl)-5-(5-methyl-pyridin-2-yl)-benzamide;
3-(5-Butyl-tetrazol-1-yl)-N—((S)-2-hydroxy-1-methyl-ethyl)-5-(5-methyl-pyridin-2-yl)-benzamide;
3-(5-Butyl-tetrazol-1-yl)-5-(5-methyl-pyridin-2-yl)-N-(1-pyrazin-2-yl-ethyl)-benzamide;
3-(5-Butyl-tetrazol-1-yl)-N-(5-methyl-pyrazin-2-ylmethyl)-5-(5-methyl-pyridine-2-yl)-benzamide;
N—[(S)-1-(5-Methyl-pyrazin-2-yl)-ethyl]-3-(5-methyl-pyridin-2-yl)-5-(5-trifluoromethyl-tetrazol-1-yl)-benzamide;
3-(5-tert-Butyl-tetrazol-1-yl)-N—((R)-2-methoxy-1-methyl-ethyl)-5-(5-methyl-pyridin-2-yl)-benzamide;
3-(5-tert-Butyl-tetrazol-1-yl)-N—((S)-2-hydroxy-1-methyl-ethyl)-5-(5-methyl-pyridin-2-yl)-benzamide;
3-(5-tert-Butyl-tetrazol-1-yl)-5-(5-methyl-pyridin-2-yl)-N-(1-pyrazin-2-yl-ethyl)-benzamide;
3-(5-tert-Butyl-tetrazol-1-yl)-N-(5-methyl-pyrazin-2-ylmethyl)-5-(5-methyl-pyridin-2-yl)-benzamide;
3-(5-Methyl-pyridin-2-yl)-5-(5-propyl-tetrazol-1-yl)-N-(1-pyrazin-2-yl-ethyl)-benzamide;
N-(5-Methyl-pyrazin-2-ylmethyl)-3-(5-methyl-pyridin-2-yl)-5-(5-propyl-tetrazol-1-yl)-benzamide;
N—((S)-2-Hydroxy-1-methyl-ethyl)-3-(5-methyl-pyridin-2-yl)-5-(5-propyl-tetrazol-1-yl)-benzamide;
3-(5-Cyclopropylmethyl-tetrazol-1-yl)-N—((S)-2-hydroxy-1-methyl-ethyl)-5-(5-methyl-pyridin-2-yl)-benzamide;
3-(5-Cyclopropylmethyl-tetrazol-1-yl)-5-(5-methyl-pyridin-2-yl)-N-(1-pyrazin-2-yl-ethyl)-benzamide;
3-(5-Cyclopropylmethyl-tetrazol-1-yl)-N-(5-methyl-pyrazin-2-ylmethyl)-5-(5-methyl-pyridin-2-yl)-benzamide;
3-(5-Methyl-pyridin-2-yl)-5-(5-methyl-tetrazol-1-yl)-N-(1-pyrazin-2-yl-ethyl)-benzamide;
N-(5-Methyl-pyrazin-2-ylmethyl)-3-(5-methyl-pyridin-2-yl)-5-(5-methyl-tetrazol-1-yl)-benzamide;
N—((S)-2-Hydroxy-1-methyl-ethyl)-3-(5-methyl-pyridin-2-yl)-5-(5-methyl-tetrazol-1-yl)-benzamide;
3-[5-(1,1-Difluoro-ethyl)-tetrazol-1-yl]-5-(5-methyl-pyridin-2-yl)-N—((S)-1-pyrazin-2-yl-ethyl)-benzamide;
3-(5-Cyclopropyl-tetrazol-1-yl)-5-(5-methyl-pyridin-2-yl)-N-(1-pyrazin-2-yl-ethyl)-benzamide;
3-(5-Cyclopropyl-tetrazol-1-yl)-N-(5-methyl-pyrazin-2-ylmethyl)-5-(5-methyl-pyridin-2-yl)-benzamide;

3-(5-Cyclopropyl-tetrazol-1-yl)-N-(2-hydroxy-1-methyl-ethyl)-5-(5-methyl-pyridin-2-yl)-benzamide;
3-(5-Ethyl-tetrazol-1-yl)-N—((S)-2-hydroxy-1-methyl-ethyl)-5-(5-methyl-pyridin-2-yl)-benzamide;
N—((S)-2-Hydroxy-1-methyl-ethyl)-3-(5-isopropyl-tetrazol-1-yl)-5-(5-methyl-pyridin-2-yl)-benzamide;
3-(5-Ethyl-tetrazol-1-yl)-N-(2-methoxy-1-methyl-ethyl)-5-(5-methyl-pyridin-2-yl)-benzamide; and
3-(5-Isopropyl-tetrazol-1-yl)-N-(2-methoxy-1-methyl-ethyl)-5-(5-methyl-pyridin-2-yl)-benzamide.

30. The compound of claim 29, wherein said compound is selected from the group consisting of:

3-(5-Isopropyl-tetrazol-1-yl)-N-(5-methyl-pyrazin-2-ylmethyl)-5-(5-methyl-pyridin-2-yl)-benzamide;
3-(5-Ethyl-tetrazol-1-yl)-N-(5-methyl-pyrazin-2-ylmethyl)-5-(5-methyl-pyridin-2-yl)-benzamide;
3-(5-Isobutyl-tetrazol-1-yl)-N-(5-methyl-pyrazin-2-ylmethyl)-5-(5-methyl-pyridin-2-yl)-benzamide;
N-(5-Methyl-pyrazin-2-ylmethyl)-3-(5-methyl-pyridin-2-yl)-5-(5-trifluoromethyl-tetrazol-1-yl)-benzamide;
N-(5-Methyl-pyrazin-2-ylmethyl)-3-(5-methyl-pyridin-2-yl)-5-(5-pentafluoroethyl-tetrazol-1-yl)-benzamide;
3-[5-(1,1-Difluoro-ethyl)-tetrazol-1-yl]-N-(5-methyl-pyrazin-2-ylmethyl)-5-(5-methyl-pyridin-2-yl)-benzamide;
3-(3-Fluoro-5-methyl-pyridin-2-yl)-N-(5-methyl-pyrazin-2-ylmethyl)-5-(5-trifluoromethyl-tetrazol-1-yl)-benzamide;
3-(5-Butyl-tetrazol-1-yl)-N-(5-methyl-pyrazin-2-ylmethyl)-5-(5-methyl-pyridin-2-yl)-benzamide;
3-(5-tert-Butyl-tetrazol-1-yl)-N-(5-methyl-pyrazin-2-ylmethyl)-5-(5-methyl-pyridin-2-yl)-benzamide;
N-(5-Methyl-pyrazin-2-ylmethyl)-3-(5-methyl-pyridin-2-yl)-5-(5-propyl-tetrazol-1-yl)-benzamide;
N-(5-Methyl-pyrazin-2-ylmethyl)-3-(5-methyl-pyridin-2-yl)-5-(5-methyl-tetrazol-1-yl)-benzamide; and
3-(5-Ethyl-tetrazol-1-yl)-N—((S)-2-hydroxy-1-methyl-ethyl)-5-(5-methyl-pyridin-2-yl)-benzamide.

* * * * *